United States Patent
Bagal et al.

(10) Patent No.: US 8,927,587 B2
(45) Date of Patent: Jan. 6, 2015

(54) CHEMICAL COMPOUNDS

(71) Applicant: Pfizer Limited, Sandwich, Kent (GB)

(72) Inventors: Sharanjeet Kaur Bagal, Great Abington (GB); Alan Daniel Brown, Great Abington (GB); Mark Ian Kemp, Sandwich (GB); Wolfgang Klute, Sandwich (GB); Laia Malet Sanz, Sandwich (GB); Brian Edward Marron, Durham, NC (US); Duncan Charles Miller, Sandwich (GB); Sarah Elizabeth Skerratt, Great Abington (GB); Mark J. Suto, Birmingham, AL (US); Christopher William West, Durham, NC (US)

(73) Assignee: Pfizer LImited, Sandwich, Kent (GB)

( * ) Notice: Subject to any disclaimer, the term of this patent is extended or adjusted under 35 U.S.C. 154(b) by 0 days.

(21) Appl. No.: 13/752,571

(22) Filed: Jan. 29, 2013

(65) Prior Publication Data
US 2013/0274243 A1 Oct. 17, 2013

Related U.S. Application Data

(60) Provisional application No. 61/594,460, filed on Feb. 3, 2012.

(51) Int. Cl.
| | | |
|---|---|---|
| A61K 31/4184 | (2006.01) | |
| C07D 235/04 | (2006.01) | |
| C07D 233/64 | (2006.01) | |
| C07D 401/04 | (2006.01) | |
| A61K 45/06 | (2006.01) | |
| A61K 31/437 | (2006.01) | |
| C07D 235/14 | (2006.01) | |
| C07D 403/04 | (2006.01) | |
| A61K 31/454 | (2006.01) | |
| C07D 235/16 | (2006.01) | |
| C07D 471/04 | (2006.01) | |

(52) U.S. Cl.
CPC .......... *A61K 31/4184* (2013.01); *C07D 233/64* (2013.01); *C07D 401/04* (2013.01); *A61K 45/06* (2013.01); *A61K 31/437* (2013.01); *C07D 235/14* (2013.01); *C07D 403/04* (2013.01); *A61K 31/454* (2013.01); *C07D 235/16* (2013.01); *C07D 471/04* (2013.01)
USPC ............ 514/387; 548/301.7; 548/304.4; 548/309.7; 514/385

(58) Field of Classification Search
CPC .............. A61K 31/4184; C07D 235/04
USPC .......... 548/301.7, 304.4, 309.7; 514/385, 387
See application file for complete search history.

(56) References Cited

U.S. PATENT DOCUMENTS

| | | | | |
|---|---|---|---|---|
| 6,106,864 | A | 8/2000 | Dolan et al. | |
| 7,816,353 | B2 * | 10/2010 | Cheng et al. | 514/235.8 |
| 2008/0261941 | A1 | 10/2008 | Fay et al. | |
| 2009/0023740 | A1 | 1/2009 | Fulp et al. | |
| 2009/0048306 | A1 | 2/2009 | Bagal et al. | |
| 2009/0143358 | A1 | 6/2009 | Marron et al. | |
| 2009/0261941 | A1 | 10/2009 | Hang et al. | |

FOREIGN PATENT DOCUMENTS

| | | |
|---|---|---|
| EP | 0266326 | 5/1988 |
| EP | 2072516 | 6/2009 |
| WO | 9111172 | 8/1991 |
| WO | 9402518 | 2/1994 |
| WO | 9855148 | 12/1998 |
| WO | 0035298 | 6/2000 |
| WO | 0228839 | 4/2002 |
| WO | 2004011439 | 2/2004 |
| WO | 2005113580 | 12/2005 |
| WO | 2007115077 | 10/2007 |
| WO | 2008047229 | 4/2008 |
| WO | 2008118758 | 10/2008 |
| WO | 2008135826 | 11/2008 |
| WO | 2008135830 | 11/2008 |
| WO | 2009012242 | 1/2009 |
| WO | 2012116440 | 9/2012 |

OTHER PUBLICATIONS

Allen et al (2008): STN International HCAPLUS database (Columbus, Ohio), accession No. 2008:1005721.*
Akopian, A. N., et al., "The Tetrodotoxin-Resistant Sodium Channel SNS Has a Specialized Function in Pain Pathways", Nature Neuroscience, Jun. 1999, pp. 541-548, 2(6).

(Continued)

*Primary Examiner* — Golam M M Shameem
(74) *Attorney, Agent, or Firm* — Richard V. Zanzalari

(57) ABSTRACT

The invention relates to benzimidazole and imidazopyridine derivatives, to their use in medicine, to compositions containing them, to processes for their preparation and to intermediates used in such processes. More particularly the invention relates to new $Na_v1.8$ modulators of formula (I)

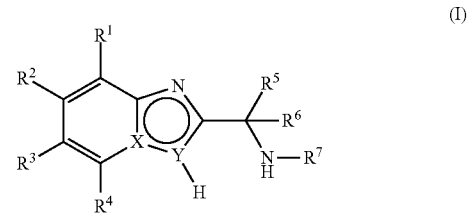

(I)

or pharmaceutically acceptable salts thereof, wherein $R^1$, $R^2$, $R^3$, $R^4$, $R^5$, $R^6$, $R^7$. X and Y are as defined in the description. $Na_v1.8$ modulators are potentially useful in the treatment of a wide range of disorders, particularly pain.

8 Claims, No Drawings

(56) References Cited

OTHER PUBLICATIONS

Akopian, A.N., et al., "A Tetrodotoxin-Resistant Voltage-Gated Sodium Channel Expressed by Sensory Neurons", Nature, Jan. 18, 1996, pp. 257-262, 379(6562).

Almarsson, O., et al., "Crystal Engineering of the Composition of Pharmaceutical Phases. Do Pharmaceutical Co-Crystals Represent a New Path to Improved Medicines?", Chemical Communications, 2004, pp. 1889-1896, vol. 17.

Black, J.A., et al., "Abnormal Expression of SNS/PN3 Sodium Channel in Cerebellar Purkinje Cells Following Loss of Myelin in the Taiep Rat", NeuroReport, Apr. 6, 1999, pp. 913-918, 10(5).

Black, J.A., et al., "Sensory Neuron-Specific Sodium Channel SNS is Abnormal Expressed in the Brains of Mice with Experimental Allergic Encephalomyelitis and Humans with Multiple Sclerosis", Proceeds National Academy of Science, Oct. 10, 2000, pp. 11598-11602, 97(21).

Bucknill, A., et al., "Nerve Fibers in Lumbar Spine Structures and Injured Spinal Roots Express the Sensory Neuron-Specific Sodium Channels SNS/PN3 and NaN/SNS2", Spine, Jan. 15, 2002, pp. 135-140, 27(2).

Cannon, S. C., "Spectrum of Sodium Channel Disturbances in the Nondystrophic Myotonias and Periodic Paralyses", Kidney International, Mar. 2000, pp. 772-779, 57(3).

Coward, K., et al., "Immunolocalization of SNS/PN3 and NaN/SNS2 Sodium Channels in Human Pain States", Pain, Mar. 1, 2000, pp. 41-50, 85(1-2).

Finnin, B., et al., "Transdermal Penetration Enhancers: Applications, Limitations, and Potential", Journal Pharmaceutical Science, Oct. 1999, pp. 955-958, 88(10).

Haleblain, John, "Characterization of Habits and Crystalline Modification of Solids and Their Pharmaceutical Applications", Journal of Pharmaceutical Science, Aug. 1975, pp. 1269-1288, 64(8).

Houge, J., et al., "Pathophysiology and First-Line Treatment of Osteoarthritis", Annals of Pharmacotherapy, Apr. 2002, pp. 679-686, 36(4).

Hubner, C.A., et al., "Ion Channel Diseases", Human Molecular Genetics, Oct. 2002, pp. 2435-2445, 11(20).

International Search Report for PCT Application No. PCT/IB2013/050555, mailed Jul. 23, 2013, 9 pages.

Lai, J., et al., "Inhibition of Neuropathic Pain by Decreased Expression of the Tetrodotoxin-Resistant Sodium Channel, NaV1.8", Pain, Jan. 2002, pp. 143-152, 95(1-2).

Laird, J., et al., "Deficits in Visceral Pain and Referred Hyperalgesia in Nav1.8 (SNS/PN3)-Null Mice", Journal of Neuroscience, Oct. 1, 2002, pp. 8352-8356, 22(19).

Liang, A., et al., "Fast-Dissolving Intraoral Drug Delivery Systems", Expert Opinion in Therapeutic Patents, Jun. 2001, pp. 981-986, 11(6).

Mellor, M., et al., "An Unexpected Rearrangement of 4-Bromo-2(3H)-Benzothiazolones", Tetrahedron, 1991, pp. 2255-2262, 47(12/13).

Millian, et al., "The Induction of Pain: An Integrative Review", Progress in Neurobiology, 1999, pp. 1-164, 57(1).

Nobel, D., "Unraveling the Genetics and Mechanisms of Cardiac Arrhythmia", Proceedings of the National Academy of Sciences, Apr. 30, 2002, pp. 5755-5756, 99(9).

Rabert, D.K., et al., "A Tetrodotoxin-Resistant Voltage-Gated Sodium Channel From Human Dorsal Root Ganglia, hPN3/SCN10A", Pain, Nov. 1, 1998, pp. 107-114, 78(2).

Shembalker, P., et al., "Increased Sodium Channel SNS/PN3 Immunoreactivity in a Causalgic Finger", European Journal of Pain, 2001, pp. 319-323, 5(3).

Tan, Z., et al., "Peptide Coupling: Insights into the Finer Issues of Native Chemical Ligation: An Approach to Cascade Ligations", Angewandte Chemie International, Ed., 2010, pp. 9500-9503, 49(9) (49).

Verma, R., et al., "Current Status of Drug Delivery Technologies and Future Directions", Pharmaceutical Technology On-line, Feb. 2001, pp. 1-14, 25(2).

Wood, J.N., et al., "Voltage-Gated Sodium Channels and Pain Pathways", Journal of Neurobiology, 2004, pp. 55-71, 61(1).

Woolf, C., et al., "Neuronal Plasticity: Increasing the Gain in Pain", Science, Jun. 9, 2000, pp. 1765-1768, 288 (5472).

Woolf, C., et al., Implications of Recent Advances in the Understanding of Pain Pathophysiology for the Assessment of Pain in Patients, Pain Supplement 6, Aug. 1999, pp. S141-S147, 82(Suppl. 1).

Yiangou, Y., et al., "SNS/PN3 and SNS2/NaN Sodium Channel-Like Immunoreactivity in Human Adult and Neonate Injured Sensory Nerves", FEBS Letters, Feb. 11, 2000, pp. 249-252, 467(2-3).

Yogeeswari, P., et al., "Ion Channels as Important Targets for Antiepileptic drug Design", Current Drug Targets, Oct. 2004, pp. 589-602, 5(7).

Woolf, C., et al., "Neuropathic pain: aetiology, symptoms, mechanisms, and management", Lancet, 1999, pp. 1959-1964, vol. 353.

US 2009/048306 published Feb. 19, 2009 equivalent to WO 2008/135826 published Nov. 13, 2008.

US 2009/143358 published Jun. 4, 2009 equivalent to WO 2008/118758 published Oct. 2, 2008.

US 2009/0023740 published Jan. 22, 2009 equivalent to WO 2009/012242 published Jan. 22, 2009.

US 2008/261941 published Oct. 23, 2008 equivalent to WO 2008/047229 published Apr. 28, 2008.

* cited by examiner

CHEMICAL COMPOUNDS

This application claims the benefit of U.S. Provisional Patent Application No. 61/594,460 filed on Feb. 3, 2012, the disclosure of which is hereby incorporated by reference in its entirety.

FIELD OF THE INVENTION

The invention relates to benzimidazole and imidazopyridine derivatives. More particularly, this invention relates to derivatives of (benzimidazol-2-yl)methylamine and (imidazo[1,2-a]pyridin-2-yl)methylamine, to their use in medicine, to compositions containing them, to processes for their preparation and to intermediates used in such processes.

BACKGROUND

The benzimidazole and imidazopyridine derivatives of the present invention are sodium channel modulators. In particular they are modulators of the $Na_v1.8$ sodium channel. Preferred benzimidazole and imidazopyridine derivatives of the invention show an activity for the $Na_v1.8$ channel which is greater than their activity for other sodium channels such as the $Na_v1.5$ sodium channel and the tetrodotoxin-sensitive sodium channels (TTX-S). The benzimidazole and imidazopyridine derivatives of the invention have a number of therapeutic applications and potential therapeutic applications. In particular they are useful in the treatment of pain.

Voltage-gated sodium channels are found in all excitable cells including myocytes of muscle and neurons of the central and peripheral nervous system. In neuronal cells, sodium channels are primarily responsible for generating the rapid upstroke of the action potential. In this manner sodium channels are essential to the initiation and propagation of electrical signals in the nervous system. Proper and appropriate function of sodium channels is therefore necessary for normal function of the neuron. Consequently, aberrant sodium channel function is thought to underlie a variety of medical disorders (see Hubner C. A., Jentsch T. J., *Hum. Mol. Genet.*, 11(20): 2435-45 (2002) for a general review of inherited ion channel disorders) including epilepsy (Yogeeswari et al., *Curr. Drug Targets*, 5(7): 589-602 (2004)), arrhythmia (Noble D., *Proc. Natl. Acad. Sci. USA*, 99(9): 5755-6 (2002)), myotonia (Cannon, S. C., *Kidney Int.* 57(3): 772-9 (2000)), and pain (Wood, J. N. et al., *J. Neurobiol.*, 61(1): 55-71 (2004)).

There are currently at least nine known members of the family of voltage-gated sodium channel (VGSC) alpha subunits. Names for this family include SCNx, SCNAx, and $Na_vx.x$. The VGSC family has been phylogenetically divided into two subfamilies $Na_v1.x$ (all but SCN6A) and $Na_v2.x$ (SCN6A). The $Na_v1.x$ subfamily can be functionally subdivided into two groups, those which are sensitive to blocking by tetrodotoxin (TTX-sensitive or TTX-S) and those which are resistant to blocking by tetrodotoxin (TTX-resistant or TTX-R).

The $Na_v1.8$ channel is a voltage-gated sodium channel which is expressed in nociceptors, the sensory neurones responsible for transducing painful stimuli. The rat channel and the human channel were cloned in 1996 and 1998 respectively (*Nature* 1996; 379: 257-262; *Pain* 1998(November); 78(2):107-114). The $Na_v1.8$ channel was previously known as SNS (sensory neurone specific) and PN3 (peripheral nerve type 3). The $Na_v1.8$ channel is atypical in that it shows resistance to the blocking effects of the puffer fish toxin tetrodotoxin and it is believed to underlie the slow-voltage-gated and tetrodotoxin-resistant (TTX-R) sodium currents recorded from dorsal root ganglion neurones. The closest molecular relative to the $Na_v1.8$ channel is the $Na_v1.5$ channel, which is the cardiac sodium channel, with which it shares approximately 60% homology. The $Na_v1.8$ channel is expressed most highly in the 'small cells' of the dorsal root ganglia (DRG). These are thought to be the C- and A-delta cells which are the putative polymodal nociceptors, or pain sensors. Under normal conditions, the $Na_v1.8$ channel is not expressed anywhere other than subpopulations of DRG neurones. The $Na_v1.8$ channels are thought to contribute to the process of DRG sensitisation and also to hyperexcitability due to nerve injury. Inhibitory modulation of the $Na_v1.8$ channels is aimed at reducing the excitability of nociceptors, by preventing them from contributing to the excitatory process.

Studies have shown that $Na_v1.8$ knock-out leads to a blunted pain phenotype, mostly to inflammatory challenges (A. N. Akopian et al., *Nat. Neurosci.* 1999; 2; 541-548) and that $Na_v1.8$ knockdown reduces pain behaviours, in this case neuropathic pain (J. Lai et al., *Pain*, 2002(January); 95(1-2): 143-152). Coward et al. and Yiangou et al., have shown that $Na_v1.8$ appears to be expressed in pain conditions (*Pain*. 2000(March); 85(1-2): 41-50 and FEBS Lett. 2000(February 11); 467(2-3): 249-252).

The $Na_v1.8$ channel has also been shown to be expressed in structures relating to the back and tooth pulp and there is evidence for a role in causalgia, inflammatory bowel conditions and multiple sclerosis (Bucknill et al., *Spine*. 2002 (January 15); 27(2):135-140: Shembalker et al., *Eur J. Pain*. 2001; 5(3): 319-323: Laird et al., *J. Neurosci.* 2002(October 1); 22(19): 8352-8356: Black et al., *Neuroreport*. 1999(April 6); 10(5): 913-918 and *Proc. Natl. Acad. Sci. USA* 2000:97: 11598-11602).

Examples of modulators of the $Na_v1.8$ sodium channel are disclosed in WO2008/135826, WO2008/135830, and WO2012/116440. There is, however, an ongoing need to provide new $Na_v1.8$ sodium channel inhibitors that are good drug candidates. These drug candidates should have one or more of the following properties: be well absorbed from the gastrointestinal tract; be metabolically stable; have a good metabolic profile, in particular with respect to the toxicity or allergenicity of any metabolites formed; or possess favourable pharmacokinetic properties whilst still retaining their activity profile as $Na_v1.8$ channel inhibitors. They should be non-toxic and demonstrate few side-effects. Ideal drug candidates should exist in a physical form that is stable, non-hygroscopic and easily formulated.

SUMMARY OF THE INVENTION

In a first aspect, the present invention provides a compound of formula (I)

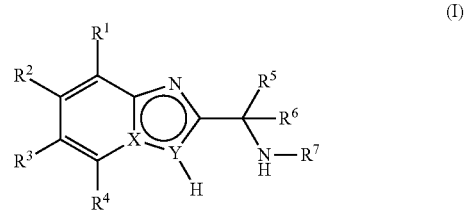

or a tautomer thereof, or a pharmaceutically acceptable salt or solvate of said compound or said tautomer, wherein:
one of X and Y is C and the other is N;

$R^1$ is selected from
  H, F, Cl and $CF_3$;
one of $R^2$ and $R^3$ is selected from
  $(C_3-C_6)$alkyl,
  $(C_3-C_6)$cycloalkyl,
  adamantyl, and
  phenyl substituted with —CN, and optionally further substituted with one or two groups independently selected from —F, —Cl, —$CF_3$ and —CN;
and the other one of $R^2$ and $R^3$ is selected from
  H and F;
$R^4$ is selected from
  H, F, $C_1$ and $CF_3$
$R^5$ is selected from
  $(C_1-C_6)$alkyl,
  $(C_1-C_6)$alkyl substituted with a group selected from
    —$CONH_2$,
    —CONH—$(C_1-C_3)$alkyl,
    —CON$((C_1-C_3)$alkyl$)_2$ wherein the $(C_1-C_3)$alkyl groups may be the same or different,
    —OH,
    —O$(C_1-C_3)$alkyl, and
    —$OCONH_2$,
  $(C_3-C_6)$cycloalkyl, and
  phenyl,
$R^6$ is selected from
  H and $(C_1-C_3)$alkyl,
or $R^5$ and $R^6$ together with the carbon atom to which they are attached may form a 3- to 6-membered cycloalkyl moiety which may optionally be benzo-fused;
$R^7$ is H or methyl,
or, when $R^5$ and $R^6$ do not form a cycloalkyl or benzo-fused cycloalkyl moiety, $R^5$ and $R^7$ together with the carbon and nitrogen atoms to which they are attached may form 4- to 6-membered monocyclic or 6- to 8-membered bicyclic saturated nitrogen heterocycle which may optionally be substituted with 1 or 2 groups selected from —$(C_1-C_3)$alkyl, —OH, and —F.

The compounds of formula (I) and their pharmaceutically acceptable salts are referred to herein as "the compounds of the invention". The definition above is referred to herein as embodiment E1 of this aspect. Further embodiments of this aspect of the invention are described in detail below.

In another aspect, the invention provides for a compound of formula (I) as described above, or in any one of the preferred embodiments, or a pharmaceutically acceptable salt or solvate thereof, for use as a medicament. In an embodiment according to this aspect the compound of formula (I), or a pharmaceutically acceptable salt or solvate thereof, is for use in the treatment of pain.

In another aspect, the invention provides for a pharmaceutical composition comprising a compound of formula (I) as described above, or in any one of the preferred embodiments, or a pharmaceutically acceptable salt or solvate thereof, and a pharmaceutically acceptable diluents or carrier In another aspect, the invention provides for a method of treating pain comprising administering a therapeutically effective amount of a compound of formula (I) as described above, or in any one of the preferred embodiments, or a pharmaceutically acceptable salt or solvate thereof, to an individual in need of such treatment.

In another aspect, the invention provides for the use of a compound of formula (I) as described above, or in any one of the preferred embodiments, or a pharmaceutically acceptable salt or solvate thereof, for the treatment of pain.

DETAILED DESCRIPTION OF THE INVENTION

Alkyl groups, containing the requisite number of carbon atoms, can be unbranched or branched. $(C_1-C_3)$Alkyl includes methyl, ethyl, n-propyl (1-propyl) and isopropyl (2-propyl, 1-methylethyl). Branched alkyl includes isopropyl (2-propyl, 1-methylethyl), sec-butyl (2-butyl, 1-methylpropyl), isobutyl (2-methylpropyl), tert-butyl (1,1-dimethylethyl), sec-pentyl (1-methylbutyl), 1-ethylpropyl, isopentyl (3-methylbutyl), tert-pentyl (1,1-dimethylpropyl), neopentyl (2,2-dimethylpropyl) and the like.

Further specific embodiments of the compounds of the invention are as follows.

In embodiment E2, there is provided a compound according to embodiment E1 of formula ($I^A$)

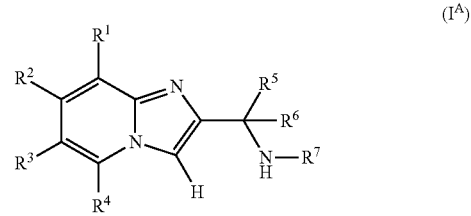

(I<sup>A</sup>)

or a pharmaceutically acceptable salt or solvate thereof, wherein
$R^1$, $R^4$, $R^5$, $R^6$ and $R^7$ are as defined for embodiment E1;
$R^2$ is selected from
  H and F, and
$R^3$ is selected from
  $(C_3-C_6)$alkyl,
  $(C_3-C_6)$cycloalkyl,
  adamantyl, and
  phenyl substituted with —CN, and optionally further substituted with one or two groups independently selected from —F, —Cl, —$CF_3$ and —CN.

In embodiment E3, there is provided a compound according to embodiment E2 or a pharmaceutically acceptable salt or solvate thereof, wherein
$R^1$ is selected from H and $CF_3$;
$R^2$ is H;
$R^3$ is selected from $(C_4-C_6)$branched alkyl and phenyl substituted at the 4-position with —CN and optionally further substituted with one or two —F groups, and
$R^4$ is selected from H, F and Cl.

In embodiment E4, there is provided a compound according to embodiment E1 of formula ($I^B$)

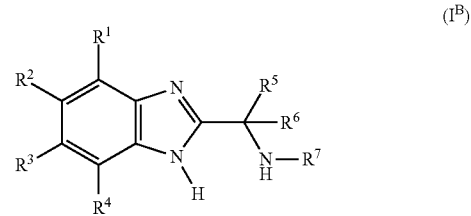

(I<sup>B</sup>)

or a tautomer thereof, or a pharmaceutically acceptable salt or solvate of said compound or tautomer, wherein
$R^1$ is selected from H, F and Cl;
$R^2$ is selected from
  $(C_3-C_6)$alkyl,
  $(C_3-C_6)$cycloalkyl,
  adamantyl, and
  phenyl substituted with —CN, and optionally further substituted with one or two groups independently selected from —F, —Cl, —$CF_3$ and —CN; and R³ is selected from
H and F; and
R⁴ is selected from H and CF₃; and
R⁵, R⁶ and R⁷ are as defined in embodiment E1.

In embodiment E5, there is provided a compound according to embodiment E4 or a tautomer thereof, or a pharmaceutically acceptable salt or solvate of said compound or tautomer, wherein R³ is H.

In embodiment E6, there is provided a compound according to embodiment E4 or E5 or a pharmaceutically acceptable salt or solvate thereof, wherein R² is $(C_4-C_6)$branched alkyl.

In embodiment E7, there is provided a compound according to any one of embodiments E4, E5 or E6 or a pharmaceutically acceptable salt or solvate thereof, wherein R² is selected from 1,1-dimethylethyl and 1,1-dimethylpropyl.

In embodiment E8, there is provided a compound according to any one of embodiments E1, E2, E3, E4, E5, E6 or E7 or a pharmaceutically acceptable salt or solvate thereof, wherein R¹ and R⁴ are both H.

In embodiment E9, there is provided a compound according to embodiment E4 of formula ($I^C$)

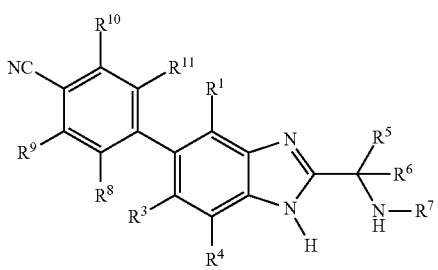

or a tautomer thereof, or a pharmaceutically acceptable salt or solvate of said compound or tautomer, wherein:
R¹, R³ and R⁴, are as defined in embodiment E4;
R⁵, R⁶ and R⁷ are as defined in embodiment E1; and
R⁸, R⁹, R¹⁰ and R¹¹ are selected from H, F, —Cl, —CF₃ and —CN, provided that at least 2 of R⁸, R⁹, R¹⁰ and R¹¹ are H.

In embodiment E10, there is provided a compound according to embodiment E9, or a tautomer thereof, or a pharmaceutically acceptable salt or solvate of said compound or tautomer, wherein:
R¹ is selected from H and —F;
R³ and R⁴ are both H;
R⁸ and R⁹ are both H;
R¹⁰ and R¹¹ are each independently selected from H and —F.

In embodiment E11, there is provided a compound according to any one of embodiments E1, E2, E3, E4, E5, E6, E7, E8, E9 or E10 of formula ($I^D$)

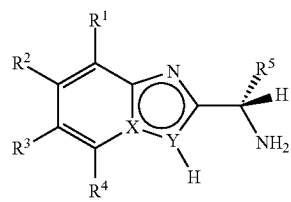

or a tautomer thereof, or a pharmaceutically acceptable salt or solvate of said compound or tautomer, having the (S) absolute configuration, wherein:

X, Y, R¹, R², R³ and R⁴ are as defined in embodiments E1, E2, E3, E4, E5, E6, E7, E8, E9 or E10; and
R⁵ is selected from $(C_1-C_6)$alkyl and $(C_3-C_6)$cycloalkyl.

In embodiment E12, there is provided a compound according to any one of embodiments E1, E2, E3, E4, E5, E6, E7, E8, E9 or E10 of formula ($I^E$)

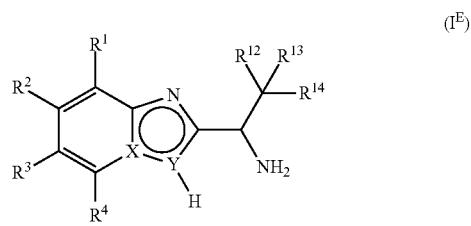

or a tautomer thereof, or a pharmaceutically acceptable salt or solvate of said compound or tautomer, wherein:
X, Y, R¹, R², R³ and R⁴ are as defined in embodiments E1, E2, E3, E4, E5, E6, E7, E8, E9 or E10;
R¹² and R¹³ are each independently —H or methyl; and
R¹⁴ is selected from —OH, —O(C₁-C₃)alkyl, —OCONH₂ and —CONH₂.

In embodiment E13, there is provided a compound according to embodiment E12 of formula ($I^G$)

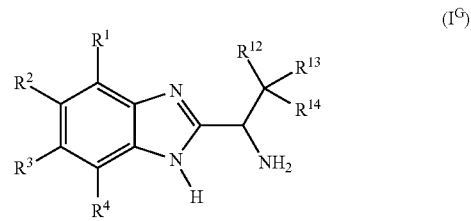

or a tautomer thereof, or a pharmaceutically acceptable salt or solvate thereof, wherein
R¹, R², R³, R⁴, R¹², R¹³ and R¹⁴ are as defined in embodiments E12.

In embodiment E14, there is provided a compound according to embodiment E13 or a pharmaceutically acceptable salt or solvate thereof, wherein R¹⁴ is selected from —OH, —O(C₁-C₃)alkyl and —OCONH₂.

In embodiment E15, there is provided a compound according to embodiment E14 of formula ($I^H$)

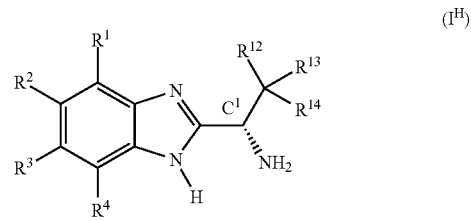

or a pharmaceutically acceptable salt thereof, having the (R) configuration at C¹.

In embodiment E16, there is provided a compound according to embodiment E14 of formula ($I^J$)

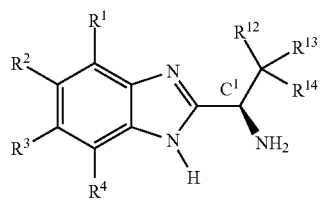
(I$^J$)

or a pharmaceutically acceptable salt thereof, having the (S) configuration at C$^1$.

In embodiment E17, there is provided a compound according to any one of embodiments E14, E15 or E16 or a pharmaceutically acceptable salt or solvate thereof, wherein
R$^{12}$ is methyl;
R$^{13}$ is H; and
R$^{14}$ is selected from —OH, —OCH$_3$ and —OCONH$_2$ In embodiment E18, there is provided a compound according to embodiment E17 of formula (I$^K$)

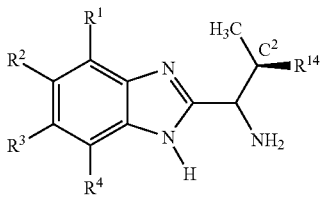
(I$^K$)

or a pharmaceutically acceptable salt thereof, having the (R) configuration at C$^2$.

In embodiment E19, there is provided a compound according to embodiment E17 of formula (I$^L$)

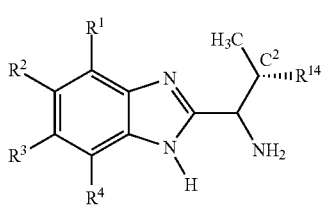
(I$^L$)

or a pharmaceutically acceptable salt thereof, having the (S) configuration at C$^2$.

In embodiment E20, there is provided a compound according to embodiment E13 or a pharmaceutically acceptable salt or solvate thereof, wherein R$^{14}$ is —CONH$_2$.

In embodiment E21, there is provided a compound according to embodiment E20 of formula (I$^M$)

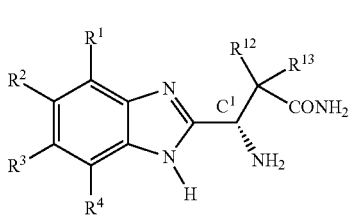
(I$^M$)

or a pharmaceutically acceptable salt thereof, having the (S) configuration at C$^1$.

In embodiment E22, there is provided a compound according to embodiment E20 of formula (I$^N$)

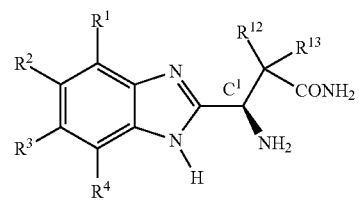
(I$^N$)

or a pharmaceutically acceptable salt thereof, having the (R) configuration at C$^1$.

In embodiment E23, there is provided a compound according to any one of embodiments E20, E21 or E22 or a pharmaceutically acceptable salt or solvate thereof, wherein R$^{12}$ is methyl and R$^{13}$ is H.

In embodiment E24, there is provided a compound according to embodiment E23 of formula (I$^P$)

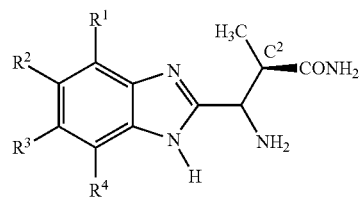
(I$^P$)

or a pharmaceutically acceptable salt thereof, having the (R) configuration at C$^2$.

In embodiment E25, there is provided a compound according to embodiment E23 of formula (I$^Q$)

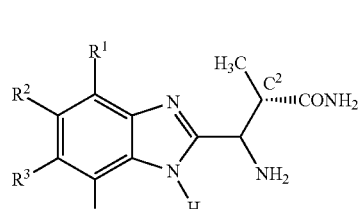
(I$^Q$)

or a pharmaceutically acceptable salt thereof, having the (S) configuration at C$^2$.

In embodiment E26, there is provided a compound according to any one of embodiments E1, E2, E3, E4, E5, E6, E7, E8, E9 or E10 of formula (I$^F$)

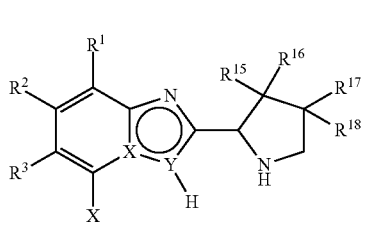
(I$^F$)

or a tautomer thereof, or a pharmaceutically acceptable salt or solvate of said compound or tautomer, wherein:
X, Y, R$^1$, R$^2$, R$^3$ and R$^4$ are as defined in embodiments E1, E2, E3, E4, E5, E6, E7, E8, E9 or E10; and $R^{15}$, $R^{16}$, $R^{17}$ and $R^{18}$ are each independently selected from H, —OH, and —F, provided that at least two of $R^{15}$, $R^{16}$, $R^{17}$ and $R^{18}$ are H.f In embodiment E27, there is provided a compound according to embodiment E26 or a pharmaceutically acceptable salt or solvate thereof, wherein
$R^{15}$ is selected from H, —(C$_1$-C$_3$)alkyl, —OH and —F,
$R^{16}$ is H,
$R^{17}$ is selected from H, —(C$_1$-C$_3$)alkyl, —OH and —F, and
$R^{18}$ is H.

In embodiment E28, there is provided a compound according to embodiment E1 of formula ($I^R$)

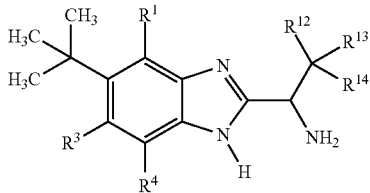

or a pharmaceutically acceptable salt or solvate thereof, wherein
$R^1$, $R^3$ and $R^4$ are each independently selected from H, —F and —Cl,
$R^{12}$ and $R^{13}$ are each independently —H or methyl; and
$R^{14}$ is selected from —OH, —O(C$_1$-C$_3$)alkyl, —OCONH$_2$ and —CONH$_2$.

In embodiment E29, there is provided a compound according to embodiment E28 of formula ($I^S$)

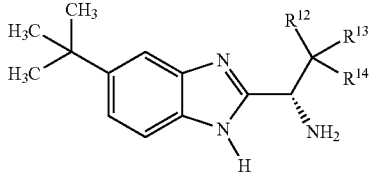

or a pharmaceutically acceptable salt or solvate thereof, wherein
$R^{12}$ and $R^{13}$ are each independently —H or methyl; and
$R^{14}$ is selected from —OH, —O(C$_1$-C$_3$)alkyl, —OCONH$_2$ and —CONH$_2$.

In embodiment E30, there is provided a compound according to embodiment E1 of formula ($I^T$)

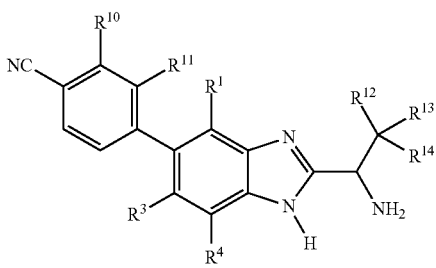

or a pharmaceutically acceptable salt or solvate thereof, wherein $R^1$, $R^3$ and $R^4$ are each independently selected from H, —F and —Cl,
$R^{10}$ and $R^{11}$ are each independently selected from H and —F,
$R^{12}$ and $R^{13}$ are each independently —H or methyl; and
$R^{14}$ is selected from —OH, —O(C$_1$-C$_3$)alkyl, —OCONH$_2$ and —CONH$_2$.

In embodiment E31, there is provided a compound according to embodiment E30 of formula ($I^U$)

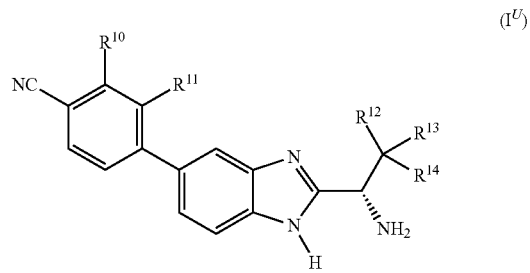

or a pharmaceutically acceptable salt or solvate thereof, wherein
$R^{10}$ and $R^{11}$ are each independently selected from H and —F,
$R^{12}$ and $R^{13}$ are each independently —H or methyl; and
$R^{14}$ is selected from —OH, —O(C$_1$-C$_3$)alkyl, —OCONH$_2$ and —CONH$_2$.

Preferred compounds of the invention include:
4-{2-[(1R,2R)-1-amino-2-methoxypropyl]-1H-benzimidazol-5-yl}-2-fluorobenzonitrile,
4-{2-[(1R,2R)-1-amino-2-methoxypropyl]-1H-benzimidazol-5-yl}benzonitrile,
4-{2-[(1R,2R)-1-amino-2-methoxypropyl]-1H-benzimidazol-5-yl}-3-fluorobenzonitrile,
4-{2-[(1R,2R)-1-amino-2-hydroxypropyl]-1H-benzimidazol-6-yl}-2-fluorobenzonitrile,
4-{2-[(1R,2R)-1-amino-2-hydroxypropyl]-1H-benzimidazol-5-yl}benzonitrile,
4-{2-[(1R,2R)-1-amino-2-methoxypropyl]-4-chloro-1H-benzimidazol-5-yl}-benzonitrile,
(2R,3S)-3-amino-3-[5-(4-cyano-3-fluorophenyl)-1H-benzimidazol-2-yl]-2-methylpropanamide,
4-{2-[(1R,2R)-1-amino-2-methoxypropyl]-4-chloro-1H-benzimidazol-5-yl}-2-fluorobenzonitrile,
4-{2-[(1R,2R)-1-amino-2-methoxypropyl]-1H-benzimidazol-6-yl}-3-chlorobenzonitrile,
(1R,2R)-1-(5-tert-butyl-1H-benzimidazol-2-yl)-2-methoxypropan-1-amine,
(2R,3S)-3-amino-3-(5-tert-butyl-1H-benzimidazol-2-yl)-2-methylpropanamide, and
(1R,2S)-1-amino-1-(6-tert-butyl-1H-benzimidazol-2-yl) propan-2-yl carbamate;
and pharmaceutically acceptable salts or solvates thereof.

The compounds of formula (I) wherein X is carbon (C) and Y is nitrogen (N) can exist in tautomeric forms. Specifically, the 2,5-disubstituted benzimidazole can exist as the (1H)-tautomer or the (3H)-tautomer. It will be understood that a 2,5-disubstituted-(3H)-benzimidazole may also be described as a 2,6-disubstituted-(1H)-benzimidazole.

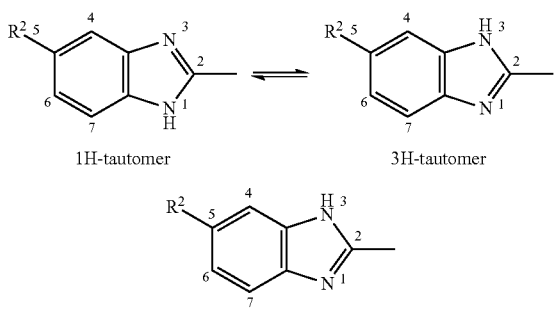

1H-tautomer    3H-tautomer

The compounds of formula (I) wherein X is carbon (C) and Y is nitrogen (N) may exist in substantially pure (1H)-tautomeric form, substantially pure (3H)-tautomeric form, or as a mixture of tautomeric forms. All such tautomers and mixtures of tautomers are included within the scope of the present invention. References herein to specific compounds should be understood to refer to the compound and/or its tautomer.

Certain compounds of formula (I) include one or more stereogenic centers and so may exist as optical isomers, such as enantiomers and diastereomers. All such isomers and mixtures thereof are included within the scope of the present invention.

Hereinafter, all references to compounds of the invention include compounds of formula (I) or pharmaceutically acceptable salts, solvates, or multi-component complexes thereof, or pharmaceutically acceptable solvates or multi-component complexes of pharmaceutically acceptable salts of compounds of formula (I), as discussed in more detail below.

Preferred compounds of the invention are compounds of formula (I) or pharmaceutically acceptable salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Hemisalts of acids and bases may also be formed, for example, hemisulphate salts.

The skilled person will appreciate that the aforementioned salts include ones wherein the counterion is optically active, for example d-lactate or l-lysine, or racemic, for example dl-tartrate or dl-arginine.

For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) may be prepared by one or more of three methods:
(i) by reacting the compound of formula (I) with the desired acid or base;
(ii) by removing an acid- or base-labile protecting group from a suitable precursor of the compound of formula (I) using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of formula (I) or pharmaceutically acceptable salts thereof may exist in both unsolvated and solvated forms. The term 'solvate' is used herein to describe a molecular complex comprising a compound of formula (I) or a pharmaceutically acceptable salt thereof and one or more pharmaceutically acceptable solvent molecules, for example, ethanol. The term 'hydrate' is employed when said solvent is water. Pharmaceutically acceptable solvates in accordance with the invention include those wherein the solvent of crystallization may be isotopically substituted, e.g. $D_2O$, $d_6$-acetone and $d_6$-DMSO.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995), incorporated herein by reference. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

Also included within the scope of the invention are multi-component complexes (other than salts and solvates) of compounds of formula (I) or pharmaceutically acceptable salts thereof wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004), incorporated herein by reference. For a general review of multi-component complexes, see J Pharm Sci, 64 (8), 1269-1288, by Haleblian (August 1975), incorporated herein by reference.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as $—COO^-Na^+$, $—COO^-K^+$, or $—SO_3^-Na^+$) or non-ionic (such as $—N^-N^+(CH_3)_3$) polar head group. For more information, see *Crystals and the Polarizing Microscope* by N. H. Hartshorne and A. Stuart, 4$^{th}$ Edition (Edward Arnold, 1970), incorporated herein by reference.

The compounds of the invention may be administered as prodrugs. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs can, for example, be produced by replacing appropriate functionalities present in a compound of formula (I) with certain moieties known to those skilled in the art as 'pro-moieties' as described, for example, in "Design of Prodrugs" by H Bundgaard (Elsevier, 1985).

Examples of prodrugs include phosphate prodrugs, such as dihydrogen or dialkyl (e.g. di-tert-butyl) phosphate prodrugs. Further examples of replacement groups in accordance with the foregoing examples and examples of other prodrug types may be found in the aforementioned references.

Also included within the scope of the invention are metabolites of compounds of formula (I), that is, compounds formed in vivo upon administration of the drug. Some examples of metabolites in accordance with the invention include, where the compound of formula (I) contains a phenyl (Ph) moiety, a phenol derivative thereof (-Ph>-PhOH);

Compounds of the invention containing one or more asymmetric carbon atoms can exist as two or more stereoisomers. Included within the scope of the invention are all stereoisomers of the compounds of the invention and mixtures of one or more thereof.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Mixtures of stereoisomers may be separated by conventional techniques known to those skilled in the art; see, for example, "Stereochemistry of Organic Compounds" by E. L. Eliel and S. H. Wilen (Wiley, New York, 1994).

The scope of the invention includes all crystal forms of the compounds of the invention, including racemates and racemic mixtures (conglomerates) thereof. Stereoisomeric conglomerates may also be separated by the conventional techniques described herein just above.

The scope of the invention includes all pharmaceutically acceptable isotopically-labelled compounds of the invention wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of the invention, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Also within the scope of the invention are intermediate compounds as hereinafter defined, all salts, solvates and complexes thereof and all solvates and complexes of salts thereof as defined hereinbefore for compounds of formula (I). The invention includes all polymorphs of the aforementioned species and crystal habits thereof.

When preparing a compound of formula (I) in accordance with the invention, a person skilled in the art may routinely select the form of intermediate which provides the best combination of features for this purpose. Such features include the melting point, solubility, processability and yield of the intermediate form and the resulting ease with which the product may be purified on isolation.

The compounds of the invention may be prepared by any method known in the art for the preparation of compounds of analogous structure. In particular, the compounds of the invention can be prepared by the procedures described by reference to the Schemes that follow, or by the specific methods described in the Examples, or by similar processes to either.

The skilled person will appreciate that the experimental conditions set forth in the schemes that follow are illustrative of suitable conditions for effecting the transformations shown, and that it may be necessary or desirable to vary the precise conditions employed for the preparation of compounds of formula (I). It will be further appreciated that it may be necessary or desirable to carry out the transformations in a different order from that described in the schemes, or to modify one or more of the transformations, to provide the desired compound of the invention.

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino or carboxylic acid groups. The protecting groups used in the preparation of the compounds of the invention may be used in conventional manner. See, for example, those described in 'Greene's Protective Groups in Organic Synthesis' by Theodora W Greene and Peter G M Wuts, third edition, (John Wiley and Sons, 1999), in particular chapters 7 ("Protection for the Amino Group") and 5 ("Protection for the Carboxyl Group"), incorporated herein by reference, which also describes methods for the removal of such groups.

All of the benzimidazole and imidazopyridine derivatives of the formula (I) can be prepared by the procedures described in the general methods presented below or by routine modifications thereof. In these general methods and schemes, unless otherwise indicated, the substituents $R^1$-$R^{13}$ have the same meanings as discussed above. The present invention also encompasses any one or more of these processes for preparing the benzimidazole and imidazopyridine derivatives of formula (I), in addition to any novel intermediates used therein.

According to a first process, compounds of formula ($I^B$) may be prepared from compounds of formula (II) and (V), as illustrated by Scheme 1.

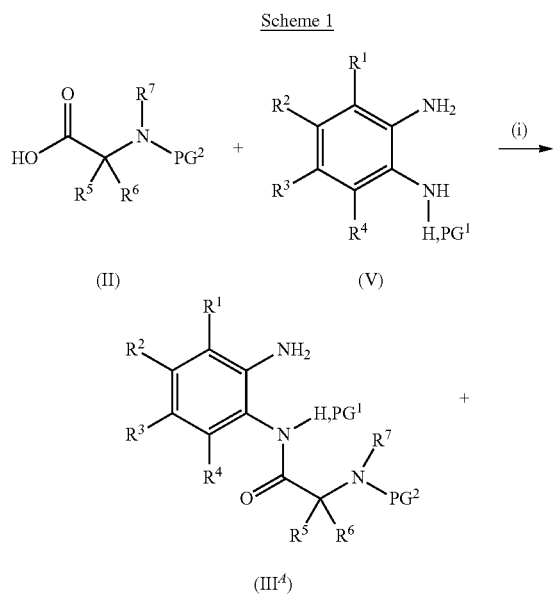

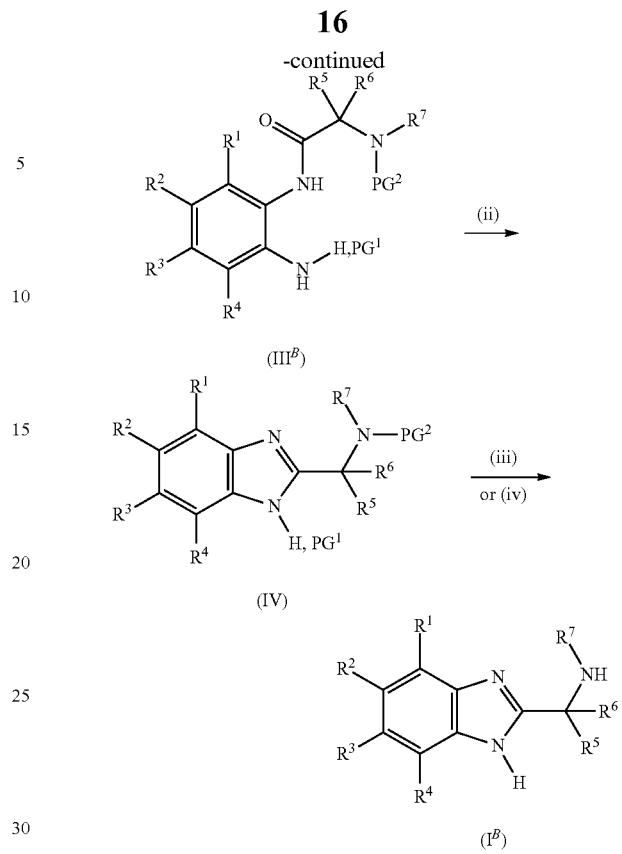

wherein $PG^1$ and $PG^2$ are suitable amine protecting groups, typically tert-butoxycarbonyl or benzyl for $PG^1$ and tert-butoxycarbonyl or benzyloxycarbonate for $PG^2$.

Compounds of formula ($I^B$) can be prepared from compounds of formula (IV) according to process step (iii), a deprotection reaction under hydrogenolysis or acidic conditions. Typical conditions are dependent on the nature of the protecting group. Where the protecting group is tert-butoxycarbonyl, conditions are acid mediated. Preferred conditions comprise an excess of HCl in 1,4-dioxane, DCM or MeOH at from 0° C. to 100° C. Where the protecting group is benzyloxycarbonyl, conditions are either acid mediated, typically using HBr in acetic acid at room temperature or by hydrogenolysis over a suitable hydrogenation catalyst, typically Pd/C or Pd(OH)$_2$/C or by the use of TMSI in DCM. Deprotection may also occur during steps (i) and (ii) to furnish compounds of formula ($I^B$). Wherein $R^7$ is Me, compounds of formula ($I^B$) may also be prepared from compounds of formula (IV) wherein $PG^1$ is H and $PG^2$ is tert-butoxycarbonyl, according to reaction step (iv), a reduction step of the tert-butoxycarbonyl protecting group to a methyl group. Typical conditions comprise LiAlH$_4$ in THF at reflux.

Compounds of formula (IV) can be prepared from compounds of formula (III$^A$ and III$^B$) according to process step (ii), a condensation reaction. Typical conditions comprise an excess of acetic acid at room or elevated temperature either neat or in a solvent such as Me-THF or using a dehydrating agent such as magnesium sulfate in a suitable solvent such as DCE at 65° C. Cyclisation may also occur during process step (i) to furnish compounds of formula (IV).

Compounds of formula (III$^A$ and III$^B$) may be prepared from compounds of formula (II) according to process step (i), by amide coupling with a compound of formula (V) in the presence of base in a suitable solvent. Typical conditions comprise converting acid (II) to an acid chloride using a suitable chlorinating agent, such as oxalyl chloride or thionyl chloride, in a suitable solvent, such as dichloromethane or toluene, optionally in the presence of catalytic DMF, at a suitable temperature, typically of between −78° C. and room temperature. The acid chloride can then be reacted with the amine (V) in the presence of a base, such as triethylamine or diisopropylethylamine, in a suitable solvent, such as dichloromethane or toluene, at a temperature of between −78° C. and room temperature. Alternatively, acid (II) can be converted to a suitable activated species with a coupling agent, such as EDCI.HCl, EDCI.MeI, HBTU, HATU, PyBop, DCC, T3P or CDI, in a suitable solvent, such as dichloromethane, acetonitrile or DMF. In the presence of EDCI.HCl or EDCI.MeI, HOBT is optionally added. A suitable base, such as triethylamine, diisopropylethylamine or NMM is also used and the reaction is typically carried out at room temperature or below. Preferred conditions comprise adding 1.2-1.4 equivalents of N-methylmorpholine followed by 1.0-1.05 equivalents of isobutyl chloroformate to 1.0 equivalent of carboxylic acid of formula (II) in acetonitrile at between 0° C.-10° C., to which is added 1.0 equivalent of diamine compound of formula (V) or using HATU, HOBt/EDCI or T3P with DIPEA, TEA or NMM in EtOAc, dioxane, DMF or DMA at from room temperature to 100° C.

Compounds of formula (II) are either commercially available or will be well-known to those skilled in the art with reference to literature precedents and/or the preparations herein.

Compounds of formula (V) are either commercially available or may be prepared according to the methods set out in Scheme 8.

According to a second process, compounds of formula (I$^C$) may be prepared from compounds of formula (IV$^A$) and (VI), as illustrated by Scheme 2.

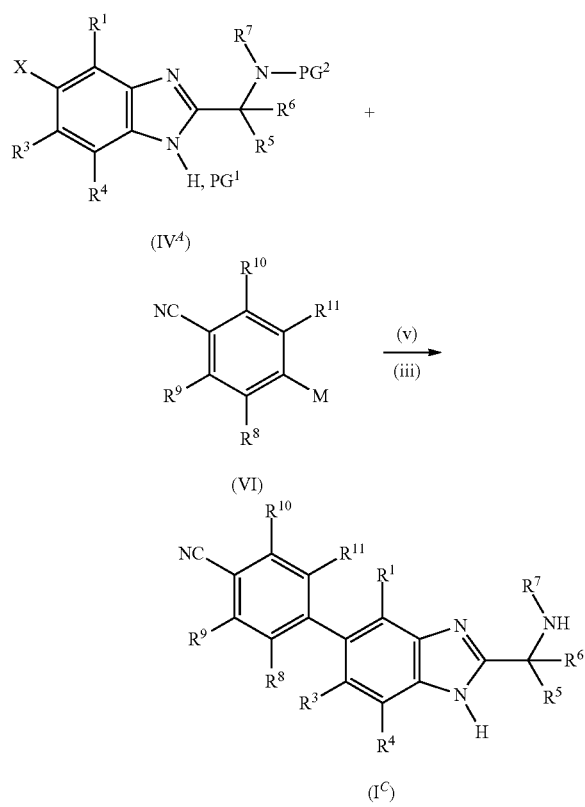

wherein X is I, Br, Cl; M is a boronic acid or ester.

Compounds of formula (I$^C$) may be prepared from compounds of formulae (IV$^A$) and (VI) according to process step (v) a metal catalysed cross-coupling reaction, followed by process step (iii), a suitable deprotection reaction as described in Scheme 1. Typical conditions for the metal catalysed cross coupling reaction comprise a palladium catalyst such as dichloro[1,1-bis(di-tert-butylphosphino)]ferrocene palladium (II) or tetrakis(triphenylphosphine)palladium (0) with a base such as sodium or potassium carbonate in THF/water or DME/water with a suitable boronic acid or ester either heating to reflux thermally, or heating up to 120° C. under microwave irradiation.

Compounds of formula (VI) are either commercially available or described in a preparation herein.

Compounds of formula (IV$^A$) may be prepared as described for compounds of formula (IV) in Scheme 1.

According to a third process, compounds of formula (I$^B$) may be prepared from compounds of formula (IV$^A$) and (VII), as illustrated by Scheme 3.

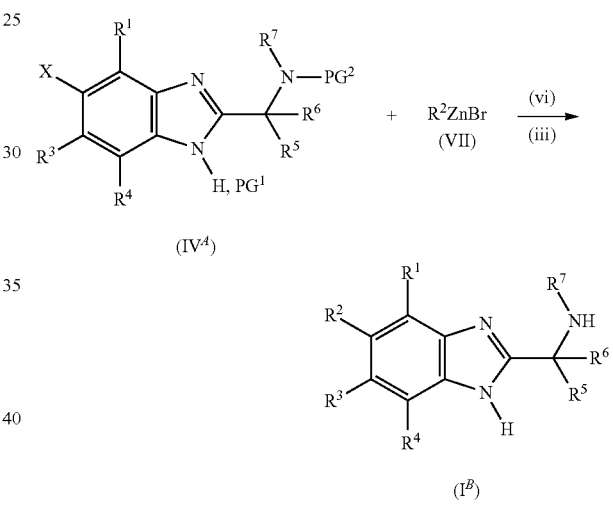

wherein X is I, Br, Cl; PG$^1$ is methoxymethyl.

Compounds of formula (I$^B$) may be prepared from compounds of formulae (IV$^A$) and (VII) according to process step (vi), a Negishi cross-coupling reaction involving an organozinc compound followed by process step (iii), a deprotection reaction. Typical conditions comprise [1,1'-bis)diphenylphosphino)ferrocene]dichloropalladium(II) with compounds of formula (VII) in THF at 65° C., followed by deprotection with boron tribromide at from 0° C. to room temperature.

Compounds of formula (VII) are commercially available.

Compounds of formula (IV$^A$) may be prepared as described in Scheme 2.

According to a fourth process, compounds of formula (I') may be prepared from compounds of formula (V) and (XII), as illustrated by Scheme 4.

Scheme 4

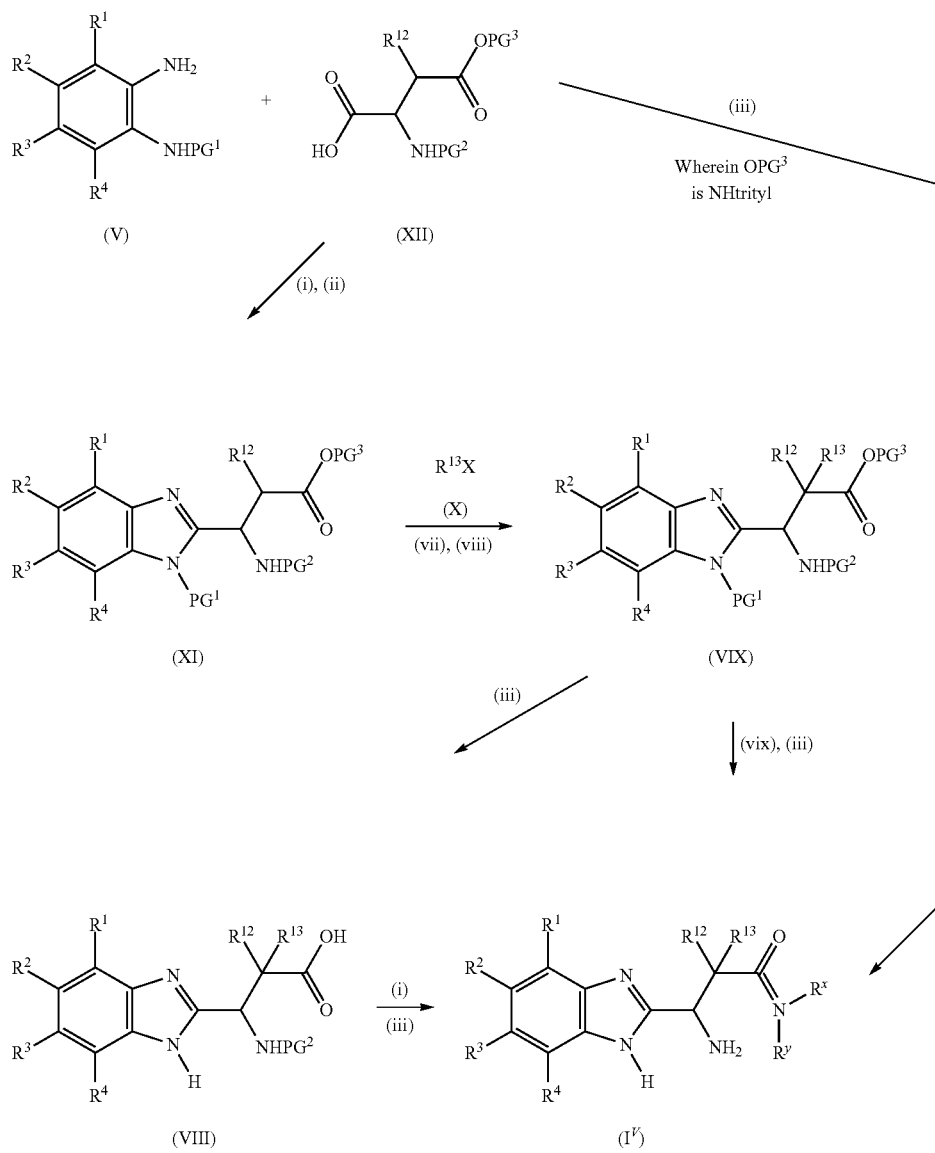

wherein PG¹ is H or benzyl; PG² is tert-butylcarbonate; PG³ is benzyl or methyl and X is I, Br, Cl, triflate, tosylate or mesylate; $R^{13}$ is as previously defined; $R^x$ and $R^y$ are H or $(C_1\text{-}C_3)$alkyl.

Compounds of formula (I$^v$) may be prepared from compounds of formula (VIII) according to process steps (i) and (iii), an amide bond coupling step in the presence of ammonium hydroxide or a suitable amine followed by a suitable deprotection reaction, both steps as described in Scheme 1. Typical conditions comprise carbonyldiimidazole in THF or EDCI with NMM in DMF at from −15° C. to room temperature followed by TFA in DCM at 0° C. or 4M HCl in dioxane.

Compounds of formula (I$^v$) may also be prepared directly from compounds of formula (VIX) according to process steps (vix) and (iii), a nucleophilic amidation reaction followed by deprotection as described in Scheme 1. Typical conditions comprise magnesium nitride in a solvent such as methanol heated to 80° C. in a sealed tube followed by 4N HCl in dioxane at room temperature or liquid ammonia at −78° C. in THF followed by 2N HCl in dioxane at room temperature.

Compounds of formula (VIII) may be prepared from compounds of formula (VIX) according to process step (iii), a suitable deprotection reaction according to the nature of the amino protecting groups. When PG¹ and PG³ are both benzyl, conditions comprise 10% palladium on carbon under hydrogenation at 40 psi. When PG³ is methyl, conditions comprise LiOH in aqueous THF at room temperature.

Compounds of formula (VIX) may be prepared from compounds of formula (XI) and (X) according to process step (vii), an alkylation reaction in the presence of a strong base followed by process step (viii), an enantiomeric purification step if required. Typical conditions comprise LiHMDS in anhydrous THF with the addition of compounds of formula (X) at −55° C. followed by KOtBu in anhydrous THF.

Compounds of formula (X) are commercially available, compounds of formula (XI) may be prepared from compounds of formula (V) and (XII) according to process steps (i) and (ii) as described in Scheme 1.

Compounds of formula (I') may also be prepared wherein OPG³ is replaced with NHtrityl. The trityl protecting group can be removed using TFA at room temperature.

According to a fifth process, compounds of formula (I$^W$) may be prepared from compounds of formula (V) and (XIII), as illustrated by Scheme 5.

Scheme 5

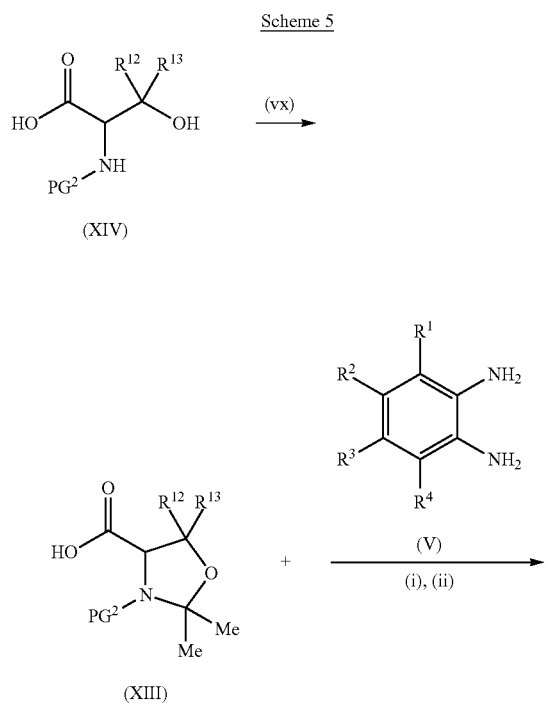

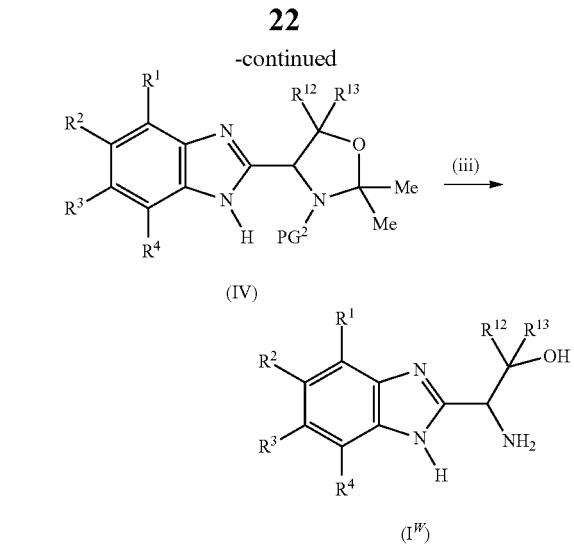

Compounds of formula (I$^W$) may be prepared from compounds of formula (IV) according to process step (iii), a deprotection step as described in Scheme 1. Preferred conditions comprise 4N HCl in dioxane at room temperature.

Compounds of formula (IV) may be prepared from compounds of formulae (V) and (XIII) according to process steps (i) and (ii) as described in Scheme 1. Preferred conditions comprise HATU and NMM in DMF at from 0° C. to room temperature.

Compounds of formula (V) may be commercially available or prepared as described in Scheme 8.

Compounds of formula (XIII) may be prepared from compounds of formula (XIV) according to process step (vx), a protection reaction. Typical conditions comprise 2,2-dimethoxypropane in THF and TBME with a catalyst such as pyridinium p-toluenesulfonate at reflux.

According to a sixth process, compounds of formulae (I$^W$) and (I$^X$) may be prepared from compounds of formulae (XIV) and (V), as illustrated by Scheme 6.

Scheme 6

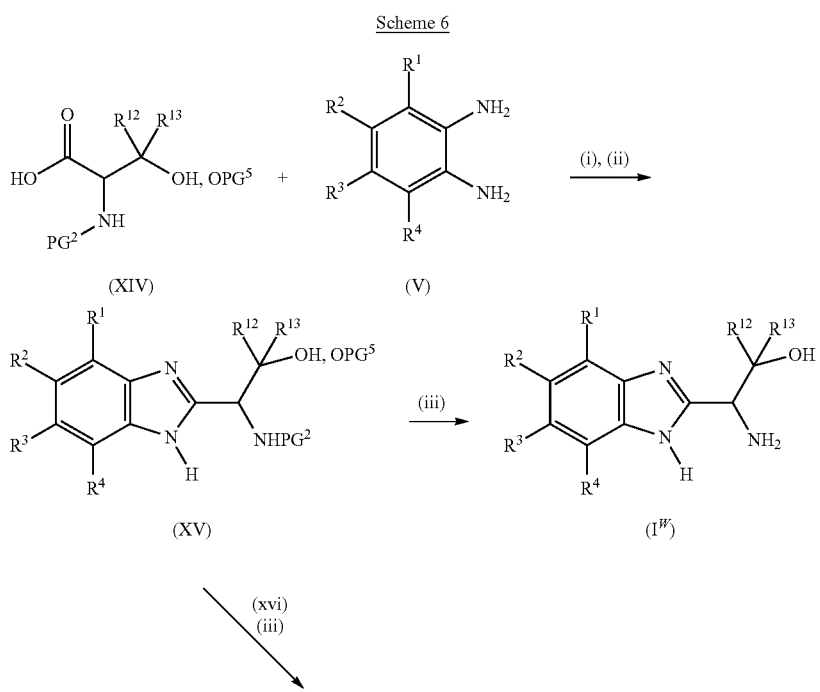

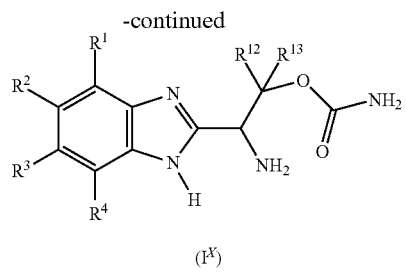

(I$^X$)

Compounds of formula (I$^X$) may be prepared from compounds of formula (XV) according to reaction step (xvi), a carbamate formation reaction followed by a deprotection reaction (iii). Typical conditions comprise N,N-disuccinimidyl carbonate and triethylamine in DCM with the addition of ammonium hydroxide at room temperature followed by TFA in DCM at room temperature.

Compounds of formula (I$^W$) may also be prepared from compounds of formula (XV) according to reaction step (iii), a deprotection step when PG$^5$ is benzyl or acetyl. Typical conditions comprise 5% palladium on carbon under a balloon of hydrogen at room temperature or 6N HCl at 60° C.

Compounds of formula (XV) may be prepared from compounds of formulae (V) and (XIV) according to process steps (i) and (ii) as described in Scheme 1. Compounds of formula (V) and (XIV) are either commercially available or described in the Preparations herein.

According to a seventh process, compounds of formula (I$^4$) may be prepared from compounds of formula (II) or (XIII) and (XVI), as illustrated by Scheme 7.

Scheme 7

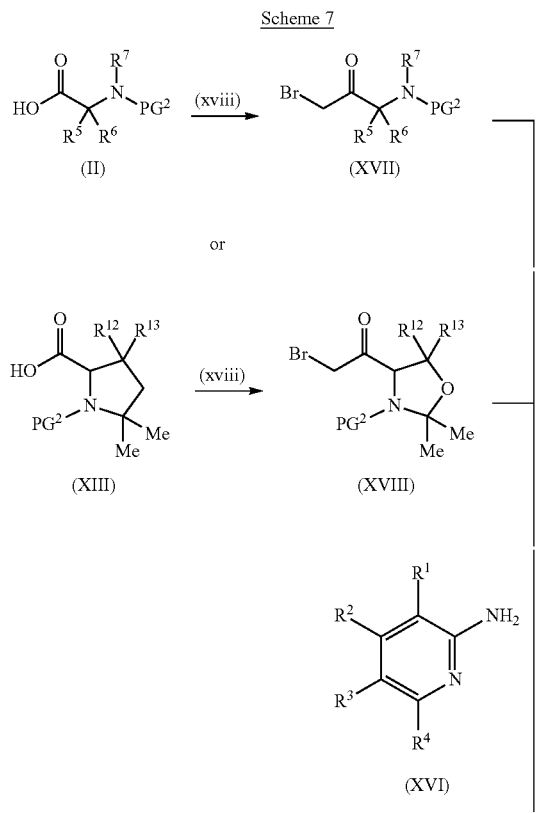

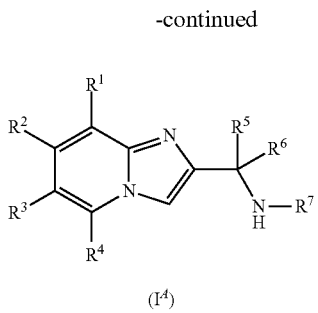

(I$^4$)

Compounds of formula (I$^4$) may be prepared from compounds of formulae (XVI) and (XVII) or (XVI) and (XVIII) according to process steps (xvii) and (iii); a heteroaromatic cyclisation reaction followed by a suitable deprotection step as described in Scheme 1. Suitable conditions comprise heating the compounds of formulae (XVII) and (XVI) or (XVI) and (XVIII) together in THF to reflux followed by deprotection under acidic conditions such as TFA in DCM or 4M HCl in dioxane, or if the final compound is protected as a lactam, ammonium hydroxide may be used to afford the primary carboxamide as R$^5$.

Compounds of formulae (XVII) and (XVIII) may be prepared from compounds of formulae (II) and (XIII) respectively according to reaction step (xviii); a diazotization reaction effected by the formation of a mixed anhydride with the addition of HBr. Preferred conditions comprise isobutylchloroformate and NMM with diazomethane at from −78° C. to 0° C. for 12 hours followed by the addition of HBr in water.

Compounds of formulae (II) or (XIII) are either commercially available, described Scheme 5 or described in the Preparations herein.

According to a eighth process, compounds of formula (V) may be prepared from compounds of formula (XXI) as illustrated by Scheme 8.

Scheme 8

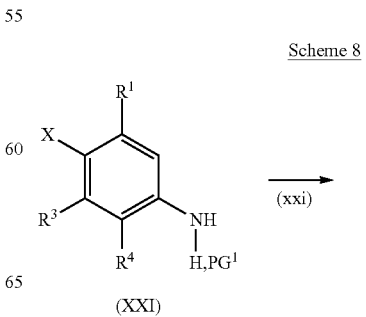

(XXI)

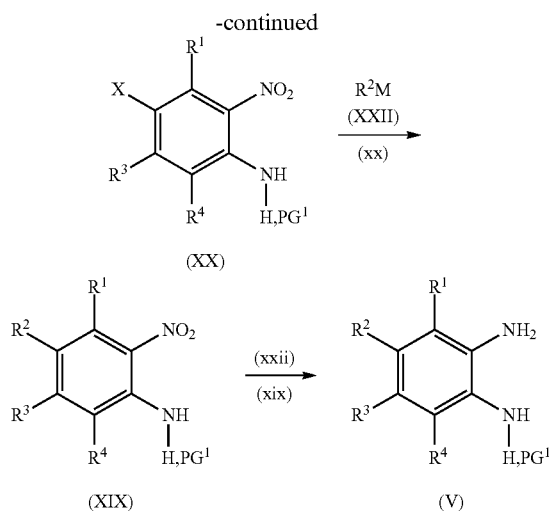

wherein M is Pd or Zn; PG$^1$ is benzyl or acetyl; X is I, Br or Cl;

Compounds of formula (V) may be prepared from compounds of formula (XIX) according to process step (xix) a reduction reaction in the presence of a suitable catalyst. Typical conditions comprise zinc dust or iron powder in the presence of ammonium chloride or calcium chloride or palladium on carbon under hydrogenation in a suitable protic solvent such as methanol or ethanol or acetic acid. Wherein PG$^1$ is acetyl, the protecting group may be removed according to process step (xxii), a hydrolysis reaction in the presence of a strong base. Typical conditions comprise aqueous sodium hydroxide at 90° C.

Compounds of formula (XIX) may be prepared from compounds of formulae (XX) and (XXII) according to process step (xx), a metal catalysed cross-coupling reaction as described in Schemes 2 and 3. Preferred conditions comprise [1,1'-bis(diphenylphosphino)ferrocene]dichloropalladium (II) or tetrakis(triphenylphosphine)palladium(0) or [1,1']bis(di-tert-butylphosphino)]ferrocene palladium (II) in a solvent such as toluene, EtOH or THF in combination with water and a suitable base such as sodium carbonate at from 60-100° C. thermally or at 140° C. under microwave irradiation.

Compounds of formula (XXII) are either commercially available or described in the Preparations herein.

Compounds of formula (XX) may be prepared from compounds of formula (XXI) according to process step (xxi), an aromatic electrophilic nitration step. Typical conditions comprise nitric acid in acetic anhydride at 0° C.

Compounds of formula (XXI) are commercially available or will be well-known to those skilled in the art with reference to literature precedents and/or the preparations herein.

Referring to the general methods above, it will be readily understood to the skilled person that where protecting groups are present, these will be generally interchangeable with other protecting groups of a similar nature, e.g. where an amine is described as being protected with a tert-butoxycarbonyl group, this may be readily interchanged with any suitable amine protecting group. Suitable protecting groups are described in 'Protective Groups in Organic Synthesis' by T. Greene and P. Wuts (3$^{rd}$ edition, 1999, John Wiley and Sons).

The present invention also relates to novel intermediate compounds as defined above, all salts, solvates and complexes thereof and all solvates and complexes of salts thereof as defined hereinbefore for benzimidazole derivatives of formula (I). The invention includes all polymorphs of the aforementioned species and crystal habits thereof.

When preparing benzimidazole derivatives of formula (I) or amino acids of formula (II) in accordance with the invention, it is open to a person skilled in the art to routinely select the best order of steps with which to synthesise the intermediates, and to choose the form of the intermediate compounds which provides the best combination of features for this purpose. Such features include the melting point, solubility, processability and yield of the intermediate form and the resulting ease with which the product may be purified on isolation.

Compounds of the invention intended for pharmaceutical use may be administered as crystalline or amorphous products or may exist in a continuum of solid states ranging from fully amorphous to fully crystalline. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

In another aspect the invention provides a pharmaceutical composition comprising a compound of the invention together with one or more pharmaceutically acceptable excipients.

Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

Suitable modes of administration include oral, parenteral, topical, inhaled/intranasal, rectal/intravaginal, and ocular/aural administration.

Formulations suitable for the aforementioned modes of administration may be formulated to be immediate and/or modified release. Modified release formulations include delayed-, sustained-, pulsed-, controlled-, targeted and programmed release.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films, ovules, sprays, liquid formulations and buccal/mucoadhesive patches.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet. Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant. Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. The formulation of tablets is discussed in "Pharmaceutical Dosage Forms: Tablets", Vol. 1, by H. Lieberman and L. Lachman (Marcel Dekker, New York, 1980).

Suitable modified release formulations for the purposes of the invention are described in U.S. Pat. No. 6,106,864. Details of other suitable release technologies such as high energy dispersions and osmotic and coated particles are to be found in "Pharmaceutical Technology On-line", 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents. Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

In the case of dry powder inhalers and aerosols, the dosage unit is determined by means of a valve which delivers a metered amount. Units in accordance with the invention are typically arranged to administer a metered dose or "puff" containing from 1 µg to 100 mg of the compound of formula (I). The overall daily dose will typically be in the range 1 µg to 200 mg which may be administered in a single dose or, more usually, as divided doses throughout the day.

The compounds of the invention may be administered rectally or vaginally, for example, in the form of a suppository, pessary, microbicide, vaginal ring or enema. Cocoa butter is a traditional suppository base, but various alternatives may be used as appropriate.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

For administration to human patients, the total daily dose of the compounds of the invention is typically in the range 1 mg to 10 g, such as 10 mg to 1 g, for example 25 mg to 500 mg depending, of course, on the mode of administration and efficacy. For example, oral administration may require a total daily dose of from 50 mg to 100 mg. The total daily dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

As noted above, the compounds of the invention are useful because they exhibit pharmacological activity in animals, i.e., $Na_v1.8$ channel modulation. More particularly, the compounds of the invention are of use in the treatment of disorders for which a $Na_v1.8$ modulator is indicated. Preferably the animal is a mammal, more preferably a human.

In a further aspect of the invention there is provided a compound of the invention for use as a medicament.

In a further aspect of the invention there is provided a compound of the invention for the treatment of a disorder for which a $Na_v1.8$ modulator is indicated.

In a further aspect of the invention there is provided use of a compound of the invention for the preparation of a medicament for the treatment of a disorder for which a $Na_v1.8$ modulator is indicated.

In a further aspect of the invention there is provided a method of treating a disorder in an animal (preferably a mammal, more preferably a human) for which a $Na_v1.8$ modulator is indicated, comprising administering to said animal a therapeutically effective amount of a compound of the invention.

Disorders for which a $Na_v1.8$ modulator is indicated include pain, particularly neuropathic, nociceptive and inflammatory pain.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a heightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertabral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:

pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;

heart and vascular pain, including pain caused by angina, myocardical infarction, mitral stenosis, pericarditis, Raynaud's phenomenon, scleredoma and skeletal muscle ischemia;

head pain, such as migraine (including migraine with aura and migraine without aura), cluster headache, tension-type headache mixed headache and headache associated with vascular disorders;

erythermalgia; and orofacial pain, including dental pain, otic pain, burning mouth syndrome and temporomandibular myofascial pain.

A $Na_v1.8$ modulator may be usefully combined with another pharmacologically active compound, or with two or more other pharmacologically active compounds, particularly in the treatment of pain. Such combinations offer the possibility of significant advantages, including patient compliance, ease of dosing and synergistic activity.

In the combinations that follow the compound of the invention may be administered simultaneously, sequentially or separately in combination with the other therapeutic agent or agents.

A $Na_v1.8$ modulator of formula (I), or a pharmaceutically acceptable salt thereof, as defined above, may be administered in combination with one or more agents selected from:

an alternative $Na_v1.8$ modulator (e.g. as disclosed in WO 2008/135826, more particularly N-[6-Amino-5-(2-chloro-5-methoxyphenyl)pyridin-2-yl]-1-methyl-1H-pyrazole-5-carboxamide);

an alternative sodium channel modulator, such as a $Na_v1.3$ modulator (e.g. as disclosed in WO2008/118758); or a $Na_v1.7$ channel modulator e.g. as disclosed in WO 2009/012242);

an inhibitor of nerve growth factor signaling, such as: an agent that binds to NGF and inhibits NGF biological activity and/or downstream pathway(s) mediated by NGF signaling (e.g. tanezumab), a TrkA antagonist or a p75 antagonists;

a compound which increases the levels of endocannabinoid, such as a compound with fatty acid amid hydrolase inhibitory (FAAH) activity, in particular those disclosed in WO 2008/047229 (e.g. N-pyridazin-3-yl-4-(3-{[5-(trifluoromethyl)pyridine-2-yl]oxy}benzylidene) piperidene-1-carboxamide);

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobartital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an $H_1$ antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl) quinazoline;

a tricyclic antidepressant, e.g. desipramine, imipramine, amitriptyline or nortriptyline;

an anticonvulsant, e.g. carbamazepine, lamotrigine, topiratmate or valproate;

a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

a vanilloid receptor agonist (e.g. resinferatoxin) or antagonist (e.g. capsazepine);

a beta-adrenergic such as propranolol;

a local anaesthetic such as mexiletine;

a corticosteroid such as dexamethasone;

a 5-HT receptor agonist or antagonist, particularly a $5-HT_{1B/1D}$ agonist such as eletriptan, sumatriptan, naratriptan, zolmitriptan or rizatriptan;

a 5-HT$_{2A}$ receptor antagonist such as R(+)-alpha-(2,3-dimethoxy-phenyl)-1-[2-(4-fluorophenylethyl)]-4-piperidinemethanol (MDL-100907);

a 5-HT$_3$ antagonist, such as ondansetron a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol®;

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)pyrazino[2′,1′:6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buproprion, buproprion metabolite hydroxybuproprion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)-amino]ethyl]-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin E$_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methyl-benzenesulfonamide or 4-[(1S)-1-({[5-chloro-2-(3-fluorophenoxy)pyridin-3-yl]carbonyl}amino)ethyl]benzoic acid;

a microsomal prostaglandin E synthase type 1 (mPGES-1) inhibitor;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl), 1,4-benzoquinone (CV-6504).

There is also included within the scope the present invention combinations of a compound of the invention together with one or more additional therapeutic agents which slow down the rate of metabolism of the compound of the invention, thereby leading to increased exposure in patients. Increasing the exposure in such a manner is known as boosting. This has the benefit of increasing the efficacy of the compound of the invention or reducing the dose required to achieve the same efficacy as an unboosted dose. The metabolism of the compounds of the invention includes oxidative processes carried out by P450 (CYP450) enzymes, particularly CYP 3A4 and conjugation by UDP glucuronosyl transferase and sulphating enzymes. Thus, among the agents that may be used to increase the exposure of a patient to a compound of the present invention are those that can act as inhibitors of at least one isoform of the cytochrome P450 (CYP450) enzymes. The isoforms of CYP450 that may be beneficially inhibited include, but are not limited to, CYP1A2, CYP2D6, CYP2C9, CYP2C19 and CYP3A4. Suitable agents that may be used to inhibit CYP 3A4 include ritonavir, saquinavir, ketoconazole, N-(3,4-difluorobenzyl)-N-methyl-2-{[(4-methoxypyridin-3-yl)amino]sulfonyl}benzamide and N-(1-

(2-(5-(4-fluorobenzyl)-3-(pyridin-4-yl)-1H-pyrazol-1-yl)acetyl)piperidin-4-yl)methanesulfonamide.

It is within the scope of the invention that two or more pharmaceutical compositions, at least one of which contains a compound of the invention, may conveniently be combined in the form of a kit suitable for coadministration of the compositions. Thus the kit of the invention comprises two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like. The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

In another aspect the invention provides a pharmaceutical product (such as in the form of a kit) comprising a compound of the invention together with one or more additional therapeutically active agents as a combined preparation for simultaneous, separate or sequential use in the treatment of a disorder for which a $Na_v1.8$ modulator is indicated.

It is to be appreciated that all references herein to treatment include curative, palliative and prophylactic treatment.

In the non-limiting Examples and Preparations that are set out later in the description, and in the aforementioned Schemes, the following the abbreviations, definitions and analytical procedures may be referred to:

AcOH is acetic acid;
APCI is atmospheric pressure chemical ionisation mass spectrum;
Arbocel is a filter agent;
br is broad;
Celite® is a filter agent;
CDI is N,N'-carbonyldiimidazole;
$Cs_2CO_3$ is caesium carbonate;
$Cu(acac)_2$ is copper (II) acetylacetonate;
CuI is copper (I) iodide;
$Cu(OAc)_2$ is copper (II) acetate;
δ is chemical shift;
d is doublet;
DABCO is 1,4-diazabicyclo[2.2.2]octane;
DAD is diode array detector;
DCM is dichloromethane; methylene chloride;
DCC is N,N'-dicyclohexylcarbodiimide;
DDQ is 2,3-Dichloro-5,6-Dicyanobenzoquinone;
DIPEA is N-ethyldiisopropylamine, N,N-diisopropylethylamine;
DMAP is 4-dimethylaminopyridine;
DMF is N,N-dimethylformamide;
DMSO is dimethyl sulphoxide;
EDCI.HCl is 1-(3-dimethylaminopropyl)-3-ethylcarbodiimide hydrochloride;
EDCI.MeI is N-(3-dimethylaminopropyl)-N'-ethylcarbodiimide methyliodide;
EDTA is ethylenediaminetetraacetic acid;
ELSD is evaporative light scattering detection;
ES is electrospray ionization;
$Et_2O$ is diethyl ether;
EtOAc is ethyl acetate;
EtOH is ethanol;
HATU is 2-(7-azabenzotriazol-1-yl)-1,1,3,3-tetramethyluronium hexafluorophosphate; HBTU is O-benzotriazol-1-yl-N,N,N',N'-tetramethyluronium hexafluorophosphate;
HCl is hydrochloric acid;
HOBT is N-hydroxybenzotriazole hydrate;
HPLC is high pressure liquid chromatography;
IPA is isopropanol;
$Ir_2(OMe)_2COD_2$ is bis(1,5-cyclooctadiene)di-p-methoxydiiridium (I);
$K_2CO_3$ is potassium carbonate;
$KHSO_4$ is potassium hydrogen sulphate;
KOAc is potassium acetate;
KOH is potassium hydroxide;
$K_3PO_4$ is potassium phosphate tribasic;
L is litre
LCMS is liquid chromatography mass spectrometry (Rt=retention time);
LiOH is lithium hydroxide;
m is multiplet;
MeOH is methanol;
2-MeTHF is 2-methyltetrahydrofuran;
$MgSO_4$ is magnesium sulphate;
m/z is mass spectrum peak;
NaH is sodium hydride;
$NaHCO_3$ is sodium hydrogencarbonate;
$Na_2CO_3$ is sodium carbonate;
$NaHSO_3$ is sodium bisulphite;
$NaHSO_4$ is sodium hydrogensulphate;
NaOH is sodium hydroxide;
$Na_2SO_4$ is sodium sulphate;
NBS is N-bromosuccinimide
$NH_4Cl$ is ammonium chloride;
NMP is N-Methyl-2-pyrrolidone;
NMR is nuclear magnetic resonance;
Pd-118 is dichloro[1,1' bis(di-tert-butylphosphino)]ferrocene palladium (II);
$PdCl_2(dtbpf)$ is dichloro[1,1'-bis(di-tert-butylphosphino)]ferrocene palladium (II);
Pd/C is palladium on carbon;
$Pd(PPh_3)_4$ is palladium tetrakis(triphenylphosphine);
$Pd(dppf)_2Cl_2.DCM$ is [1,1'-bis(diphenylphosphino)ferrocene]dichloropalladium(II), complex with dichloromethane;
$Pd_2(dba)_3$ is tris(dibenzylideneacetone)dipalladium(0);
$Pd(OAc)_2$ is palladium acetate;
$Pd(OH)_2/C$ is palladium hydroxide on carbon;
Prep is preparation;
$POBr_3$ is phosphorus oxybromide;
psi is pounds per square inch;
PyBop is (Benzotriazol-1-yloxy)tripyrrolidinophosphonium hexafluorophosphate;
q is quartet;
Rt is retention time;
s is singlet;
SPhos is 2-Dicyclohexylphosphino-2',6'-dimethoxybiphenyl;
t is triplet;
T3P is propylphosphonic acid anhydride;
TBAF is tetrabutyl ammonium fluoride;
TBME is tert-butyl dimethyl ether;
THF is tetrahydrofuran;
THP is tetrahydropyran;
TLC is thin layer chromatography;
UV is ultraviolet; and WSCDI is 1-(3-dimethylaminopropyl)-3-ethylcarbodiimide hydrochloride Certain compounds of the Examples and Preparations were purified using Automated Preparative High Performance Liquid Chromatography (HPLC). Reversed-phase HPLC conditions were on FractionLynx systems. Samples were submitted dissolved in 1 mL of DMSO. Depending on the nature of the compounds and the results of a pre-analysis, the purification was performed under either acidic conditions ('A-HPLC') or basic conditions ('B-HPLC') at ambient temperature. Acidic runs were carried out on a Sunfire Prep C18 OBD column (19×100 mm, 5 µm), basic runs were carried out on an Xterra Prep MS C18 (19×100 mm, 5 µm), both from Waters. A flow rate of 18 mL/min was used with mobile phase A: water+0.1% modifier (v/v) and B: acetonitrile+0.1% modifier (v/v). For acidic runs the modifier was formic acid, for basic run the modifier was diethylamine. A Waters 2525 binary LC pump supplied a mobile phase with a composition of 5% B for 1 min then ran from 5% to 98% B over 6 min followed by a 2 min hold at 98% B. Detection was achieved using a Waters 2487 dual wavelength absorbance detector set at 225 nm followed in series by a Polymer Labs PL-ELS 2100 detector and a Waters ZQ 2000 4 way MUX mass spectrometer in parallel. The PL 2100 ELSD was set at 30° C. with 1.6 L/min supply of Nitrogen. The Waters ZQ MS was tuned with the following parameters:

| | |
|---|---|
| ES+ Cone voltage: 30 V | Capillary: 3.20 kV |
| ES– Cone voltage: –30 V | Capillary: –3.00 kV |
| Desolvation gas: 600 L/hr | |
| Source Temp: 120° C. | |
| Scan range 150-900 Da | |

The fraction collection was triggered by both MS and ELSD. Quality control (QC) analysis was performed using a LCMS method. Acidic runs were carried out on a Sunfire C18 (4.6×50 mm, 5 µm), basic runs were carried out on a Xterra C18 (4.6×50 mm, 5 µm), both from Waters. A flow rate of 1.5 mL/min was used with mobile phase A: water+0.1% modifier (v/v) and B: acetonitrile+0.1% modifier (v/v). For acidic runs the modifier was formic acid, for basic run the modifier was ammonia. A Waters 1525 binary LC pump ran a gradient elution from 5% to 95% B over 3 min followed by a 1 min hold at 95% B. Detection was achieved using a Waters MUX UV 2488 detector set at 225 nm followed in series by a Polymer Labs PL-ELS 2100 detector and a Waters ZQ 2000 4 way MUX mass spectrometer in parallel. The PL 2100 ELSD was set at 30° C. with 1.6 L/min supply of Nitrogen. The Waters ZQ MS was tuned with the following parameters:

| | |
|---|---|
| ES+ Cone voltage: 25 V | Capillary: 3.30 kV |
| ES– Cone voltage: –30 V | Capillary: –2.50 kV |
| Desolvation gas: 800 L/hr | |
| Source Temp: 150° C. | |
| Scan range 160-900 Da | |

The Preparations and Examples that follow illustrate the invention but do not limit the invention in any way. All starting materials are available commercially or described in the literature. All temperatures are in ° C. Flash column chromatography was carried out using Merck silica gel 60 (9385). Thin layer chromatography (TLC) was carried out on Merck silica gel 60 plates (5729). "$R_f$" represents the distance traveled by a compound divided by the distance traveled by the solvent front on a TLC plate. Melting points were determined using a Gallenkamp MPD350 apparatus and are uncorrected.

$^1$H-NMR spectra were recorded on a Varian Mercury 300 or 400 MHz, Bruker Avance 400 MHz NMR or Jeol ECX 400 MHz. NMR spectra were obtained as DMSO-$d_6$ solutions (reported in ppm). Other NMR solvents were used as needed. When peak multiplicities are reported, the following abbreviations are used: s=singlet, d=doublet, t=triplet, m=multiplet, br=broadened, dd=doublet of doublets, dt=doublet of triplets.

LCMS indicates liquid chromatography mass spectrometry (Rt=retention time). Where ratios of solvents are given, the ratios are by volume.

Mass spectra (MS) were recorded using either electrospray ionisation (ESI) or atmospheric pressure chemical ionisation (APCI). Mass spectroscopy was carried out using a Finnigan Navigator single quadrupole electrospray mass spectrometer, Finnigan aQa APCI mass spectrometer or Applied Biosystem Q-Trap For the avoidance of doubt, named compounds used herein have been named using ACD Labs Name Software v7.11™.

Where it is stated that compounds were prepared in the manner described for an earlier Preparation or Example, the skilled person will appreciate that reaction times, number of equivalents of reagents and reaction temperatures may have been modified for each specific reaction, and that it may nevertheless be necessary, or desirable, to employ different work-up or purification conditions.

Where compounds are purified by HPLC, the methods used are shown below:
LCMS/HPLC
Preparative HPLC Conditions for Library Protocols 1,6,7
    8 minute prep LC-MS gradient and instrument conditions
A: 0.1% TFA in water
B: acetonitrile
Column: C18 phase Sepax BR 100×21.2 mm
Gradient: 96-33% A over 8 min, 30 mL/min flow rate
Temperature: ambient
System A: AB01
Column: Welch XB-C18 2.1×50 mm 5 µm, 50° C., mobile phase A: 0.0375% TFA in water; mobile phase B: 0.01875% TFA in acetonitrile. Initial gradient 1% B; 0.60 mins 5% B, 4.00 mins 100% B, 4.30 mins 1% B, 4.70 mins 1% B. Flow rate 0.8 mL/min.
System B: 2 Minute Run
    2 minute LC-MS gradient and instrument conditions
A: 0.1% formic acid in water
B: 0.1% formic acid in acetonitrile
Column: C18 phase Phenomenex 20×4.0 mm with 3 micron particle size
Gradient: 70-2% A over 1.5 min, 0.3 min hold, 0.2 re-equilibration, 1.8 mL/min flow rate
UV: 210 nm-450 nm DAD
Temperature: 75° C.
System C: 5 Minute Run with Formic Acid
    5 minute LC-MS gradient and instrument conditions
A: 0.1% formic acid in water
B: 0.1% formic acid in acetonitrile
Column: C18 phase Waters Sunfire 50×4.6 mm with 5 micron particle size
Gradient: 95-5% A over 3 min, 1 min hold, 1 min re-equilibration, 1.5 mL/min flow rate
UV: 225 nm—ELSD-MS
Temperature: ambient
System D: 5 Minute Run with Ammonium Hydroxide
    5 minute LC-MS gradient and instrument conditions
A: 0.1% ammonium hydroxide in water
B: 0.1% ammonium hydroxide in acetonitrile Column: C18 phase XTerra 50×4.6 mm with 5 micron particle size
Gradient: 95-5% A over 3 min, 1 min hold, 1 min re-equilibration, 1.5 mL/min flow rate
UV: 225 nm—ELSD-MS
Temperature: ambient
System E: 5 Minute Run with TFA
 5 minute LC-MS gradient and instrument conditions
A: 0.0375% TFA in water
B: 0.01875% TFA in acetonitrile
Column: C18 phase Welch XB 50×2.1 mm with 5 micron particle size
Gradient: 99-0% A over 4 min, 0.70 min re-equilibration, 0.8 mL/min flow rate
UV: 225 nm—ELSD-MS
Temperature: 50° C.
System F: 5 Minute Run with Formic Acid
 5 minute LC-MS gradient and instrument conditions
A: 0.05% formic acid in water
B: acetonitrile
Column: C18 phase XBridge 50×4.6 mm with 5 micron particle size
Gradient: 90-10% A over 3 min, 1 min hold, 1 min re-equilibration, 1.2 mL/min flow rate
UV: 200 nm-260 nm DAD
Temperature: 25° C.
System G: 5 Minute Run with Ammonium Acetate
 5 minute LC-MS gradient and instrument conditions
A: 10 mM ammonium acetate in water
B: acetonitrile
Column: C18 phase Gemini NX 50×4.6 mm with 5 micron particle size
Gradient: 90-10% A over 3 min, 1 min hold, 1 min re-equilibration, 1.2 mL/min flow rate
UV: 200 nm-260 nm DAD
Temperature: 25° C.
System H: 7 Minute Run
Column:Symmetry-C18 2.1×50 mm 3.5 μm
Mobile phase—A=ACN, B=0.1% FA IN WATER;
Time(min)% B=0/90, 1.5/90, 2/15, 4.5/15, 6.5/90, 7/90
Flow: 0.5 mL/min, Column Temp=45° C.; Diluent: ACN
System I: 7 Minute Run
Column:Symmetry-C18 2.1×50 mm 3.5 μm
Mobile phase—A=0.1% FA in ACN, B=0.1% FA in Water;
Time(min)% B=0/90, 0.5/90, 2.0/55, 3.0/55, 3.5/10, 6/10, 7/90;
Flow: 0.5 mL/min, Column Temp=45° C.; Diluent: MeOH
System J: 20 Minute Run
Column: NUCLEODUR C18 150×4.6 mm,
Column ID: ANL_C18__187
Mobile Phase: D=ACN, B=10 mM NH4OAC
Time/% B: 0/80, 2/80, 6/10, 18/10, 19/80, 20/80.
Flow Rate: 1.0 ml/min
Column Temp: 40° C.
Diluent: MeOH
System K: 25 Minute Run
A: 0.05% formic acid in water
B: 0.05% formic acid in acetonitrile
Column: Luna C18 3 μm 150×4.6 mm
Gradient: 95% of A to 5% of A over 22.5 minutes, 0.5 ml/min flow rate
Temperature: 25° C.
System L: 25 Minute Run
A: 20 mmol ammonium formate in water
B: 100% acetonitrile
Column: Luna C18 3 μm 150×4.6 mm
Gradient: 95% of A to 5% of A over 22.5 minutes, 0.5 ml/min flow rate
Temperature: 25° C.
CMA 80 eluant conditions: 80% CHCl$_3$: 20% (9:1 MeOH: NH$_4$OH).

EXAMPLES

Library Protocol 1

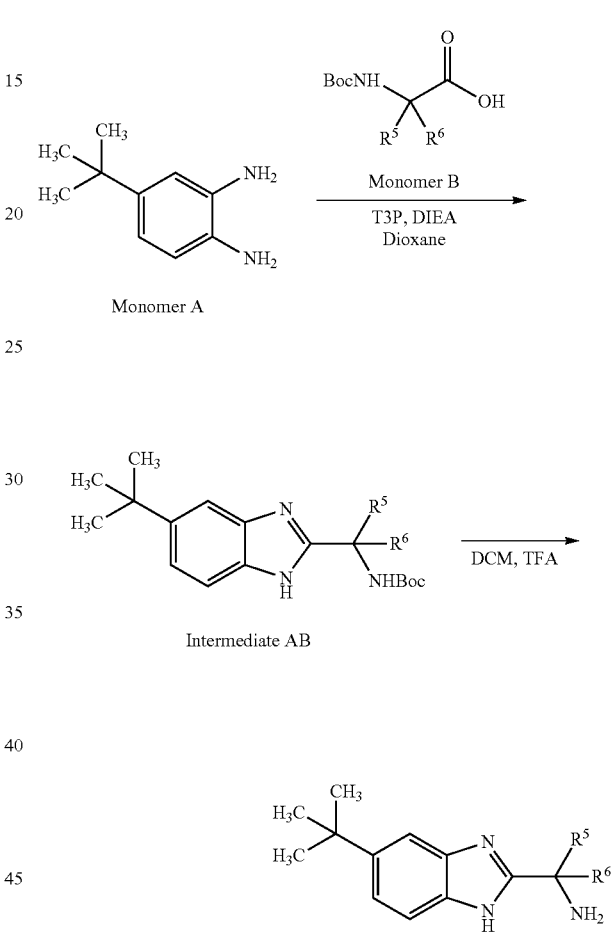

Step 1
To Monomer B (100 μmol, 1 eq) was added 4-tert-butyl-1, 2-diaminobenzene (0.2M solution in dioxane, 500 μL, 100 μmol, 1 eq) followed by DIEA (300 μL, 3 eq) and T3P (50% solution in EtOAc, 200 μmol, 2 eq). The reaction was shaken at 100° C. for 16 hours before concentrating in vacuo and purifying by preparative HPLC to afford Intermediate AB.

Step 2
To Intermediate AB was added a solution of TFA in DCM (2 mL, TFA/DCM V/V=1/5) and the reaction was shaken at 30° C. for 5 hours before concentrating in vacuo to afford the final compounds as their TFA salts unless otherwise described.
LCMS QC: Welch XB-C18 2.1×50 mm 5 μm/0.05% TFA
The following Examples were prepared according to Library Protocol 1 using 4-tert-butyl-1,2-diaminobenzene and the appropriate amino acids for Monomer B as described.

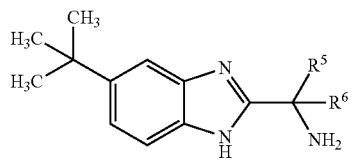

1. (1S)-1-(5-tert-Butyl-1H-benzimidazol-2-yl)-4-methylpentan-1-amine

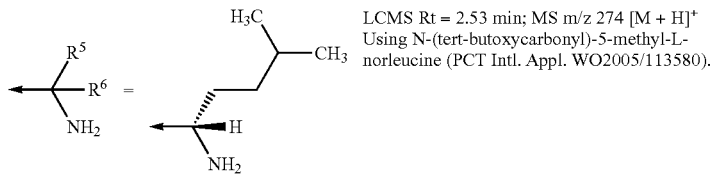

LCMS Rt = 2.53 min; MS m/z 274 [M + H]⁺
Using N-(tert-butoxycarbonyl)-5-methyl-L-norleucine (PCT Intl. Appl. WO2005/113580).

2. 2-(5-tert-Butyl-1H-benzimidazol-2-yl)-2,3-dihydro-1H-inden-2-amine

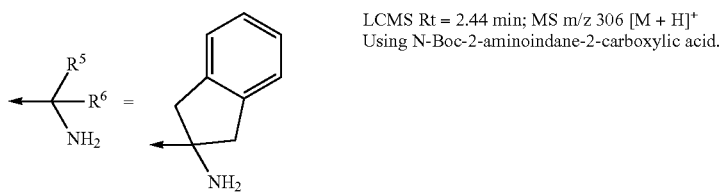

LCMS Rt = 2.44 min; MS m/z 306 [M + H]⁺
Using N-Boc-2-aminoindane-2-carboxylic acid.

3. (S)-1-(5-tert-Butyl-1H-benzimidazol-2-yl)-1-cyclopentylmethanamine

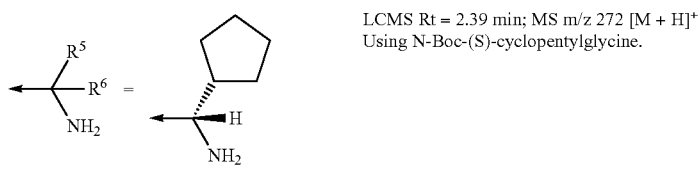

LCMS Rt = 2.39 min; MS m/z 272 [M + H]⁺
Using N-Boc-(S)-cyclopentylglycine.

4. 1-(5-tert-Butyl-1H-benzimidazol-2-yl)cyclobutanamine

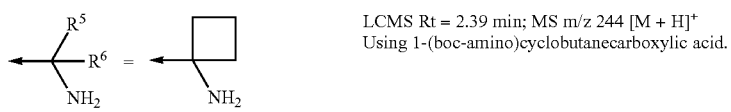

LCMS Rt = 2.39 min; MS m/z 244 [M + H]⁺
Using 1-(boc-amino)cyclobutanecarboxylic acid.

5. (1S)-1-(5-tert-Butyl-1H-benzimidazol-2-yl)-2-methylpropan-1-amine

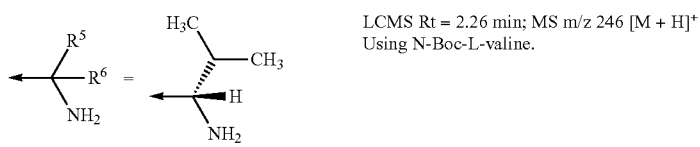

LCMS Rt = 2.26 min; MS m/z 246 [M + H]⁺
Using N-Boc-L-valine.

6. (1S)-1-(5-tert-Butyl-1H-benzimidazol-2-yl)-2,2-dimethylpropan-1-amine

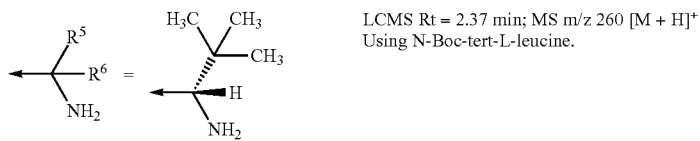

LCMS Rt = 2.37 min; MS m/z 260 [M + H]⁺
Using N-Boc-tert-L-leucine.

7. (1S)-1-(5-tert-Butyl-1H-benzimidazol-2-yl)ethanamine

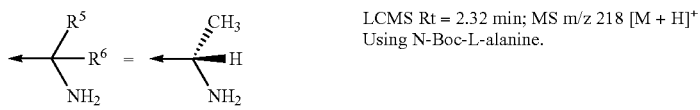

LCMS Rt = 2.32 min; MS m/z 218 [M + H]⁺
Using N-Boc-L-alanine.

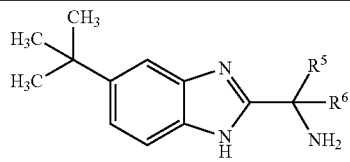

8. (1R)-1-(5-tert-Butyl-1H-benzimidazol-2-yl)-3-methylbutan-1-amine

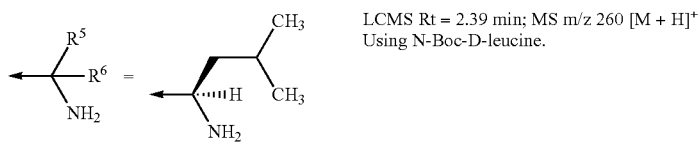

LCMS Rt = 2.39 min; MS m/z 260 [M + H]+
Using N-Boc-D-leucine.

9. (1R)-1-(5-tert-Butyl-1H-benzimidazol-2-yl)-2-methylpropan-1-amine

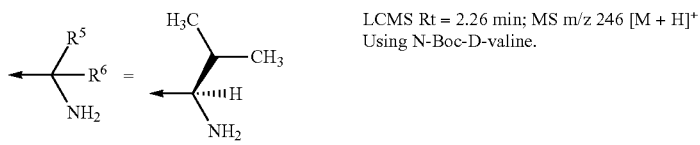

LCMS Rt = 2.26 min; MS m/z 246 [M + H]+
Using N-Boc-D-valine.

10. (1R)-1-(5-tert-Butyl-1H-benzimidazol-2-yl)ethanamine

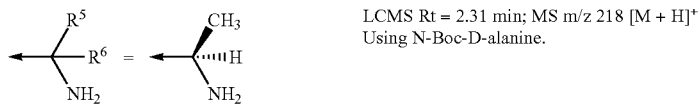

LCMS Rt = 2.31 min; MS m/z 218 [M + H]+
Using N-Boc-D-alanine.

11. (1S)-1-(5-tert-Butyl-1H-benzimidazol-2-yl)pentan-1-amine

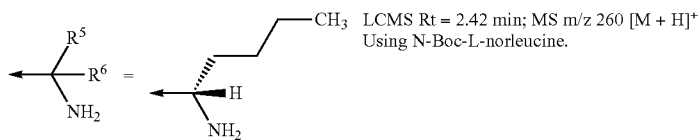

LCMS Rt = 2.42 min; MS m/z 260 [M + H]+
Using N-Boc-L-norleucine.

12. (1R)-1-(5-tert-Butyl-1H-benzimidazol-2-yl)-2-methoxyethanamine

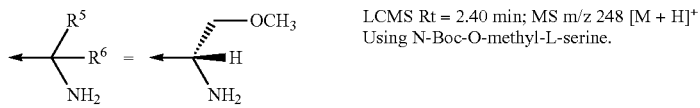

LCMS Rt = 2.40 min; MS m/z 248 [M + H]+
Using N-Boc-O-methyl-L-serine.

13. 1-(5-tert-Butyl-1H-benzimidazol-2-yl)cyclopentanamine

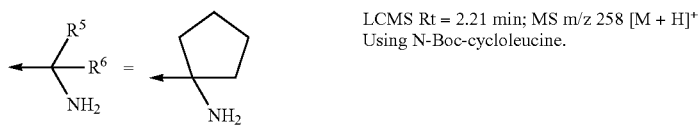

LCMS Rt = 2.21 min; MS m/z 258 [M + H]+
Using N-Boc-cycloleucine.

14. (1S)-1-(5-tert-Butyl-1H-benzimidazol-2-yl)-3-methylbutan-1-amine

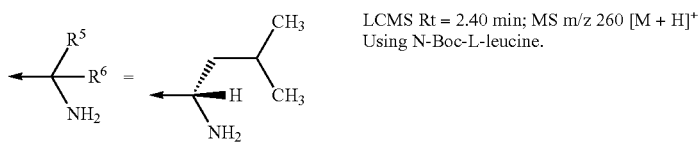

LCMS Rt = 2.40 min; MS m/z 260 [M + H]+
Using N-Boc-L-leucine.

15. (1R)-1-(5-tert-Butyl-1H-benzimidazol-2-yl)-2,2-dimethylpropan-1-amine

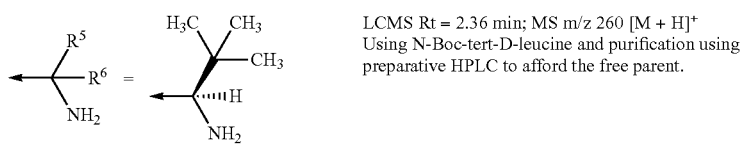

LCMS Rt = 2.36 min; MS m/z 260 [M + H]+
Using N-Boc-tert-D-leucine and purification using preparative HPLC to afford the free parent.

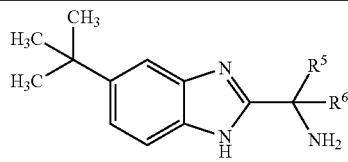

16. (1S,2S)-1-Amino-1-(5-tert-butyl-1H-benzimidazol-2-yl)propan-2-ol

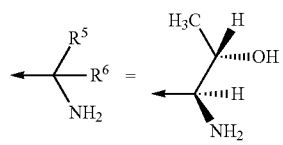

LCMS Rt = 2.36 min; MS m/z 248 [M + H]+
Using N-Boc-D-threonine and purification using preparative HPLC to afford the free parent.

17. 1-(5-tert-Butyl-1H-benzimidazol-2-yl)cyclohexanamine

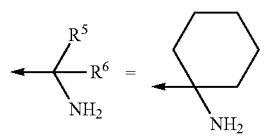

LCMS Rt = 2.28 min; MS m/z 272 [M + H]+
Using 1-(boc-amino)cyclohexanecarboxylic acid and purification using preparative HPLC to afford the free parent.

Example 18

(1S,2R)-1-Amino-1-(5-tert-butyl-1H-benzimidazol-2-yl)propan-2-ol

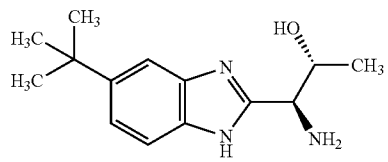 [SMILES: C[C@@H](O)[C@@H](N)c1nc2cc(C(C)(C)C)ccc2[nH]1]

The title compound was prepared according to the method described in Library Protocol 1 using N-boc-D-allo-threonine. The crude material was diluted with saturated aqueous NaHCO$_3$ solution (10 mL) and extracted with DCM (30 mL). The organic layer was separated using a separation cartridge and concentrated in vacuo.

The residue was purified using silica gel column chromatography eluting with 80:20:2 DCM:MeOH:NH$_3$ $^1$H NMR (400 MHz, CDCl$_3$): δ ppm 1.20 (d, 3H), 1.35 (s, 9H), 4.10-4.20 (m, 2H), 7.35 (m, 1H), 7.55 (m, 1H), 7.55 (m, 1H).

Example 19

(1R,2S)-1-Amino-1-(5-tert-butyl-1H-benzimidazol-2-yl)propan-2-ol

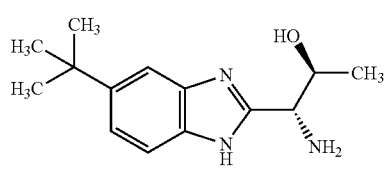 [SMILES: C[C@H](O)[C@H](N)c1nc2cc(C(C)(C)C)ccc2[nH]1]

The title compound was prepared according to the method described in Library Protocol 1 using N-boc-L-allo-threonine. The crude material was diluted with saturated aqueous NaHCO$_3$ solution (10 mL) and extracted with DCM (30 mL). The organic layer was separated using a separation cartridge and concentrated in vacuo. The residue was purified using silica gel column chromatography eluting with 80:20:2 DCM:MeOH:NH$_3$ $^1$H NMR (400 MHz, CDCl$_3$): δ ppm 1.20 (d, 3H), 1.35 (s, 9H), 3.95-4.00 (m, 2H), 7.30 (m, 1H), 7.45 (m, 1H), 7.55 (m, 1H).

Library Protocol 2

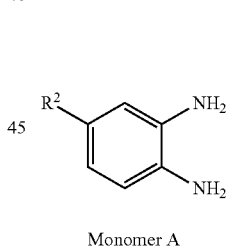

Monomer A

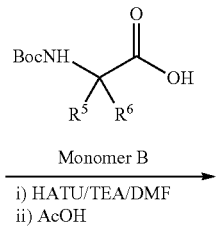

Monomer B i) HATU/TEA/DMF
ii) AcOH

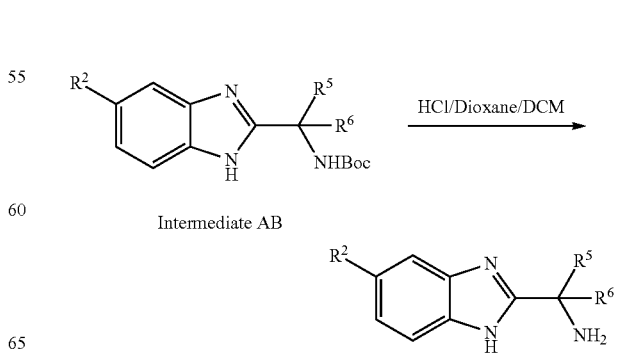

Intermediate AB

HCl/Dioxane/DCM

Step 1

To 4-tert-butyl-1,2-diaminobenzene (100 μmol, 1 eq) was added a solution of Monomer B in DMF (0.2M, 500 μL, 100 μmol, 1 eq) followed by TEA (28 μL, 200 μmol, 2 eq) and a solution of HATU in DMF (0.2 M, 500 μL, 100 μmol, 1 eq). The reaction was shaken at 60° C. for 16 hours before cooling and concentrating in vacuo to afford crude uncyclised Intermediate AB.

Step 2

To crude uncyclised Intermediate AB was added acetic acid (1000 μL) and the reaction was shaken at 80° C. for 1 hour. The reaction was cooled, concentrated in vacuo and dissolved in DMSO. The solution was filtered and purified using preparative HPLC to afford Intermediate AB.

Step 3

To Intermediate AB was added DCM (1800 μmol) followed by 4M HCl in dioxane (200 μL) and the reaction was shaken at 30° C. for 1.5 hours. The reaction was concentrated in vacuo to afford the final compounds as their HCl salts.

Example 20

(2R)-2-Amino-2-(5-tert-butyl-1H-benzimidazol-2-yl)ethanol

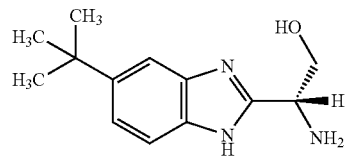 [SMILES: CC(C)(C)c1ccc2[nH]c([C@@H](N)CO)nc2c1]

Prepared according to Library Protocol 2 using N-Boc-L-serine with purification by preparative HPLC:

Preparative HPLC: Phenomenex Gemini C18; 250×21.2 mm×10 um; Acetonitrile:NH$_4$OH eluting with 41-71% MeCN over 8.5 minute gradient time. Flow rate 30 mL/min.

LCMS Rt=2.28 minutes MS m/z 234 [M+H]+

LCMS QC: AB01; Column: Welch XB-C18 2.1×50 mm 5 μm, 50° C., mobile phase A: 0.0375% TFA in water; mobile phase B: 0.01875% TFA in acetonitrile. Initial gradient 1% B; 0.60 mins 5% B, 4.00 mins 100% B, 4.30 mins 1% B, 4.70 mins 1% B. Flow rate 0.8 mL/min.

Library Protocol 3

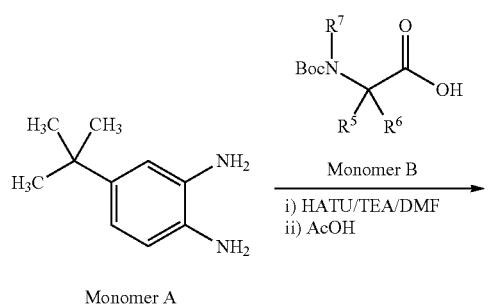

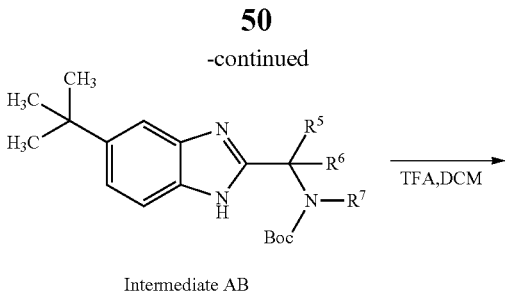

Intermediate AB

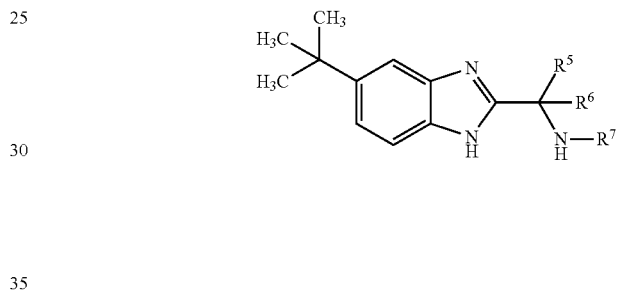

Step 1

To a 0.325M solution of Monomer B in DMF (400 μL, 125 μmol, 1 eq) was added a 0.325M solution of 4-tert-butyl-1,2-diaminobenzene in DMF (400 μL, 125 μmol, 1 eq), a 0.325M solution of HATU in DMF (400 μL, 125 μmol, 1 eq) and TEA (35 μL, 250 μmol, 2 eq). The reaction was shaken at 60° C. for 16 hours before concentrating in vacuo. To the residue was added HOAc (1.25 mL) and the reaction shaken at 80° C. for 3 hours. The reaction was cooled, concentrated in vacuo and purified using preparative HPLC to afford Intermediate AB.

Step 2

To Intermediate AB was added a solution of TFA/DCM (V/V=1/5, 2 mL) and the reaction was shaken at 30° C. for 1 hour. The reaction was concentrated in vacuo to afford the final compounds as their TFA salts.

LCMS QC: AB01; Column: Welch XB-C18 2.1×50 mm 5 μm, 50° C., mobile phase A: 0.0375% TFA in water; mobile phase B: 0.01875% TFA in acetonitrile. Initial gradient 1% B; 0.60 mins 5% B, 4.00 mins 100% B, 4.30 mins 1% B, 4.70 mins 1% B. Flow rate 0.8 mL/min.

Preparative HPLC: Phenomenex Gemini C18; 250×21.2 mm×10 um; Acetonitrile:NH$_4$OH eluting with a gradient specific to each compound (see table) over an 8-10 minute gradient time. Flow rate 30/35 mL/min unless otherwise specified.

The following Examples were prepared according to Library Protocol 3 using 4-tert-butyl-1,2-diaminobenzene and the appropriate amino acid for Monomer B as described.

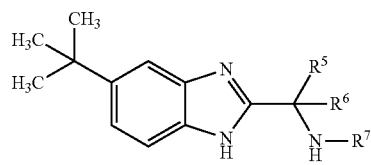

21. (1R,2R)-1-(5-tert-Butyl-1H-benzimidazol-2-yl)-2-methoxypropan-1-amine

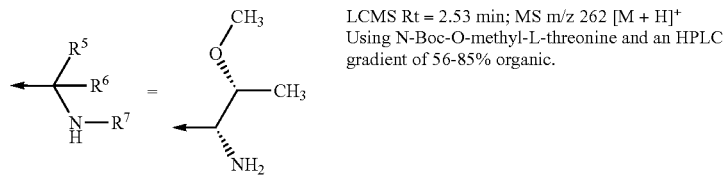

LCMS Rt = 2.53 min; MS m/z 262 [M + H]+
Using N-Boc-O-methyl-L-threonine and an HPLC gradient of 56-85% organic.

22. (3S,5S)-5-(5-tert-Butyl-1H-benzimidazol-2-yl)pyrrolidin-3-ol

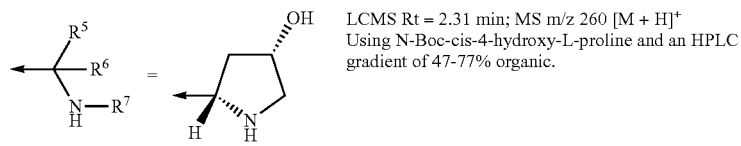

LCMS Rt = 2.31 min; MS m/z 260 [M + H]+
Using N-Boc-cis-4-hydroxy-L-proline and an HPLC gradient of 47-77% organic.

23. (1R,2R)-1-(5-tert-Butyl-1H-benzimidazol-2-yl)-2-methylbutan-1-amine

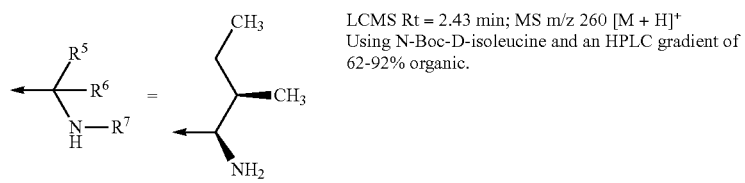

LCMS Rt = 2.43 min; MS m/z 260 [M + H]+
Using N-Boc-D-isoleucine and an HPLC gradient of 62-92% organic.

24. (3R,5R)-5-(5-tert-Butyl-1H-benzimidazol-2-yl)pyrrolidin-3-ol

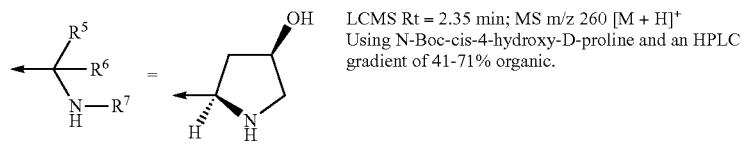

LCMS Rt = 2.35 min; MS m/z 260 [M + H]+
Using N-Boc-cis-4-hydroxy-D-proline and an HPLC gradient of 41-71% organic.

25. 5-tert-Butyl-2-[(2R)-pyrrolidin-2-yl]-1H-benzimidazole

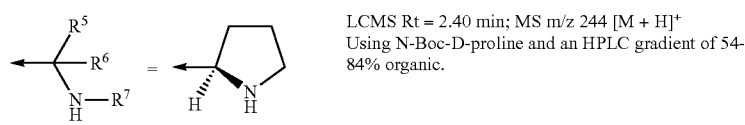

LCMS Rt = 2.40 min; MS m/z 244 [M + H]+
Using N-Boc-D-proline and an HPLC gradient of 54-84% organic.

26. (3R,5S)-5-(5-tert-Butyl-1H-benzimidazol-2-yl)pyrrolidin-3-ol

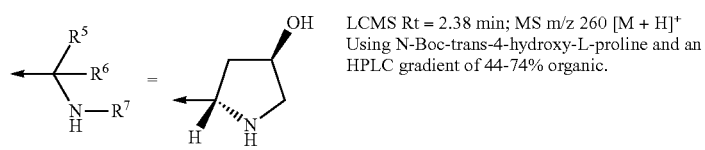

LCMS Rt = 2.38 min; MS m/z 260 [M + H]+
Using N-Boc-trans-4-hydroxy-L-proline and an HPLC gradient of 44-74% organic.

27. 1-(5-tert-Butyl-1H-benzimidazol-2-yl)-2-methoxy-2-methylpropan-1-amine

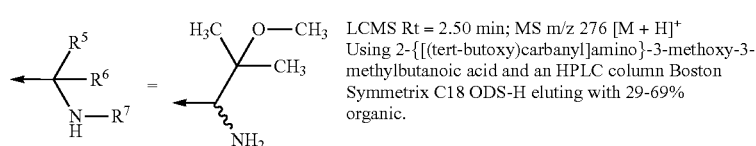

LCMS Rt = 2.50 min; MS m/z 276 [M + H]+
Using 2-{[(tert-butoxy)carbanyl]amino}-3-methoxy-3-methylbutanoic acid and an HPLC column Boston Symmetrix C18 ODS-H eluting with 29-69% organic.

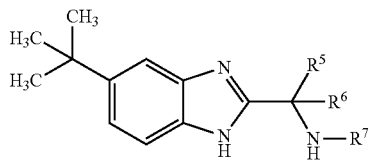

28. (3R)-3-Amino-3-(5-tert-butyl-1H-benzimidazol-2-yl)propanamide

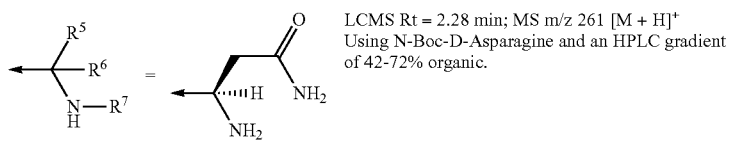

LCMS Rt = 2.28 min; MS m/z 261 [M + H]⁺
Using N-Boc-D-Asparagine and an HPLC gradient of 42-72% organic.

Library Protocol 4

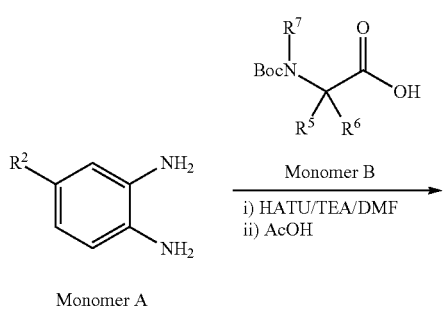

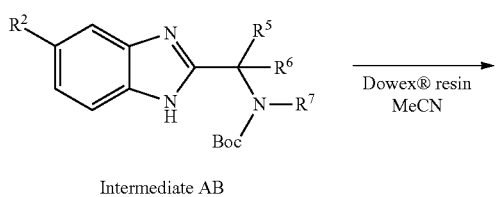

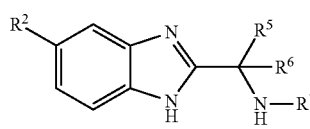

Step 1

A 0.2M solution of Monomer B in DMF (500 μL, 100 μmol) was added to a 0.2M solution of Monomer A in DMF (500 μL, 100 μmol) followed by HATU (100 μmol) and TEA (200 μmol). The reaction was stirred at 60° C. for 16 hours. The reaction was concentrated in vacuo and AcOH (10 mL) was added to the residue. The reaction was stirred at 80° C. for 12 hours, cooled and concentrated in vacuo to afford crude Intermediate AB.

Step 2

To crude Intermediate AB was added MeCN (20 mL) followed by MSC Dowex® resin (150 mg) and the reaction was stirred at 25° C. for 16 hours. The resin was washed with 1:1 MeCN:MeOH followed by 5% $NH_3$/MeOH. The combined solvents were concentrated in vacuo, dissolved in DMSO (1 mL) and purified using preparative HPLC to afford the final compounds.

LCMS QC Method 1: Column: RESTEK C18 2.1×30 mm 3 μm, mobile phase A: 0.05% formic acid in water; mobile phase B: Acetonitrile. Initial gradient 2% B; 0.75 mins 2% B, 1.00 mins 10% B, 2.00 mins 98% B, 2.90 mins 2% B, 3.00 mins 2% B. Flow rate 1.5 mL/min.

LCMS QC Method 2: Column: Xbridge C18 2.1×50 mm 5 μm, mobile phase A: 10 mM ammonium acetate in water; mobile phase B: Acetonitrile. Initial gradient 5% B; 0.50 mins 5% B, 1.00 mins 25% B, 1.50 mins 45% B, 2.00 mins 90% B, 2.90 mins 5% B, 3.00 mins 5% B. Flow rate 1.5 mL/min.

Preparative HPLC: Xterra 250×19 mm, 10μ or X-Bridge 50×19 mm, 5μ; mobile phase A: acetonitrile, mobile phase B: 0.05% $NH_3$ in water; eluting with a gradient specific to each compound (see table) over a 7, 16, 18 or 22 minute gradient time. Flow rate between 13-20 mL/min unless otherwise specified.

The following Examples were prepared according to Library Protocol 4 using either 4-(1,1-dimethylpropyl)benzene-1,2-diamine (Preparation 75) or 3',4'-diaminobiphenyl-4-carbonitrile (Preparation 82) and the appropriate amino acid for Monomer B as described.

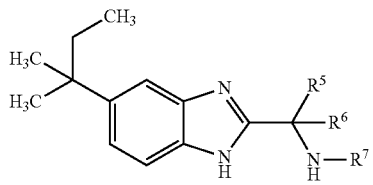

29. (3S,5S)-5-[5-(2-Methylbutan-2-yl)-1H-benzimidazol-2-yl]pyrrolidin-3-ol

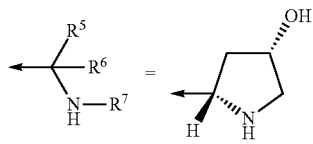

LCMS Rt = 1.35 min; MS m/z 274 [M + H]+
Using N-Boc-cis-4-hydroxy-L-proline and an HPLC gradient of 5-50% organic.

30. (3S)-3-Amino-3-[5-(2-methylbutan-2-yl)-1H-benzimidazol-2-yl]propanamide

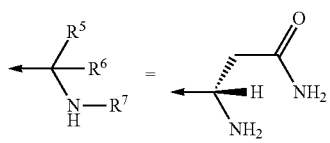

LCMS Rt = 1.33 min; MS m/z 275 [M + H]+
Using N-Boc-L-Asparagine and an HPLC gradient of 10-40% organic.

31. (1R)-2-Methoxy-1-[5-(2-methylbutan-2-yl)-1H-benzimidazol-2-yl]ethanamine

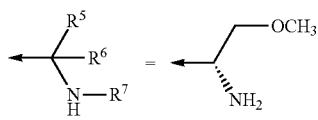

LCMS Rt = 1.37 min; MS m/z 262 [M + H]+
Using N-Boc-O-methyl-L-serine and an HPLC gradient of 10-70% organic.

32. 4-{2-[(S)-Amino(cyclopentyl)methyl]-1H-benzimidazol-5-yl}benzonitrile

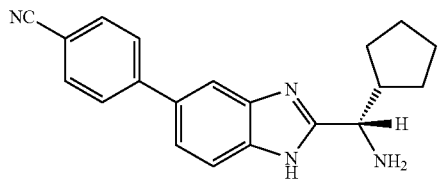 [SMILES: N#Cc1ccc(-c2ccc3[nH]c([C@@H](N)C4CCCC4)nc3c2)cc1]

LCMS Rt = 1.39 min; MS m/z 317 [M + H]+
Using N-Boc-L-cyclopentylglycine and an HPLC gradient of 10-60% organic.

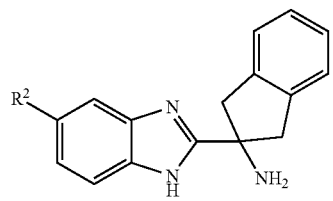

33. 2-[5-(2-Methylbutan-2-yl)-1H-benzimidazol-2-yl]-2,3-dihydro-1H-inden-2-amine

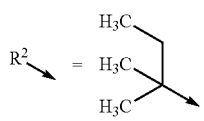

LCMS Rt = 1.45 min; MS m/z 320 [M + H]+
Using N-Boc-2-aminoindane-2-carboxylic acid and an HPLC gradient of 5-60% organic.

34. 4-[2-(2-Amino-2,3-dihydro-1H-inden-2-yl)-1H-benzimidazol-5-yl]benzonitrile

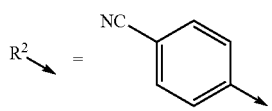

LCMS Rt = 1.40 min; MS m/z 351 [M + H]+
Using N-Boc-2-aminoindane-2-carboxylic acid and an HPLC gradient of 5-50% organic.

35. (1S)-1-[5-(2-Methylbutan-2-yl)-1H-benzimidazol-2-yl]ethanamine

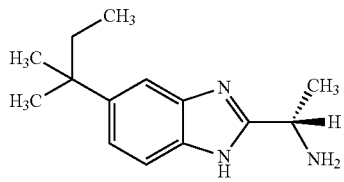 [SMILES: CCC(C)(C)c1ccc2[nH]c([C@H](C)N)nc2c1]

LCMS Rt = 1.35 min; MS m/z 232 [M + H]+
Using N-Boc-L-alanine and an HPLC gradient of 5-40% organic.

36. 4-{2-[(R)-Amino(phenyl)methyl]-1H-benzimidazol-5-yl}benzonitrile

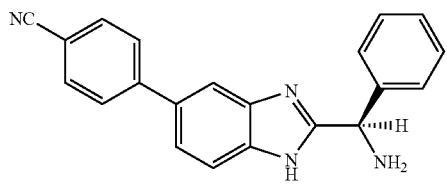 [SMILES: N#Cc1ccc(-c2ccc3[nH]c([C@H](N)c4ccccc4)nc3c2)cc1]

LCMS Rt = 1.40 min; MS m/z 325 [M + H]+
Using N-boc-D-phenylglycine and an HPLC gradient of 10-60% organic.

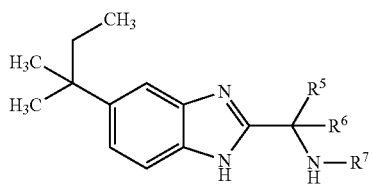

37. (2R,3S)-2-[5-(2-Methylbutan-2-yl)-1H-benzimidazol-2-yl]pyrrolidin-3-ol

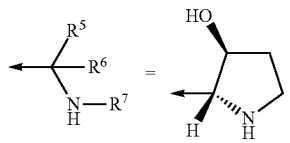

LCMS Rt = 1.36 min; MS m/z 274 [M + H]+
Using N-Boc-trans-3-hydroxy-L-proline and an HPLC gradient of 10-70% organic.

38. (1R,2R)-2-Methoxy-1-[5-(2-methylbutan-2-yl)-1H-benzimidazol-2-yl]propan-1-amine

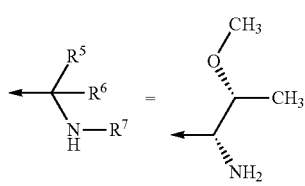

LCMS Rt = 1.39 min; MS m/z 276 [M + H]+
Using N-Boc-O-Methyl-L-threonine using an HPLC gradient of 5-50% organic.

39. (1R,2R)-1-Amino-1-[5-(2-methylbutan-2-yl)-1H-benzimidazol-2-yl]propan-2-ol

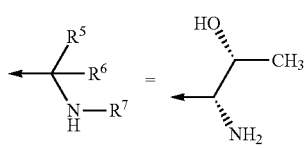

LCMS Rt = 1.35 min; MS m/z 262 [M + H]+
Using N-Boc-L-threonine and an HPLC gradient of 5-40% organic.

40. 4-{2-[(1R,2R)-1-Amino-2-hydroxypropyl]-1H-benzimidazol-5-yl}benzonitrile

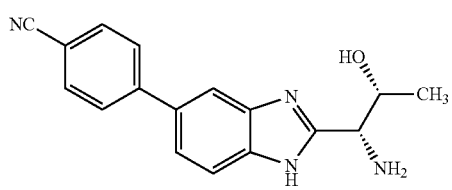 [SMILES: C[C@@H](O)[C@H](N)c1nc2cc(-c3ccc(C#N)cc3)ccc2[nH]1]

LCMS Rt = 1.32 min; MS m/z 293 [M + H]+
Using N-Boc-L-threonine and an HPLC gradient of 5-40% organic.

| | |
|---|---|
| 41. (1R)-1-[5-(2-Methylbutan-2-yl)-1H-benzimidazol-2-yl]ethanamine | |
| 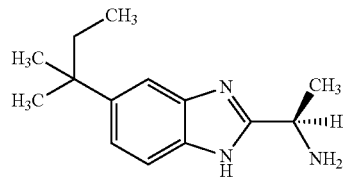 [SMILES: CCC(C)(C)c1ccc2[nH]c([C@@H](C)N)nc2c1] | LCMS Rt = 1.35 min; MS m/z 232 [M + H]$^+$<br>Using N-Boc-D-alanine and an HPLC gradient of 5-50% organic. |

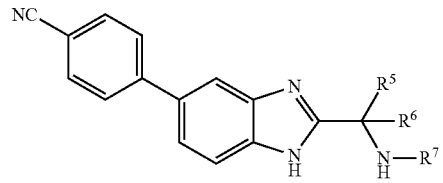

| | |
|---|---|
| 42. 4-{2-[(S)-Amino(phenyl)methyl]-1H-benzimidazol-5-yl}benzonitrile | |
| 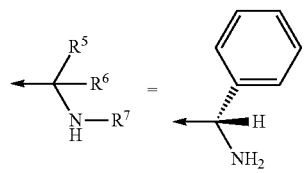 | LCMS Rt = 1.40 min; MS m/z 325 [M + H]$^+$<br>Using N-boc-L-phenylglycine and an HPLC gradient of 10-60% organic. |
| 43. 4-{2-[(2R,4R)-4-Hydroxypyrrolidin-2-yl]-1H-benzimidazol-5-yl}benzonitrile | |
| 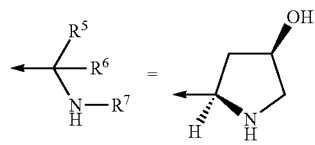 | LCMS Rt = 1.31 min; MS m/z 305 [M + H]$^+$<br>Using N-Boc-cis-4-hydroxy-D-proline and an HPLC gradient of 5-40% organic. |
| 44. (3R)-3-Amino-3-[5-(4-cyanophenyl)-1H-benzimidazol-2-yl]propanamide | |
| 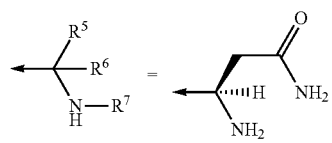 | LCMS Rt = 1.28 min; MS m/z 306 [M + H]$^+$<br>Using N-Boc-D-Asparagine and an HPLC gradient of 10-50% organic. |
| 45. (3S)-3-Amino-3-[5-(4-cyanophenyl)-1H-benzimidazol-2-yl]propanamide | |
| 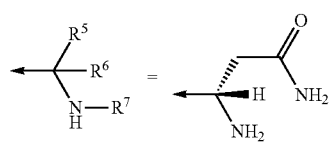 | LCMS Rt = 1.29 min; MS m/z 306 [M + H]$^+$<br>Using N-Boc-L-Asparagine and an HPLC gradient of 10-45% organic. |
| 46. 4-{2-[(2S,4R)-4-Hydroxypyrrolidin-2-yl]-1H-benzimidazol-5-yl}benzonitrile | |
| 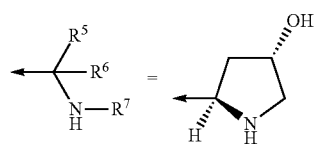 | LCMS Rt = 1.31 min; MS m/z 305 [M + H]$^+$<br>Using N-Boc-trans-4-hydroxy-D-proline and an HPLC gradient of 5-40% organic. |
| 47. 4-{2-[(1R)-1-Amino-3-methylbutyl]-1H-benzimidazol-5-yl}benzonitrile | |
| 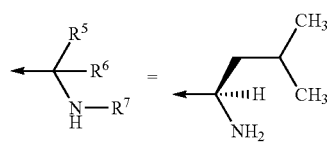 | LCMS Rt = 1.39 min; MS m/z 305 [M + H]$^+$<br>Using and N-Boc-D-leucine and an HPLC gradient of 5-45% organic. |

48. 4-{2-[(1R)-1-Amino-2,2-dimethylpropyl]-1H-benzimidazol-5-yl}benzonitrile

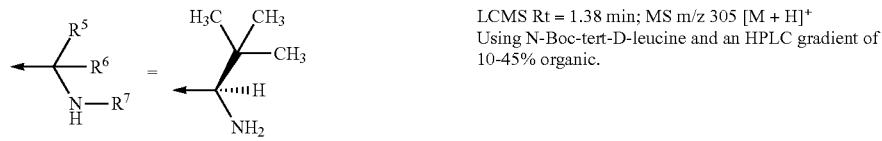

LCMS Rt = 1.38 min; MS m/z 305 [M + H]⁺
Using N-Boc-tert-D-leucine and an HPLC gradient of 10-45% organic.

49. 4-{2-[(2S,4S)-4-Hydroxypyrrolidin-2-yl]-1H-benzimidazol-5-yl}benzonitrile

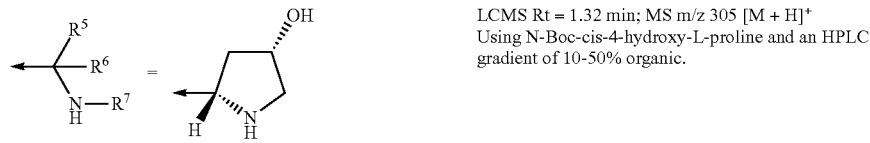

LCMS Rt = 1.32 min; MS m/z 305 [M + H]⁺
Using N-Boc-cis-4-hydroxy-L-proline and an HPLC gradient of 10-50% organic.

50. 4-{2-[(2R,3S)-3-Hydroxypyrrolidin-2-yl]-1H-benzimidazol-5-yl}benzonitrile

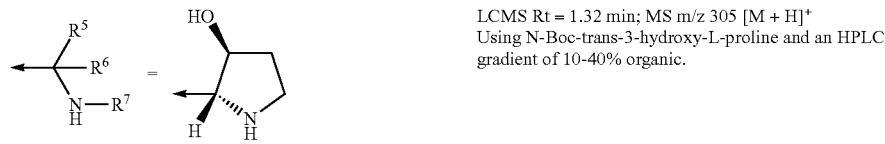

LCMS Rt = 1.32 min; MS m/z 305 [M + H]⁺
Using N-Boc-trans-3-hydroxy-L-proline and an HPLC gradient of 10-40% organic.

Library Protocol 5

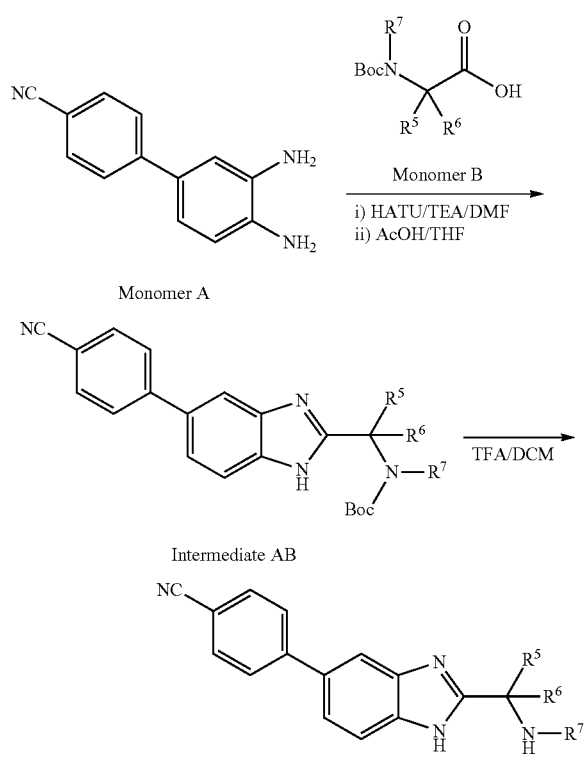

Step 1

A 0.25M solution of Monomer B in DMF (500 µL, 125 µmol) was added to a 0.25M solution of Monomer A in DMF (500 µL, 125 µmol) followed by HATU (125 µmol) and TEA (18 µl, 125 µmol). The reaction was stirred at 60° C. for 16 hours. The reaction was concentrated in vacuo and a solvent mixture of AcOH:THF (1:5, 1 mL) was added to the residue. The reaction was stirred at 60° C. for 16 hours, cooled and concentrated in vacuo. The residue was dissolved in DCM (500 µL) and purified using silica gel column chromatography (Biotage Quad-111) eluting with 20% acetone in hexane to afford intermediate AB.

Step 2

Intermediate AB was dissolved in DCM (800 µL), cooled to 5-10° C. and TFA (200 µL) was added. The reaction was stirred at room temperature for 16 hours before concentrating in vacuo. The residue was dissolved in a solution of 20% TEA in DMF (1 mL). A 10 µL aliquot was removed, diluted to 200 µL with DMSO and purified using preparative HPLC to afford the final compounds.

LCMS QC: Column: RESTEK C18 2.1×30 mm 3 µm, mobile phase A: 0.05% formic acid in water; mobile phase B: Acetonitrile. Initial gradient 2% B; 0.75 mins 2% B, 1.00 mins 10% B, 2.00 mins 98% B, 2.90 mins 2% B, 3.00 mins 2% B. Flow rate 1.5 mL/min.

Preparative HPLC: XBRIDGE C18 (250×19 mm, 5µ) or (50×19 mm, 5µ); mobile phase A: acetonitrile, mobile phase B: 0.1% NH₃ in water, over a 7, 18, 22, 23 or 24 minute gradient time; flow rate between 16-20 mL/min; eluting with a gradient specific to each compound (see table).

The following Examples were prepared according to Library Protocol 5 using 3',4'-diaminobiphenyl-4-carbonitrile (Preparation 82) and the appropriate amino acid for Monomer B as described.

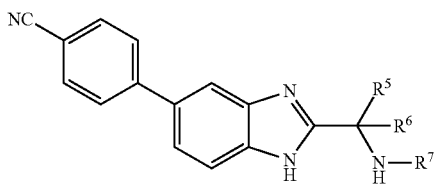

51. 4-{2-[(2S)-Piperidin-2-yl]-1H-benzimidazol-5-yl}benzonitrile

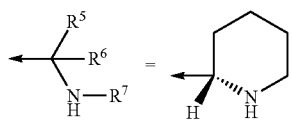

LCMS Rt = 1.34 min; MS m/z 303 [M + H]⁺
Using (S)-1-N-Boc-piperidine-2-carboxylic acid and an HPLC gradient of 10-45% organic.

52. 4-{2-[(1S)-1-amino-2-methylpropyl]-1H-benzimidazol-5-yl}benzonitrile

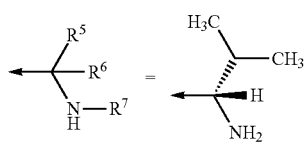

LCMS Rt = 1.35 min; MS m/z 291 [M + H]⁺
Using N-Boc-L-valine and an HPLC gradient of 10-45% organic.

53. 4-{2-[(1R)-1-aminopropyl]-1H-benzimidazol-5-yl}benzonitrile

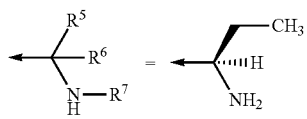

LCMS Rt = 1.33 min; MS m/z 277 [M + H]⁺
Using (R)-N-Boc-2-aminobutyric acid and an HPLC gradient of 10-40% organic.

54. 4-{2-[(1R)-1-aminoethyl]-1H-benzimidazol-5-yl}benzonitrile

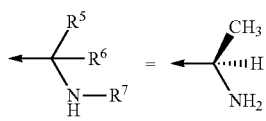

LCMS Rt = 1.30 min; MS m/z 263 [M + H]⁺
Using N-Boc-D-alanine and an HPLC gradient of 10-45% organic.

55. 4-{2-[(1R,2S,5S)-6,6-dimethyl-3-azabicyclo[3.1.0]hex-2-yl]-1H-benzimidazol-5-yl}benzonitrile

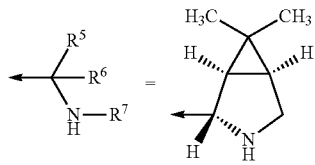

LCMS Rt = 1.37 min; MS m/z 329 [M + H]⁺
Using (1R,2S,5S)-3-(tert-butoxycarbonyl)-6,6-dimethyl-3-azabicyclo[3.1.0]hexane-2-carboxylic acid and an HPLC gradient of 10-60% organic.

56. 4-{2-[(1R)-1-amino-2-methylpropyl]-1H-benzimidazol-5-yl}benzonitrile

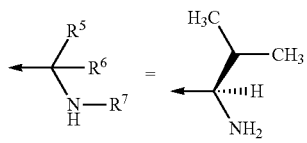

LCMS Rt = 1.35 min; MS m/z 291 [M + H]⁺
Using N-Boc-D-valine and an HPLC gradient of 10-45% organic.

57. 4-{2-[(1S)-1-amino-2,2-dimethylpropyl]-1H-benzimidazol-5-yl}benzonitrile

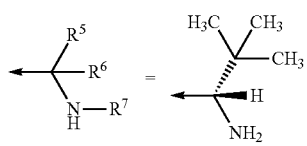

LCMS Rt = 1.38 min; MS m/z 305 [M + H]⁺
Using N-Boc-L-tert-leucine and an HPLC gradient of 10-50% organic.

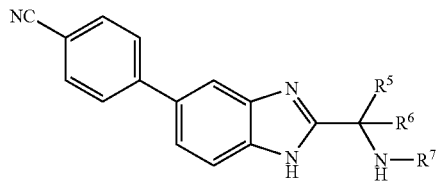

58. 4-{2-[(1R)-1-aminopentyl]-1H-benzimidazol-5-yl}benzonitrile

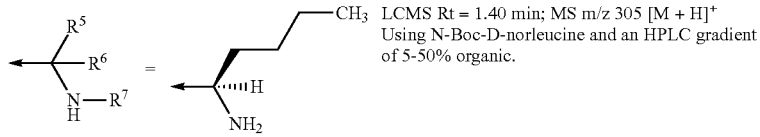

LCMS Rt = 1.40 min; MS m/z 305 [M + H]+
Using N-Boc-D-norleucine and an HPLC gradient of 5-50% organic.

59. 4-[2-(1-aminocyclopentyl)-1H-benzimidazol-5-yl]benzonitrile

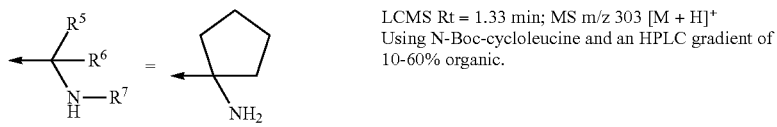

LCMS Rt = 1.33 min; MS m/z 303 [M + H]+
Using N-Boc-cycloleucine and an HPLC gradient of 10-60% organic.

60. 4-{2-[(1S)-1-aminopentyl]-1H-benzimidazol-5-yl}benzonitrile

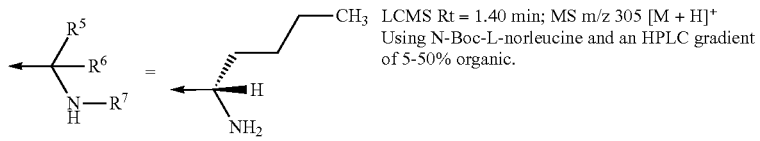

LCMS Rt = 1.40 min; MS m/z 305 [M + H]+
Using N-Boc-L-norleucine and an HPLC gradient of 5-50% organic.

61. 4-{2-[(2S,4S)-4-fluoropyrrolidin-2-yl]-1H-benzimidazol-5-yl}benzonitrile

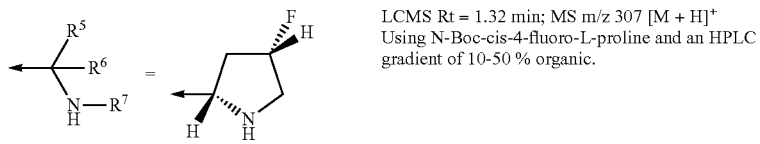

LCMS Rt = 1.32 min; MS m/z 307 [M + H]+
Using N-Boc-cis-4-fluoro-L-proline and an HPLC gradient of 10-50 % organic.

62. 4-{2-[(1S,2S)-1-amino-2-hydroxypropyl]-1H-benzimidazol-5-yl}benzonitrile

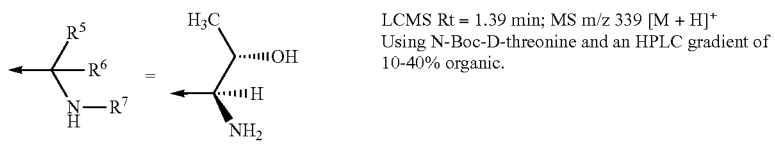

LCMS Rt = 1.39 min; MS m/z 339 [M + H]+
Using N-Boc-D-threonine and an HPLC gradient of 10-40% organic.

63. (This Example is intentionally omitted)
64. 4-{2-[(1S)-1-aminoethyl]-1H-benzimidazol-5-yl}benzonitrile

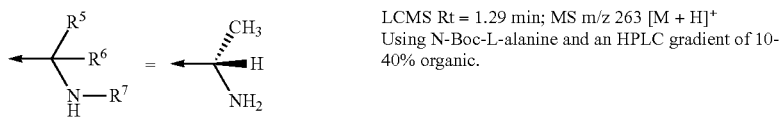

LCMS Rt = 1.29 min; MS m/z 263 [M + H]+
Using N-Boc-L-alanine and an HPLC gradient of 10-40% organic.

Library Protocol 6

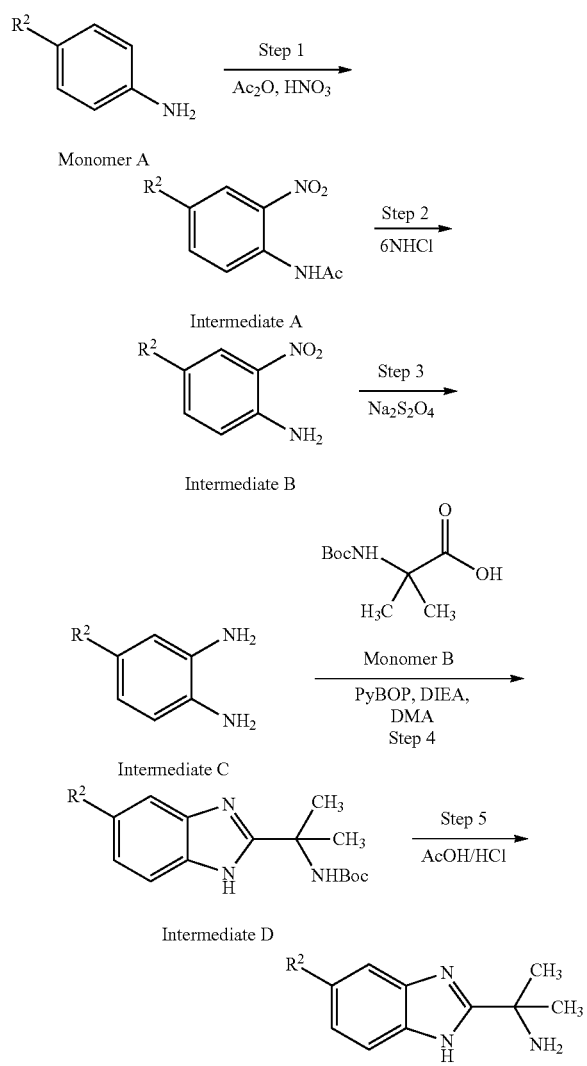

Step 1

Acetic anhydride (500 μL) was added to Monomer A (150 μmol, 1 eq) followed by concentrated HNO₃ (120 μL) at 0° C. The reaction was shaken at 0° C. for 30 minutes.

Ice-water was added (1 mL) followed by ammonium hydroxide (500 μL) to reach pH=9. The mixture was extracted with EtOAc (3×1 mL), the organic layer collected, dried over Na₂SO₄ and concentrated in vacuo to afford intermediate A.

Step 2

To crude intermediate A was added 6N HCl (500 μL) and the reaction shaken at 100° C. for 2 hours. After cooling ammonium hydroxide (500 μL) was added to reach pH=9 and the mixture was extracted with EtOAc (3×1 mL). The combined organic layers were dried over Na₂SO₄ and concentrated in vacuo to afford intermediate B.

Step 3

To crude intermediate B (125 μmol) was added dioxane (1 mL) followed by a 2M solution of potassium carbonate in water (300 μL, 10 μmol), a 2.08M solution of Na₂S₂O₄ in water (300 μL, 625 μmol) and a 0.033M solution of methyl viologen in water (300 μL, 10 μmol). The reaction was shaken at 30° C. for 16 hours. The reaction was extracted with EtOAc (3×2 mL), the organic layers collected, dried over Na₂SO₄ and concentrated in vacuo to afford intermediate C.

Step 4

DMA (800 μL) was added to N-boc-2-amino-isobutyric acid (100 μmol) and PyBOP (55 mg, 110 μmol). The mixture was shaken at 30° C. for 30 minutes. A solution of crude intermediate C in DMA (400 μL) was added to the reaction followed by DIEA (75 μL, 300 μmol). The reaction was shaken at 30° C. for 16 hours before concentrating in vacuo to afford intermediate D.

Step 5

To crude intermediate D (75 μmol) was added acetic acid (400 μmol) followed by 6N HCl (150 μL). The reaction was shaken at 100° C. for 2 hours. The reaction was cooled, concentrated in vacuo and purified using preparative HPLC to afford the final compounds.

LCMS QC: Column Welch XB-C18 2.1×50 mm 5 μm, mobile phase A: Acetonitrile; mobile phase B: 0.05% TFA.

The following Examples were prepared according to Library Protocol 6 and isolated as their TFA salts. The appropriate aniline for Monomer B was used as described.

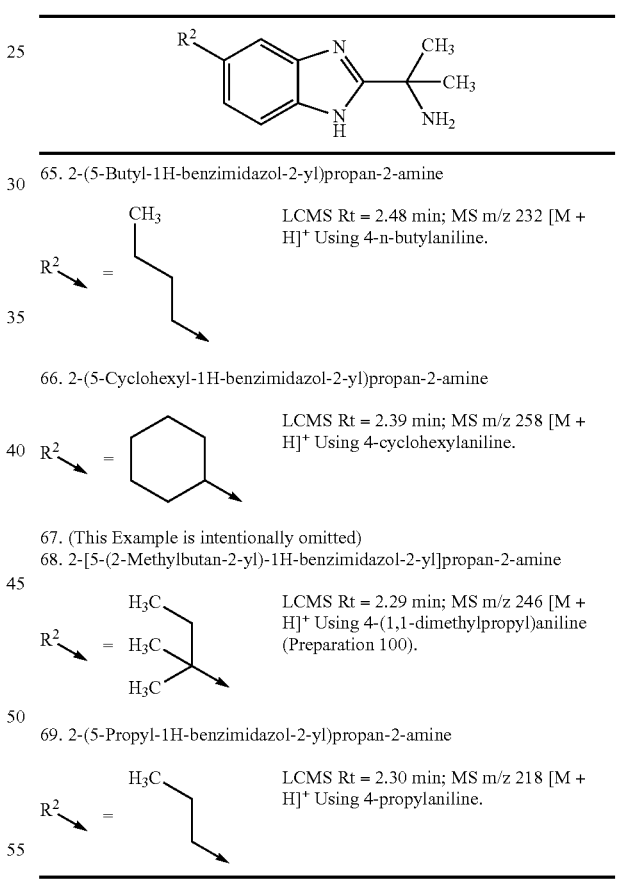

65. 2-(5-Butyl-1H-benzimidazol-2-yl)propan-2-amine

LCMS Rt = 2.48 min; MS m/z 232 [M + H]⁺ Using 4-n-butylaniline.

66. 2-(5-Cyclohexyl-1H-benzimidazol-2-yl)propan-2-amine

LCMS Rt = 2.39 min; MS m/z 258 [M + H]⁺ Using 4-cyclohexylaniline.

67. (This Example is intentionally omitted)

68. 2-[5-(2-Methylbutan-2-yl)-1H-benzimidazol-2-yl]propan-2-amine

LCMS Rt = 2.29 min; MS m/z 246 [M + H]⁺ Using 4-(1,1-dimethylpropyl)aniline (Preparation 100).

69. 2-(5-Propyl-1H-benzimidazol-2-yl)propan-2-amine

LCMS Rt = 2.30 min; MS m/z 218 [M + H]⁺ Using 4-propylaniline.

Library Protocol 7

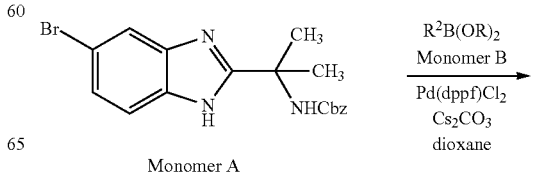

Monomer A

-continued

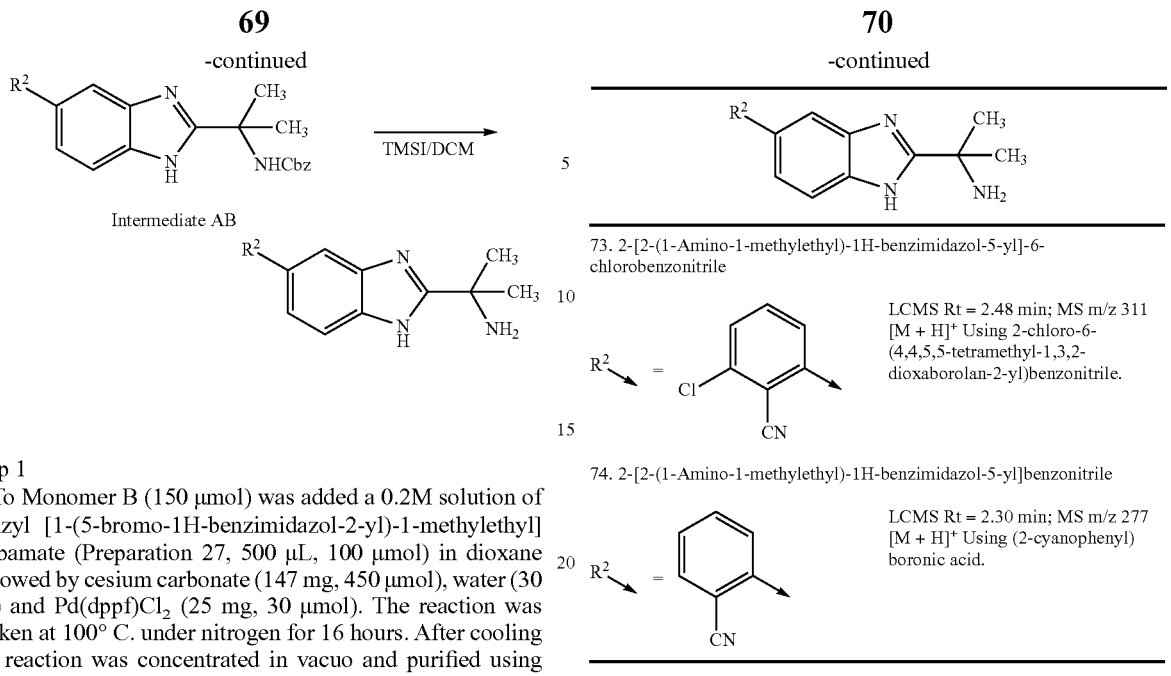

Intermediate AB

Step 1

To Monomer B (150 μmol) was added a 0.2M solution of benzyl [1-(5-bromo-1H-benzimidazol-2-yl)-1-methylethyl]carbamate (Preparation 27, 500 μL, 100 μmol) in dioxane followed by cesium carbonate (147 mg, 450 μmol), water (30 μL) and Pd(dppf)Cl$_2$ (25 mg, 30 μmol). The reaction was shaken at 100° C. under nitrogen for 16 hours. After cooling the reaction was concentrated in vacuo and purified using preparative HPLC to afford Intermediate AB.

Step 2

Intermediate AB was dissolved in DCM (1 mL) and TMSI (75 μL, 108 mg) was added. The reaction was shaken at 30° C. for 1 hour before the addition of water (100 μL) and MeOH (500 μL). The mixture was concentrated in vacuo and purified by preparative HPLC to afford the final compounds.

LCMS QC: Column Welch XB-C18 2.1×50 mm 5 μm, mobile phase A: Acetonitrile; mobile phase B: 0.05% TFA.

The following Examples were prepared according to Library Protocol 7 and isolated as their TFA salts. The appropriate boronic acid or boronate ester was used for Monomer B as described.

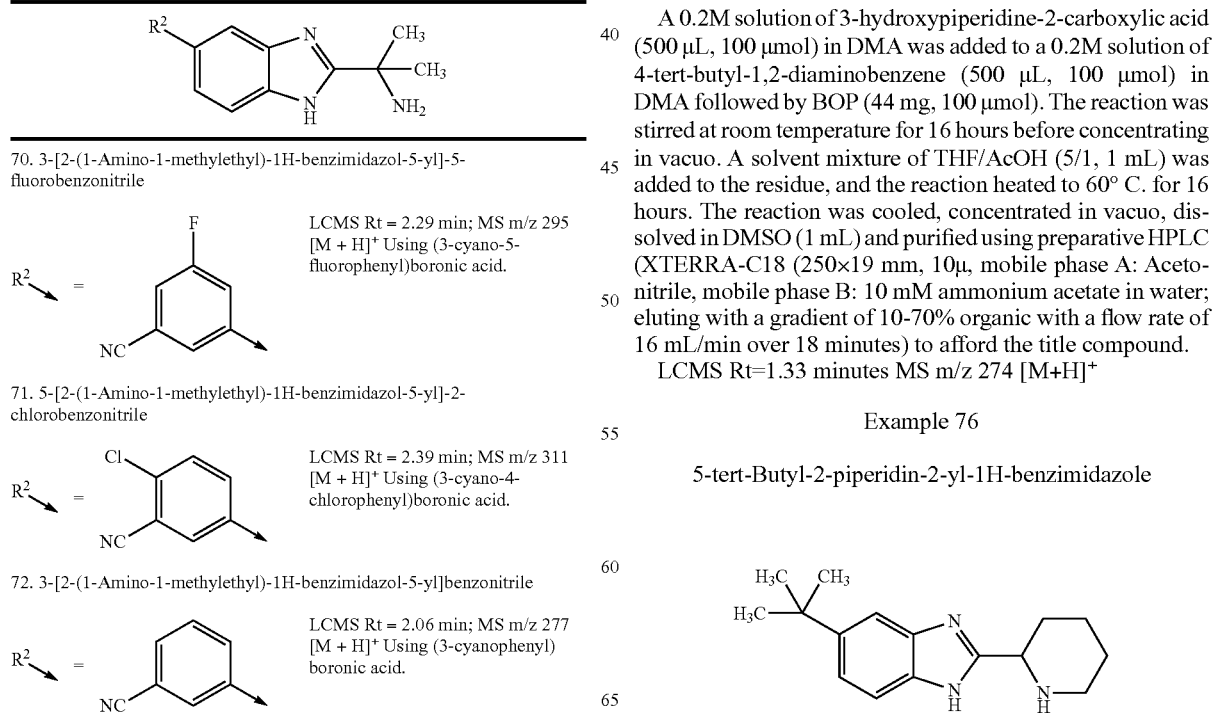

70. 3-[2-(1-Amino-1-methylethyl)-1H-benzimidazol-5-yl]-5-fluorobenzonitrile

| | |
|---|---|
| R² = (3-cyano-5-fluorophenyl) | LCMS Rt = 2.29 min; MS m/z 295 [M + H]⁺ Using (3-cyano-5-fluorophenyl)boronic acid. |

71. 5-[2-(1-Amino-1-methylethyl)-1H-benzimidazol-5-yl]-2-chlorobenzonitrile

| | |
|---|---|
| R² = (3-cyano-4-chlorophenyl) | LCMS Rt = 2.39 min; MS m/z 311 [M + H]⁺ Using (3-cyano-4-chlorophenyl)boronic acid. |

72. 3-[2-(1-Amino-1-methylethyl)-1H-benzimidazol-5-yl]benzonitrile

| | |
|---|---|
| R² = (3-cyanophenyl) | LCMS Rt = 2.06 min; MS m/z 277 [M + H]⁺ Using (3-cyanophenyl)boronic acid. |

73. 2-[2-(1-Amino-1-methylethyl)-1H-benzimidazol-5-yl]-6-chlorobenzonitrile

| | |
|---|---|
| R² = (2-chloro-6-cyanophenyl) | LCMS Rt = 2.48 min; MS m/z 311 [M + H]⁺ Using 2-chloro-6-(4,4,5,5-tetramethyl-1,3,2-dioxaborolan-2-yl)benzonitrile. |

74. 2-[2-(1-Amino-1-methylethyl)-1H-benzimidazol-5-yl]benzonitrile

| | |
|---|---|
| R² = (2-cyanophenyl) | LCMS Rt = 2.30 min; MS m/z 277 [M + H]⁺ Using (2-cyanophenyl)boronic acid. |

Example 75

2-(5-tert-Butyl-1H-benzimidazol-2-yl)piperidin-3-ol

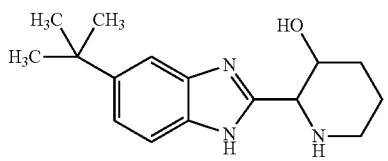 [SMILES: CC(C)(C)c1ccc2[nH]c(C3NCCCC3O)nc2c1]

A 0.2M solution of 3-hydroxypiperidine-2-carboxylic acid (500 μL, 100 μmol) in DMA was added to a 0.2M solution of 4-tert-butyl-1,2-diaminobenzene (500 μL, 100 μmol) in DMA followed by BOP (44 mg, 100 μmol). The reaction was stirred at room temperature for 16 hours before concentrating in vacuo. A solvent mixture of THF/AcOH (5/1, 1 mL) was added to the residue, and the reaction heated to 60° C. for 16 hours. The reaction was cooled, concentrated in vacuo, dissolved in DMSO (1 mL) and purified using preparative HPLC (XTERRA-C18 (250×19 mm, 10μ, mobile phase A: Acetonitrile, mobile phase B: 10 mM ammonium acetate in water; eluting with a gradient of 10-70% organic with a flow rate of 16 mL/min over 18 minutes) to afford the title compound.

LCMS Rt=1.33 minutes MS m/z 274 [M+H]⁺

Example 76

5-tert-Butyl-2-piperidin-2-yl-1H-benzimidazole

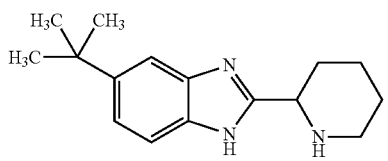 [SMILES: CC(C)(C)c1ccc2[nH]c(C3CCCCN3)nc2c1]

The title compound may be prepared according to the protocol described for Example 75 using piperidine-2-carboxylic acid and purification using preparative HPLC as described with an organic gradient of 10-65%.

LCMS Rt=1.28 minutes MS m/z 258 [M+H]+

Example 77

2-{2-[(1R,2R)-1-Amino-2-methoxypropyl]-1H-benzimidazol-5-yl}benzonitrile

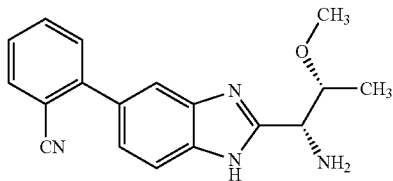 [SMILES: CO[C@H](C)[C@H](N)c1nc2cc(-c3ccccc3C#N)ccc2[nH]1]

To 4-bromo-1,2-benzenediamine (2.3 g, 12.3 mmol) and N-boc-O-methyl-L-threonine (2.9 g, 12.3 mmol) was added DCM (100 mL) followed by DIEA (3 mL, 17.5 mmol) and HATU (4.7 g, 12.3 mmol). The reaction was stirred at 30° C. for 16 hours before concentrating in vacuo. To the residue was added AcOH (120 mL) and the reaction heated to 50° C. for 2 hours. The reaction was cooled, concentrated in vacuo and diluted with a 2M solution of LiOH in water (250 mL). The aqueous layer was extracted with EtOAc (2×150 mL), the organic layers combined, dried over Na₂SO₄ and concentrated in vacuo. The residue was dissolved in dioxane to obtain a 0.075M solution.

To an aliquot of this solution (1 mL) was added cesium carbonate (75 mg, 225 µmol), 2-cyanophenylboronic acid (112.5 µol), water (30 µL), and nitrogen was bubbled through for 30 seconds. Pd(dppf)Cl₂ (6 mg, 7.5 µmol) was then added and the reaction shaken at 90° C. for 16 hours before cooling and filtering. MeOH (200 µL) was then added followed by 4M HCl in dioxane (300 µL) and the reaction shaken at 30° C. for 16 hours. The reaction was concentrated in vacuo and purified using preparative HPLC (Boston Symmetrix ODS-H; 150×30 mm×5µ; mobile phase A: Acetonitrile, mobile phase B: 0.225% TFA in water; eluting with a gradient of 22-52% organic, over 10 minutes with a flow rate of 30 mL/min) to afford the title compound as the TFA salt.

LCMS Rt=2.42 minutes MS m/z 307 [M+H]+

Example 78

(1R,2R)-1-Amino-1-(5-tert-butyl-1H-benzimidazol-2-yl)propan-2-ol

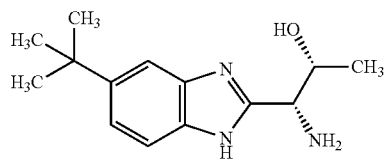 [SMILES: C[C@@H](O)[C@H](N)c1nc2cc(C(C)(C)C)ccc2[nH]1]

Step 1

To a stirred solution of 4-tert-butyl-1,2-diaminobenzene (375 mg, 2.28 mmol) in dioxane (4 mL) was added a solution of N-Boc-L-threonine (500 mg, 2.28 mmol) in dioxane (4 mL) followed by triethylamine (636 µL, 456 mmol) and T3P (1520 mg, 2.40 mmol). The reaction was stirred at room temperature for 10 minutes followed by heating to 100° C. for 18 hours. The reaction was cooled and diluted with EtOAc (50 mL) and saturated aqueous sodium bicarbonate solution (40 mL). The organic layer was collected, washed with brine, dried over MgSO₄ and concentrated in vacuo. The residue was purified using silica gel column chromatography eluting with 15-100% TBME in heptanes to afford tert-butyl [(1R,2R)-1-(5-tert-butyl-1H-benzimidazol-2-yl)-2-hydroxypropyl]carbamate.

Step 2

To tert-butyl [(1R,2R)-1-(5-tert-butyl-1H-benzimidazol-2-yl)-2-hydroxypropyl]-carbamate (105 mg, 0.302 mmol) was added DCM (5 mL) followed by TFA (700 µL) at 0° C. The reaction was allowed to warm to room temperature for 4 hours before cooling back to 0° C. and quenching with saturated aqueous NaHCO₃ solution (20 mL). The mixture was extracted with DCM, the organic layer collected, dried over MgSO₄ and concentrated in vacuo. The residue was purified using silica gel column chromatography eluting with DCM:MeOH:NH₃ (80:20:2) to afford the title compound (21 mg, 28%).

¹H NMR (400 MHz, CDCl₃): δ ppm 1.20 (s, 3H), 1.35 (s, 9H), 4.00 (m, 1H), 4.37 (m, 1H), 7.25 (m, 1H), 7.42 (m, 1H), 7.50 (m, 1H).

LCMS (2 minute run) Rt=1.02 minutes MS m/z 246 [M−H]−

Example 79

(1R,2R)-1-(5-tert-Butyl-1H-benzimidazol-2-yl)-1-(methylamino)propan-2-ol

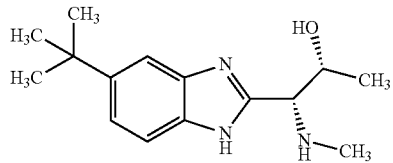 [SMILES: CN[C@H](c1nc2cc(C(C)(C)C)ccc2[nH]1)[C@@H](C)O]

To a stirred suspension of 2M Lithium aluminum hydride in THF (0.09 mL, 0.180 mmol) was added a solution of the intermediate product from Example 78, Step 1; tert-butyl [(1R,2R)-1-(5-tert-butyl-1H-benzimidazol-2-yl)-2-hydroxypropyl]carbamate (50 mg, 0.15 mmol) in THF (2 mL) dropwise at 0° C. The reaction mixture was then refluxed for 18 hours. The reaction was cooled, quenched by the addition of Na₂SO₄.10H₂O portionwise followed by anhydrous Na₂SO₄ and THF (5 mL) and stirred at room temperature for 30 minutes. The suspension was filtered through arbocel and the filtrated concentrated in vacuo. The residue was purified using silica gel column chromatography twice eluting both times with 90:10:1 DCM:MeOH:NH₃ to afford the title compound.

LCMS Rt=1.80 minutes MS m/z 262 [M+H]+

Example 80

(2S)-2-Amino-2-(5-tert-butyl-1H-benzimidazol-2-yl)propan-1-ol

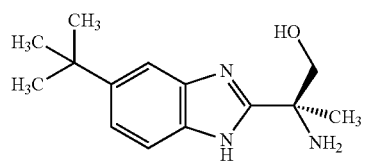 [SMILES: CC(C)(C)c1ccc2[nH]c([C@](C)(N)CO)nc2c1]

To a solution of tert-butyl [(1S)-1-(5-tert-butyl-1H-benzimidazol-2-yl)-2-hydroxy-1-methylethyl]carbamate (Preparation 26, 94 mg, 0.27 mmol) in dioxane (3 mL) was added 4M HCl in dioxane (4 mL) and the reaction stirred at room temperature for 3 hours. The reaction was concentrated in vacuo, azeotroping with toluene (2×10 mL) to afford a gummy solid. The residue was triturated with TBME (15 mL) to afford the title compound as the bis HCl salt (90 mg, 83%).

Microanalysis: Theory C: 52.66%; H: 6.58%; N: 13.17%. Found: C: 51.11%; H, 7.31%; N, 12.37%.

$^1$H NMR (400 MHz, DMSO-d$_6$): δ ppm 1.34 (s, 9H), 1.70 (s, 3H), 3.85 (m, 2H), 7.40 (m, 1H), 7.55 (m, 2H), 8.80 (br s, 4H).

Example 81

4-{2-[(1S)-1-Aminopropyl]-1H-benzimidazol-5-yl}benzonitrile

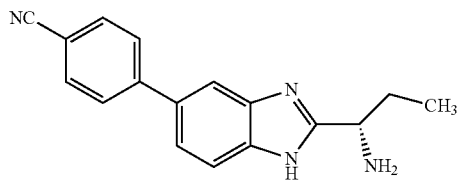 [SMILES: CC[C@H](N)c1nc2cc(-c3ccc(C#N)cc3)ccc2[nH]1]

Method 1
Step 1

To a stirred solution of (S)-2-(tert-butoxycarbonylamino)butanoic acid (391 mg, 1.92 mmol) in acetonitrile (6 mL) at 0° C. was added NMM (0.30 rL, 2.7 mmol) followed by isobutylchloroformate (0.25 mL, 1.90 mmol) dropwise over 15 minutes. This solution was added dropwise to 3',4'-diaminobiphenyl-4-carbonitrile (Preparation 82, 401 mg, 1.92 mmol) in acetonitrile (4 mL) at 0° C. over 15 minutes, and the reaction allowed to warm to room temperature for 18 hours. The reaction mixture was diluted with EtOAc (25 mL) and 5% aqueous citric acid solution (12.5 mL). The organic layer was separated and washed with 5% aqueous citric acid solution (2×12.5 mL). The organic layer was collected, washed with brine, dried over sodium sulphate and concentrated in vacuo.

Step 2

To this residue was added AcOH (6 mL) and the reaction allowed to stir at room temperature for 4 days. The reaction was diluted with 10% aqueous potassium carbonate solution (5 mL) and EtOAc (10 mL). The organic layer was collected washed with brine, dried over sodium sulphate and concentrated in vacuo. The residue was purified using silica gel column chromatography eluting with 0-50% EtOAc in heptanes.

Step 3

The residue was dissolved in dioxane (10 mL) and 4M HCl in dioxane (8.8 mL) was added, and the reaction stirred at room temperature for 2 hours. The reaction was concentrated in vacuo and purified using an SCX cartridge eluting with MeOH followed by 2M NH$_3$ in MeOH. The resulting oil was further purified using silica gel column chromatography eluting with DCM:MeOH:NH$_3$ 90:10:1 to afford a white solid that was triturated in ether to afford the title compound (215 mg, 45%).

$^1$H NMR (400 MHz, DMSO-d$_6$): δ ppm 0.85 (t, 3H), 1.75 (m, 1H), 1.80 (m, 1H), 3.90 (m, 1H), 7.50 (m, 1H), 7.55 (m, 1H), 7.80 (br s, 1H), 7.85 (m, 4H).

LCMS (5 minute run) Rt=1.44 minutes MS m/z 277 [M+H]$^+$

Example 82

4-{2-[(1R)-1-Amino-2-hydroxyethyl]-1H-benzimidazol-5-yl}benzonitrile

The title compound was prepared according to Method 1 using (S)-3-(tert-butoxycarbonyl)-2,2-dimethyloxazolidine-4-carboxylic acid and 3',4'-diaminobiphenyl-4-carbonitrile (Preparation 82). The residue was purified through an SCX cartridge followed by reverse phase column chromatography eluting with 0-60% MeCN in water.

LCMS (2 minute run) Rt=0/7 minutes MS m/z 279 [M+H]$^+$

Example 83

(1S,2R)-1-(5-tert-Butyl-1H-benzimidazol-2-yl)-2-methoxypropan-1-amine

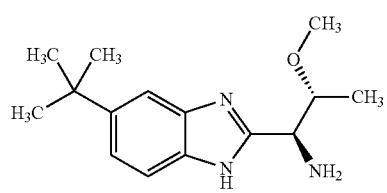 [SMILES: CO[C@H](C)[C@@H](N)c1nc2cc(C(C)(C)C)ccc2[nH]1]

The title compound was prepared according to Method 1 using N-Boc-allo-O-Methyl-D-threonine and 4-(tert-butyl)benzene-1,2-diamine. The residue was dissolved in MeOH and purified through an SCX cartridge eluting with MeOH followed by 7N NH$_3$ in MeOH (120 mg, 84%).

LCMS (5 minute run) Rt=1.47 minutes MS m/z 262 [M+H]$^+$

Example 84

4-{2-[(1R,2R)-1-Amino-2-methoxypropyl]-1H-benzimidazol-5-yl}-3-chlorobenzonitrile

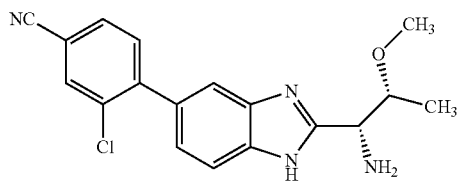 [SMILES: CO[C@H](C)[C@H](N)c1nc2cc(-c3ccc(C#N)cc3Cl)ccc2[nH]1]

Method 2

To tert-butyl [(1R,2R)-1-(5-bromo-1H-benzimidazol-2-yl)-2-methoxypropyl]carbamate (Preparation 22, 400 mg, 1.04 mmol) in THF/water (8 mL/2 mL) was added 2-(2-chloro-4-cyanophenyl)-4,4,5,5-tetramethyl-1,3,2-dioxaborolane (411 mg, 1.56 mmol) and sodium carbonate (275 mg, 2.60 mmol) and the mixture degassed with nitrogen for 20 minutes. Dichloro [1,1' bis(di-tert-butylphosphino)]ferrocene palladium (II) (18 mg, 0.031 mmol) was added and the reaction heated to 60° C. for 18 hours. The reaction was cooled, diluted with MeOH (100 mL) and filtered through celite. The filtrate was concentrated in vacuo and the residue dissolved in EtOAc (100 mL). The organic solution was washed with water (20 mL), dried over $Na_2SO_4$ and concentrated in vacuo. The residue was purified using silica gel column chromatography and dissolved in 4M HCl in dioxane (2 mL). The reaction was stirred at room temperature for 2 hours before the addition of saturated aqueous $NaHCO_3$ solution (20 mL), and extraction into EtOAc (3×20 mL). The organic layers were combined, dried over $MgSO_4$ and concentrated in vacuo. The residue was purified using reverse phase column chromatography eluting with 0-30% acetonitrile in 0.1% formic acid in water to afford the title compound as the formate salt (98 mg, 28%).

$^1$H NMR (400 MHz, MeOD): δ ppm 1.20 (d, 3H), 3.42 (s, 3H), 3.86 (m, 1H), 4.26 (d, 1H), 7.38 (d, 1H), 7.62 (d, 1H), 7.70 (m, 2H), 7.77 (d, 1H), 7.98 (s, 1H), 8.40 (br s, 1H).

LCMS (4.5 minute run) Rt=1.84 minutes MS m/z 341 [M+H]$^+$

Example 85

4-{2-[(1R,2R)-1-Amino-2-methoxypropyl]-1H-benzimidazol-5-yl}-2-fluorobenzonitrile

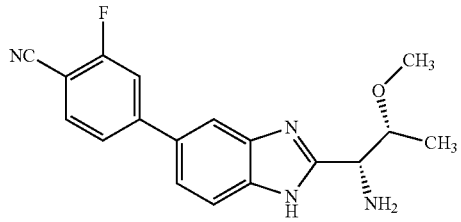 [SMILES: CO[C@H](C)[C@H](N)c1nc2cc(-c3ccc(C#N)c(F)c3)ccc2[nH]1]

The title compound was prepared according to Method 2 using 3-fluoro-4-cyanophenylboronic acid and isopropanol to quench the first step and filter through celite. The final residue was purified using reverse phase column chromatography eluting with 0-40% acetonitrile in 0.1% formic acid in water to afford the title compound as the formate salt (212 mg, 51%).

$^1$H NMR (400 MHz, MeOD): δ ppm 1.39 (d, 3H), 3.42 (s, 3H), 3.87 (m, 1H), 4.32 (d, 1H), 7.62 (d, 1H), 7.65 (m, 3H), 7.83 (m, 1H), 7.95 (s, 1H), 8.40 (br s, 1H).

Example 86

4-{2-[(1R,2R)-1-Amino-2-methoxypropyl]-1H-benzimidazol-5-yl}-3-(trifluoromethyl)-benzonitrile

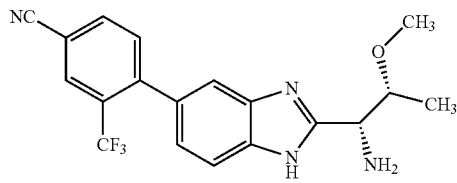 [SMILES: CO[C@H](C)[C@H](N)c1nc2cc(-c3ccc(C#N)cc3C(F)(F)F)ccc2[nH]1]

The title compound was prepared according to Method 2 using 2-[4-bromo-2-(trifluoromethyl)phenyl]-4,4,5,5-tetramethyl-1,3,2-dioxaborolane (Preparation 102) and isolated as the formate salt.

$^1$H NMR (400 MHz, MeOD): δ ppm 1.18 (d, 3H), 3.46 (s, 3H), 3.93 (m, 1H), 4.37 (d, 1H), 7.26 (d, 1H), 7.40 (s, 1H), 7.64 (d, 1H), 8.02 (d, 1H), 8.21 (s, 1H), 8.45 (s, 1H).

LCMS (4.5 minute run) Rt=1.91 minutes MS m/z 375 [M+H]$^+$

Example 87

4-{2-[(1R,2R)-1-Amino-2-methoxypropyl]-1H-benzimidazol-5-yl}-2,6-difluorobenzonitrile

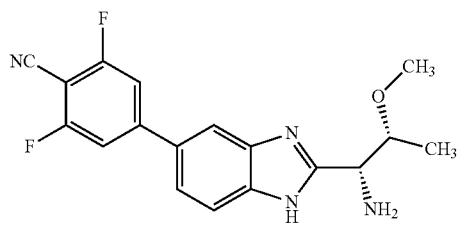 [SMILES: CO[C@H](C)[C@H](N)c1nc2cc(-c3cc(F)c(C#N)c(F)c3)ccc2[nH]1]

The title compound was prepared according to Method 2 using 2,6-difluoro-4-(4,4,5,5-tetramethyl-1,3,2-dioxaborolan-2-yl)benzonitrile (Preparation 103). The residue was purified using reverse phase column chromatography eluting with from 5% MeCN in water (0.1% formic acid) to 100% MeCN with 0.1% formic acid.

$^1$H NMR (400 MHz, MeOD): δ ppm 1.17 (d, 3H), 3.44 (s, 3H), 3.83-3.93 (m, 1H), 4.33 (d, 1H), 7.59 (s, 1H), 7.61 (s, 1H), 7.65 (m, 1H), 7.73 (d, 1H), 7.97 (s, 1H), 8.43 (br s, 1H).

Example 88

4-{2-[(1R,2R)-1-Amino-2-hydroxypropyl]-1H-benzimidazol-5-yl}benzene-1,2-dicarbonitrile

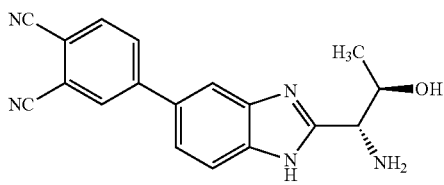 [SMILES: C[C@@H](O)[C@H](N)c1nc2cc(-c3ccc(C#N)c(C#N)c3)ccc2[nH]1]

The title compound was prepared according to Method 2 using tert-butyl (4R,5R)-4-(5-bromo-1H-benzimidazol-2-yl)-2,2,5-trimethyl-1,3-oxazolidine-3-carboxylate (Preparation 21) and 3,4-dicyanophenylboronic acid (Preparation 104). Following the amide bond forming step the residue was purified using silica gel column chromatography eluting with 40-80% EtOAc in heptanes. The final residue was purified using reverse phase column chromatography eluting with 5-70% acetonitrile in 0.1% formic acid in water to afford the formate salt.

$^1$H NMR (400 MHz, MeOD): δ ppm 1.20 (d, 3H), 4.13-4.27 (m, 2H), 7.64-7.66 (m, 1H), 7.72-7.75 (m, 1H), 7.97 (s, 1H), 8.01-8.03 (m, 1H), 8.15 (m, 1H), 8.31 (s, 1H).

LCMS Rt=1.82 minutes MS m/z 318 [M+H]$^+$

Example 89

4-{2-[(1R,2R)-1-Amino-2-hydroxypropyl]-1H-benzimidazol-5-yl}-2,6-difluorobenzonitrile

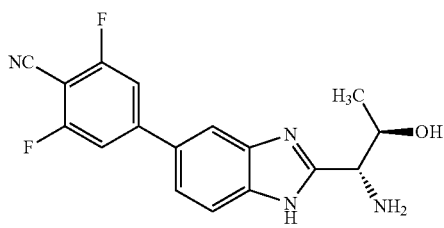 [SMILES: C[C@@H](O)[C@H](N)c1nc2cc(-c3cc(F)c(C#N)c(F)c3)ccc2[nH]1]

The title compound was prepared according to Method 2 using tert-butyl (4R,5R)-4-(5-bromo-1H-benzimidazol-2-yl)-2,2,5-trimethyl-1,3-oxazolidine-3-carboxylate (Preparation 21) and 3,5-difluoro-4-cyanophenylboronic acid (Preparation 105). Following the amide bond forming step the residue was purified using silica gel column chromatography eluting with 30-60% EtOAc in heptanes. The final residue was purified using reverse phase column chromatography eluting with 5-100% acetonitrile in 0.1% formic acid in water to afford the formate salt.

$^1$H NMR (400 MHz, MeOD): δ ppm 1.20 (d, 3H), 4.21-4.30 (m, 2H), 7.59 (s, 1H), 7.61 (s, 1H), 7.64-7.66 (m, 1H), 7.73 (d, 1H), 7.97 (s, 1H), 8.44 (s, 1H).

LCMS Rt=1.80 minutes MS m/z 329 [M+H]$^+$

Example 90

4-{2-[(1R,2R)-1-Amino-2-methoxypropyl]-1H-benzimidazol-5-yl}-3-fluorobenzonitrile

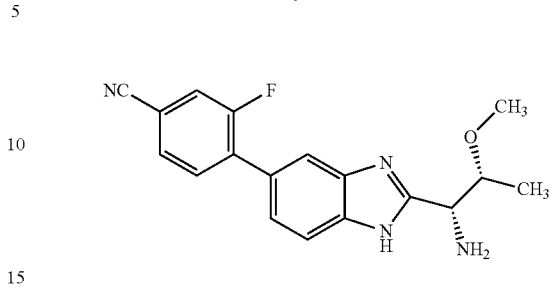

To tert-butyl [(1R,2R)-1-(5-bromo-1H-benzimidazol-2-yl)-2-methoxypropyl]carbamate (Preparation 22, 120 mg, 0.312 mmol) in THF/water (5 mL/1 mL) was added 2-fluoro-4-cyanophenylboronic acid (77 mg, 0.531 mmol) and sodium carbonate (83 mg, 0.780 mmol) and the mixture degassed with nitrogen for 10 minutes. Dichloro[1,1' bis(di-tert-butylphosphino)]ferrocene palladium (II) (6 mg, 0.00937 mmol) was added and the reaction heated to 60° C. for 18 hours. The reaction was cooled and filtered through celite. The filtrate was diluted with water and extracted with EtOAc (3×20 mL). The organic layers were combined, dried over Na$_2$SO$_4$ and concentrated in vacuo. The residue was purified using silica gel column chromatography and dissolved in a mixture of TFA and DCM (1 mL/5 mL). The reaction was stirred at room temperature for 3 hours before concentrating in vacuo. The residue was purified by filtering through Amberlist-21 followed by reverse phase column chromatography eluting with 0-40% acetonitrile in 0.1% formic acid in water to afford the title compound as the formate salt (32 mg, 30%).

$^1$H NMR (400 MHz, MeOD): δ ppm 1.18 (s, 3H), 3.43 (s, 3H), 3.87 (br s, 1H), 4.32 (br s, 1H), 7.52 (d, 1H), 7.65-7.80 (m, 4H), 7.87 (br s, 1H).

LCMS (4.5 minute run) Rt=1.79 minutes MS m/z 325 [M+H]$^+$

Example 91

4-{2-[(1R,2R)-1-Amino-2-methoxypropyl]-6-fluoro-1H-benzimidazol-5-yl}benzonitrile

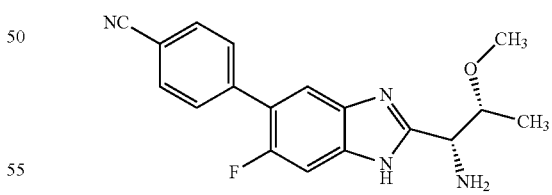

Isobutylchloroformate (0.17 g, 0.125 mmol) was added to a cooled mixture of N-(tert-butoxycarbonyl)-O-methyl-L-threonine (Preparation 51, 0.28 g, 0.12 mmol) and NMM (0.137 g, 0.135 mmol) in THF (10 mL) at −78° C. The reaction was stirred at this temperature for 1 hour and then added dropwise to a cooled solution of 4',5'-diamino-2'-fluorobiphenyl-4-carbonitrile (Preparation 76, 0.28 g, 0.12 mmol) at −78° C. and stirred at this temperature for 3 hours. The reaction was partitioned between EtOAc (70 mL) and saturated aqueous NaHCO$_3$ solution (30 mL), the organic layer was collected and concentrated in vacuo to afford a brown residue that was dissolved in AcOH (5 mL) and heated to 40° C. for 2 days followed by 50° C. for 1 day. The reaction was concentrated in vacuo and purified using silica gel column chromatography to afford a beige solid that was dissolved in TFA/DCM (0.2 mL/3 mL) and stirred at room temperature for 5 hours. The reaction was partitioned between saturated aqueous $Na_2CO_3$ solution (10 mL) and EtOAc (30 mL). The organic layer was collected and concentrated in vacuo. The residue was purified using reverse phase column chromatography eluting with a gradient of acetonitrile in 0.5% formic acid in water followed by elution through an SCX cartridge to afford the title compound that contains some of the other diastereomer.

$^1$H NMR (400 MHz, MeOD): δ ppm 1.08 (m, 3H), 3.22 (s, 3H), 3.82 (m, 1H), 4.36-4.50 (m, 1H), 7.42 (m, 1H), 7.69 (m, 1H), 7.76 (m, 2H), 7.82 (m, 2H), 8.40 (br s, 1H).

LCMS (4.5 minute run) Rt=1.80 minutes MS m/z 325 $[M+H]^+$

Example 92

4-{2-[(1R,2R)-1-Amino-2-methoxypropyl]-1H-benzimidazol-5-yl}benzonitrile

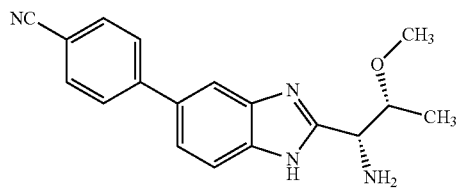 [SMILES: CO[C@H](C)[C@H](N)c1nc2cc(-c3ccc(C#N)cc3)ccc2[nH]1]

To a stirred solution of N-(tert-butoxycarbonyl)-O-methyl-L-threonine (Preparation 51, 1.696 g, 7.27 mmol) in acetonitrile (25 mL) at 0° C. was added NMM (1.12 mL, 10.2 mmol) followed by isobutylchloroformate (0.943 mL, 7.27 mmol) dropwise. The reaction was stirred at 0° C. for 35 minutes forming a white precipitate (NMM.HCl salt). This suspension was added dropwise filtering through a cotton wool plug to a solution of 3',4'-diaminobiphenyl-4-carbonitrile (Preparation 82, 1.521 g, 7.271 mmol) in acetonitrile (25 mL) and the reaction stirred at room temperature for 18 hours. The reaction was diluted with EtOAc (100 mL) and 5% aqueous citric acid (50 mL). The organic layer was separated, washed further with 5% aqueous citric acid (50 mL), brine, dried over $MgSO_4$ and concentrated in vacuo. The residue was dissolved in AcOH (20 mL) and stirred at room temperature for 4 days. The reaction was concentrated to dryness and partitioned between saturated aqueous $NaHCO_3$ solution (50 mL) and EtOAc (100 mL). The organic layer was collected, dried over $Na_2SO_4$ and concentrated in vacuo. The residue was purified using silica gel column chromatography eluting with 0-50% EtOAc in heptanes to afford an orange/brown foam that was dissolved in 4M HCl in dioxane (30 mL) and stirred at room temperature for 2 hours. The reaction was concentrated in vacuo and diluted with 4M NaOH to pH=9. The aqueous solution was extracted with EtOAc (2×40 mL), the organic layers were combined and concentrated in vacuo. The residue was purified using silica gel column chromatography eluting with 95:5:0.5 DCM:MeOH:$NH_3$ to afford the title compound (1 g, 46%).

$^1$H NMR (400 MHz, $CDCl_3$): δ ppm 1.20 (d, 3H), 3.40 (s, 3H), 3.90 (m, 1H), 4.25 (m, 1H), 7.45 (d, 2H), 7.60-7.75 (m, 6H).

LCMS (5 minute run) Rt=1.44 minutes MS m/z 307 $[M+H]^+$

Example 93

4-{2-[(1S,2S)-1-Amino-2-methoxypropyl]-1H-benzimidazol-5-yl}benzonitrile

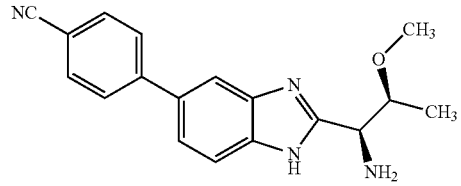 [SMILES: CO[C@@H](C)[C@@H](N)c1nc2cc(-c3ccc(C#N)cc3)ccc2[nH]1]

The title compound was prepared according to Method 1 using N-(tert-butoxycarbonyl)-O-methyl-D-threonine. The residue was purified using preparative HPLC.

LCMS (5 minute run) Rt=1.48 minutes MS m/z 307 $[M+H]^+$

Example 94

(1S,2S)-1-(5-tert-Butyl-1H-benzimidazol-2-yl)-2-methoxypropan-1-amine

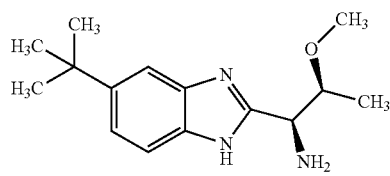 [SMILES: CO[C@@H](C)[C@@H](N)c1nc2cc(C(C)(C)C)ccc2[nH]1]

The title compound was prepared according to Method 1 using N-(tert-butoxycarbonyl)-O-methyl-D-threonine and 4-tert-butyl-1,2-diaminobenzene. The residue was purified by elution through an SCX cartridge with MeOH followed by 2M $NH_3$ in MeOH followed by silica gel column chromatography eluting with 90:10:1 DCM:MeOH:$NH_3$.

$^1$H NMR (400 MHz, $CDCl_3$): δ ppm 1.00 (m, 3H), 1.25 (s, 9H), 3.20 (s, 3H), 3.60 (m, 1H), 3.95 (m, 1H), 7.20 (m, 1H), 7.20-7.35 (br s, 2H), 11.90 (br s, 1H).

LCMS (5 minute run) Rt=1.36 minutes MS m/z 260 $[M-H]^-$

Example 95

(3S)-3-Amino-3-[5-(propan-2-yl)-1H-benzimidazol-2-yl]propanamide

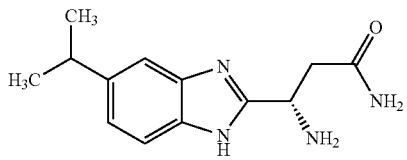 [SMILES: CC(C)c1ccc2[nH]c([C@@H](N)CC(N)=O)nc2c1]

Magnesium nitride (137 mg, 1.36 mmol) and methanol (5 ml) were added to benzyl (3S)-3-[(tert-butoxycarbonyl)

amino]-3-(5-isopropyl-1H-benzimidazol-2-yl)propanoate (Preparation 36, 85 mg, 0.194 mmol) in a sealed tube, and the reaction heated to 80° C. for 18 hours. The reaction mixture was acidified with dilute HCl and neutralized with saturated aqueous NaHCO₃ solution and extracted with ethyl acetate. The organic layer was dried over sodium sulphate and concentrated in vacuo. The residue was purified by preparative HPLC and dissolved in 1,4-dioxane (5 mL). The solution was cooled to 0° C. and 4N HCl in dioxane (5 mL) was added and the reaction stirred at room temperature for 2 hours. The reaction was concentrated in vacuo and purified through an SCX-2 cartridge to afford the title compound (4 mg, 40%).

¹H NMR (400 MHz, MeOD): δ ppm 2.04 (s, 3H), 2.20 (s, 3H), 3.20-3.40 (m, 3H), 4.50 (s, 1H), 7.20-7.38 (m, 2H), 7.42 (s, 1H), 8.20 (s, 1H).

LCMS (20 minute run) Rt=7.54 minutes MS m/z 247 [M+H]⁺

Example 96

(1R,2R)-1-[5-(2,2-Dimethylpropyl)-5-fluoro-1H-benzimidazol-2-yl]-2-methoxypropan-1-amine

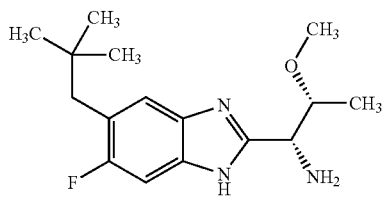 [SMILES: CO[C@H](C)[C@H](N)c1nc2cc(CC(C)(C)C)c(F)cc2[nH]1]

Method 3

To a suspension of Boc-Thr(Me)-OH (23.8 mg, 0.102 mmol) in acetonitrile (0.4 mL) was added 4-methylmorpholine (0.025 mL, 0.23 mmol) and isobutyl chloroformate (0.014 mL, 0.11 mmol). After stirring for 45 minutes 4-fluoro-5-neopentylbenzene-1,2-diamine (Preparation 73, 22 mg, 0.11 mmol) was added and the reaction was stirred for 18 hours. The solution was concentrated in vacuo, redissolved in acetic acid (0.4 mL, 7 mmol) and heated to 65° C. for 5 hours. After cooling, the solution was concentrated in vacuo, redissolved in methylene chloride and washed with aqueous saturated sodium hydrogen carbonate solution (2×). The organic layer was dried over anhydrous magnesium sulphate, filtered, and concentrated in vacuo. The residue was purified using silica gel column chromatography eluting with a 0-100% ethyl acetate/hexanes gradient to afford the protected benzimidazole as a clear oil. The oil was dissolved in methylene chloride (3 mL) and treated with trifluoroacetic acid (0.5 mL, 6 mmol). After stirring for 2 hours, the solution was concentrated in vacuo, redissolved in methylene chloride and treated with saturated aqueous sodium hydrogen carbonate solution. The aqueous layer was extracted with methylene chloride (2×). The organic layers were combined, dried over anhydrous magnesium sulphate, filtered, and concentrated in vacuo. The residue was purified using silica gel column chromatography eluting with a 0-100% CMA80/methylene chloride gradient to afford the title compound (15 mg, 15%) as a white solid.

¹H NMR (400 MHz, DMSO-d₆): δ ppm 0.93 (s, 9H), 1.00 (d, 3H), 2.61 (s, 2H), 3.25 (s, 3H), 3.68 (m, 1H), 3.97 (d, 1H), 7.27 (m, 2H).

LCMS Rt=1.16 minutes MS m/z 294 [M+H]⁺

Example 97

(1R)-1-(5-tert-Butyl-1H-benzimidazol-2-yl)propan-1-amine

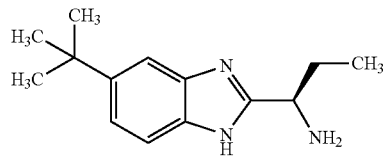 [SMILES: CC[C@@H](N)c1nc2cc(C(C)(C)C)ccc2[nH]1]

The title compound was prepared according to Method 3 using 4-tert-butyl-1,2-diaminobenzene and (tert-butoxycarbonyl)-D-2-aminobutyric acid.

LCMS (2 minute run) Rt=0.75 minutes MS m/z 232 [M+H]⁺

Example 98

4-{2-[(1R,2R)-1-Amino-2-hydroxypropyl]-4-fluoro-1H-benzimidazol-5-yl}benzonitrile

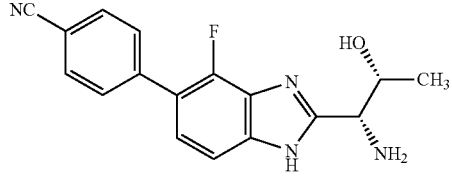 [SMILES: C[C@@H](O)[C@H](N)c1nc2c(F)c(-c3ccc(C#N)cc3)ccc2[nH]1]

The title compound was prepared according to Method 1 using (4S,5R)-3-(tert-butoxycarbonyl)-2,2,5-trimethyl-1,3-oxazolidine-4-carboxylic acid (Preparation 57) and 3',4'-diamino-2'-fluorobiphenyl-4-carbonitrile (Preparation 77). After the final deprotection step, the residue was purified using reverse phase column chromatography eluting with acetonitrile in 0.1% formic acid in water to afford the formate salt.

¹H NMR (400 MHz, MeOD): δ ppm 1.21 (d, 3H), 4.26 (br s, 2H), 7.40 (m, 1H), 7.51 (d, 1H), 7.78 (d, 2H), 7.83 (d, 2H), 8.44 (br s, 1H).

LCMS Rt=1.69 minutes MS m/z 311 [M+H]⁺

Example 99

4-{2-[(1R,2R)-1-Amino-2-hydroxypropyl]-4-chloro-1H-benzimidazol-5-yl}benzonitrile

The title compound was prepared according to Method 3 using (4S,5R)-3-(tert-butoxycarbonyl)-2,2,5-trimethyl-1,3-oxazolidine-4-carboxylic acid (Preparation 57) and 3',4'-diamino-2'-chlorobiphenyl-4-carbonitrile (Preparation 78).

The acetic acid cyclisation step was performed at room temperature. Following TFA deprotection the residue was purified by reverse phase column chromatography eluting with acetonitrile in 0.1% formic acid in water to afford the formate salt.

LCMS Rt=1.67 minutes MS m/z 327 [M+H]+

Example 100

4-{2-[(1R,2R)-1-Amino-2-hydroxypropyl]-1H-benzimidazol-5-yl}-3-(trifluoromethyl)benzonitrile

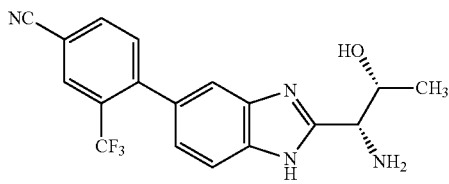 [SMILES: C[C@@H](O)[C@H](N)c1nc2cc(-c3ccc(C#N)cc3C(F)(F)F)ccc2[nH]1]

The title compound was prepared according to Method 2 using 4-(4,4,5,5-tetramethyl-1,3,2-dioxaborolan-2-yl)-3-(trifluoromethyl)benzonitrile (Preparation 102) and tert-butyl (4R,5R)-4-(5-bromo-1H-benzimidazol-2-yl)-2,2,5-trimethyl-1,3-oxazolidine-3-carboxylate (Preparation 21). The residue was purified using reverse phase column chromatography eluting with MeCN/0.1% formic acid in water and freeze dried for 18 hours to afford the formate salt (320 mg, 81%).

$^1$H NMR (400 MHz, MeOD): δ ppm 1.21 (d, 3H), 4.27 (m, 2H), 7.24 (d, 1H), 7.58 (s, 1H), 7.62 (d, 1H), 7.68 (d, 1H), 8.02 (dd, 1H), 8.20 (s, 1H), 8.43 (s, 1H).

$^{19}$F NMR (400 MHz, MeOD): δ ppm—58.16
LCMS Rt=1.91 minutes.

Example 101

4-{2-[(1R,2R)-1-Amino-2-hydroxypropyl]-1H-benzimidazol-5-yl}-3-fluorobenzonitrile

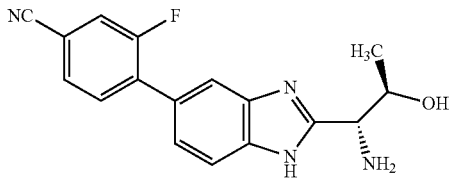 [SMILES: C[C@@H](O)[C@H](N)c1nc2cc(-c3ccc(C#N)cc3F)ccc2[nH]1]

To a solution of (4S,5R)-3-(tert-butoxycarbonyl)-2,2,5-trimethyl-1,3-oxazolidine-4-carboxylic acid (Preparation 57, 778 mg, 3 mmol) and HOBt (551 mg, 3.60 mmol) in DMF (23 mL) was added NMM (0.33 mL, 3 mmol) and the mixture cooled to −5° C. EDCI (690 mg, 3.60 mmol) was added and the reaction stirred at −5° C. for 90 minutes. A solution of 3',4'-diamino-2-fluorobiphenyl-4-carbonitrile (Preparation 79, 750 mg, 3.30 mmol) in DMF (7 mL) was added and the reaction was allowed to warm to room temperature for 3 days. The reaction was poured in EtOAc (120 mL), washed with 3% aqueous NaHCO$_3$ solution (4×120 mL), brine (30 mL), dried over Na$_2$SO$_4$ and concentrated in vacuo. The residue was purified using silica gel column chromatography eluting with EtOAc:Heptane 1:1. The residue was dissolved in AcOH (7 mL) and stirred at 40° C. for 18 hours. The reaction was concentrated in vacuo and treated with saturated aqueous NaHCO$_3$ solution (15 mL), extracted into EtOAc (2×15 mL), the organic layers combined, dried over Na$_2$SO$_4$ and concentrated in vacuo. The residue was purified using silica gel column chromatography eluting with acetone:heptanes 1:3. The residue was dissolved in 4M HCl in dioxane with 1 drop of water and stirred at room temperature for 2 hours. The reaction was eluted through an SCX column washing through with MeOH followed by 3N NH$_3$ in MeOH and the filtrate concentrated in vacuo. The residue was treated with water (1 mL) and MeOH (0.5 mL) and freeze dried to afford the title compound (125 mg, 75%).

$^1$H NMR (400 MHz, MeOD): δ ppm 1.19 (d, 3H), 3.99 (d, 1H), 4.06 (m, 1H), 7.46 (d, 1H), 7.61-7.79 (m, 5H).
LCMS Rt=1.82 minutes MS m/z 311 [M+H]+

Example 102

(1R)-1-Amino-1-(5-tert-butyl-1H-benzimidazol-2-yl)-2-methylpropan-2-ol

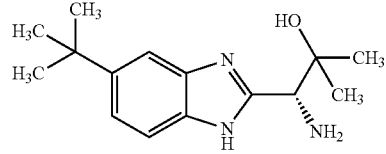 [SMILES: CC(C)(C)c1ccc2[nH]c([C@@H](N)C(C)(C)O)nc2c1]

A solution of 4-tert-butyl-1,2-diaminobenzene (1 g, 6 mmol), N-boc-3-hydroxy-L-valine (1.4 g, 6 mmol) and triethylamine (1.5 mL, 15.1 mmol) in dioxane (50 mL) was stirred at 0° C. for 15 minutes. T3P (50% w/w in EtOAc, 4.6 mL, 7.3 mmol) was added dropwise and the reaction continued stirring at this temperature for 30 minutes. The reaction was then heated to reflux for 5 hours before cooling and diluting with EtOAc. The solution was washed with saturated aqueous sodium carbonate solution twice, dried over Na$_2$SO$_4$ and concentrated in vacuo. The residue was purified using silica gel column chromatography eluting with 0-50% EtOAc in heptanes. The residue was dissolved in dioxane (10 mL) at 0° C. and treated with 4M HCl in dioxane (10 mL). The reaction was stirred at room temperature for 2 hours before concentrating in vacuo. The residue was washed with EtOAc and pentane before basifying with saturated aqueous NaOH solution and extracting into EtOAc. The organic layer was collected, dried over Na$_2$SO$_4$, concentrated in vacuo and triturated with 10% EtOH in pentane (5 mL) to afford the title compound (25 mg, 2%).

$^1$H NMR (400 MHz, DMSO-d$_6$): δ ppm 1.08-1.1 (m, 6H), 1.21-1.39 (m, 9H), 2.17-2.27 (m, 2H), 3.81 (s, 1H), 4.87 (s, 1H), 7.18-7.21 (m, 1H), 7.41 (m, 2H), 11.9 (br s, 1H).
MS m/z 262 [M+H]+

Example 103

(2R,3S)-3-Amino-3-(5-tert-butyl-1H-benzimidazol-2-yl)-2-methylpropanamide

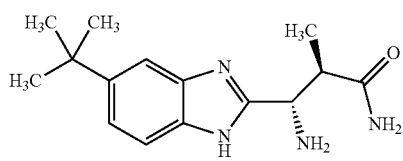 [SMILES: C[C@@H](C(N)=O)[C@H](N)c1nc2cc(C(C)(C)C)ccc2[nH]1]

A solution of tert-butyl [(1S)-3-amino-1-(5-tert-butyl-1H-benzimidazol-2-yl)-2-methyl-3-oxopropyl]carbamate (Preparation 29, 3.07 g, 8.2 mmol) in DCM (50 mL) and TFA (10 mL) was stirred at room temperature for 3 hours before concentrating in vacuo. Saturated aqueous NaHCO$_3$ solution (100 mL) was added and the product extracted with 2-MeTHF (4×100 mL). The organic layers were combined, washed with brine, dried over Na$_2$SO$_4$ and concentrated in vacuo. The residue was purified using reverse phase column chromatography eluting with 0-40% acetonitrile in water. The resulting solid was dissolved in MeCN (40 mL) at 50° C. and methanol added before allowing the solution to cool. The resulting white precipitate was collected, dried, and further triturated with EtOAc (5 mL) twice to afford a white solid as the desired (2R,3S) diastereomer.

$^1$H NMR (400 MHz, MeOD): δ ppm 1.03 (d, 3H), 1.38 (s, 9H), 2.84 (m, 1H), 4.18 (d, 1H), 7.33 (m, 1H), 7.46 (m, 1H), 7.54 (m, 1H).

LCMS Rt=2.32 minutes MS m/z 275 [M+H]$^+$

Example 104

(2S,3S)-3-Amino-3-(5-tert-butyl-1H-benzimidazol-2-yl)-2-methylpropanamide

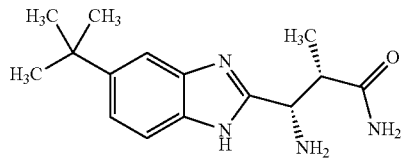 [SMILES: C[C@H](C(N)=O)[C@H](N)c1nc2cc(C(C)(C)C)ccc2[nH]1]

The diastereomeric mixture from the Example above may be separated according to the following chiral HPLC conditions to obtain the title compound:

Chiralpak IC 70/30/0.1 heptane/IPA/DEA to afford the two separate diastereomers:

Peak 1 (2.5 minute acidic run) Rt=0.67 minutes MS m/z 275 [M+H]+ (Example 103) Peak 2 (2.5 minute acidic run) Rt=0.62 minutes MS m/z 275 [M+H]+ (Example 104)

$^1$H NMR (400 MHz, MeOD): δ ppm 1.20 (d, 3H), 1.38 (s, 9H), 2.92 (m, 1H), 4.35 (d, 1H), 7.33 (m, 1H), 7.46 (m, 1H), 7.54 (m, 1H).

Example 105

(2R,3S)-3-Amino-3-(5-tert-butyl-1H-benzimidazol-2-yl)-2-($^{13}$CD$_3$-methyl)propanamide

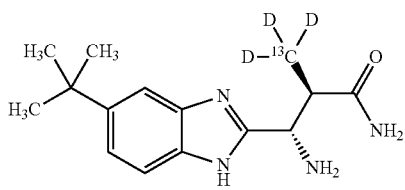 [SMILES: [2H][13C]([2H])([2H])[C@@H](C(N)=O)[C@H](N)c1nc2cc(C(C)(C)C)ccc2[nH]1]

tert-Butyl-[(1S,2R)-3-amino-1-(5-tert-butyl-1H-benzimidazol-2-yl)-2-($^{13}$CD$_3$-methyl-3-oxopropyl]carbamate (Preparation 1, 0.95 g, 2.5 mmol) was dissolved in CH$_2$Cl$_2$ (20 mL) in a round bottom flask. The reaction was cooled to 0° C. and TFA (3.0 mL) was added drop-wise while stirring. The reaction was stirred at room temperature for 4 hours. The reaction was concentrated in vacuo and azeotroped twice with toluene (20 mL). The residue was dissolved in CH$_2$Cl$_2$ (20 mL) and washed with 1N NaOH to pH=6, followed by brine, dried over sodium sulfate, filtered and concentrated in vacuo. The residue was triturated with MeOH and filtered to give a white solid as the title compound (0.512 g, 73%).

$^1$H NMR (400 MHz, CDCl$_3$): δ ppm 1.30 (s, 9H), 3.20 (m, 1H), 4.25 (m, 1H), 5.65 (br s, 1H), 6.45 (br s, 1H), 7.30-7.35 (m, 1H), 7.45-7.60 (m, 2H).

MS m/z 277 [M−H]$^-$

Example 106

(1R,2S)-1-Amino-1-(5-tert-butyl-1H-benzimidazol-2-yl)propan-2-yl carbamate

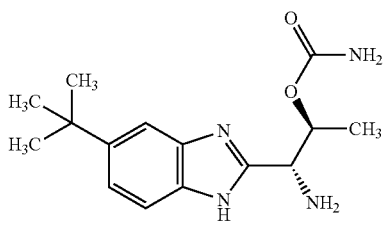 [SMILES: C[C@H](OC(N)=O)[C@H](N)c1nc2cc(C(C)(C)C)ccc2[nH]1]

tert-Butyl [(1R,2S)-1-(5-tert-butyl-1H-benzimidazol-2-yl)-2-hydroxypropyl]carbamate (Preparation 24, 60 g, 172 mmol) was dissolved in MeCN (2 L) and cooled to 13° C. N,N'-disuccinimidylcarbonate (58.8 g, 207 mmol) was added portionwise and the mixture stirred at room temperature for 5 hours before cooling back to 3° C. Ammonium hydroxide (200 mL) was added and the reaction warmed to room temperature for 18 hours. The reaction was concentrated to low volume and diluted with EtOAc (2 L), washed with saturated aqueous NaHCO$_3$ solution (3×300 mL), water (2×400 mL), brine (2×400 mL), dried over Na$_2$SO$_4$ and concentrated in vacuo. The residue was purified using silica gel column chromatography eluting with a gradient of 4:1 to 1:1 cyclohexane in acetone. The pure intermediate (55.10 g) was dissolved in dioxane (1 L) and cooled to 3° C. 4M HCl in dioxane (1 L) was added maintaining the internal temperature at <10° C. The reaction was stirred at room temperature for 5 hours before concentrating in vacuo. The crude solid was sonicated in ether (14 filtered and reslurried in acetonitrile (10 with further sonication for 1 hour. The solid was filtered, washed with acetonitrile and dried to afford the title compound as the bis HCl salt (47 g, 90%).

$^1$H NMR (400 MHz, DMSO-$d_6$): δ ppm 1.18 (d, 3H), 1.38 (s, 9H), 5.00 (m, 1H), 5.19 (m, 1H), 6.80 (br s, 2H), 7.60 (m, 1H), 7.78 (m, 2H), 9.37 (br s, 3H).

LCMS (25 minute run) Rt=9.18 minutes MS m/z 291 [M+H]$^+$

Example 107

(1R,2R)-1-Amino-1-(6-tert-butyl-1H-benzimidazol-2-yl)propan-2-yl carbamate

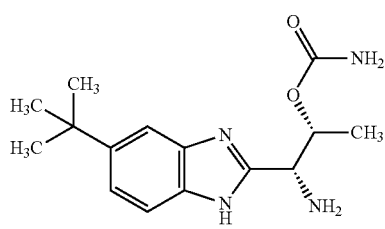 [SMILES: C[C@@H](OC(N)=O)[C@H](N)c1nc2cc(C(C)(C)C)ccc2[nH]1]

The title compound was prepared according to Example 106 using tert-butyl-[(1R,2R)-1-(5-tert-butyl-1H-benzimidazol-2-yl)-2-hydroxypropyl]carbamate (Preparation 25). The crude residue was triturated with ether followed by acetonitrile and further purified using preparative HPLC and isolated by freeze drying.

$^1$H NMR (400 MHz, MeOD): δ ppm 1.40 (d, 3H), 1.42 (s, 9H), 5.12 (d, 1H), 5.37-5.43 (m, 1H), 7.71-7.78 (m, 2H), 7.81 (s, 1H).

LCMS Rt=1.52 minutes MS m/z 291 [M+H]$^+$

Example 108

(2R,3S)-3-Amino-3-(6-tert-butyl-1H-benzimidazol-2-yl)-N,2-dimethylpropanamide

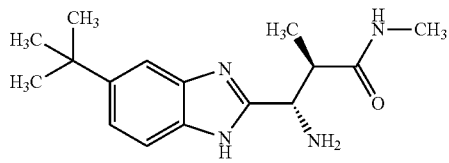 [SMILES: CNC(=O)[C@H](C)[C@H](N)c1nc2cc(C(C)(C)C)ccc2[nH]1]

1-Ethyl-3-(3-dimethylaminopropyl)carbodiimide hydrochloride (90 mg, 0.47 mmol) was added to a stirred solution of ((3S)-3-[(tert-butoxycarbonyl)amino]-3-(5-tert-butyl-1H-benzimidazol-2-yl)-2-methylpropanoic acid (Preparation 30,140 mg, 0.39 mmol), N-methylmorpholine in DMF (5 mL) at 0° C. The reaction mixture was stirred for 15 minutes at 0° C. and charged with solution of methylamine in water (40%, 0.07 mL, 0.78 mmol). The reaction mixture was allowed to stay at −18° C. for 24 hours. The reaction mixture was recharged with 1-ethyl-3-(3-dimethylaminopropyl)carbodiimide hydrochloride (100 mg, 0.50 mmol) and stirred at 0° C. for 30 minutes and stored at −18° C. for a further 72 hours. The reaction mixture was diluted with EtOAc (20 mL) and washed with saturated sodium bicarbonate solution (2×10 mL). The organic layer was evaporated to dryness and purified by silica gel column chromatography eluting with a gradient of DCM/tert-butyl methyl ether to separate the diastereomers to afford the title diastereomer as a white solid (50 mg, 30%).

$^1$H NMR (400 MHz, CDCl$_3$): δ ppm 1.18 (d, 3H), 1.40 (s, 9H), 1.48 (s, 9H), 2.90 (m, 3H), 3.32 (m, 1H), 5.02 (m, 1H), 6.52 (m, 1H), 6.60 (m, 1H), 7.29-7.80 (m, 3H).

HCl in 1,4-dioxane (4M, 2 mL, 8.00 mmol) was added to a stirred solution of tert-butyl ((1S,2R)-1-(5-(tert-butyl)-1H-benzo[d]imidazol-2-yl)-2-methyl-3-(methylamino)-3-oxo-propyl)carbamate (50 mg, 0.13 mmol) in 1,4-dioxane (1 mL). The reaction mixture was stirred at room temperature for 4 hours before concentrating in vacuo. The residue was sonicated in diethyl ether (0.5 mL) for 30 minutes, the organic solvent was decanted and the fine precipitate dried under high vacuum to afford the title compound as the hydrochloride salt as a white solid (43.4 mg, quant).

$^1$H NMR (400 MHz, MeOD): δ ppm 1.26 (d, 3H), 1.40 (s, 9H), 2.78 (s, 3H), 3.34 (m, 1H), 5.07 (d, 1H), 7.73 (m, 2H), 7.80 (s, 1H).

LCMS Rt=1.56 minutes MS m/z 289 [M+H]$^+$

Example 109

(2R,3S)-3-Amino-3-[5-(4-cyano-3-fluorophenyl)-1H-benzimidazol-2-yl]-2-methylpropanamide

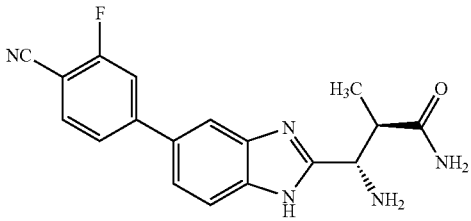 [SMILES: C[C@@H](C(N)=O)[C@H](N)c1nc2cc(-c3ccc(C#N)c(F)c3)ccc2[nH]1]

The title compound was prepared according to Preparation 28 using ammonium hydroxide and (2R,3S)-3-[(tert-butoxycarbonyl)amino]-3-[5-(4-cyano-3-fluorophenyl)-1H-benzimidazol-2-yl]-2-methylpropanoic acid (Preparation 32). The residue was sonicated in DCM:cyclohexane 5:1 to afford the boc protected amide intermediate. The residue was dissolved in 4M HCl in dioxane and stirred at room temperature for 3 hours. The solvent was removed in vacuo and the residue dissolved in MeOH and passed through an SCX cartridge eluting first with MeOH followed by 3M NH$_3$ in MeOH. The residue was purified using silica gel column chromatography eluting with DCM:MeOH:NH$_3$ (90:10:0.5) to afford the title compound (55 mg, 71%).

$^1$H NMR (400 MHz, MeOD): δ ppm 1.09 (d, 3H), 2.92-2.95 (m, 1H), 4.25 (d, 1H), 7.60 (d, 1H), 7.65-7.70 (m, 3H), 7.80-7.83 (m, 1H), 7.89 (s, 1H).

LCMS Rt=1.90 minutes MS m/z 338 [M+H]$^+$

Example 110

(2R,3S)-3-Amino-3-[4-chloro-5-(4-cyano-3-fluorophenyl)-1H-benzimidazol-2-yl]-2-methylpropanamide

The title compound was prepared according to Preparations 34 and 30 followed by Example 108 using 3',4'-diamino-2'-chloro-3-fluorobiphenyl-4-carbonitrile (Preparation 80) and (2S)-4-(benzyloxy)-2-[(tert-butoxycarbonyl)amino]-3-methyl-4-oxobutanoic acid (Preparation 66).

LCMS Rt=1.94 minutes MS m/z 372 [M+H]$^+$

Example 111

(2R,3S)-3-Amino-3-[4-chloro-5-(4-cyanophenyl)-1H-benzimidazol-2-yl]-2-methylpropanamide

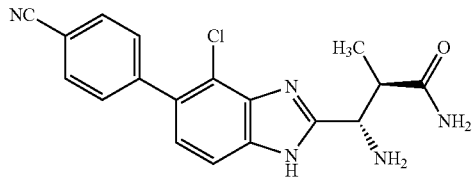 [SMILES: C[C@@H](C(N)=O)[C@H](N)c1nc2c(Cl)c(-c3ccc(C#N)cc3)ccc2[nH]1]

The title compound was prepared according to Preparations 34 and 30 followed by Example PF-108 using 3',4'-diamino-2'-chlorobiphenyl-4-carbonitrile (Preparation 78) and (2S)-4-(benzyloxy)-2-[(tert-butoxycarbonyl)amino]-3-methyl-4-oxobutanoic acid (Preparation 66).

LCMS Rt=1.73 minutes MS m/z 354 [M+H]$^+$

Example 112

(1S)-1-[5-(2,2-Dimethylpropyl)-1H-benzimidazol-2-yl]propan-1-amine

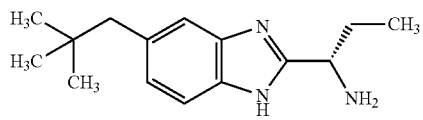 [SMILES: CC[C@H](N)c1nc2cc(CC(C)(C)C)ccc2[nH]1]

Argon was bubbled through a mixture of (S)-tert-butyl (1-(5-bromo-1H-benzo[d]imidazol-2-yl)propyl)carbamate (Preparation 18, 150 mg, 0.42 mmol), [1,1'-bis(diphenylphosphino)ferrocene]dichloropalladium(II) (48.2 mg, 0.0659 mmol), and neopentylzinc bromide in tetrahydrofuran (0.5 M, 2.5 mL, 1.3 mmol) for 5 minutes. The mixture was then heated under microwave irradiation for 10 minutes at 140° C. After cooling, the reaction was concentrated in vacuo, redissolved in dichloromethane (9 mL) and treated with trifluoroacetic acid (1 mL, 13 mmol). After stirring for 2.5 hours, the reaction was concentrated in vacuo and redissolved in a saturated solution of hydrogen chloride in methanol and stirred for 18 hours. The fully deprotected product was concentrated in vacuo and purified by preparative HPLC followed by silica gel column chromatography eluting with 0-50% CMA80/methylene chloride to afford the title compound (10 mg, 15%) as a white solid.

$^1$H NMR (400 MHz, DMSO-d$_6$): δ ppm 0.86 (m,12H), 1.70 (m, 1H), 1.83 (m, 1H), 2.59 (s, 2H), 3.91 (t, 1H), 6.90 (m, 1H), 7.25 (m, 1H), 7.40 (m, 1H), 12.0 (m, 1H).

LCMS Rt=0.83 minutes MS m/z 246 [M+H]$^+$

Example 113

1-(5-Cyclobutyl-1H-benzimidazol-2-yl)propylamine

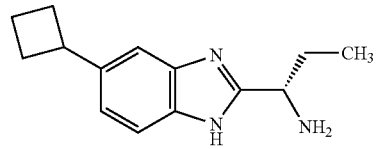 [SMILES: CC[C@H](N)c1nc2cc(C3CCC3)ccc2[nH]1]

Argon was bubbled through a mixture of (S)-tert-butyl (1-(6-bromo-1-(methoxymethyl)-1H-benzo[d]imidazol-2-yl)propyl)carbamate (Preparation 19, 218 mg, 0.55 mmol), [1,1-bis(diphenylphosphino)ferrocene]dichloropalladium (11) (45.0 mg, 0.0615 mmol), and cyclobutylzinc bromide in tetrahydrofuran (0.5 M, 5.5 mL, 2.8 mmol) for 5 minutes. The mixture was then heated at reflux for 18 hours. After cooling, the reaction was concentrated in vacuo, redissolved in ethyl acetate, and washed with water and brine. The organic layer was dried over anhydrous magnesium sulphate, filtered, and concentrated in vacuo. The residue was purified using silica gel column chromatography eluting with a 0-100% ethyl acetate/hexanes gradient to afford the fully protected intermediate as a brown oil. To this oil, cooled in an ice water bath, was added boron tribromide (0.5 mL, 5 mmol) and the reaction was allowed to warm to room temperature and stirred for 5 days. The resulting mixture was then purified by preparative HPLC to provide the title compound (32 mg, 13%) as a white solid.

$^1$H NMR (400 MHz, DMSO-d$_6$): δ ppm 0.88 (t, 3H), 1.85 (m, 1H), 2.02 (m, 3H), 2.15 (m, 2H), 2.32 (m, 2H), 3.62 (m, 1H), 4.54 (m, 1H), 7.15 (m, 1H), 7.43 (m, 1H), 7.54 (d, 1H), 8.61 (m, 2H).

LCMS Rt=0.84 minutes MS m/z 230 [M+H]$^+$

Example 114

4-[2-(2-Amino-2,3-dihydro-1H-inden-2-yl)-1H-benzimidazol-5-yl]-2-fluorobenzonitrile

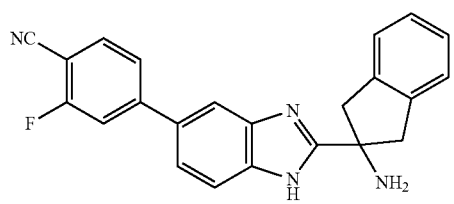 [SMILES: N#Cc1ccc(-c2ccc3[nH]c(C4(N)Cc5ccccc5C4)nc3c2)cc1F]

Argon was bubbled through a mixture of tert-butyl (2-(5-bromo-1H-benzo[d]imidazol-2-yl)-2,3-dihydro-1H-inden-2-yl)carbamate (Preparation 20, 179 mg, 0.42 mmol), tetrakis (triphenylphosphine)palladium(0) (64 mg, 0.055 mmol), 4-cyano-3-fluorophenylboronic acid (97 mg, 0.59 mmol), aqueous potassium carbonate (2M, 0.45 mL, 0.90 mmol), and 1,2-dimethoxyethane (2 mL) for 5 minutes. The mixture was then heated under microwave irradiation for 45 minutes at 120° C. After cooling, the reaction was diluted with ethyl acetate, and washed with water and brine. The organic layer was dried over anhydrous magnesium sulphate, filtered, and concentrated in vacuo. The residue was purified using silica gel column chromatography eluting with a 0-100% ethyl acetate/hexanes gradient to afford the protected intermediate as a clear oil. The oil was dissolved in dichloromethane (5 mL) and treated with trifluoroacetic acid (0.5 mL, 7 mmol). After stirring for 2 hours, the reaction was concentrated in vacuo and purified by silica gel column chromatography eluting with a 0-100% CMA80/methylene chloride gradient to afford the title compound (15.2 mg, 10%) as a white solid.

$^1$H NMR (400 MHz, DMSO-$d_6$): δ ppm 3.41 (d, 2H), 3.82 (d, 2H), 7.32 (m, 2H), 7.40 (m, 2H), 7.72 (m, 2H), 7.84 (dd, 1H), 7.99 (dd, 1H), 8.03 (t, 1H), 8.15 (m, 1H), 12.9 (br s, 1H).

LCMS Rt=0.97 minutes MS m/z 369 [M+H]$^+$

Example 115

2-Amino-2-[6-(2,2-dimethylpropyl)-1H-benzimidazol-2-yl]propan-1-ol

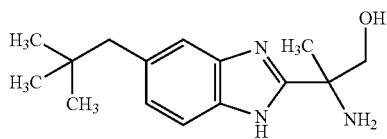 [SMILES: CC(C)(C)Cc1ccc2[nH]c(C(C)(N)CO)nc2c1]

To a solution of 2-((tert-butoxycarbonyl)amino)-3-hydroxy-2-methylpropanoic acid (Preparation 53, 186 mg, 0.85 mmol) acetonitrile (4.0 mL) and 4-methylmorpholine (0.15 mL, 1.4 mmol) cooled in an ice/brine bath was added isobutylchloroformate (0.050 mL, 0.38 mmol). The mixture was stirred for 30 minutes and then 4-neopentylbenzene-1,2-diamine (Preparation 83, 139 mg, 0.78 mmol) was added. The reaction mixture was allowed to warm to room temperature and stir for 4 days. The solvent was evaporated and the resulting oil was dissolved in acetic acid (3.0 mL, 50 mmol) and stirred at room temperature for 16 hours and then heated to 70° C. for 5 hours. After cooling, the solvent was removed in vacuo and the residue purified by silica gel column chromatography eluting with a 0-100% ethyl acetate/hexanes gradient. The resulting oil was dissolved in methylene chloride (5 mL) and treated with trifluoroacetic acid (0.5 mL, 6 mmol). After stirring for 2 hours, the reaction mixture was concentrated in vacuo and purified by silica gel column chromatography eluting with a 0-100% CMA80/methylene chloride gradient to provide the title compound (20.6 mg, 10%) as an off-white solid.

$^1$H NMR (400 MHz, DMSO-$d_6$): δ ppm 0.94 (s, 9H), 1.64 (s, 3H), 2.65 (s, 2H), 3.78 (m, 4H), 5.76 (m, 1H), 7.03 (m, 1H), 7.35 (s, 1H), 7.51 (m, 1H), 8.62 (br s, 2H).

LCMS Rt=0.85 minutes MS m/z 263 [M+H]$^+$

Example 116

2-[6-(2,2-Dimethylpropyl)-1H-benzimidazol-2-yl]-2,3-dihydro-1H-inden-2-amine

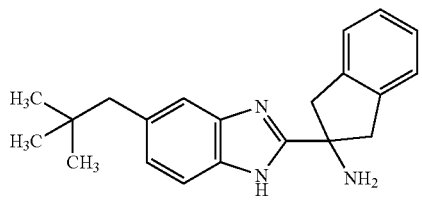 [SMILES: CC(C)(C)Cc1ccc2[nH]c(C3(N)Cc4ccccc4C3)nc2c1]

To a solution of Boc-2-aminoindane-2-carboxylic acid (107 mg, 0.386 mmol) in acetonitrile (2.0 mL) and 4-methylmorpholine (0.11 mL, 1.0 mmol) cooled in an ice/brine bath was added isobutylchloroformate (0.050 mL, 0.38 mmol). The mixture was stirred for 30 minutes and then 4-neopentylbenzene-1,2-diamine (Preparation 83, 82 mg, 0.46 mmol) was added. The reaction mixture was allowed to warm to room temperature and stir for 4 hours. The solvent was evaporated and the resulting oil was dissolved in acetic acid (3.0 mL, 50 mmol) and heated at 65° C. for 16 hours. After cooling, the solvent was removed in vacuo and the residue purified by silica gel column chromatography eluting with a 0-100% ethyl acetate/hexanes gradient. The resulting oil was dissolved in methylene chloride (5 mL) and treated with trifluoroacetic acid (0.5 mL, 6 mmol). After stirring for 2 hours, the reaction mixture was concentrated in vacuo and purified by silica gel column chromatography eluting with a 0-100% CMA80/methylene chloride gradient. This provided the title compound (63.7 mg, 52%) as a white solid.

$^1$H NMR (400 MHz, DMSO-$d_6$): δ ppm 0.91 (s, 9H), 2.62 (s, 2H), 3.52 (d, 2H), 3.83 (d, 2H), 5.41 (m, 1H), 7.06 (d, 1H), 7.32 (m, 3H), 7.47 (m, 2H), 7.67 (m, 1H), 8.96 (br s, 2H).

LCMS Rt=1.02 minutes MS m/z 320 [M+H]$^+$

Example 117

(3S)-3-Amino-3-[5-(4-cyano-3-fluorophenyl)-1H-benzimidazol-2-yl]propanamide

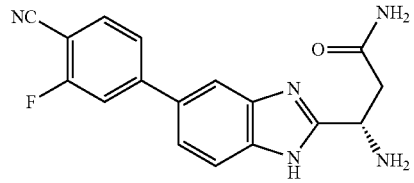 [SMILES: N#Cc1ccc(-c2ccc3[nH]c([C@@H](N)CC(N)=O)nc3c2)cc1F]

(S)-tert-butyl(1-(5-(4-cyano-3-fluorophenyl)-1H-benzo[d]imidazol-2-yl)-3-oxo-3-(tritylamino)propyl)carbamate (Preparation 17, 28 mg, 0.042 mmol) was dissolved in trifluoroacetic acid (1.1 mL, 14 mmol) and stirred for 2.5 hours. The reaction mixture was concentrated in vacuo, azeotroped with methanol (3×), and purified by silica gel column chromatography eluting with 0-100% CMA80/methylene chloride to afford the title compound (9 mg, 37%) as a white solid.

$^1$H NMR (400 MHz, DMSO-$d_6$): δ ppm 2.70 (dd, 1H), 2.89 (dd, 1H), 4.60 (m, 1H), 7.00 (m, 1H), 7.55 (m, 1H), 7.64 (m, 2H), 7.79 (dd, 1H), 7.91 (m, 1H), 7.99 (m, 2H).

LCMS Rt=0.80 minutes MS m/z 325 [M+H]$^+$

Example 118

(3S)-3-Amino-3-[5-(2,2-dimethylpropyl)-1H-benzimidazol-2-yl]propanamide

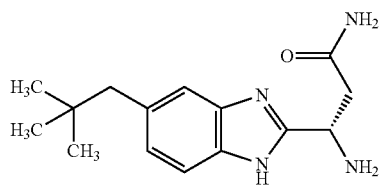 [SMILES: CC(C)(C)Cc1ccc2[nH]c([C@@H](N)CC(N)=O)nc2c1]

To a solution of (S)-tert-butyl (1-(5-neopentyl-1H-benzo[d]imidazol-2-yl)-3-oxo-3-(tritylamino)propyl)carbamate (Preparation 16, 107 mg, 0.173 mmol) in methylene chloride (5 mL) was added triethylsilane (0.15 mL, 0.94 mmol) and trifluoroacetic acid (1.0 mL, 13 mmol). The reaction mixture was stirred at room temperature for 3 days and then concentrated in vacuo. The residue was purified by preparative HPLC to afford the trifluoroacetic acid salt. The salt was suspended in methylene chloride and treated with aqueous saturated sodium hydrogen carbonate solution. The layers were separated and the aqueous layer washed with methylene chloride (2×). The organic layers were combined, dried over anhydrous magnesium sulphate, filtered, and concentrated in vacuo to provide the desired product (25 mg, 52%) as an off white solid.

$^1$H NMR (400 MHz, DMSO-$d_6$): δ ppm 0.88 (s, 9H), 2.58 (s, 2H), 2.89 (dd, 1H), 2.97 (dd, 1H), 4.84 (m, 1H), 7.03 (m, 1H), 7.19 (m, 1H), 7.33 (m, 1H), 7.49 (d, 1H), 7.67 (m, 1H), 8.57 (br s, 2H).

LCMS Rt=0.88 minutes MS m/z 275 [M+H]$^+$

Example 119

(3S)-3-Amino-3-[5-(2-chloro-4-cyanophenyl)-1H-benzimidazol-2-yl]propanamide

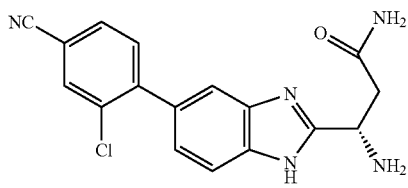 [SMILES: N#Cc1ccc(-c2ccc3[nH]c([C@@H](N)CC(N)=O)nc3c2)c(Cl)c1]

To (S)-tert-butyl (1-(6-(2-chloro-4-cyanophenyl)-1H-benzo[d]imidazol-2-yl)-3-oxo-3-(tritylamino)propyl)carbamate (Preparation 15, 35 mg, 0.051 mmol) was added trifluoroacetic acid (1.3 mL, 17 mmol) and the mixture stirred at room temperature for 2 hours. The reaction solution was concentrated in vacuo and azeotroped with methanol. The residue was purified using silica gel column chromatography eluting with 0-100% CMA80/methylene chloride to afford the title compound (14 mg, 65%) as a light yellow solid.

$^1$H NMR (400 MHz, DMSO-$d_6$): δ ppm 2.60 (m, 1H), 2.75 (m, 1H), 4.55 (m, 1H), 7.00 (m, 1H), 7.25 (m, 1H), 7.60 (m, 4H), 7.90 (m, 1H), 8.25 (m, 1H).

LCMS Rt=0.75 minutes MS m/z 340 [M+H]$^+$

Example 120

4-{2-[(1R,2R)-1-Amino-2-methoxypropyl]-4-chloro-1H-benzimidazol-5-yl}-2-fluorobenzonitrile

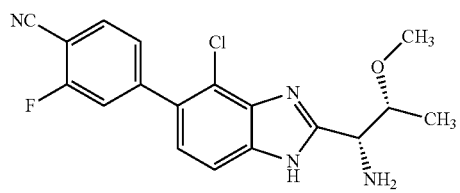 [SMILES: CO[C@H](C)[C@H](N)c1nc2c(Cl)c(-c3ccc(C#N)c(F)c3)ccc2[nH]1]

Method 4

Step 1

To a solution of N-(tert-butoxycarbonyl)-O-methyl-L-threonine (Preparation 51, 280 mg, 1.20 mmol) in DMF (15 mL) was added NMM (175 mg, 1.73 mmol) and HATU (525 mg, 1.38 mmol) at 0° C. The reaction was stirred at 0° C. for 2 hours before a solution of 3',4'-diamino-2'-chloro-3-fluoro-biphenyl-4-carbonitrile (Preparation 80, 300 mg, 1.15 mmol) in DMF (5 mL) was added with heating to 50° C. for 18 hours. The reaction was diluted with water (80 mL) and brine (80 mL), and extracted into EtOAc (3×30 mL). The organic layers were combined, washed with brine (2×100 mL), dried over Na$_2$SO$_4$ and concentrated in vacuo to afford a brown oil that was dissolved in DMSO (1 mL) and purified using reverse phase column chromatography eluting with 0-100% acetonitrile in 0.1% formic acid in water over 30 minutes to afford a pale brown foam.

Step 2

The foam was dissolved in AcOH (15 mL) and heated to 40° C. for 18 hours. The reaction was concentrated in vacuo aeotroping with DCM. The residue was purified using silica gel column chromatography eluting with 0-15% EtOAc in DCM to afford a brown solid.

Step 3

The solid was dissolved in 4M HCl in dioxane (3 mL) and stirred at room temperature for 3 hours.

The solvent was removed in vacuo and the residue was dissolved in MeOH (1 mL) and 0.7N NH$_3$ (10 mL). The solvents were removed in vacuo and the residue purified using silica gel column chromatography eluting with DCM:MeOH:NH$_3$ (99:1:0.1 to 96:4:0.1) to afford a white solid (49 mg, 45%).

$^1$H NMR (400 MHz, MeOD): δ ppm 1.16 (d, 3H), 3.35 (s, 3H) 3.68-3.74 (m, 1H), 4.09 (d, 1H), 7.28 (d, 1H), 7.49-7.53 (m, 2H), 7.59 (d, 1H), 7.84 (dd, 1H).

LCMS (4.5 minute run) Rt=1.90 minutes MS m/z 359 [M+H]$^+$

Example 121

4-{2-[(1R,2R)-1-Amino-2-hydroxypropyl]-4-chloro-1H-benzimidazol-5-yl}-2-fluorobenzonitrile

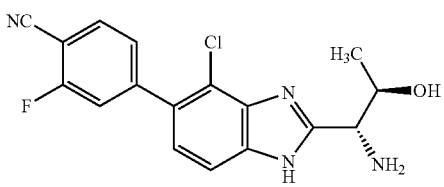 [SMILES: C[C@@H](O)[C@H](N)c1nc2c(Cl)c(-c3ccc(C#N)c(F)c3)ccc2[nH]1]

The title compound was prepared according to Method 4 using (4S,5R)-3-(tert-butoxycarbonyl)-2,2,5-trimethyl-1,3-oxazolidine-4-carboxylic acid (Preparation 57) and 3',4'-diamino-2'-chloro-3-fluorobiphenyl-4-carbonitrile (Preparation 80). The final residue was purified using silica gel column chromatography eluting with DCM:MeOH (7N NH$_3$), 97:3 to 93:7 and freeze dried for 18 hours.

$^1$H NMR (400 MHz, MeOD): δ ppm 1.17 (d, 3H), 3.98-4.01 (m, 1H), 4.04-4.11 (m, 1H), 7.30 (d, 1H), 7.49-7.54 (m, 2H), 7.59 (d, 1H), 7.82-7.86 (m, 1H).

LCMS Rt=1.83 minutes MS m/z 345 [M+H]$^+$

Example 122

4-{2-[(1R,2R)-1-Amino-2-hydroxypropyl]-1H-benzimidazol-6-yl}-3-chlorobenzonitrile

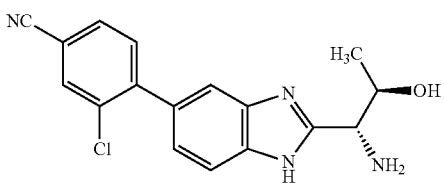 [SMILES: C[C@@H](O)[C@H](N)c1nc2cc(-c3ccc(C#N)cc3Cl)ccc2[nH]1]

The title compound was prepared according to Method 4 using (4S,5R)-3-(tert-butoxycarbonyl)-2,2,5-trimethyl-1,3-oxazolidine-4-carboxylic acid (Preparation 57) and 2-chloro-4-(4,4,5,5-tetramethyl-1,3,2-dioxaborolan-2-yl)benzonitrile. The final residue was purified using reverse phase column chromatography eluting with 0-30% acetonitrile in 0.1% formic acid in water to afford the formate salt.

$^1$H NMR (400 MHz, D$_2$O): δ ppm 1.12 (d, 3H), 4.23 (m, 1H), 4.44 (d, 1H), 7.22 (m, 1H), 7.42 (m, 1H), 7.55-7.65 (m, 3H), 7.78 (m, 1H), 8.27 (s, 1H).

Example 123

(1R,2R)-2-Methoxy-1-[5-(propan-2-yl)-1H-benzimidazol-2-yl]propan-1-amine

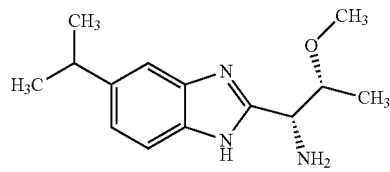 [SMILES: CO[C@H](C)[C@H](N)c1nc2cc(C(C)C)ccc2[nH]1]

The title compound was prepared according to Method 4 using 4-(1-methylethyl)-1,2-benzenediamine and N-(tert-butoxycarbonyl)-O-methyl-L-threonine (Preparation 51). The residue was purified by elution through an SCX cartridge.

$^1$H NMR (400 MHz, DMSO-d$_6$): δ ppm 0.96 (d, 3H), 1.19 (s, 6H), 2.93-2.98 (m, 1H), 3.20 (s, 3H), 3.64 (m, 1H), 4.15 (d, 1H), 7.0 (d, 1H), 7.25-7.41 (m, 2H), 11.95 (br s, 1H).

LCMS (GVK 5 minute run) Rt=2.40 minutes MS m/z 248 [M+H]$^+$

Example 124

(This Example is intentionally omitted)

Example 125

(1R,2R)-1-Amino-3-methyl-1-[5-(propan-2-yl)-1H-benzimidazol-2-yl]butan-2-ol

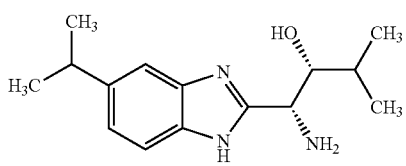 [SMILES: CC(C)c1ccc2[nH]c([C@@H](N)[C@H](O)C(C)C)nc2c1]

The title compound was prepared according to Method 4 using (4S,5R)-3-(tert-butoxycarbonyl)-5-isopropyl-2,2-dimethyl-1,3-oxazolidine-4-carboxylic acid (Preparation 60) and 4-(1-methylethyl)-1,2-benzenediamine.

$^1$H NMR (400 MHz, DMSO-d$_6$): δ ppm 0.80-1.00 (m, 6H), 1.30-1.40 (m, 6H), 1.50-1.60 (m, 1H), 2.90-3.10 (m, 2H), 3.40-3.50 (m, 1H), 4.00 (d, 1H), 4.80 (s, 1H), 7.00 (d, 1H), 7.20-7.40 (m, 2H), 12.10 (br s, 1H).

LCMS (7 minute run) Rt=3.24 minutes MS m/z 262 [M+H]$^+$

Example 126

(1R,2R)-1-Amino-1-[5-(propan-2-yl)-1H-benzimidazol-2-yl]butan-2-ol

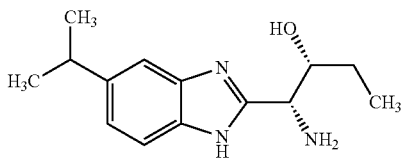 [SMILES: CC[C@@H](O)[C@H](N)c1nc2cc(C(C)C)ccc2[nH]1]

The title compound was prepared according to Method 4 using name (Preparation 61) and 4-(1-methylethyl)-1,2-benzenediamine.

$^1$H NMR (400 MHz, DMSO-d$_6$): δ ppm 0.85 (t, 3H), 1.25 (s, 6H), 1.30-1.45 (m, 2H), 2.0 (br m, 2H), 2.92-3.00 (m, 1H), 3.6 (s, 1H), 3.82 (d, 1H), 4.76 (s, 1H), 7.0 (d, 1H), 7.40 (br s, 2H), 12.00 (br s, 1H).

LCMS (5 minute run) Rt=1.84 minutes MS m/z 248 [M+H]$^+$

Example 127

(1R,2S)-2-Methoxy-1-[5-(propan-2-yl)-1H-benzimidazol-2-yl]propan-1-amine

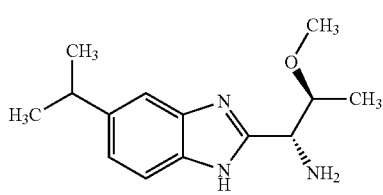 [SMILES: CO[C@@H](C)[C@H](N)c1nc2cc(C(C)C)ccc2[nH]1]

The title compound was prepared according to Method 4 using N-boc-(2S,3S)-2-amino-3-methoxybutanoic acid and 4-(1-methylethyl)-1,2-benzenediamine.

$^1$H NMR (400 MHz, DMSO-d$_6$): δ ppm 1.0 (s, 3H), 1.2 (s, 6H), 2.2 (br m, 2H), 2.98 (m, 1H), 3.2 (s, 3H), 3.65 (m, 1H), 4.15 (d, 1H), 7.0 (d, 1H), 7.20-7.45 (m, 2H), 11.95 (br s, 1H). MS m/z 248 [M+H]$^+$

Example 128

(1R,2S)-1-(5-tert-Butyl-1H-benzimidazol-2-yl)-2-methoxypropan-1-amine

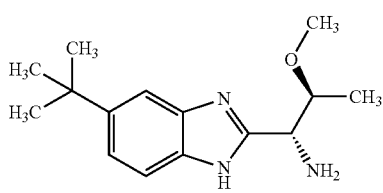 [SMILES: CO[C@@H](C)[C@H](N)c1nc2cc(C(C)(C)C)ccc2[nH]1]

The title compound was prepared according to Method 4 using N-boc-(2S,3S)-2-amino-3-methoxybutanoic acid and 4-tert-butyl-1,2-diaminobenzene.

$^1$H NMR (400 MHz, DMSO-d$_6$): δ ppm 1.02 (d, 3H), 1.35 (s, 9H), 2.15 (brs, 2H), 3.25 (s, 3H), 3.60-3.70 (m, 1H), 4.16 (d, 1H), 7.2 (d, 1H), 7.25-7.55 (m, 2H), 11.95 (s, 1H).

MS m/z 262 [M+H]$^+$

Example 129

2-[(2S)-Azetidin-2-yl]-5-tert-butyl-1H-benzimidazole

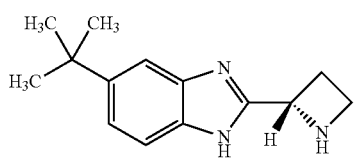 [SMILES: CC(C)(C)c1ccc2[nH]c([C@@H]3CCN3)nc2c1]

The title compound was prepared according to Method 4 using (S)—N-Boc-azetidine carboxylic acid and 4-tert-butyl-1,2-diaminobenzene. The final deprotection was effected with ethereal HCl in DCM. After removal of solvent the solid was triturated with ether to afford the title compound as the HCl salt.

$^1$H NMR (400 MHz, DMSO-d$_6$): δ ppm 1.35 (s, 9H), 2.85-2.95 (m, 1H), 3.00-3.15 (m, 1H), 3.90-4.20 (m, 2H), 5.75 (br s, 1H), 7.5 (d, 1H), 7.7 (d, 2H), 9.85 (d, 2H).

MS m/z 230 [M+H]$^+$

Example 130

2-[(2R)-Azetidin-2-yl]-5-tert-butyl-1H-benzimidazole

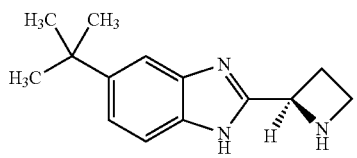 [SMILES: CC(C)(C)c1ccc2[nH]c([C@H]3CCN3)nc2c1]

The title compound was prepared according to Method 4 using (R)—N-Boc-azetidine carboxylic acid and 4-tert-butyl-1,2-diaminobenzene. The final deprotection was effected with ethereal HCl in DCM. After removal of solvent the solid was triturated with ether to afford the title compound as the HCl salt.

$^1$H NMR (300 MHz, DMSO-d$_6$): δ ppm 1.35 (s, 9H), 2.80-2.95 (m, 1H), 3.00-3.20 (m, 1H), 3.90-4.18 (m, 2H), 5.8 (br s, 1H), 7.5 (d, 1H), 7.60-7.75 (m, 2H), 9.9 (d, 2H).

MS m/z 230 [M+H]$^+$

Example 131

5-tert-Butyl-2-[(2S,4R)-4-fluoropyrrolidin-2-yl]-1H-benzimidazole

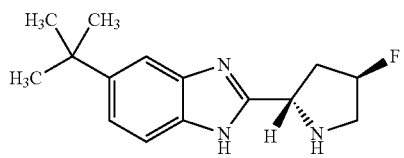 [SMILES: CC(C)(C)c1ccc2[nH]c([C@@H]3C[C@@H](F)CN3)nc2c1]

The title compound was prepared according to Method 4 using N-Boc-trans-4-fluoro-L-proline and 4-tert-butyl-1,2-diaminobenzene. The final residue was washed with ethyl acetate and diluted with water, basified with saturated lithium hydroxide solution (pH=8), extracted with ethyl acetate and dried over anhydrous $Na_2SO_4$ and concentrated under reduced pressure.

$^1$H NMR (300 MHz, DMSO-$d_6$): δ ppm 1.34 (s, 9H), 2.10-2.30 (m, 1H), 2.40-2.50 (m, 2H), 3.05-3.20 (m, 2H), 4.50-4.55 (m, 1H), 5.25-5.40 (m, 1H), 7.2 (d, 1H), 7.30-7.50 (m, 2H), 12.0 (br s, 1H).

MS m/z 262 [M+H]$^+$

Example 132

5-tert-Butyl-2-[(2S,4S)-4-fluoropyrrolidin-2-yl]-1H-benzimidazole

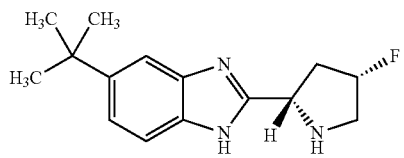 [SMILES: CC(C)(C)c1ccc2[nH]c([C@@H]3C[C@H](F)CN3)nc2c1]

The title compound was prepared according to Method 4 using N-Boc-cis-4-fluoro-L-proline and 4-tert-butyl-1,2-diaminobenzene. The final residue was washed with ethyl acetate and diluted with water, basified with saturated lithium hydroxide solution (pH=8), extracted with ethyl acetate and dried over anhydrous $Na_2SO_4$ and concentrated under reduced pressure.

$^1$H NMR (300 MHz, DMSO-$d_6$): δ ppm 1.34 (s, 9H), 2.10-2.30 (m, 1H), 2.50-2.60 (m, 2H), 3.08-3.20 (m, 2H), 4.30-4.40 (m, 1H), 5.25-5.40 (m, 1H), 7.2 (d, 1H), 7.30-7.50 (m, 2H), 11.95 (br s, 1H).

MS m/z 262 [M+H]$^+$

Example 133

(1R,2R)-1-Amino-1-(5-tert-butyl-1H-benzimidazol-2-yl)-3-methylbutan-2-ol

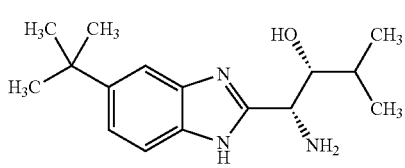 [SMILES: CC(C)[C@@H](O)[C@H](N)c1nc2cc(C(C)(C)C)ccc2[nH]1]

The title compound was prepared according to Method 4 using (4S,5R)-3-(tert-butoxycarbonyl)-5-isopropyl-2,2-dimethyl-1,3-oxazolidine-4-carboxylic acid (Preparation 60) and 4-tert-butyl-1,2-diaminobenzene. The final residue was washed with ethyl acetate and diluted with water, basified with saturated lithium hydroxide solution (pH=8), extracted with ethyl acetate and dried over anhydrous $Na_2SO_4$ and concentrated under reduced pressure.

$^1$H NMR (300 MHz, DMSO-$d_6$): δ ppm 0.86 (d, 6H), 1.32 (s, 9H), 1.50-1.60 (m, 1H), 2.2 (br s, 2H), 3.42-3.50 (m, 1H), 3.90 (d, 1H), 4.75 (d, 1H), 7.2 (d, 1H), 7.32-7.55 (m, 2H), 12.00 (br s, 1H).

MS m/z 276 [M+H]$^+$

Example 134

(3R)-3-Amino-3-(5-tert-butyl-1H-benzimidazol-2-yl)propan-1-ol

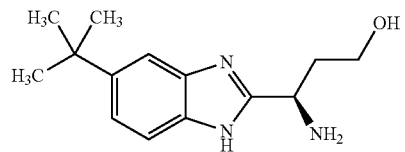 [SMILES: CC(C)(C)c1ccc2[nH]c([C@H](N)CCO)nc2c1]

The title compound was prepared using Method 4 Steps 1 and 2 followed by the method described for Example 140 using 4-tert-butyl-1,2-diaminobenzene and N-α-t-Butyloxylcarbonyl-O-benzyl-D-homoserine. The residue was diluted with water and washed with EtOAc. Dilute aqueous LiOH solution was added to pH=10 and extracted with EtOAc. The organic layer was collected, dried over $Na_2SO_4$ and concentrated in vacuo (56 mg, 79%).

$^1$H NMR (300 MHz, DMSO-$d_6$): δ ppm 1.32 (s, 9H), 1.72-1.84 (m, 1H), 1.90-2.20 (m, 3H), 3.42-3.59 (m, 2H), 4.05-4.12 (m, 1H), 4.6 (brs, 1H), 7.2 (d, 1H), 7.41 (s, 2H), 11.95 (br s, 1H).

MS m/z 248 [M+H]$^+$

Example 135

(4R)-4-Amino-4-(5-tert-butyl-1H-benzimidazol-2-yl)butan-1-ol

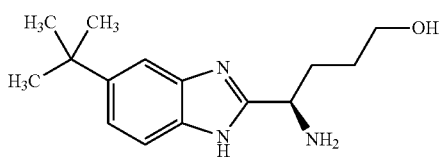 [SMILES: CC(C)(C)c1ccc2[nH]c([C@H](N)CCCO)nc2c1]

The title compound was prepared according to Method 4 using (4R)-3-(tert-butoxycarbonyl)-2,2-dimethyl-1,3-oxazepane-4-carboxylic acid (Preparation 48) and 4-tert-butyl-1,2-diaminobenzene.

The residue was diluted with water, basified with 10% NaOH solution and extracted with EtOAc. The organic layer was dried over anhydrous $Na_2SO_4$ and concentrated under reduced pressure to afford a solid that was triturated with n-pentane and diethyl ether (68 mg, 52%).

$^1$H NMR (400 MHz, DMSO-$d_6$): δ ppm 1.32 (s, 9H), 1.62-1.74 (m, 2H), 1.76-1.85 (m, 2H), 3.30-3.40 (m, 2H), 3.9 (t, 1H), 7.2 (d, 1H), 7.30-7.50 (m, 2H), 11.9 (br s, 1H).

MS m/z 262 [M+H]$^+$

Example 136

(2R,3R)-2-(5-tert-Butyl-1H-benzimidazol-2-yl)pyrrolidin-3-ol

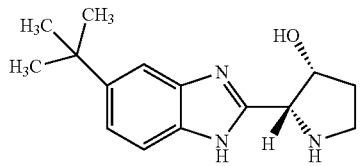 [SMILES: CC(C)(C)c1ccc2[nH]c([C@H]3NCC[C@H]3O)nc2c1]

The title compound was prepared according to Method 4 Steps 1 and 2 using (3R)-3-acetoxy-1-(tert-butoxycarbonyl)-L-proline (Preparation 47) and 4-tert-butyl-1,2-diaminobenzene. The residue was dissolved in 6N HCl (5 mL) at 0° C. and then heated to 60° C. for 4 hours. The reaction was cooled, concentrated in vacuo and purified through an SCX cartridge (47 mg, 66%).

$^1$H NMR (300 MHz, DMSO-$d_6$): δ ppm 1.36 (s, 9H), 1.68-1.8 (m, 1H), 1.90-2.03 (m, 1H), 2.83-3.02 (m, 2H), 3.15 (q, 1H), 4.10 (d, 1H), 4.30-4.40 (m, 1H), 4.70 (br s, 1H), 7.19 (d, 1H), 7.3-7.45 (m, 2H), 11.90 (br s, 1H).

MS m/z 260 [M+H]$^+$

Example 137

4-{2-[(1S,2R)-1-Amino-2-hydroxypropyl]-1H-benzimidazol-5-yl}benzonitrile

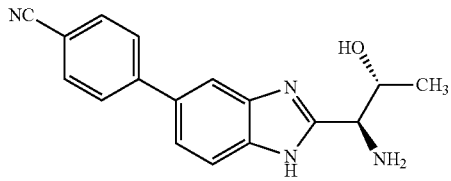 [SMILES: C[C@@H](O)[C@@H](N)c1nc2cc(-c3ccc(C#N)cc3)ccc2[nH]1]

The title compound was prepared according to Method 4 using (4R,5R)-3-(tert-butoxycarbonyl)-2,2,5-trimethyl-1,3-oxazolidine-4-carboxylic acid (Preparation 59A) and 3',4'-diaminobiphenyl-4-carbonitrile (Preparation 82). The reaction mixture was concentrated in vacuo and purified by SCX-2 cartridge (16 mg, 72%).

$^1$H NMR (400 MHz, DMSO-$d_6$): δ ppm 1.05 (s, 3H), 4.00 (s, 2H), 5.00 (s, 1H), 7.45-8.00 (7H), 12.2 (s, 1H), MS m/z 291 [M−H]$^-$

Example 138

4-{2-[(1R,2S)-1-Amino-2-hydroxypropyl]-1H-benzimidazol-5-yl}benzonitrile

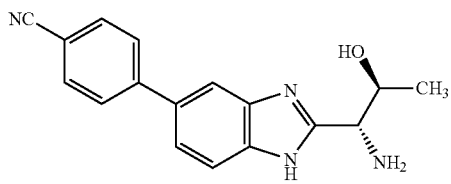 [SMILES: C[C@H](O)[C@H](N)c1nc2cc(-c3ccc(C#N)cc3)ccc2[nH]1]

The title compound was prepared according to Method 4 using (4S,5S)-3-(tert-butoxycarbonyl)-5-isopropyl-2,2-dimethyl-1,3-oxazolidine-4-carboxylic acid (Preparation 59B) and 3',4'-diaminobiphenyl-4-carbonitrile (Preparation 82). The reaction mixture was concentrated in vacuo and purified by SCX-2 cartridge (16 mg, 72%).

$^1$H NMR (300 MHz, DMSO-$d_6$): δ ppm 1.1 (d, 3H), 4.2 (d, 2H), 5.25 (brs, 1H), 7.5 (d, 1H), 7.60-7.70 (m, 1H), 7.9 (brs, 5H).

MS m/z 293 [M+H]$^+$

Example 139

(1R,2R)-1-Amino-1-(5-tert-butyl-1H-benzimidazol-2-yl)butan-2-ol

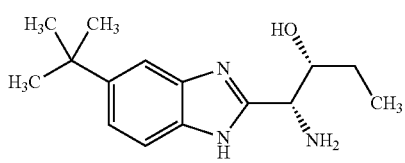 [SMILES: CC[C@@H](O)[C@H](N)c1nc2cc(C(C)(C)C)ccc2[nH]1]

The title compound was prepared according to Method 4 using name (Preparation 61) and 4-(tert-butyl)benzene-1,2- diamine. The residue was neutralized with saturated aqueous NaHCO₃ solution and extracted with ethyl acetate. The organic layer was dried over sodium sulphate, concentrated in vacuo and triturated with ether.

¹H NMR (300 MHz, DMSO-d₆): δ ppm 0.80 (t, 3H), 1.20 (s, 11H), 2.00 (br s, 2H), 3.60 (s, 1H), 3.80 (d, 1H), 4.80 (d, 1H), 7.20 (d, 1H), 7.40 (br m, 2H), 12.00 (br s, 1H).

MS m/z 260 [M−H]⁻

Example 140

(4S)-4-Amino-4(5-tert-butyl-1H-benzimidazol-2-yl)butan-1-ol

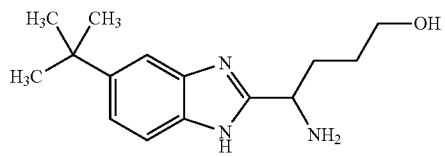 [SMILES: CC(C)(C)c1ccc2[nH]c(C(N)CCCO)nc2c1]

Wet 5% Pd/C (150 mg) was added to a solution of tert-butyl [(1S)-4-(benzyloxy)-1-(5-tert-butyl-1H-benzimidazol-2-yl)butyl]carbamate (Preparation 35, 390 mg, 0.864) in EtOAc (150 mL) and stirred for 48 hours at room temperature under an H₂ balloon pressure. The reaction was filtered through celite and the filtrate concentrated in vacuo. The residue was purified by silica gel column chromatography eluting with 30-40% EtOAc in petroleum ether. The resulting solid was suspended in dioxane (4 mL) and treated with 4N HCl in dioxane (4 mL) at 0° C. The reaction was stirred warming to room temperature for 3 hours. The reaction was concentrated in vacuo and purified through an SCX cartridge to furnish the title compound (38 mg, 45%).

¹H NMR (300 MHz, DMSO-d₆): δ ppm 1.34 (s, 9H), 1.48-1.62 (m, 1H), 1.80-1.90 (m, 1H), 2.80-2.92 (m, 2H), 3.16-3.22 (m, 1H), 4.58 (br s, 1H), 7.19 (d, 1H), 7.37 (d, 1H), 7.40 (s, 1H).

MS m/z 262 [M+H]⁺

Example 141

(3S)-3-Amino-3-(5-tert-butyl-1H-benzimidazol-2-yl)-2,2-dimethylpropanamide

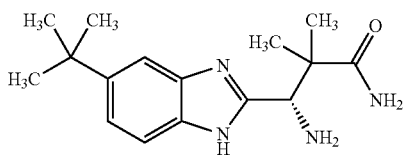 [SMILES: CC(C)(C)c1ccc2[nH]c([C@@H](N)C(C)(C)C(N)=O)nc2c1]

To a solution of benzyl (3S)-3-amino-3-(5-tert-butyl-1H-benzimidazol-2-yl)-2,2-dimethylpropanoate (Preparation 13, 150 mg, 0.312 mmol) in THF (10 mL) was added freshly condensed liquid NH₃ (20 mL) at −78° C. and the reaction was stirred at room temperature for 24 hours. The reaction mixture was evaporated and purified by preparative TLC eluting with 70% EtOAc in petroleum ether. The residue was dissolved in dioxane (6 mL), cooled to 0° C. and treated with 2N HCl in dioxane (4 mL). The reaction was stirred at room temperature for 4 hours before concentrating in vacuo. The residue was purified through an SCX cartridge to afford the title compound (25 mg, 30%).

¹H NMR (400 MHz, DMSO-d₆): δ ppm 1.03 (s, 3H), 1.15 (s, 3H), 1.32 (s, 9H), 6.85 (br s, 1H), 7.20 (d, 1H), 7.30-7.60 (m, 3H), 11.90 (br s, 1H).

MS m/z 289 [M+H]⁺

Example 142

4-[2-(1-Amino-2-methoxy-2-methylpropyl)-1H-benzimidazol-5-yl]benzonitrile

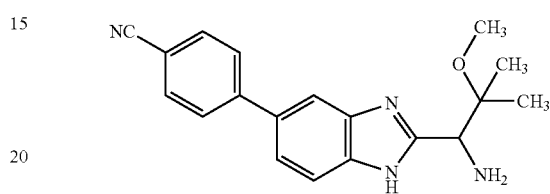

The title compound was prepared according to Method 4 using T3P and triethylamine in the first step with 2-{[(tert-butoxy)carbonyl]amino}-3-methoxy-3-methylbutanoic acid and 3',4'-diaminobiphenyl-4-carbonitrile (Preparation 82). The reaction was concentrated to dryness, triturated with ether and purified using preparative HPLC. Rt=3.21 minutes MS m/z 321 [M+H]⁺

Example 143

(R)-2-Amino-2-(5-(tert-butyl)-1H-benzo[d]imidazol-2-yl)ethyl carbamate

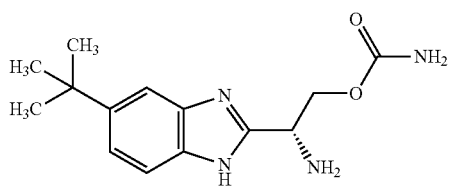 [SMILES: CC(C)(C)c1ccc2[nH]c([C@@H](N)COC(N)=O)nc2c1]

(R)-tert-Butyl (1-(6-(tert-butyl)-1H-benzo[d]imidazol-2-yl)-2-hydroxyethyl)carbamate (Preparation 12, 35 mg, 0.10 mmol) was dissolved in dichloromethane and triethylamine (10.8 mg, 0.11 mmol) was added followed by N,N-disuccinimidyl carbonate (27 mg, 0.11 mmol). The reaction was shaken at room temperature for 4 hours. 28% aqueous ammonium hydroxide solution (2 mL) was added and the reaction mixture stirred vigorously at 50° C. in a sealed vial for 18 hours. The reaction mixture was washed successively with 0.5N hydrochloric acid and brine, then dried over anhydrous magnesium sulfate and filtered. The solvent was removed in vacuo to give the BOC protected product which was taken forward without purification. The protected product was dissolved in dichloromethane (2 mL) and trifluoroacetic acid (25 mL) was added. The reaction mixture was shaken for 6 hours then the solvent removed in vacuo. The residue was dissolved dichloromethane and neutralized with macroporous triethylammonium methylpolystyrene carbonate resin. The reaction mixture was evaporated onto celite and purified by silica gel column chromatography eluting with 0-100% CMA80 in dichloromethane to afford the title compound (13.8 mg).

$^1$H NMR (300 MHz, DMSO-d$_6$): δ ppm 1.33 (s, 9H), 2.15 (br s, 2H), 4.12-4.27 (m, 3H), 6.47 (br s, 2H), 7.21 (d, 1H), 7.32-7.55 (m, 2H), 12.05 (br s, 1H).

LCMS Rt=0.82 minutes MS m/z 277 [M+H]$^+$

Example 144

(R)-2-((S)-Amino-(6-(tert-butyl)-1H-benzo[d]imidazol-2-yl)methyl)butanamide

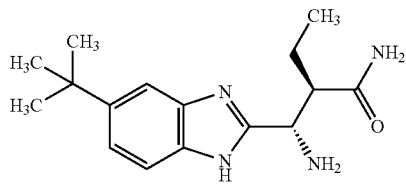 [SMILES: CC[C@@H](C(N)=O)[C@H](N)c1nc2cc(C(C)(C)C)ccc2[nH]1]

(2S,3R)-1-(tert-Butyldimethylsilyl)-3-ethyl-4-oxoazetidine-2-carboxylic acid (Tetrahedron, 46(7), 2255-62; 1990, 100 mg, 0.388 mmol) was dissolved in N,N-dimethylformamide (2 mL) and N,N,N',N'-tetramethyl-O-(7-azabenzotriazol-1-yl)uronium hexafluorophosphate (418 mg, 1.10 mmol) was added. The reaction mixture was stirred for 20 minutes then 4-(tert-butyl)benzene-1,2-diamine (165 mg, 1.00 mmol) was added and the reaction mixture stirred at ambient temperature for 18 hours. The reaction mixture was diluted with water and extracted three times with ethyl ether. The combined organic phase was dried over anhydrous magnesium sulfate, filtered and the solvent removed in-vacuo. The residue was purified by silica gel column chromatography eluting with 0-100% ethyl acetate in hexanes to afford the amide as a mixture of isomers.

The amide intermediate was stirred in acetic acid (2 mL) at 60° C. for 18 hours. The acetic acid was removed in vacuo and the residue was dissolved in dichloromethane (2 mL) then 4-dimethylaminopyridine (0.12 g, 0.97 mmol) and di-tert-butyldicarbonate (0.2 g, 1 mmol) were added. The reaction mixture was stirred at room temperature for 2 days. The reaction mixture was washed with aqueous saturated sodium bicarbonate solution and the organic phase dried over anhydrous magnesium sulfate then filtered and the solvent removed in vacuo. The residue was purified by silica gel column chromatography eluting with 0-50% ethyl acetate in hexanes to afford the BOC protected benzimidazole.

The benzimidazole was dissolved in tetrahydrofuran (3 mL) with 28% aqueous ammonium hydroxide (1 mL) and stirred for 48 hours at ambient temperature. The solvent was removed in vacuo and the residue was dissolved in 4N HCl in 1,4-dioxane and stirred for 2 hours. The solvent was removed in vacuo and the residue was taken into methanol/dichloromethane and treated with macroporous triethylammonium methylpolystyrene carbonate resin to neutralize excess acid. The reaction mixture was filtered and the solvent removed in vacuo. The residue was purified by silica gel column chromatography eluting with 0-80% CMA80 in dichloromethane to afford the title compound (38 mg).

$^1$H NMR (300 MHz, DMSO-d$_6$): δ ppm 0.81 (t, 3H), 1.31-1.45 (m, 11H), 2.94 (m, 1H), 4.62 (m, 1H), 7.29-7.37 (m, 2H), 7.47-7.59 (m, 2H), 7.74 (br s, 1H), 8.54 (br s, 2H), 12.7 (br s, 1H).

LCMS Rt=1.01 minutes, MS m/z 289 [M+H]$^+$

Example 145

(1R,2R)-1-(5-Cyclopentyl-1H-benzo[d]imidazol-2-yl)-2-methoxypropan-1-amine

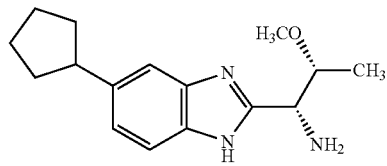 [SMILES: CO[C@H](C)[C@H](N)c1nc2cc(C3CCCC3)ccc2[nH]1]

To a solution of Boc-Thr(Me)-OH (113 mg, 0.48 mmol) in N,N-dimethylformamide (3.0 mL) was added HATU (225 mg, 0.592 mmol). The mixture was stirred for 30 minutes and then 4-cyclopentylbenzene-1,2-diamine (Compound 84, 118 mg, 0.669 mmol) was added. After stirring for 2 days, the solution was diluted with ethyl acetate, washed with water and brine, dried over anhydrous magnesium sulphate, filtered, and concentrated in vacuo. To the resulting residue was added acetic acid (3 mL, 50 mmol) and the mixture allowed to stir for 2 days. The reaction mixture was then concentrated in vacuo and purified by silica gel column chromatography eluting with 0-100% ethyl acetate in hexanes. The resulting brown oil was dissolved in methylene chloride (5 mL) and treated with trifluoroacetic acid (0.5 mL, 6 mmol). After stirring for 3 hours, the reaction mixture was concentrated in vacuo, redissolved in methylene chloride, and washed with saturated aqueous sodium hydrogen carbonate solution.

The organic layer was dried over anhydrous magnesium sulphate, filtered and concentrated in vacuo. The residue was purified by silica gel column chromatography eluting with 0-100% methylene chloride/CMA80 gradient to afford the title compound (10.4 mg, 8%) as a white solid.

$^1$H NMR (300 MHz, DMSO-d$_6$): δ ppm 1.06 (d, 3H), 1.65 (m, 4H), 1.80 (m, 2H), 2.08 (m, 2H), 3.15 (m, 1H), 3.24 (s, 3H), 3.65 (m, 1H), 3.96 (d, 1H), 7.05 (m, 1H), 7.47 (m, 2H), 11.80 (m, 1H).

LCMS Rt=1.08 minutes MS m/z 275 [M+H]$^+$

Example 146

4-{2-[(1S)-1-Aminobutyl]-1H-benzimidazol-5-yl}-2-fluorobenzonitrile

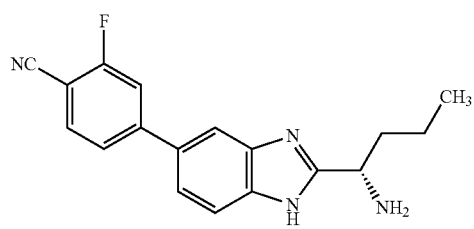 [SMILES: CCC[C@H](N)c1nc2cc(-c3ccc(C#N)c(F)c3)ccc2[nH]1]

Argon was bubbled through a mixture of (S)-tert-butyl (1-(5-bromo-1H-benzo[d]imidazol-2-yl)butyl)carbamate (Preparation 11, 109 mg, 0.296 mmol), tetrakis(triphenylphosphine)palladium(0) (50.2 mg, 0.043 mmol), 4-cyano-3-fluorophenylboronic acid (117 mg, 0.71 mmol), aqueous potassium carbonate (2.0 M, 0.50 mL, 1.0 mmol), and 1,2-dimethoxyethane (2.0 mL) for 5 minutes. The mixture was then heated in a microwave for 45 minutes at 120° C.

After cooling, the reaction was diluted with ethyl acetate, and washed with water and brine. The organic layer was dried over MgSO₄, filtered, and concentrated in vacuo. The residue was purified using silica gel chromatography eluting with 0-100% ethyl acetate in hexanes to afford the protected intermediate as a clear oil. The oil was dissolved in dichloromethane (5.0 mL) and treated with trifluoroacetic acid (0.5 mL, 7 mmol). After stirring for 2 hours, the reaction was concentrated in vacuo and purified using silica gel column chromatography eluting with 0-50% methylene chloride/CMA80 gradient. This provided the title compound (40.3 mg, 44%) as a white solid.

$^1$H NMR (300 MHz, DMSO-d$_6$): δ ppm 0.92 (t, 3H), 1.31 (m, 2H), 1.68 (m, 1H), 1.83 (m, 1H), 4.03 (m, 1H), 7.58 (m, 2H), 7.77 (m, 1H), 7.98 (m, 3H).

MS m/z 309 [M+H]$^+$

Example 147

4-{2-[(1S)-1-Aminobutyl]-1H-benzimidazol-5-yl}benzonitrile

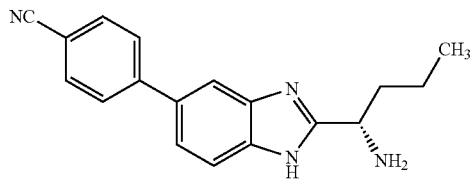 [SMILES: CCC[C@H](N)c1nc2cc(-c3ccc(C#N)cc3)ccc2[nH]1]

To a solution of (S)-tert-butyl (1-(5-bromo-1H-benzo[d]imidazol-2-yl)butyl)carbamate (Preparation 11, 101 mg, 0.274 mmol) and 4-cyanophenylboronic acid (100 mg, 0.68 mmol) in 1,2-dimethoxyethane (4.0 mL) was added aqueous potassium carbonate (2.0 M, 0.41 mL, 0.82 mmol) followed by tetrakis(triphenylphosphine)palladium(0) (32 mg, 0.027 mmol). Argon was bubbled through the reaction mixture for 5 minutes and it was then heated for 45 minutes under microwave irradiation at 120° C. After cooling, the mixture was diluted with ethyl acetate and washed with water and then brine. The organic layer was dried over anhydrous magnesium sulphate, filtered, and concentrated in vacuo. The residue was purified using silica gel column chromatography eluting with 0-100% ethyl acetate in hexanes to afford the protected intermediate as an oil. This oil was dissolved in methylene chloride (5 mL), treated with trifluoroacetic acid (1 mL, 10 mmol), and stirred for 2 hours. The reaction mixture was concentrated in vacuo and purified by silica gel column chromatography eluting with 0-40% methylene chloride/CMA80 gradient to provide the title compound (15.0 mg, 20%) as a white solid.

$^1$H NMR (300 MHz, DMSO-d$_6$): δ ppm 0.92 (m, 3H), 1.31 (m, 2H), 1.69 (m, 1H), 1.81 (m, 1H), 4.04 (m, 1H), 7.53 (m, 2H), 7.85 (m, 1H), 7.96 (m, 4H), 12.25 (br s, 1H).

LCMS Rt=0.88 minutes MS m/z 291 [M+H]$^+$

Example 148

(1S,2R)-1-Amino-1-[5-(propan-2-yl)-1H-benzimidazol-2-yl]propan-2-ol

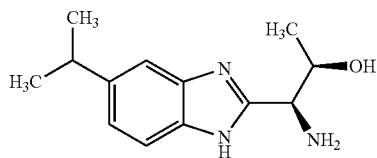 [SMILES: CC(C)c1ccc2[nH]c([C@H](N)[C@@H](C)O)nc2c1]

The title compound was prepared according to Method 4 using N-Boc-D-allo-threonine (Preparation 55) and 4-(1-methylethyl)-1,2-benzenediamine. The residue was purified using preparative HPLC using the following conditions:

Phenomenex Gemini C18 250×21.2 mm×10 um; eluting with 28-58% acetonitrile in NH₄OH (pH=10); with a flow rate of 30 mL per minute.

LCMS (ABO1) Rt=1.95 minutes MS m/z 234 [M+H]$^+$

Example 149

(2R,3S)-3-Amino-3-(5-tert-butyl-1H-benzimidazol-2-yl)-N,N,2-trimethylpropanamide

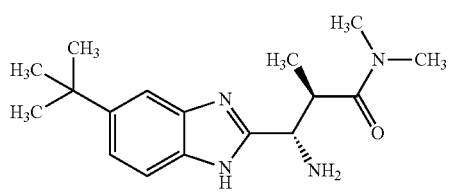 [SMILES: C[C@@H](C(=O)N(C)C)[C@H](N)c1nc2cc(C(C)(C)C)ccc2[nH]1]

1-Ethyl-3-(3-dimethylaminopropyl)carbodiimide hydrochloride (90 mg, 0.47 mmol) was added to a stirred solution of (2R,3S)-3-((tert-butoxycarbonyl)amino)-3-(5-(tert-butyl)-1H-benzo[d]imidazol-2-yl)-2-methylpropanoic acid (Preparation 31, 140 mg, 0.39 mmol), N-methylmorpholine (0.10 mL, 0.78 mmol) in DMF (5 mL) at 0° C. The reaction mixture was stirred for 15 minutes at 0° C. and charged with solution of dimethylamine in THF (2M, 0.30 mL, 0.60 mmol). The reaction mixture was allowed to stay at −18° C. for 24 hours. The reaction mixture was recharged with solution of dimethylamine in THF (2M, 0.30 mL, 0.60 mmol) and stored at −18° C. for 72 hours. The reaction mixture was diluted with EtOAc (20 mL), washed with saturated sodium bicarbonate (2×10 mL). The organic layer was evaporated to dryness to afford the crude residue that had partially epimerised. The mixture of diastereoisomers was purified by silica gel column chromatography eluting with a gradient of Heptane/EtOAc to afford the pure diastereomer, that was dissolved in dioxane (1 mL). The solution was treated with 4M HCl in dioxane (2 mL) and the reaction was stirred at room temperature for 4 hours. The reaction was concentrated in vacuo, sonicated in ether for 30 minutes, filtered and dried to afford the title compound as the HCl salt (20 mg, 32%)

$^1$H NMR (400 MHz, CDCl₃): δ ppm 1.20 (d, 3H), 1.42 (s, 9H), 3.00 (s, 3H), 3.17 (s, 3H), 3.98 (m, 1H), 5.13 (d, 1H), 7.77 (m, 2H), 7.81 (s, 1H).

LCMS Rt=1.66 minutes MS m/z 303 [M+H]$^+$

Example 150

4-(2-(2-Amino-1-hydroxypropan-2-yl)-1H-benzo[d]imidazol-5-yl)-2-fluorobenzonitrile

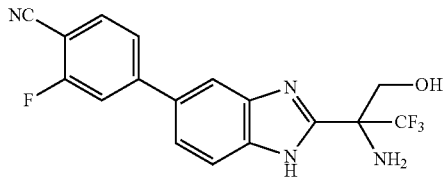 [SMILES: N#Cc1ccc(-c2ccc3[nH]c(C(N)(CO)C(F)(F)F)nc3c2)cc1F]

A solution of 4M hydrogen chloride in 1,4-dioxane (0.3 mL) was added to tert-butyl (2-(5-(4-cyano-3-fluorophenyl)-1H-benzo[d]imidazol-2-yl)-1-hydroxypropan-2-yl)carbamate (Preparation 10, 10 mg, 0.024 mmol) and stirred at room temperature for 30 minutes then concentrated in vacuo. The residue was triturated with anhydrous diethyl ether then dried under vacuum to give the product as a hydrochloric acid salt.

The product was dissolved in water, basified with 1N sodium hydroxide solution, extracted with ethyl acetate, dried over anhydrous sodium sulfate, filtered and concentrated. The residue was purified using silica gel column chromatography eluting with 0-10% methanol in dichloromethane followed by 0-70% chloroform/methanol/aqueous ammonium hydroxide solution (80/18/2) in dichloromethane to afford the title compound as a white solid (1 mg, 12%).

$^1$H NMR (300 MHz, DMSO-$d_6$): δ ppm 1.44 (s, 3H), 3.55 (d, 1H), 3.69 (d, 1H), 5.00 (br s, 1H), 7.61 (m, 2H), 7.79 (d, 1H), 7.84-8.05 (m, 3H).

LCMS Rt=0.98 minutes MS m/z 311 [M+H]$^+$

Example 151

(1R,2S)-1-(5-((3R,5R,7R)-Adamantan-1-yl)-1H-benzo[d]imidazol-2-yl)-1-aminopropan-2-yl carbamate

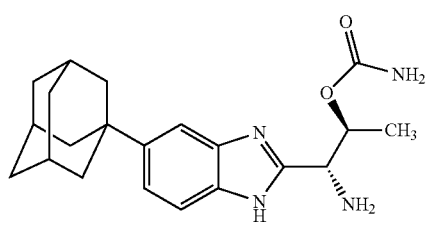 [SMILES: C[C@H](OC(N)=O)[C@H](N)c1nc2cc(C34CC5CC(CC(C5)C3)C4)ccc2[nH]1]

tert-Butyl ((1R,2S)-1-(6-((3R,5R,7R)-adamantan-1-yl)-1H-benzo[d]imidazol-2-yl)-2-(carbamoyloxy)propyl)carbamate (Preparation 7, 26 mg, 0.055 mmol) was placed in a reaction vial. A solution of 4M hydrogen chloride in 1,4-dioxane (0.75 mL) was added. The reaction mixture was stirred at room temperature for 1 hour then concentrated in vacuo to give the deprotected product. The product was triturated with anhydrous diethyl ether then dried under vacuum for 18 hours to afford the title compound as the hydrochloric acid salt (12 mg, 54%).

$^1$H NMR (300 MHz, DMSO-$d_6$): δ ppm 1.21 (d, 3H), 1.79 (m, 6H), 1.96 (m, 6H), 2.12 (m, 3H), 4.91 (d, 1H), 5.21 (m, 1H), 7.50 (d, 1H), 7.64 (s, 1H), 7.70 (d, 1H), 9.07 (br s, 3H).

LCMS Rt=1.21 minutes MS m/z 369 [M+H]$^+$

Example 152

(3S)-3-Amino-3-[5-(tricyclo[3.3.1.1$^{3,7}$]dec-1-yl)-1H-benzimidazol-2-yl]propanamide

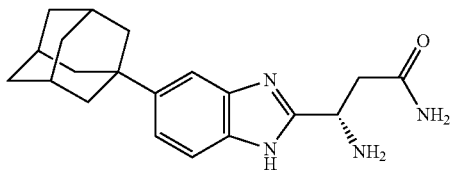 [SMILES: NC(=O)C[C@H](N)c1nc2cc(C34CC5CC(CC(C5)C3)C4)ccc2[nH]1]

Trifluoroacetic acid (3.2 mL, 41 mmol) was added to tert-butyl ((S)-1-(6-(3S,5S,7S)-adamantan-1-yl)-1H-benzo[d]imidazol-2-yl)-3-oxo-3-(tritylamino)propyl)carbamate (Preparation 8, 82 mg, 0.12 mmol) and stirred at room temperature for 2 hours. The reaction solution was concentrated in vacuo. The residue was dissolved in methanol and concentrated in vacuo, then dried under vacuum for 18 hours. The residue was dissolved in dimethyl sulfoxide, purified by preparative HPLC and lyophilized for 48 hours to afford the title compound as the trifluoroacetic acid salt (13 mg, 32%, white powder).

$^1$H NMR (300 MHz, DMSO-$d_6$): δ ppm 1.79 (m, 6H), 1.95 (m, 6H), 2.12 (m, 3H), 2.95 (dd, 2H), 4.88 (br s, 2H), 7.23 (s, 1H), 7.34 (dd, 1H), 7.51 (d, 1H), 7.56 (d, 1H), 7.70 (br s, 1H), 8.59 (br s, 2H).

LCMS Rt=1.20 minutes MS m/z 339 [M+H]$^+$

Example 153

4-{2-[(1R)-1-Amino-2-methoxyethyl]-1H-benzimidazol-5-yl}benzonitrile

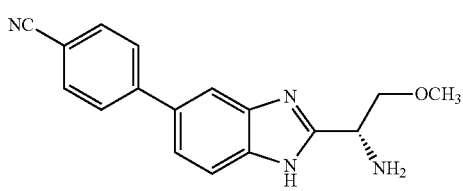 [SMILES: COC[C@H](N)c1nc2cc(-c3ccc(C#N)cc3)ccc2[nH]1]

The title compound was prepared according to Method 1 using N-Boc-O-methyl-serine and 3',4'-diaminobiphenyl-4-carbonitrile (Preparation 82).

$^1$H NMR (300 MHz, DMSO-$d_6$): δ ppm 3.25 (m, 3H), 3.50-3.70 (m, 2H), 4.20 (m, 1H), 7.50-7.60 (m, 2H), 7.80-7.90 (m, 5H).

LCMS Rt=1.25 minutes MS m/z 293 [M+H]$^+$

Example 154

4-{2-[(1R,2R)-1-Amino-2-hydroxypropyl]imidazo[1,2-a]pyridin-6-yl}benzonitrile

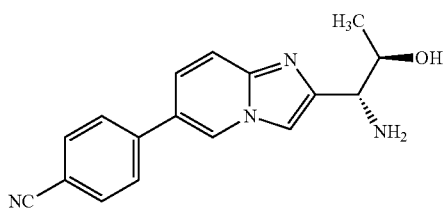 [SMILES: C[C@@H](O)[C@H](N)c1cn2cc(-c3ccc(C#N)cc3)ccc2n1]

A solution of tert-butyl (4S,5R)-4-(bromoacetyl)-2,2,5-trimethyl-1,3-oxazolidine-3-carboxylate (Preparation 58, 400 mg, 1.2 mmol) and 4-(6-aminopyridin-3-yl)benzonitrile (0.234 mg, 1.2 mol) in THF (5 mL) was heated to reflux for 18 hours. The reaction was filtered, concentrated in vacuo and purified using silica gel column chromatography eluting with 20-50% EtOAc in heptanes. The residue was dissolved in 4M HCl in dioxane (4 mL) and stirred at room temperature for 5 hours. The reaction was concentrated in vacuo and treated with 10% aqueous $K_2CO_3$ solution (6 mL) and stirred for 1 hour before extracting with EtOAc. The organic layer was dried over $Na_2SO_4$ and concentrated in vacuo. The residue was purified using preparative HPLC to afford the title compound as the formate salt.

$^1$H NMR (400 MHz, MeOD): δ ppm 1.18 (d, 3H), 4.18-4.25 (m, 2H), 7.70 (d, 1H), 7.73 (dd, 1H), 7.86-7.89 (br d, 4H), 8.02 (s, 1H), 8.50 (br s, 1H), 8.87 (s, 1H).

LCMS Rt=1.53 minutes MS m/z 293 [M+H]$^+$

Example 155

(2R)-2-Amino-2-(6-tert-butylimidazo[1,2-a]pyridin-2-yl)ethanol

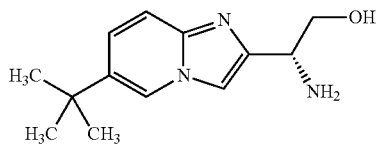 [SMILES: CC(C)(C)c1ccc2nc([C@@H](N)CO)cn2c1]

Cold conc HCl (0.5 mL) was added to tert-butyl [(1R)-2-(benzyloxy)-1-(6-tert-butylimidazo[1,2-a]pyridin-2-yl)ethyl]carbamate (Preparation 41, 15 mg, 0.035 mmol) at 0° C., and the reaction mixture was stirred at room temperature for 14 hours. The reaction was concentrated in vacuo and the residue was washed with diethyl ether and dried under vacuum to afford the title compound as the HCl salt (7 mg, 73%).

$^1$H NMR (400 MHz, MeOD): δ ppm 1.4 (s, 9H), 3.30 (m, 1H), 4.00-4.16 (m, 2H), 7.9 (d, 1H), 8.4 (d, 1H), 8.55 (s, 1H), 8.8 (s, 1H)

MS m/z 234 [M+H]$^+$

Example 156

(2R,3S)-3-Amino-3-[6-(4-cyanophenyl)imidazo[1,2-a]pyridin-2-yl]-2-methylpropanamide

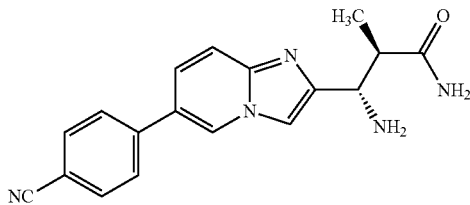 [SMILES: C[C@@H](C(N)=O)[C@H](N)c1cn2cc(-c3ccc(C#N)cc3)ccc2n1]

To a solution of benzyl (2R,3S)-3-[(tert-butoxycarbonyl)amino]-3-[6-(4-cyanophenyl)imidazo[1,2-a]pyridin-2-yl]-2-methylpropanoate (Preparation 42, 100 mg, 0.196 mmol) in THF/water (2.5 mL/0.5 mL) was added LiOH (6 mg, 0.250 mmol) and the reaction was stirred at room temperature for 18 hours. The reaction was quenched by the addition of saturated aqueous $KHSO_4$ solution to pH=5-6 and extracted with EtOAc. The organic layer was collected, dried over $MgSO_4$ and concentrated in vacuo. The residue was purified using silica gel column chromatography eluting with EtOAc. The residue was dissolved in dioxane (10 mL) and EDCI (72 mg, 0.31 mmol), HOBt (83 mg, 0.46 mmol) and NMM (62 mg, 0.62 mmol) were added and the reaction stirred for 1.5 hours. The reaction was cooled to 0° C. and 0.5M $NH_3$ in dioxane (1.86 mL) was added and the reaction continued stirring for 3 hours before concentrating in vacuo. The residue was purified using reverse phase column chromatography eluting with 0-60% MeCN in water. The residue was dissolved in 4M HCl in dioxane (1 mL) and stirred at room temperature for 3 hours. The reaction was quenched by the addition of saturated aqueous $NaHCO_3$ solution (10 mL) and extracted with 2-MeTHF (3×30 mL). The organic layers were combined, dried over $MgSO_4$ and concentrated in vacuo. The residue was purified by silica gel column chromatography eluting with DCM:MeOH:$NH_3$ 70:30:0.7 followed by preparative HPLC to afford the title compound as the formate salt.

$^1$H NMR (400 MHz, MeOD): δ ppm 1.18 (d, 3H), 3.13 (m, 1H), 4.57 (d, 1H), 7.72 (m, 2H), 7.83 (m, 3H), 8.01 (s, 1H), 8.43 (s, 1H), 8.88 (s, 1H).

LCMS Rt=2.02 minutes MS m/z 320 [M+H]$^+$

Example 157

(2R,3S)-3-Amino-3-(6-tert-butylimidazo[1,2-a]pyridin-2-yl)-2-methylpropanamide

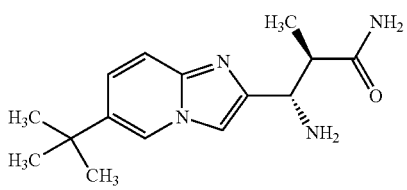 [SMILES: C[C@@H](C(N)=O)[C@H](N)c1cn2cc(C(C)(C)C)ccc2n1]

tert-Butyl((1S,2R)-3-amino-1-(6-(tert-butyl)imidazo[1,2-a]pyridin-2-yl)-2-methyl-3-oxopropyl)carbamate (Preparation 37, 311 mg) was dissolved in dichloromethane (ca 4 mL) and excess trifluoroacetic acid (ca 0.5 mL) was added. The reaction mixture was stirred for 18 hours then the solvent was removed in vacuo. The residue was dissolved in dichloromethane and washed with saturated aqueous sodium bicarbonate. The product stayed in the aqueous phase. The aqueous phase was adjusted to pH=10 with 1N sodium hydroxide, then sodium chloride was added until the solution was saturated. The aqueous phase was extracted three times with ethyl acetate. The combined organic phase was dried over anhydrous magnesium sulfate, filtered and the solvent removed in vacuo. The residue was purified by silica gel column chromatography eluting with 0-100% CMA80 in dichloromethane to afford 233 mg of the title compound as a white solid.

$^1$H NMR (400 MHz, DMSO-d$_6$): δ ppm 0.89 (d, 3H), 1.33 (s, 9H), 1.90 (br s, 2H), 2.66 (m, 1H), 3.93 (d, 1H), 6.77 (br s, 1H), 7.35 (dd, 1H), 7.40-7.49 (m, 2H), 7.72 (s, 1H), 8.38 (m, 1H).

LCMS Rt=0.36 minutes MS m/z 275 [M+H]$^+$

PREPARATIONS

Preparation 1 tert-Butyl [(1S,2R)-3-amino-1-(5-tert-butyl-1H-benzimidazol-2-yl)-2-($^{13}$CD$_3$-methyl-3-oxopropyl]carbamate (2R,3S)-3-[(tert-butoxycarbonyl)amino]-3-(5-tert-butyl-1H-benzimidazol-2-yl)-2-($^{13}$CD$_3$-methyl)propanoic acid (Preparation 2, 1.8 g, 4.74 mmol) was dissovled in anhydrous THF (35 mL) and cooled to −9° C. in a water-ice/acetone bath. To the reaction mixture under N$_2$ was added carbonyldiimidazole (0.92 g, 5.67 mmol). The reaction temperature continued to fall reaching −14° C. After 45 minutes at −15° C. the cooling bath was removed and temperature was allowed to rise to 15° C. over 30 minutes. Stirring was continued for another hour at room temperature and then the reaction was cooled to −11° C. Ammonium hydroxide (2.7 mL 23.7 mmol) was added rapidly followed by stirring for 1 hour at −12° C. Citric acid (0.5M, 40 mL) was added quickly over 1 minute. EtOAc (25 mL) was added, the ice bath was removed and stirring continued for 5 minutes. The organic layer was separated, and the aqueous layer was washed with EtOAc (3×25 mL). The combined organic layers were washed with brine, dried over sodium sulfate and concentrated in vacuo. The residue was purified using silica gel column chromatography eluting with 0-20% MeOH in DCM to afford the title compound as a white solid that was taken directly on to the next step (1.0 g, 56%).

Preparation 2

(2R,3S)-3-[(tert-Butoxycarbonyl)amino]-3-(5-tert-butyl-1H-benzimidazol-2-yl)-2-($^{13}$CD$_3$-methyl)propanoic acid To a solution of benzyl (2R,3S)-3-(1-benzyl-5-tert-butyl-1H-benzimidazol-2-yl)-3-[(tert-butoxycarbonyl)amino]-2-($^{13}$CD$_3$-methyl)propanoate (Preparation 3, 3.15 g, 5.6 mmol) in EtOH (35 mL) was added 10% Pd/C (700 mg) and the mixture hydrogenated at 40 psi for 18 hours followed by the addition of more catalyst (300 mg) and further hydrogenation for 24 hours. The reaction was filtered through celite and the filter cake washed with CH$_2$Cl$_2$/MeOH 1:1. The filtrate was concentrated in vacuo to afford the title compound as a white hard foam that was taken directly on to the next step (1.8 g, 85%).

Preparation 3

Benzyl (2R,3S)-3-(1-benzyl-5-tert-butyl-1H-benzimidazol-2-yl)-3-[(tert-butoxycarbonyl)amino]-2-($^{13}$CD$_3$-methyl)propanoate Benzyl (2S,3S)-3-(1-benzyl-5-tert-butyl-1H-benzimidazol-2-yl)-3-[(tert-butoxy-carbonyl)amino]-2-($^{13}$CD$_3$-methyl)propanoate (Preparation 4, 4.53 g, 8.1 mmol) was dissolved in anhydrous THF (58 mL), flushed with N$_2$ and cooled to −61° C. (internal temperature). KOtBu (25 mL, 1M in THF) was added drop-wise over 2 minutes. The internal temperature rose to −51° C. during the addition. The yellow solution was allowed to warm up to −30° C. over 55 minutes. The reaction was stirred for 2 hours maintaining the temperature between −41° C. and −29° C. The mixture was quenched at −31° C. with glacial acetic (2.3 mL) and the temperature of the reaction rose to approximately −20° C. The cooling bath was removed and water (50 mL) was added in one portion together with NaOH (1N, 17 mL) until pH=9. The organic layer was separated, and the aqueous layer washed with methyl tert-butyl ether (2×40 mL). The combined organic extracts were washed with brine, dried over sodium sulfate, filtered and the solvent removed under reduced pressure. The residue was purified by filtration through a celite pad eluting with EtOAc/Hexane 1:1 and 2:1 to afford the title compound that was taken directly on to the next step as a hard foam (3.15 g, 70%).

Preparation 4

Benzyl (2S,3S)-3-(1-benzyl-5-tert-butyl-1H-benzimidazol-2-yl)-3-[(tert-butoxycarbonyl)amino]-2-($^{13}$CD$_3$-methyl)propanoate Benzyl (3S)-3-(1-benzyl-5-tert-butyl-1H-benzimidazol-2-yl)-3-[(tert-butoxycarbonyl)amino]propanoate (Preparation 5, 2.2 g, 4.06 mmol) was dissolved in anhydrous THF (22 mL) under N$_2$. The reaction mixture was cooled to −55° C. and 1M LiHMDS in THF (10.5 mL) was added drop-wise over 2 minutes, maintaining a reaction temperature<−50° C. The reaction was stirred for 1 hour, over the first 15 minutes the reaction was allowed to warm up to −25° C., then cooled back to −50° C. followed by warming up to −27° C. over the next 25 minutes and cooling back to −40° C. Finally the reaction was cooled to −56° C. and $^{13}$CD$_3$I (1.0 g, 6.85 mmol) was added. The reaction was stirred between −45° C. and −55° C. for the next 2.5 hours. The reaction was quenched by the addition of glacial acetic acid (1.4 mL) followed by water (30 mL). The solution (pH=6) was extracted with t-butyl methyl ether (2×40 mL). The combined organic extracts were washed with brine and dried over sodium sulfate, filtered and the solvent removed under reduced pressure. The crude product was obtained as an amber oil and used without further purification (2.27 g, quant).

Preparation 5

Benzyl (3S)-3-(1-benzyl-5-tert-butyl-1H-benzimidazol-2-yl)-3-[(tert-butoxycarbonyl)amino]propanoate Step 1

A 100 mL reactor was charged with N-1-benzyl-4-tert-butylbenzene-1,2-diamine (Preparation 106, 7.254 g) and ethyl acetate (60 mL) and stirred for 5 minutes. The mixture was cooled to 15° C., then (S)-4-(benzyloxy)-2-(tert-butoxycarbonylamino)-4-oxobutanoic acid (9.218 g) and ethyl acetate (12.5 mL) were added. Triethylamine (5.16 mL) was added in one portion, followed by a solution of propylphosphonic anhydride (50 wt % in ethyl acetate, 22.1 mL) over 7 minutes. After 3 hours, water (24 mL) was added, the mixture is stirred for 20 minutes, then allowed to settle and the phases were separated. Water (24 mL) was added to the organic phase, the mixture was stirred for 20 minutes, then allowed to settle and the phases were separated. The organic layer was concentrated to low volume to give a concentrated ethyl acetate solution of (S)-benzyl-4-(2-benzylamino)-5-tert-butylphenylamino-3-(tert-butyxoycarbonylamino)-4-oxobutanoate.

$^1$H NMR (400 MHz, DMSO-d$_6$): δ ppm 1.18 (s, 9H), 1.38 (s, 9H), 2.74 (m, 1H), 2.92 (m, 1H), 4.30 (m, 2H), 4.52 (m, 1H), 5.10 (m, 2H), 5.38 (m, 1H), 6.42 (m, 1H), 6.97 (m, 1H), 7.06 (m, 1H), 7.20 (m, 1H), 7.27-7.39 (m, 10H), 9.36 (s, 1H).

Step 2

Acetonitrile (150 mL) was added to the concentrated ethyl acetate solution of (S)-benzyl 4-(2-benzylamino)-5-tert-butylphenylamino-3-(tert-butyxoycarbonylamino)-4-oxobutanoate prepared in the previous step. The solution was concentrated in vacuo until approximately 20% of the initial amount remained. Acetonitrile (58 mL) was added and the solution heated to 30° C. Water (15 mL) and trifluoroacetic acid (3.2 mL) were added. After 68 hours, the mixture was diluted with 2-methyltetrahydrofuran (160 mL). The organic phase was washed once with 7.5 w/w % sodium bicarborate in water (80 mL) and then once with water (80 mL). The final organic phase was concentrated in vacuo until approximately 25% of the initial amount remained. 2-Propanol (160 mL) was added, and the solution concentrated in vacuo until approximately 25% of the initial amount remained. Additional 2-propanol (77 mL) was added, followed by water (42 mL), and the mixture allowed to stir at room temperature. After 16 hours, the mixture was heated to 45° C. then cooled to room temperature. On cooling, crystallization commenced. After an additional 23 hours, water (28 mL) was added and the slurry allowed to stir for an additional 23 hours at room temperature. The slurry was filtered and the filter cake was washed once with 1:1 v/v 2-propanol:water (37.5 mL). The filter cake was dried by passing nitrogen gas through the cake for 2 hours to provide 9.530 g of the title compound.

$^1$H NMR (400 MHz, DMSO-d$_6$): δ ppm 1.26 (s, 9H), 1.32 (s, 9H), 2.99 (m, 1H), 3.38 (m, 1H), 5.07 (m, 2H), 5.40-5.45 (m, 2H), 5.54 (m, 1H), 7.14-7.27 (m, 12H), 7.59 (s, 1H), 7.72 (m, 1H).

Preparation 6 tert-Butyl ((1R,2S)-1-(5-((3R,5R,7R)-adamantan-1-yl)-1H-benzo[d]imidazol-2-yl)-2-hydroxypropyl)carbamate HATU (340 mg, 0.849 mmol) was added to a solution of (2S,3S)-2-((tert-butoxycarbonyl)amino)-3-hydroxybutanoic acid (Preparation 43, 186 mg, 0.849 mmol) in N,N-dimethylformamide (1.3 mL). The reaction solution was stirred for 10 minutes then a solution of 4-((3R,5R,7R)-adamantan-1-yl)benzene-1,2-diamine (Preparation 74, 137 mg, 0.28 mmol) in N,N-dimethylformamide (1.2 mL) was added and the reaction mixture was stirred at room temperature for 36 hours. Saturated sodium bicarbonate solution was added and the mixture was extracted with ethyl acetate (3×). The organic phases were combined, washed with brine, dried over anhydrous sodium sulfate, filtered, concentrated in vacuo and then dried under vacuum for 18 hours to afford the intermediate product as a brown thick oil.

A solution of the above intermediate in acetic acid (4.7 mL) was heated at 65° C. for 2 hours. Acetic acid was removed in vacuo and the residue partitioned between ethyl acetate and saturated sodium bicarbonate solution. The organic phase was separated and washed with brine, dried over anhydrous sodium sulfate, filtered, concentrated in vacuo and dried. The residue was purified using silica gel column chromatography eluting with 0% to 100% ethyl acetate in dichloromethane to afford the title compound (96 mg).

LCMS Rt=1.30 minutes MS m/z 426 [M+H]$^+$

Preparation 7 tert-Butyl ((1R,2S)-1-(5-((3R,5R,7R)-adamantan-1-yl)-1H-benzo[d]imidazol-2-yl)-2-(carbamoyloxy) propyl)carbamate Triethylamine (16 uL, 0.114 mmol) was added to a solution of the tert-butyl ((1R,2S)-1-(5-((3R,5R,7R)-adamantan-1-yl)-1H-benzo[d]imidazol-2-yl)-2-hydroxypropyl)carbamate (Preparation 6, 38 mg, 0.076 mmol) in dichloromethane (1 mL), followed by addition of the N,N'-disuccinimidylcarbonate (22.7 mg, 0.084 mmol). The reaction mixture was stirred at room temperature for 18 hours. The reaction solution was concentrated in vacuo then dried under vacuum to give the intermediate product.

Tetrahydrofuran (1.5 mL) was added to the above intermediate, followed by the addition of aqueous ammonium hydroxide solution (1.5 mL). The reaction mixture was stirred vigorously at room temperature for 2 hours. The organic layer was separated and the aqueous layer was extracted with ethyl acetate (2×). The organic layers were combined, washed with water (3×), brine, dried over anhydrous sodium sulfate, filtered and concentrated in vacuo. The residue was purified twice using silica gel column chromatography eluting with 0% to 100% ethyl acetate in dichloromethane and 1% to 5% methanol in dichloromethane to afford the title compound (26 mg) as an off white solid.

LCMS Rt=1.36 minutes MS m/z 469 [M+H]$^+$

Preparation 8 tert-Butyl ((S)-1-(5-((3S,5S,7S)-adamantan-1-yl)-1H-benzo[d]imidazol-2-yl)-3-oxo-3-(tritylamino) propyl)carbamate A mixture of (S)-tert-butyl (1-(5-bromo-1H-benzo[d]imidazol-2-yl)-3-oxo-3-(tritylamino)propyl)carbamate (Preparation 9, 525 mg, 0.839 mmol), [1,1-bis(diphenyl phosphino) ferrocene]dichloropalladium(II) (61 mg, 0.084 mmol) and 0.5 M 1-adamantylzinc bromide in tetrahydrofuran (3.4 mmol, 6.8 mL) was heated at 110° C. for 2 hours under microwave irradiation. The reaction solution was cooled to room temperature, quenched with water, diluted with ethyl acetate, washed with saturated sodium bicarbonate solution, brine, dried over anhydrous sodium sulphate and concentrated in vacuo. The residue was purified three times using silica gel column chromatography eluting with dichloromethane followed by 0% to 100% methanol/ethyl acetate (5/95) in dichloromethane for the first run, 0% to 50% ethyl acetate in dichloromethane for the second run, and dichloromethane/hexanes (1/1) to 0.35% methanol in dichloromethane/hexanes (1/1) for the third run to afford the title compound (82 mg).

LCMS Rt=1.54 minutes MS m/z 681 [M+H]$^+$

Preparation 9

(S)-tert-Butyl (1-(5-bromo-1H-benzo[d]imidazol-2-yl)-3-oxo-3-(tritylamino)propyl)carbamate To a solution of (S)-2-((tert-butoxycarbonyl)amino)-4-oxo-4-(tritylamino)butanoic acid (4.25 g, 8.96 mmol) in anhydrous tetrahydrofuran (20 mL, 200 mmol) cooled in an ice water bath was added 4-methylmorpholine (1.48 mL, 13.4 mmol) and isobutyl chloroformate (1.28 mL, 9.85 mmol). The reaction mixture was stirred for 1 hour at 0° C. and then 4-bromo-1,2-benzenediamine (1.68 g, 8.96 mmol) was added. The reaction mixture was allowed to warm to room temperature over 2 hours and stirred at room temperature for additional 2 hours. The reaction mixture was concentrated in vacuo and dried under vacuum for 18 hours to give the intermediate product.

Acetic acid (48 mL, 850 mmol) was added to the above intermediate and heated at 65° C. for 2 hours. The reaction solution was concentrated and the residue was taken up in ethyl acetate, washed with water, saturated sodium bicarbonate solution, brine, dried over anhydrous sodium sulfate, filtered and concentrated in vacuo to half of the original volume. A solid precipitated out during concentration and was collected by filtration to give 2.48 g of the title compound as a pale pink solid. The filtrate was concentrated onto celite and was purified using silica gel column chromatography eluting with 0% to 100% ethyl acetate in dichloromethane to afford additional compound (0.97 g, pale tan solid). A total of 3.45 g of the product was obtained.

LCMS Rt=1.47 minutes MS m/z 625 [M+H]$^+$

Preparation 10 tert-Butyl (2-(5-(4-cyano-3-fluorophenyl)-1H-benzo[d]imidazol-2-yl)-1-hydroxypropan-2-yl)carbamate A solution of 1-propylphosphonic anhydride (50% in ethyl acetate, 165 mg, 0.259 mmol) in N,N-dimethylformamide (0.5 mL) was added to a solution of the 2-((tert-butoxycarbonyl)amino)-3-hydroxy-2-methylpropanoic acid (Preparation 53, 52.2 mg, 0.238 mmol), 3',4'-diamino-3-fluoro-[1,1'-biphenyl]-4-carbonitrile (49 mg, 0.220 mmol) and triethylamine (106 uL, 0.756 mmol) in N,N-dimethylformamide (0.5 mL) and stirred at room temperature for 18 hours. The reaction mixture was diluted with water and extracted with ethyl acetate (3×). The combined organic extracts were washed successively with saturated sodium bicarbonate solution, 50% brine and saturated brine, dried over anhydrous sodium sulfate, filtered and concentrated in vacuo then dried under vacuum to give the crude intermediate product as a brown solid, which was used in the next step without further purification.

Acetic acid (1.6 mL) was added to the above intermediate and the resulting solution was heated at 65° C. for 2 hours. Acetic acid was removed in vacuo and the residue was partitioned between ethyl acetate and saturated sodium bicarbonate solution. The organic phase was separated and aqueous phase was extracted with ethyl acetate (2×). The combined organic phase was washed with water and brine, dried over anhydrous sodium sulfate, filtered and concentrated to give the crude final product, which was purified via silica gel column chromatography eluting with 0-100% ethyl acetate in dichloromethane. The product was purified again via silica gel column chromatography eluting with 0-5% methanol in dichloromethane to afford 10 mg of the pure product as a light yellow solid.

LCMS Rt=1.10 minutes MS m/z 411 [M+H]$^+$

Preparation 11

(S)-tert-Butyl (1-(5-bromo-1H-benzo[d]imidazol-2-yl)butyl)carbamate

To a solution of Boc-NVA-OH (4.5 g, 21 mmol) in acetonitrile (68 mL) and 4-methylmorpholine (2.41 mL, 21.9 mmol) cooled to –20° C. was added isobutyl chloroformate (2.7 mL, 21 mmol) dropwise. The mixture was stirred for 120 minutes at –20° C. and then 4-bromo-1,2-benzenediamine (3.87 g, 20.7 mmol) was added. The reaction mixture was allowed to warm to room temperature and stirred for 18 hours. The solvent was evaporated, redissolved in ethyl acetate, washed with water, saturated aqueous solution of sodium hydrogen carbonate, and brine. The organic layer was dried over anhydrous magnesium sulfate, filtered, and concentrated in vacuo. The resulting residue was dissolved in acetic acid (20 mL, 400 mmol) and stirred at 70° C. for 6 hours. The acetic acid was removed in vacuo and the mixture was redissolved in ethyl acetate, washed with saturated aqueous solution of sodium hydrogen carbonate, and brine. The organic layer was dried over anhydrous magnesium sulfate, filtered, and concentrated in vacuo. The resulting oil was redissolved in dichloromethane, treated with activated carbon and filtered through a plug of celite. Purification by silica gel column chromatography eluting with a 0-100% ethyl acetate/hexanes gradient to afford the title compound (5.95 g, 78%) as a white solid.

$^1$H NMR (400 MHz, CDCl$_3$): δ ppm 0.92 (t, 3H), 1.41 (m, 11H), 1.90 (m, 1H), 2.11 (m, 1H), 4.85 (m, 1H), 5.65 (m, 1H), 7.11 (m, 0.5H), 7.25 (m, 0.5H), 7.31 (m, 0.5H), 7.37 (m, 0.5H), 7.52 (m, 0.5H), 7.80 (m, 0.5H), 11.20 (m, 1H).

LCMS Rt=1.19 minutes MS m/z 366, 368 [$^{79}$Br, $^{81}$Br M+H]$^+$

Preparation 12

(R)-tert-Butyl (1-(5-(tert-butyl)-1H-benzo[d]imidazol-2-yl)-2-hydroxyethyl)carbamate (S)-2-((tert-Butoxycarbonyl)amino)-3-hydroxypropanoic acid (226 mg, 1.10 mmol) was dissolved in N,N-dimethylformamide (5 mL) and 1-[bis(dimethylamino)methylene]-1H-1,2,3-triazolo[4,5-b]pyridinium-3-oxid-hexafluorophosphate (440 mg, 1.10 mmol) was added. The reaction was stirred for 10 minutes then 4-(tert-butyl)benzene-1,2-diamine (164 mg, 1.00 mmol) was added and the reaction mixture stirred for 18 hours. The reaction mixture was diluted with water and extracted twice with ethyl ether. The combined organic phase was dried over anhydrous magnesium sulfate, filtered and the solvent removed in vacuo. The residue was dissolved in 1,2-dichloroethane and anhydrous magnesium sulfate was added. The reaction was stirred at 65° C. for 18 hours to complete the dehydration. The reaction mixture was filtered and loaded directly onto a 4 g silica gel column for purification. The column was eluted with 0-10% methanol in dichloromethane to afford 73 mg of product as a white solid.

$^1$H NMR (400 MHz, DMSO-d$_6$): δ ppm 1.33 (s, 9H), 1.40 (s, 9H), 3.72 (m, 2H), 4.76 (m, 1H), 4.95 (t, 1H), 7.03, (m, 1H), 7.21 (m, 1H), 7.34-7.52 (m, 2H), 11.95 (m, 1H).

LCMS Rt=1.03 minutes MS m/z 334 [M+H]$^+$

Preparation 13

Benzyl (3S)-3-amino-3-(5-tert-butyl-1H-benzimidazol-2-yl)-2,2-dimethylpropanoate The title compound was prepared according to Method 1 Steps 1 and 2 using (2S)-4-(benzyloxy)-2-[(tert-butoxycarbonyl)amino]-3,3-dimethyl-4-oxobutanoic acid (Preparation 44) and 4-tert-butyl-1,2-diaminobenzene.

$^1$H NMR (400 MHz, DMSO-$d_6$): δ ppm 1.20 (d, 6H), 1.30 (s, 9H), 5.08 (d, 2H), 5.27-5.31 (m, 1H), 7.15-7.34 (m, 7H), 7.36-7.40 (m, 1H), 7.42-7.51 (m, 1H), 12.02 (d, 1H).

Preparation 14

(S)-tert-Butyl (1-(5-bromo-1H-benzo[d]imidazol-2-yl)-3-oxo-3-(tritylamino)propyl)carbamate To a solution of Boc-Asn(Trt)-OH (1.05 g, 2.21 mmol) in anhydrous tetrahydrofuran (4 mL) cooled in an ice water bath was added 4-methylmorpholine (0.365 mL, 3.32 mmol) and isobutyl chloroformate (0.316 mL, 2.43 mmol). The reaction mixture was stirred for 1 hour at 0° C. and then 4-bromo-1, 2-benzenediamine (414 mg, 2.21 mmol) was added. The reaction mixture was allowed to warm to room temperature over 2 hours and then stirred an additional 2 hours. The reaction mixture was concentrated in vacuo and dried. To the resulting residue was added acetic acid (12 mL, 210 mmol) and the mixture stirred at 65° C. for 2 hours. The reaction was concentrated in vacuo and the residue taken up in ethyl acetate, washed with water, saturated aqueous sodium hydrogen carbonate solution, and brine. The organic layer was dried over anhydrous magnesium sulphate, filtered, and concentrated in vacuo to give crude product that was purified by silica gel column chromatography eluting with a 0-100% ethyl acetate/methylene chloride gradient. This provided the title compound (1.38 g, 61%) as a light tan solid.

LCMS Rt=1.54 minutes MS m/z 625, 627 [$^{79}$Br, $^{81}$Br, M+H]+

Preparation 15

(S)-tert-Butyl (1-(5-(2-chloro-4-cyanophenyl)-1H-benzo[d]imidazol-2-yl)-3-oxo-3-(tritylamino)propyl)carbamate A mixture of (S)-tert-butyl (1-(5-bromo-1H-benzo[d]imidazol-2-yl)-3-oxo-3-(tritylamino)propyl)carbamate (Preparation 14, 87 mg, 0.14 mmol), 2-chloro-4-cyanophenylboronic acid (34 mg, 0.19 mmol) and aqueous sodium carbonate solution (2M, 150 µL, 0.30 mmol) in 1,2-dimethoxyethane (0.95 mL) was sparged with argon three times, then tetrakis(triphenylphosphine)palladium(0) (8 mg, 0.007 mmol) was added. The reaction mixture was heated under microwave irradiation at 120° C. for 60 minutes. The reaction mixture was diluted with ethyl acetate, washed with water and brine, dried over anhydrous sodium sulphate, and concentrated in vacuo to give the crude product. The residue was purified using silica gel column chromatography eluting with a 0-100% ethyl acetate/hexanes gradient to afford the title compound (45 mg, 48%) as a pale tan solid.

LCMS Rt=1.30 minutes MS m/z 682 [M+H]+

Preparation 16

(S)-tert-Butyl (1-(5-neopentyl-1H-benzo[d]imidazol-2-yl)-3-oxo-3-(tritylamino)propyl)carbamate To a solution of Boc-Asn(Trt)-OH (101 mg, 0.213 mmol) in acetonitrile (2.0 mL) cooled in an ice water bath was added 4-methylmorpholine (0.059 mL, 0.53 mmol) and isobutyl chloroformate (0.027 mL, 0.21 mmol). After stirring for 45 minutes 4-neopentylbenzene-1,2-diamine (Preparation 83, 34 mg, 0.19 mmol) was added and the mixture allowed to warm to room temperature. After stirring for 2.5 hours, the reaction mixture was concentrated in vacuo and acetic acid (1.0 mL, 18 mmol) was added. The reaction was stirred for 18 hours, concentrated in vacuo, redissolved in ethyl acetate, washed with water, aqueous saturated sodium hydrogen carbonate solution, and brine. The organic layer was dried over anhydrous magnesium sulfate, filtered and concentrated in vacuo. The residue was purified by silica gel column chromatography eluting with a 0-100% ethyl acetate/hexanes gradient to afford the title compound (108 mg, 93%) as an offwhite solid that was taken directly on to the next step.

Preparation 17

(S)-tert-Butyl (1-(5-(4-cyano-3-fluorophenyl)-1H-benzo[d]imidazol-2-yl)-3-oxo-3-(tritylamino)propyl)carbamate To a solution of Boc-Asn(Trt)-OH (100.4 mg, 0.2116 mmol) in acetonitrile (2.0 mL) cooled in an ice water bath was added 4-methylmorpholine (0.059 mL, 0.53 mmol) and isobutyl chloroformate (0.027 mL, 0.21 mmol). After stirring for 60 minutes, 3',4'-diamino-3-fluoro-[1,1-biphenyl]-4-carbonitrile (Preparation 81, 42.7 mg, 0.188 mmol) was added and the mixture allowed to warm to room temperature. After stirring for 18 hours the reaction mixture was concentrated in vacuo and redissolved in acetic acid. After stirring at room temperature for 6.5 hours, the mixture was concentrated in vacuo, redissolved in ethyl acetate, washed with water, 0.5M HCl, and brine. The organic layer was dried over anhydrous magnesium sulphate, filtered, and concentrated in vacuo. The residue was purified using silica gel column chromatography eluting with a 0-100% ethyl acetate/hexanes gradient to afford the title compound (75 mg, 60%).

LCMS Rt=1.44 minutes MS m/z 666 [M+H]+

Preparation 18

(S)-tert-Butyl (1-(5-bromo-1H-benzo[d]imidazol-2-yl)propyl)carbamate

To a solution of Boc-Abu-OH (2.979 g, 14.66 mmol) in acetonitrile (50 mL) and 4-methylmorpholine (1.78 mL, 16.2 mmol) cooled to −20° C. was added isobutyl chloroformate (1.92 mL, 14.8 mmol) dropwise. The mixture was stirred for an additional 90 minutes at −20° C. and then 4-bromo-1,2-benzenediamine (2.86 g, 15.3 mmol) was added. The reaction mixture was allowed to warm to room temperature and stirred for 5 hours. The solvent was evaporated, redissolved in ethyl acetate, washed with water, saturated aqueous solution of sodium hydrogen carbonate, and brine. The organic layer was dried over anhydrous magnesium sulfate, filtered, and concentrated in vacuo. The resulting residue was dissolved in acetic acid (5.0 mL, 88 mmol) and stirred at room temperature for 18 hours. The acetic acid was removed in vacuo and purified by silica gel column chromatography eluting with a 0-100% ethyl acetate/hexanes gradient. The residue was recrystallised from a mixture of ethyl acetate/hexanes to afford the title compound (2.65 g, 51%) as a white solid.

$^1$H NMR (400 MHz, DMSO-$d_6$): δ ppm 1.05 (t, 3H), 1.44 (s, 9H), 2.02 (m, 1H), 2.26 (m, 1H), 4.76 (m, 1H), 5.30 (d, 1H), 7.24 (m, 0.5H), 7.36 (m, 1H), 7.53 (m, 0.5H), 7.60 (m, 0.5H), 7.91 (m, 0.5H).

LCMS Rt=1.03 minutes MS m/z 354, 356 [$^{79}$Br, $^{81}$Br, M+H]$^+$

Preparation 19

(S)-tert-Butyl (1-(6-bromo-1-(methoxymethyl)-1H-benzo[d]imidazol-2-yl)propyl)carbamate To a solution of (S)-tert-butyl (1-(6-bromo-1H-benzo[d]imidazol-2-yl)propyl)carbamate (Preparation 18, 0.97 g, 2.7 mmol) in N,N-dimethylformamide (10 mL) was added potassium carbonate (1.35 g, 9.77 mmol) and chloromethyl methyl ether (0.40 mL, 5.3 mmol), and the reaction was stirred at room temperature for 16 hours. The reaction was diluted with ethyl acetate and washed with water and brine. The organic layer was dried over MgSO$_4$, filtered, and concentrated in vacuo. The residue was purified by silica gel column chromatography eluting with a 0-100% ethyl acetate/hexanes gradient to afford the title compound (580 mg, 53%) as a white solid.

LCMS Rt=1.27 minutes MS m/z 398, 400 [$^{79}$Br, $^{81}$Br, M+H]$^+$

Preparation 20 tert-Butyl (2-(5-bromo-1H-benzo[d]imidazol-2-yl)-2,3-dihydro-1H-inden-2-yl)carbamate To a solution of N-Boc-2-aminoindane-2-carboxylic acid (3.30 g, 11.9 mmol) in N,N-dimethylformamide (15.0 mL) and 4-methylmorpholine (2.20 mL, 20.0 mmol) cooled to −20° C. was added a solution of isopropyl chloroformate in toluene (1.0 M, 20.0 mL, 20.0 mmol) dropwise over one hour. The mixture was stirred for an additional 60 minutes at −20° C. and then 4-bromo-1,2-benzenediamine (3.30 g, 17.6 mmol) was added. The reaction mixture was allowed to warm to room temperature for 18 hours. The solvent was evaporated, redissolved in ethyl acetate, washed with water, saturated aqueous solution of sodium hydrogen carbonate, and brine. The organic layer was dried over anhydrous magnesium sulphate, filtered, and concentrated in vacuo. The resulting residue was dissolved in acetic acid (20.0 mL, 352 mmol) and heated at 60° C. for 2 hours. After cooling, the solvent was removed in vacuo and then purified by silica gel column chromatography eluting with a 0-100% ethyl acetate/hexanes gradient to afford the title compound (3.05 g, 60%) as a brown solid.

$^1$H NMR (400 MHz, DMSO-d$_6$): δ ppm 1.44 (s, 9H), 3.60 (m, 2H), 3.93 (m, 2H), 5.41 (m, 1H), 7.21 (m, 6H), 7.31 (m, 1H).

LCMS Rt=1.24 minutes MS m/z 428, 430 [$^{79}$Br, $^{81}$Br, M+H]$^+$

Preparation 21 tert-Butyl (4R,5R)-4-(5-bromo-1H-benzimidazol-2-yl)-2,2,5-trimethyl-1,3-oxazolidine-3-carboxylate To a solution of (4S,5R)-3-(tert-butoxycarbonyl)-2,2,5-trimethyl-1,3-oxazolidine-4-carboxylic acid (Preparation 57, 15 g, 57.9 mmol) in DMF (100 mL) was added HATU (24.2 g, 63.7 mmol) and DIPEA (25.9 mL, 144.7 mmol) and the mixture allowed to stir for 10 minutes at 0° C. 4-bromophenyl-1,2-diamine (10.8 g, 57.9 mmol) was added and the reaction stirred at room temperature for 18 hours. The reaction was diluted with water and extracted with EtOAc. The organic layer was collected, dried over MgSO$_4$ and concentrated in vacuo. The residue was purified using silica gel column chromatography eluting with 15-20% EtOAc in petroleum ether and the resulting intermediate was dissolved in AcOH (100 mL) and heated to 50° C. for 16 hours. The reaction was concentrated in vacuo and diluted with water, basified with saturated aqueous Na$_2$CO$_3$ solution and extracted with EtOAc. The organic layer was collected, dried over Na$_2$SO$_4$ and concentrated in vacuo. The residue was triturated with diethyl ether to afford the title compound (11.7 g, 74%).

$^1$H NMR (400 MHz, DMSO-d$_6$): δ ppm 0.90 (s, 7H), 1.30 (d, 3H), 1.40 (s, 2H), 1.50-1.70 (m, 6H), 4.30 (br s, 1H), 4.50 (d, 1H), 7.30 (d, 1H), 7.50 (d, 1H), 7.80 (s, 1H), 12.60 (d, 1H).

Preparation 22 tert-Butyl [(1R,2R)-1-(5-bromo-1H-benzimidazol-2-yl)-2-methoxypropyl]carbamate

A solution of tert-butyl {(1S,2R)-1-[(2-amino-4-bromophenyl)carbamoyl]-2-methoxypropyl}carbamate (Preparation 23, 6.5 g, 16.17 mmol) in AcOH (5 mL) was stirred at room temperature for 3 days followed by 40° C. for 18 hours. The reaction was diluted by the addition of dioxane and concentrated in vacuo. The residue was purified using reverse phase column chromatography eluting with 0-40% acetonitrile in 0.1% formic acid in water to afford the title compound as a white solid (1.8 g, 29%).

$^1$H NMR (400 MHz, MeOD): δ ppm 1.18 (d, 3H), 1.55 (s, 9H), 3.27 (s, 3H), 3.87 (m, 1H), 4.87 (m, 1H), 7.52 (d, 1H), 7.65 (m, 1H), 7.88 (m, 1H).

Preparation 23 tert-Butyl {(1S,2R)-1-[(2-amino-4-bromophenyl)carbamoyl]-2-methoxypropyl}carbamate To a solution of N-(tert-butoxycarbonyl)-O-methyl-L-threonine (Preparation 51, 4 g, 17.15 mmol) in anhydrous THF (150 mL) was added NMM (2.43 g, 24.01 mmol) and isobutyl chloroformate (2.58 g, 18.86 mmol) at −78° C. and the reaction was stirred at this temperature for 1 hour. This solution was then added to a solution of 4-bromophenyl-1,2-diamine (3.85 g, 20.58 mmol) in THF (50 mL) at −78° C. and the reaction was stirred warming to room temperature for 18 hours. The reaction was quenched by the addition of water and extracted with EtOAc (3×50 mL). The organic layers were combined, dried over Na$_2$SO$_4$ and concentrated in vacuo. The residue was purified using reverse phase column chromatography eluting with 0-60% acetonitrile in 0.1% formic acid in water to afford the title compound (6.60 g, 96%).

$^1$H NMR (400 MHz, MeOD): δ ppm 0.95-1.20 (m, 3H), 1.45 (s, 9H), 3.38 (s, 3H), 3.85 (m, 1H), 4.20 (m, 1H), 6.60-7.20 (m, 3H).

Preparation 24 tert-Butyl [(1R,2S)-1-(5-tert-butyl-1H-benzimidazol-2-yl)-2-hydroxypropyl]carbamate N-Boc-L-allo-threonine (Preparation 54, 67.12 g, 306 mmol), 4-tert-butyl-diaminobenzene (60.3 g, 367 mmol) and HOBt (56.3 g, 367 mmol) were dissolved in DMF (500 mL). NMM (67 mL, 612 mmol) was added and the mixture cooled to 0° C. EDCI (65.6 g, 336 mmol) was added portionwise over 1.5 hours and the reaction was stirred at room temperature for 18 hours. EtOAc (2 L) was added followed by water (10 and the mixture stirred vigorously for 15 minutes. The aqueous layer was removed and washed further with EtOAc (2×30 mL). The organic layers were combined, dried over Na$_2$SO$_4$ and concentrated in vacuo. The residue was sonicated in pentane/DCM 10/1 twice and filtered to afford a pale pink solid that was dissolved in AcOH (500 mL) and stirred at 40° C. for 24 hours followed by room temperature for 2 days. The solvent was removed in vacuo and the residue dissolved in EtOAc (1.5 L). Saturated aqueous NaHCO$_3$ (500 mL) was added and the mixture stirred vigorously. The organic layer was collected, washed with NaHCO$_3$ solution (2×200 mL), dried over Na$_2$SO$_4$ and concentrated in vacuo. The residue was dissolved in DCM (500 mL) and purified using silica gel column chromatography eluting with 0-20% acetone in cyclohexaneto afford the title compound as an off-white solid (89 g, quant).

$^1$H NMR (400 MHz, MeOD): δ ppm 1.17 (d, 3H), 1.40 (s, 9H), 1.43 (s, 9H), 4.17 (m, 1H), 4.80 (m, 1H), 7.30 (m, 1H), 7.45 (m, 1H), 7.55 (m, 1H).

LCMS Rt=1.87 minutes MS m/z 348 [M+H]$^+$

Preparation 25 tert-Butyl [(1R,2R)-1-(5-tert-butyl-1H-benzimidazol-2-yl)-2-hydroxypropyl]carbamate The title compound was prepared according to Method 4 Steps 1 and 2 using N-Boc-L-threonine (Preparation 52) and 4-tert-butyl-diaminobenzene.

$^1$H NMR (400 MHz, CDCl$_3$): δ ppm 1.33 (d, 3H), 1.38 (s, 9H), 1.45 (s, 9H), 4.64-4.73 (m, 3H), 5.61 (d, 1H), 7.35 (d, 1H), 7.43-7.64 (m, 2H).

LCMS Rt=1.90 minutes MS m/z 348 [M+H]$^+$

Preparation 26 tert-Butyl [(1S)-1-(5-tert-butyl-1H-benzimidazol-2-yl)-2-hydroxy-1-methylethyl]carbamate and tert-butyl [(1R)-1-(5-tert-butyl-1H-benzimidazol-2-yl)-2-hydroxy-1-methylethyl]carbamate and To a stirred solution of Rac-N-Boc-2-methylserine (Preparation 53, 700 mg, 3.19 mmol) in dioxane (30 mL) was added 4-tert-butyl-1,2-diaminobenzene (787 mg, 4.79 mmol), T3P (2130 mg, 3.35 mmol) and TEA (0.89 mL, 6.39 mmol) and the reaction heated to 100° C. for 4 hours. The reaction was cooled and partitioned between EtOAc and saturated aqueous NaHCO$_3$ solution. The organic layer was collected and concentrated in vacuo. The residue was first purified using silica gel column chromatography eluting with 2/8 to 0/1 heptane in TBDME followed by chiral separation using a Chiralpak-IC column, 220 nM eluting with heptanes:iPrOH 80:20 to afford two enantiomers:
Peak 1: 11.24 minutes, 89% ee
Peak 2: 16.94 minutes, 99% ee.
Peak 1 was taken through to the next step and assumed (S).

Preparation 27

Benzyl [1-(5-bromo-1H-benzimidazol-2-yl)-1-methylethyl]carbamate

A solution of benzyl {2-[(2-amino-5-bromophenyl)amino]-1,1-dimethyl-2-oxoethyl}carbamate (Preparation 28, 80 g, 0.2 mol) and p-TsOH (34 g, 0.2 mol) in anhydrous MeOH (1 L) was heated to reflux for 48 hours. The reaction was cooled, concentrated in vacuo and partitioned between DCM (1 L) and water (500 mL). The organic layer was collected, washed with water (200 mL), brine (200 mL), dried over Na$_2$SO$_4$ and concentrated to low volume to enable the precipitation of a yellow solid. The solid was collected and dried to afford the title compound (18 g, 23%).

$^1$H NMR (400 MHz, DMSO-d$_6$): δ ppm 1.61 (s, 6H), 4.93 (br s, 2H), 7.24-7.81 (br m, 8H), 12.32 (br s, 1H).

Preparation 28

Benzyl {2-[(2-amino-5-bromophenyl)amino]-1,1-dimethyl-2-oxoethyl}carbamate

To a stirred solution of N-[(benzyloxy)carbonyl]-2-methylalanine (Preparation 56, 35 g, 0.15 mmol) in DCM (600 mL) was added HOBt (25 g, 0.18 mmol) followed by EDCI.HCl (35.5 g, 0.18 mmol) and the reaction stirred at room temperature for 30 minutes. 4-Bromobenzene-1,2-diamine (30.7 g, 0.16 mmol) was added and the reaction heated to reflux for 24 hours. The reaction was cooled and poured into water (500 mL). The organic layer was separated, washed with water (200 mL), brine (100 mL) dried over Na$_2$SO$_4$ and concentrated in vacuo. The residue was purified using silica gel column chromatography to afford the title compound as a brown solid that was taken directly on to the next step (80 g, 66%).

Preparation 29 tert-Butyl [(1S)-3-amino-1-(5-tert-butyl-1H-benzimidazol-2-yl)-2-methyl-3-oxopropyl]carbamate A mixture of (3S)-3-[(tert-butoxycarbonyl)amino]-3-(5-tert-butyl-1H-benzimidazol-2-yl)-2-methylpropanoic acid (Preparation 30, 7.25 g, 19.33 mmol), Boc$_2$O (5.9 g, 27.0 mmol), pyridine (1 mL) and NaHCO$_3$ (2 g, 25 mmol) in THF/DMF (200 mL/100 mL) was stirred at room temperature for 18 hours. 0.5M Ammonia in dioxane (150 mL) was added and the reaction continued stirring at room temperature for a further 18 hours. The reaction was concentrated to dryness and diluted with saturated aqueous NaHCO$_3$ solution. The solution was extracted with 2-MethylTHF and concentrated in vacuo. The residue was purified using reverse phase column chromatography eluting with 5-70% acetonitrile in 0.1% formic acid in water to afford the title compound as a mixture of diastereomers (3 g, 43%).

LCMS Rt=2.20 minutes MS m/z 375 [M+H]$^+$

Preparation 30

(3S)-3-[(tert-Butoxycarbonyl)amino]-3-(5-tert-butyl-1H-benzimidazol-2-yl)-2-methylpropanoic acid A mixture of methyl (3S)-3-[(tert-butoxycarbonyl)amino]-3-(5-tert-butyl-1H-benzimidazol-2-yl)-2-methylpropanoate (Preparation 33, 7.25 g, 18.65 mmol) and lithium hydroxide (0.67 g, 27.95 mmol) in THF and water (100 mL/10 mL) was stirred at room temperature for 18 hours. The THF was evaporated and the remaining aqueous solution was diluted with water (100 mL). A solution of KHSO$_4$ in water was added resulting in a white precipitate. The solid was filtered and dried to afford the title compound that was taken directly on to the next step.

Preparation 31

(2R,3S)-3-((tert-Butoxycarbonyl)amino)-3-(5-(tert-butyl)-1H-benzo[d]imidazol-2-yl)-2-methylpropanoic acid To a cooled solution (−78° C.) of (2S,3R)-4-(benzyloxy)-2-((tert-butoxycarbonyl)amino)-3-methyl-4-oxobutanoic acid (Preparation 66, 4.10 g, 12.2 mmol) in tetrahydrofuran (50 mL) was added N-methylmorpholine (2.0 mL, 18.23 mmol) followed by isobutyl chloroformate (1.67 mL, 12.8 mmol) and the resulting white suspension stirred at −78° C. for 30 minutes. A solution of 4-(tert-butyl)benzene-1,2-diamine (2.40 g, 14.6 mmol) in tetrahydrofuran (5 mL) was added. The reaction mixture was allowed to warm up to room temperature and stirred at room temperature for 1 hour. The reaction mixture was concentrated in vacuo. The crude product was dissolved in ethyl acetate (200 mL) and washed with aqueous saturated sodium bicarbonate (3×50 mL), water (2×50 mL). The organic layer was concentrated in vacuo and purified by silica gel column chromatography eluting with a gradient of dichloromethane: EtOAc. The residue was dissolved in methanol (50 mL) and palladium hydroxide was added (20% wt % on carbon, 0.43 g). The reaction mixture was stirred under a hydrogen atmosphere (2 atm) at room temperature for 1 hour. The reaction mixture was filtered through a small pad of Arbocel and concentrated in vacuo. The residue was dissolved in acetic acid (100 mL) and stirred at room temperature for 72 hours. The reaction mixture was concentrated in vacuo. The crude product was purified by reverse phase column chromatography eluting with a gradient of water/MeCN to afford the title compound as off-white solid (3.54 g, 78%).

$^1$H NMR (400 MHz, CDCl$_3$): δ ppm 1.13 (d, 3H), 1.26 (s, 9H), 1.37 (s, 9H), 3.41 (m, 1H), 5.40 (br. s, 1H), 5.54 (m, 1H), 7.08 (m, 1H), 7.40 (m, 1H), 7.58 (m, 1H), 7.62 (s, 1H)

LCMS (system 1, acidic, 4.5 min): Rt=2.09 minutes MS m/z 376 [M+H]$^+$

Preparation 32

(2R,3S)-3-[(tert-Butoxycarbonyl)amino]-3-[5-(4-cyano-3-fluorophenyl)-1H-benzimidazol-2-yl]-2-methylpropanoic acid The title compound was prepared according to the method described for Preparation 30 using benzyl (2R,3S)-3-[(tert-butoxycarbonyl)amino]-3-[5-(4-cyano-3-fluorophenyl)-1H-benzimidazol-2-yl]-2-methylpropanoate (Preparation 34), (163 mg, 84%).

$^1$H NMR (400 MHz, MeOD): δ ppm 1.25 (d, 3H), 1.46 (s, 9H), 3.30 (m, 1H), 5.14 (d, 1H), 7.57-7.60 (m, 1H), 7.64-7.69 (m, 3H), 7.78-7.82 (m, 1H), 7.86 (m, 1H).

LCMS Rt=2.39 minutes MS m/z 439 [M+H]$^+$

Preparation 33

Methyl (3S)-3-[(tert-butoxycarbonyl)amino]-3-(5-tert-butyl-1H-benzimidazol-2-yl)-2-methylpropanoate A solution of (2S)-2-[(tert-butoxycarbonyl)amino]-4-methoxy-3-methyl-4-oxobutanoic acid (Preparation 62, 8.45 g, 32.3 mmol) in THF (300 mL) was cooled to −78° C. and NMM (5.3 mL, 48.5 mmol) was added followed by a solution of isobutylchloroformate (4.44 mL, 34 mmol) in THF (20 mL) dropwise over 30 minutes. The resulting solution was added to a solution of 4-tert-butyl-1,2-diaminobenzene (5.95 g, 36.22 mmol) in THF (100 mL) via cannula at −78° C. The reaction was stirred at −78° C. for 1 hour, then allowed to warm to room temperature for 3 hours. The reaction was concentrated in vacuo and diluted with EtOAc (300 mL). The solution was washed with saturated aqueous NaHCO$_3$ solution (2×100 mL), brine (3×100 mL), dried over Na$_2$SO$_4$ and concentrated in vacuo. The residue was dissolved in AcOH (150 mL) and stirred at room temperature for 4 days. The reaction was evaporated to dryness azeotroping with dioxane. The residue was purified using reverse phase column chromatography eluting with 5-40% MeCN in 0.1% formic acid in water. The acetonitrile was evaporated and the remaining aqueous solution was basified with saturated aqueous NaHCO$_3$ solution. The product was extracted with EtOAc, dried over Na$_2$SO$_4$ and concentrated in vacuo. The crude residue was purified using silica gel column chromatography eluting with DCM/TBME 9/1 to afford the title compound as a yellow solid (7.25 g, 58%).

$^1$H NMR (400 MHz, CDCl$_3$): δ ppm 1.10-1.55 (m, 21H), 3.25 and 3.52 (m, 1H, diastereomers 1:2 ratio), 3.65 and 3.72 (s, 3H, diastereomers 1:2 ratio), 5.18 and 5.21 (m, 1H, diastereomers 1:2 ratio), 5.60 and 6.25 (m, 1H, diastereomers 1:2 ratio), 7.28-7.80 (m, 3H).

LCMS Rt=2.59 minutes MS m/z 390 [M+H]$^+$

Preparation 34

Benzyl (2R,3S)-3-[(tert-butoxycarbonyl)amino]-3-[5-(4-cyano-3-fluorophenyl)-1H-benzimidazol-2-yl]-2-methylpropanoate To a solution of (2S)-4-(benzyloxy)-2-[(tert-butoxycarbonyl)amino]-3-methyl-4-oxobutanoic acid (Preparation 66, 713 mg, 2.11 mmol) in DMF (15 mL) was added NMM (267 mg, 2.64 mmol) and the mixture was cooled to 0° C. HATU (871 mg, 2.29 mmol) was added and the reaction stirred warming to room temperature for 2 hours. 3',4'-diamino-3-fluoro-[1,1'-biphenyl]-4-carbonitrile (Preparation 81, 400 mg, 1.76 mmol) was added and the reaction stirred at room temperature for 18 hours. The reaction was diluted with water and extracted with EtOAc. The organic layer was collected, dried over Na$_2$SO$_4$ and concentrated in vacuo. The residue was purified using silica gel column chromatography eluting with 20-40% EtOAc in heptanes. The residue was dissolved in AcOH (10 mL) and heated to 40° C. for 2 days. The reaction was cooled and concentrated in vacuo, azeotroping with DCM to afford a foam. The residue was purified using silica gel column chromatography eluting with DCM:EtOAc 94:6 to afford the title compound.

$^1$H NMR (400 MHz, MeOD): δ ppm 1.25 (d, 3H), 1.46 (s, 9H), 3.39 (m, 1H), 5.08 (m, 2H), 5.18 (m, 1H), 7.17-7.20 (m, 3H), 7.59-7.84 (m, 3H).

Preparation 35 tert-Butyl [(1S)-4-(benzyloxy)-1-(5-tert-butyl-1H-benzimidazol-2-yl)butyl]carbamate The title compound was prepared according to Method 4 Steps 1 and 2 using 5-(benzyloxy)-N-(tert-butoxycarbonyl)-L-norvaline and 4-tert-butyl-1,2-diaminobenzene. The crude product was purified by silica gel column chromatography eluting with 30-40% EtOAc in petroleum ether (430 mg, 52%).

$^1$H NMR (300 MHz, DMSO-d$_6$): δ ppm 1.32 (s, 9H), 1.40 (s, 9H), 1.43-1.65 (m, 2H), 1.76-1.90 (m, 1H), 1.95-2.05 (m, 1H), 3.43 (t, 2H), 4.42 (s, 2H), 4.70-4.80 (m, 1H), 7.18-7.35 (m, 7H), 7.40 (s, 1H), 7.45 (d, 1H), 11.98 (d, 1H).
MS m/z 452 [M+H]+

Preparation 36

Benzyl (3S)-3-[(tert-butoxycarbonyl)amino]-3-(5-isopropyl-1H-benzimidazol-2-yl)propanoate The title compound was prepared according to Method 4 Steps 1 and 2 using 4-(1-methylethyl)-1,2-benzenediamine and N-boc-L-asp-4-benzyl ester and used directly in the next reaction.

Preparation 37 tert-Butyl ((1S,2R)-3-amino-1-(6-(tert-butyl)imidazo [1,2-a]pyridin-2-yl)-2-methyl-3-oxopropyl)carbamate (2S,3R)-tert-butyl 2-(6-(tert-butyl)imidazo[1,2-a]pyridin-2-yl)-3-methyl-4-oxoazetidine-1-carboxylate (Preparation 38) was dissolved in THF (10 mL) and excess 28% aqueous ammonium hydroxide solution (ca 3 mL) added. The reaction was stirred in a sealed vial at 50° C. for 18 hours. The solvent was removed in vacuo to afford 311 mg of the title compound.
LCMS Rt=0.98 minutes MS m/z 375 [M+H]+

Preparation 38

(2S,3R)-tert-Butyl 2-(6-(tert-butyl)imidazo[1,2-a] pyridin-2-yl)-3-methyl-4-oxoazetidine-1-carboxylate (3R,4S)-4-(6-(tert-butyl)imidazo[1,2-a]pyridin-2-yl)-3-methylazetidin-2-one (Preparation 39) was dissolved in THF (15 mL) and 4-dimethylaminopyridine (89 mg, 0.71 mmol) was added, followed by excess di-tert-butyl dicarbonate (1560 mg, 7.14 mmol) and triethylamine (721 mg, 7.14 mmol). The reaction mixture was stirred for 4 hours at ambient temperature then the solvent removed in vacuo. The residue was purified by silica gel column chromatography eluting with 0-100% ethyl acetate in hexanes to afford the title compound.
LCMS Rt=1.04 minutes MS m/z 358 [M+H]+

Preparation 39

(3R,4S)-4-(6-(tert-Butyl)imidazo[1,2-a]pyridin-2-yl)-3-methylazetidin-2-one (3R,4S)-4-(6-(tert-butyl)imidazo[1,2-a]pyridin-2-yl)-1-(tert-butyldimethylsilyl)-3-methylazetidin-2-one (Preparation 40) was dissolved in THF and 1 M tetrabutylammonium fluoride in THF (3 mL, 10 mmol) was added. The reaction mixture was stirred for 2 hours then the solvent was removed in vacuo. The intermediate was purified by silica gel column chromatography eluting with 0-100% CMA80 in dichloromethane to afford the title compound.
LCMS Rt=0.37 minutes MS m/z 258 [M+H]+

Preparation 40

(3R,4S)-4-(6-(tert-Butyl)imidazo[1,2-a]pyridin-2-yl)-1-(tert-butyldimethylsilyl)-3-methylazetidin-2-one (3R,4S)-4-(2-bromoacetyl)-1-(tert-butyldimethylsilyl)-3-methylazetidin-2-one (Preparation 72, 1144 mg, 3.57 mmol) and 5-(tert-butyl)pyridin-2-amine (537 mg, 3.57 mmol) were mixed in acetonitrile (10 mL) and the reaction mixture stirred for 18 hours at room temperature, then an additional 18 hours at 65° C. to complete the dehydration. The reaction solvent was removed in vacuo and the residue was purified by silica gel column chromatography eluting with 0-100% ethyl acetate in hexanes to afford the title compound which was immediately taken to the next step.
LCMS Rt=0.99 minutes MS m/z 372 [M+H]+

Preparation 41 tert-Butyl [(1R)-2-(benzyloxy)-1-(6-tert-butylimidazo[1,2-a]pyridin-2-yl)ethyl]carbamate A mixture of tert-butyl {(1S)-1-[(benzyloxy)methyl]-3-bromo-2-oxopropyl}carbamate (3.72 g, 10.0 mmol) and 2-amino-6-tert-butylpyridine (1.5 g, 10.0 mmol) in toluene (50 mL) was stirred at room temperature for 14 hours and then refluxed for 5 hours. The reaction mixture was cooled and concentrated in vacuo. The crude product was purified by silica gel column chromatography eluting with 30% EtOAc in petroleum ether. The residue was treated with cold conc. HCl (5 mL) at 0° C. followed by stirring at room temperature for 18 hours. The reaction mixture was basified with saturated aqueous $Na_2CO_3$ solution, extracted with EtOAc, dried over $Na_2SO_4$ and concentrated in vacuo to afford a residue which was purified further by preparative TLC eluting with 20% MeOH in EtOAc to afford the title compound (21 mg, 25%).
MS m/z 234 [M+H]+

Preparation 42

Benzyl (2R,3S)-3-[(tert-butoxycarbonyl)amino]-3-[6-(4-cyanophenyl)imidazo[1,2-a]pyridin-2-yl]-2-methylpropanoate To a solution of benzyl (2R,3S)-5-bromo-3-[(tert-butoxycarbonyl)amino]-2-methyl-4-oxopentanoate (Preparation 65, 400 mg, 0.966 mmol) in THF (15 mL) was added 4-(6-aminopyridin-3-yl)benzonitrile and the reaction stirred at room temperature for 3 days followed by 40° C. for 18 hours. The reaction was diluted with saturated aqueous $NaHCO_3$ solution (80 mL), and extracted with EtOAc (3×50 mL). The organic layers were collected, dried over $MgSO_4$ and concentrated in vacuo. The residue was purified by reverse phase column chromatography eluting with 0-60% MeCN in water followed by silica gel column chromatography eluting with 40% EtOAc in heptanes to afford the title compound.
$^1$H NMR (400 MHz, $CDCl_3$): δ ppm 1.23 (d, 3H), 1.45 (s, 9H), 3.44 (m, 1H), 5.00 (s, 1H), 5.18 (m, 2H), 6.00 (d, 1H), 7.20 (m, 4H), 7.42 (m, 2H), 7.60 (m, 3H), 7.82 (d, 2H), 8.18 (s, 1H).

Preparation 43

(2S,3S)-2-((tert-Butoxycarbonyl)amino)-3-hydroxybutanoic acid

Di-tert-butyldicarbonate (550 mg, 2.52 mmol) was added to a mixture of L-allo-threonine (250 mg, 2.10 mmol) and sodium bicarbonate (529 mg, 6.30 mmol) in methanol (2.5 mL) and water (2.5 mL) at 0° C. The reaction mixture was then allowed to warm to room temperature and stirred at room temperature for 18 hours. The reaction mixture was concentrated to remove methanol and the residual aqueous phase was acidified with 6N hydrochloric acid solution (pH 3~4), extracted with ether (3×), the organic phases were combined and washed with water and brine, dried over anhydrous sodium sulfate, filtered and concentrated in vacuo, then dried under vacuum for 24 hours to afford the title compound (304 mg) as a white solid.

LCMS Rt=0.36 minutes MS m/z 220 [M+H]$^+$ MS m/z 218 [M−H]−

Preparation 44

(2S)-4-(Benzyloxy)-2-[(tert-butoxycarbonyl)amino]-3,3-dimethyl-4-oxobutanoic acid To a solution of 4-benzyl 1-methyl N-(tert-butoxycarbonyl)-3,3-dimethyl-L-aspartate (Preparation 45, 2 g, 5.47 mmol) in MeCN (30 mL) and water (0.6 mL) was added triethylamine (2.3 mL, 16.41 mmol) followed by LiBr (4.75 g, 54.73 mmol). The reaction mixture was stirred at room temperature for 3 days. The reaction was acidified with 1N HCl and extracted with ethyl acetate. The organic layer was dried over sodium sulphate and concentrated in vacuo to afford the title compound that was used directly in the next step (1.5 g).

$^1$H NMR (400 MHz, DMSO-d$_6$): δ ppm 1.2 (s, 6H), 1.36 (s, 9H), 4.6 (d, 1H), 5.00-5.15 (m, 2H), 7.1 (d, 1H), 7.22-7.40 (m, 5H), 12.82 (br s, 1H).

Preparation 45

4-Benzyl 1-methyl N-(tert-butoxycarbonyl)-3,3-dimethyl-L-aspartate

1M LiHMDS in THF (111 mL, 111.12 mmol) was added to 4-benzyl 1-methyl N-(tert-butoxycarbonyl)-L-aspartate (Preparation 46, 7.5 g, 22.23 mmol) in THF (500 mL) at −78° C. and stirred for 2 hours under nitrogen. The solution was treated with MeI (5.5 mL, 88.92 mmol) and the reaction stirred at −78° C. for a further 1 hour followed by room temperature for 18 hours. The solution was quenched with saturated aqueous NH$_4$Cl solution and extracted with EtOAc. The organic layer was dried over sodium sulphate and concentrated in vacuo. The residue was purified using preparative HPLC to afford the title compound (2.5 g, 31%).

LCMS (7 minute run) Rt=4.59 minutes MS m/z 266 [M-Boc+H]$^+$

Preparation 46

4-Benzyl 1-methyl N-(tert-butoxycarbonyl)-L-aspartate

Anhydrous K$_2$CO$_3$ (10.2 g, 74.22 mmol) and methyl iodide (4.6 mL, 74.22 mmol) were added to a solution of Boc-D-Asp-OBzl ester (8 g, 24.741.8 mol) in acetone (150 mL) and stirred at room temperature for 16 hours. The reaction mixture was concentrated in vacuo, triturated with dichloromethane and the filtrate was concentrated to afford the title compound that was taken directly on to the next step (7.5 g, 89%).

Preparation 47

(3R)-3-Acetoxy-1-(tert-butoxycarbonyl)-L-proline

Pyridine (5 mL) and acetic anhydride (2 mL) were added to N-boc-cis-3-hydroxy-L-proline (400 mg, 1.73 mmol) and the reaction was stirred for 4 hours at room temperature. The reaction was diluted with water, acidified with 1N HCl and extracted with EtOAc. The organic layer was dried over anhydrous Na$_2$SO$_4$ and concentrated under reduced pressure to afford the title compound (370 mg, 78%).

$^1$H NMR (400 MHz, DMSO-d$_6$): δ ppm 1.34 (d, 9H), 1.83-1.98 (m, 4H), 2.05-2.20 (m, 1H), 3.25-3.44 (m, 2H), 4.3 (d, 1H), 5.34-5.42 (m, 1H), 12.7 (br s, 1H).

Preparation 48

(4R)-3-(tert-Butoxycarbonyl)-2,2-dimethyl-1,3-oxazepane-4-carboxylic acid

Wet 5% Pd/C (400 mg) was added to a solution of 4-benzyl 3-tert-butyl (4R)-2,2-dimethyl-1,3-oxazepane-3,4-dicarboxylate (Preparation 49, 2.5 g, 6.87 mmol) in 50% EtOH in THF (100 mL) and stirred for 4 hours at room temperature under an H$_2$ balloon. The reaction was filtered through celite and the filtrate was concentrated under reduced pressure to afford the title compound (1.6 g, 85%).

$^1$H NMR (300 MHz, DMSO-d$_6$): δ ppm 1.40 (s, 12H), 1.42 (s, 3H), 1.60-1.76 (m, 1H), 1.78-1.90 (m, 1H), 2.10-2.30 (m, 2H), 3.70-3.90 (m, 3H), 12.1 (br s, 1H).

Preparation 49

4-Benzyl 3-tert-butyl (4R)-2,2-dimethyl-1,3-oxazepane-3,4-dicarboxylate

To the solution of benzyl N-(tert-butoxycarbonyl)-5-hydroxy-D-norvalinate (Preparation 50, 3 g, 9.28 mmol) in THF (20 mL) was added 2,2-dimethoxypropane (12.07 mL, 92.8 mmol) and PPTS (catalytic amount), and the reaction was stirred for 5 hours at 60° C. The reaction mixture was poured into cold water and extracted with EtOAc. The organic layer was dried over Na$_2$SO$_4$ and concentrated under reduced pressure to afford the title compound (2.5 g, 74%).

$^1$H NMR (300 MHz, DMSO-d$_6$): δ ppm 1.40 (s, 12H), 1.43 (s, 3H), 1.65-1.80 (m, 1H), 1.80-1.90 (m, 1H), 2.30-2.40 (m, 2H), 3.70-3.90 (m, 3H), 5.1 (s, 2H), 7.26-7.40 (m, 5H).

Preparation 50

Benzyl N-(tert-butoxycarbonyl)-5-hydroxy-D-norvalinate

Triethylamine (12.4 mL, 89.02 mmol) and ethyl chloroformate (11.57 mL, 89.02 mL) were added to the solution of N-Boc-D-Glu(OBzI)OH (10 g, 29.6 mmol) in THF (100 mL) at −10° C. under an argon atmosphere. The mixture was stirred for 1 hour at −10° C. NaBH$_4$ (4.39 g, 118.4 mmol) in water (100 mL) was added drop-wise to the reaction mixture at −10° C., then the reaction mixture was stirred for 4 hours at room temperature. The reaction mixture was quenched with saturated aqueous NH$_4$Cl solution, extracted with EtOAc, dried over Na$_2$SO$_4$, and concentrated in vacuo. The residue was purified by silica gel column chromatography eluting with 30-40% EtOAc in petroleum ether to afford the title compound (3.1 g, 33%).

$^1$H NMR (300 MHz, CDCl$_3$): δ ppm 1.42 (s, 9H), 1.70-1.95 (m, 2H), 2.40-2.50 (m, 2H), 3.53-3.70 (m, 3H), 4.8 (br s, 1H), 5.1 (s, 2H), 7.30-7.40 (m, 5H).

MS m/z 224 [M-Boc+H]$^+$

Preparation 51

N-(tert-Butoxycarbonyl)-O-methyl-L-threonine

To a solution of O-methyl-L-threonine (10 g, 75.11 mmol) in THF (350 mL) and water (350 mL) was added NaHCO$_3$ (18.93 g, 225.32 mmol) and Boc$_2$O (24.59 g, 112.66 mmol) at 0° C. and the reaction was allowed to stir warming to room temperature for 18 hours. The reaction was quenched by the addition of aqueous KHSO$_4$ solution to pH=4 and extracted with EtOAc (5×150 mL). The combined organic layers were dried over Na$_2$SO$_4$ and concentrated in vacuo. The residue was triturated with heptanes to afford the title compound as a white solid (16.50 g, 94%).

$^1$H NMR (400 MHz, CDCl$_3$): δ ppm 1.22 (d, 3H), 1.45 (s, 9H), 3.28 (s, 3H), 3.98 (br d, 1H), 4.38 (d, 1H), 5.28 (d, 1H), 10.40-10.60 (br s, 1H).

Preparation 52

N-Boc-L-threonine

To a solution of L-threonine (400 mg, 3.36 mmol) in MeOH (5 mL) was added NaHCO$_3$ (434 mg, 5.17 mmol) in water (5 mL) followed by Boc$_2$O (1.07 g, 4.90 mmol) and the reaction stirred at room temperature for 3 days. The solvent was removed in vacuo and the residue diluted with water (20 mL) and washed with ether (2×20 mL).

The aqueous layer was acidified with saturated aqueous NaHSO$_4$ solution and extracted with 2-MeTHF. The organic layer was dried over Na$_2$SO$_4$ and concentrated in vacuo to afford the title compound as a white solid (730 mg, 99%).

$^1$H NMR (400 MHz, CDCl$_3$): δ ppm 1.24 (d, 3H), 1.44 (s, 9H), 4.26 (d, 1H), 4.40 (d, 1H), 5.52 (d, 1H), 5.69 (br s, 1H).

LCMS Rt=1.68 minutes MS m/z 218 [M+H]$^+$

Preparation 53

2-((tent-Butoxycarbonyl)amino)-3-hydroxy-2-methylpropanoic acid

Di-tert-butyldicarbonate (3.44 g, 15.7 mmol) was added to a mixture of αmethyl-DL-serine (1.25 g, 10.5 mmol) and sodium bicarbonate (2.64 g, 31.5 mmol) in methanol (5 mL) and water (5 mL) at 0° C. The ice bath was removed and the reaction mixture was allowed to warm to room temperature for 18 hours. The reaction mixture was concentrated to remove methanol and the residual aqueous phase then was acidified with 6N hydrochloric acid solution (pH 3~4), extracted with ether (3×). The combined organic phases were washed with water and brine, dried over anhydrous sodium sulfate, filtered and concentrated, then dried in vacuo to give the crude product, which was purified via silica gel column chromatography eluting with 0-10% methanol in dichloromethane to afford the title compound (450 mg) as a white solid.

LCMS Rt=0.37 minutes MS m/z 220 [M+H]$^+$ MS m/z 218 [M−H]$^−$

Preparation 54

N-Boc-L-allo-threonine

To a solution of L-allo-threonine (40 g, 335.8 mmol) in MeOH (500 mL) at 0° C. was added a solution of NaHCO$_3$ in water (43.44 g, 517 mmol in 500 mL) and the reaction stirred at this temperature for 10 minutes. Boc$_2$O (107 g, 490 mmol) was added and the reaction stirred at room temperature for 18 hours. Further Boc$_2$O (10 g) was added and the reaction continued for 5 hours. The solvent was removed in vacuo and the residue acidified to pH=4/5 using saturated aqueous KHSO$_4$ solution before extraction with EtOAc (8×300 mL) and 2-MeTHF (3×300 mL). The organic layers were combined, dried over MgSO$_4$ and concentrated in vacuo. The residue was triturated with pentane (2×30 mL) to afford the title compound (72 g, 98%).

$^1$H NMR (400 MHz, CDCl$_3$): δ ppm 1.20 (m, 3H), 1.45 (s, 9H), 4.20 (m, 1H), 4.38 (m, 1H), 5.45 (m, 1H).

Preparation 55

N-Boc-D-allo-threonine

The title compound was prepared according to Preparation 51 using D-allo-threonine with NaOH and tert-BuOH, and used directly in the next step.

Preparation 56

N-[(Benzyloxy)carbonyl]-2-methylalanine

To a solution of 2-methylalanine (50 g, 0.49 mmol) and Na$_2$CO$_3$ (156 g, 1.47 mol) in water (1 L) was added a solution of CbzCl (91 g, 0.54 mmol) in dioxane (500 mL) at 0° C. over 15 minutes. The resulting solution was stirred at room temperature for 18 hours. The reaction was extracted with Et$_2$O (2×500 mL), and the aqueous layer collected, acidified to pH=1 with cHCl and extracted with EtOAc (2×500 mL). The organic layers were combined, washed with brine, dried over Na$_2$SO$_4$ and concentrated in vacuo to afford a white solid as the title compound that was used directly in the next step (111 g, 97%).

Preparation 57

(4S,5R)-3-(tert-Butoxycarbonyl)-2,2,5-trimethyl-1,3-oxazolidine-4-carboxylic acid Boc-L-threonine (600 g, 2.74 mol) was added to methyl-tert-butyl ether (3.6 L) and THF (1.2 L) followed by 2,2-dimethoxypropane (1710 g, 16.42 mol) and pyridinium p-toluenesulfonate (171.9 g, 684 mmol) and the suspension heated to reflux for 20 hours. The reaction was cooled and diluted with water (3 L) and stirred to achieve a solution. The organic layer was collected, washed with water (1.8 L), and diluted with methyl-tert-butyl ether (4.2 L). A solution of NaOH in water (109 g in 120 mL) was added and the mixture stirred for 20 minutes. The mixture was concentrated to low volume to effect precipitation. The resulting solid was filtered and collected as the sodium salt of the title compound.

$^1$H NMR (400 MHz, DMSO-d$_6$): δ ppm 1.20 (d, 3H), 1.29 (s, 9H), 1.42 (s, 6H), 3.43 (m, 1H), 3.94 (m, 1H).

Preparation 58 tert-Butyl (4S,5R)-4-(bromoacetyl)-2,2,5-trimethyl-1,3-oxazolidine-3-carboxylate The title compound was prepared according to Preparation 65. The residue was purified using silica gel column chromatography eluting with 10-15% EtOAc in heptanes to afford a white solid (1.23 g, 45%).

LCMS Rt=2.72 minutes MS m/z 238 [M-Boc]$^−$

Preparation 59A and Preparation 59B (4R,5R)-3-(tert-Butoxycarbonyl)-2,2,5-trimethyl-1,3-oxazolidine-4-carboxylic acid (Preparation 59A) and (4S,5S)-3-(tert-butoxycarbonyl)-2,2,5-trimethyl-1,3-oxazolidine-4-carboxylic acid (Preparation 59B)

The title compounds were prepared according to Preparation 60 using N-Boc-D-allothreonine and N-Boc-L-allothreonine.

$^1$H NMR (400 MHz, DMSO-$d_6$): δ ppm 1.25 (d, 3H), 1.30-1.60 (15H), 4.14-4.20 (m, 1H), 4.35-4.45 (m, 1H), 12.70 (s, 1H).

Preparation 60

(4S,5R)-3-(tert-Butoxycarbonyl)-5-isopropyl-2,2-dimethyl-1,3-oxazolidine-4-carboxylic acid 2,2-Dimethoxypropane (10 mL, 10 mmol) and catalytic amount of camphor sulphonic acid (0.1 g, 0.3 mmol) were added to the stirred ice cooled solution of (3R)-L-Leucine-N-[(1,1-dimethylethoxy)carbonyl]-3-hydroxy (Angew.Chem. Int. Ed., 49 (9), 9500-9503, (2010), 250 mg, 1 mmol) in dry THF (30 mL) under nitrogen atmosphere and stirred at 90° C. for 16 hours. The reaction mixture was concentrated under reduced pressure, and the residue was dissolved in DCM and washed with water followed by brine. The organic layer was dried over anhydrous $Na_2SO_4$ and concentrated in vacuo to afford the title compound (0.25 g, 86%) which was used in next reaction without purification.

$^1$H NMR (400 MHz, DMSO-$d_6$): δ ppm 0.9 (d, 6H), 1.30-1.42 (m, 9H), 1.50 (d, 6H), 1.75-1.85 (m, 1H), 3.68-3.78 (m, 1H), 3.90 (d, 1H), 12.90 (br s, 1H).

Preparation 61

(4S,5R)-3-(tert-Butoxycarbonyl)-5-ethyl-2,2-dimethyl-1,3-oxazolidine-4-carboxylic acid The title compound was prepared according to Preparation 57 using PTSA in DCM at room temperature.

$^1$H NMR (400 MHz, DMSO-$d_6$): δ ppm 0.90 (t, 3H), 1.30-1.70 (m, 17H), 3.80-3.85 (m, 1H), 3.86-3.95 (m, 1H), 12.90 (s, 1H).

Preparation 62

(2S)-2-[(tert-Butoxycarbonyl)amino]-4-methoxy-3-methyl-4-oxobutanoic acid (2S)-2-amino-4-methoxy-3-methyl-4-oxobutanoic acid (Preparation 63, 23 g, 82.55 mmol) was dissolved in NMM:MeOH (1:1, 100 mL) and evaporated to dryness. The residue was dissolved in MeOH (200 mL) and cooled to 0° C. $Boc_2O$ (21.6 g, 99 mmol) and triethylamine (23 mL, 105 mmol) were added and the reaction stirred at room temperature for 18 hours. The reaction was concentrated in vacuo and triturated with heptane. The solid was dissolved in EtOAc (200 mL), washed with 10% $KHSO_4$ in brine. The aqueous was back-washed with EtOAc (7×100 mL) and the organic layers combined, washed with brine, dried over $Na_2SO_4$ and concentrated in vacuo. The residue was purified using silica gel column chromatography eluting with DCM/MeOH 95/5 to afford the title compound in a diastereomeric ratio of 2:1 (12 g, 57%).

$^1$H NMR (400 MHz, $CDCl_3$): δ ppm 1.20-1.30 (m, 3H), 1.43 (m, 9H), 3.03 and 3.27 (m, 1H, diastereomers 1:2 ratio), 3.71 (m, 3H), 4.53 and 4.67 (1H, m, diastereomers 2:1 ratio), 5.30 and 5.50 (m, 1H, diastereomers 2:1 ratio).

LCMS Rt=2.29 minutes MS m/z 262 [M+H]$^+$

Preparation 63

(2S)-2-Amino-4-methoxy-3-methyl-4-oxobutanoic acid

A mixture of dimethyl 3-methyl-L-aspartate (Preparation 64, 23 g, 82.55 mmol), $CuCO_3.Cu(OH)_2$ (21.9 g, 99.05 mmol) in water (250 mL) was heated to 70° C. for 4 hours. The resulting precipitate was filtered and the filtrate cooled to 0° C. Ammonium sulfide (20% in water, 67.5 mL, 198 mmol) was added slowly ensuring the temperature did not rise above 5° C. The reaction was filtered through arbocel to remove the copper residues and the filtrate concentrated in vacuo. The residue was redissolved in MeOH and filtered through arbocel, with concentration of the filtrate to dryness to afford the title compound as an oil that was used directly in the next step.

$^1$H NMR (400 MHz, $D_2O$): δ ppm 1.10-1.20 (m, 3H), 3.13 (m, 1H), 3.60-3.65 (m, 3H), 3.93 (m, 1H). Diastereoisomers are evident in a 2:1 ratio.

Preparation 64

Dimethyl 3-methyl-L-aspartate

A solution of dimethyl N-(tert-butoxycarbonyl)-3-methyl-L-aspartate (Preparation 67, 22.7 g, 0.083 mol) in formic acid (100 mL) was stirred at 40° C. for 2 hours. The reaction was concentrated in vacuo azeotroping with water (3×300 mL) to afford the title compound as a colourless oil as the formate salt that was used directly in the next reaction.

Preparation 65

Benzyl (2R,3S)-5-bromo-3-[(tert-butoxycarbonyl)amino]-2-methyl-4-oxopentanoate

To a solution of (2S)-4-(benzyloxy)-2-[(tert-butoxycarbonyl)amino]-3-methyl-4-oxobutanoic acid (Preparation 66, 1 g, 2.96 mmol) in THF (60 mL) at −78° C. was added NMM (0.36 mL, 3.26 mmol) followed by isobutylchloroformate (0.42 mL, 3.26 mmol) and the reaction was stirred for 1 hour warming from −78° C. to −60° C. The resultant white precipitate was filtered off and the filtrate cooled to 0° C. To the solution was added a pre-prepared solution of diazomethane in ether (1.97 g Diazald, 90 mL ether) and the reaction stirred at 0° C. for 12 hours. A 48% solution of HBr in water was added and the reaction stirred for 30 minutes before being diluted with EtOAc. The organic layer was collected, washed with saturated aqueous $NaHCO_3$ solution, brine, dried over $Na_2SO_4$ and concentrated in vacuo to afford the title compound.

$^1$H NMR (400 MHz, $CDCl_3$): δ ppm 1.28 (d, 3H), 1.45 (s, 9H), 3.40 (m, 1H), 4.20 (s, 2H), 4.57 (dd, 1H), 5.10 (m, 2H), 5.63 (d, 1H), 7.20-7.40 (m, 5H).

LCMS Rt=3.51 minutes MS m/z 436 [M+Na]$^+$

Preparation 66

(2S)-4-(Benzyloxy)-2-[(tert-butoxycarbonyl)amino]-3-methyl-4-oxobutanoic acid

To a solution of 4-benzyl 1-methyl N-(tert-butoxycarbonyl)-3-methyl-L-aspartate (Preparation 68, 0.5 g, 1.52 mmol)

in THF/water (50 mL/10 mL) was added lithium hydroxide (34 mg, 1.42 mmol) at 0° C. and the reaction stirred warming slowly to room temperature for 18 hours. The reaction was extracted with heptane and the aqueous was acidified with 10% aqueous $KHSO_4$ solution. The solution was extracted with EtOAc, washed with brine, dried over $Na_2SO_4$ and concentrated in vacuo. The residue was purified using reverse phase column chromatography eluting with 0-60% MeCN in 0.1% formic acid in water to afford the title compound (182 mg, 38%).

$^1$H NMR (400 MHz, $CDCl_3$): δ ppm 1.28 (d, 3H), 1.43 (s, 9H), 3.31 (m, 1H), 4.54 (m, 1H), 5.17 (m, 2H), 5.53 (m, 1H), 7.30-7.45 (m, 5H).

Preparation 67

Dimethyl N-(tert-butoxycarbonyl)-3-methyl-L-aspartate

To a solution of hexamethyldisilazane (88 mL, 0.421 mol), in THF (500 mL) at −30° C. was added BuLi (2.5M in hexanes, 169 mL, 0.423 mol) and the mixture stirred at this temperature for 15 minutes before cooling to −78° C. A solution of dimethyl N-(tert-butoxycarbonyl)-L-aspartate (Preparation 70, 50 g, 0.19 mol) in THF (200 mL) was added slowly over 15 minutes and the reaction stirred at −78° C. for 2 hours. MeI (14.3 mL, 0.23 mol) was added over 30 minutes and the reaction continued stirring at −78° C. for 18 hours. The reaction was quenched by pouring into an aqueous solution of $KHSO_4$ (80 g in 600 mL, pH=3). THF was then removed in vacuo and the product extracted into EtOAc. The organic layer was collected, washed with brine, dried over $Na_2SO_4$ and concentrated in vacuo. The residue was purified using silica gel column chromatography eluting with 0-10% EtOAc in heptane to afford the title compound as a mixture of diastereomers in a ratio 7:3.

$^1$H NMR (400 MHz, $CDCl_3$): δ ppm 1.25 (d, 3H), 1.45 (s, 9H), 3.29 (m, 1H), 3.66 (m, 2×3H), 4.52 (dd, 1H), 5.42 (br d, 1H).

Preparation 68

4-Benzyl 1-methyl N-(tert-butoxycarbonyl)-3-methyl-L-aspartate

The title compound was prepared according to Preparation 67 using 4-benzyl 1-methyl N-(tert-butoxycarbonyl)-L-aspartate (Preparation 69). The crude residue was purified using reverse phase column chromatography eluting with 0-60% MeCN in 0.1% formic acid in water followed by silica gel column chromatography eluting with heptane:acetone 95:5 to afford one major diastereomer assumed to be (2R),(3S).

$^1$H NMR (400 MHz, $CDCl_3$): δ ppm 1.25 (d, 3H), 1.43 (s, 9H), 3.28 (m, 1H), 3.62 (s, 3H), 4.54 (m, 1H), 5.14 (m, 2H), 5.40 (m, 1H), 7.30-7.40 (m, 5H).

Preparation 69

4-Benzyl 1-methyl N-(tert-butoxycarbonyl)-L-aspartate

To a solution of N-Boc-O-Bn-L-Asp (25 g, 77.3 mmol) and $KHCO_3$ (15.5 g, 154.6 mmol) in DMF (300 mL) was added MeI (9.6 mL, 154.6 mmol) and the reaction stirred at room temperature for 18 hours. The reaction was diluted with EtOAc, washed with saturated aqueous $NaHCO_3$ solution, water, dried over $Na_2SO_4$ and concentrated in vacuo. The residue was purified using silica gel column chromatography eluting with DCM/TBME 4/1 to afford the title compound as a white solid (26 g, 96%).

$^1$H NMR (400 MHz, $CDCl_3$): δ ppm 1.43 (s, 9H), 2.8-3.1 (m, 2H), 3.70 (s, 3H), 4.58 (m, 1H), 5.13 (m, 2H), 5.47 (m, 1H), 7.30-7.40 (m, 5H).

Preparation 70

Dimethyl N-(tert-butoxycarbonyl)-L-aspartate

To a solution of dimethyl L-aspartate hydrochloride (Preparation 71, 160 g, 0.75 mol) in MeOH (600 mL) at −78° C. was added triethylamine (200 mL, 1.50 mol) followed by $Boc_2O$ (180 g, 0.83 mol) and the reaction stirred at room temperature for 18 hours. The reaction was concentrated in vacuo and triturated with THF. The triethylamine hydrochloride was filtered off and the filtrate evaporated to dryness. The residue was dissolved in DCM and purified using silica gel column chromatography eluting with DCM:TBME 100:1 to afford the title compound as a white solid (153.7 g, 78%).

$^1$H NMR (400 MHz, $CDCl_3$): δ ppm 1.40 (s, 9H), 2.70-3.10 (m, 2H), 3.69 (s, 3H), 3.76 (s, 3H), 4.59 (m, 1H), 5.46 (m, 1H).

Preparation 71

Dimethyl L-aspartate hydrochloride

Acetyl chloride (160 mL) was added dropwise to MeOH (600 mL) at −78° C. followed by L-aspartic acid (100 g, 0.75 mol) and the reaction stirred warming to room temperature for 3 days. The reaction was concentrated in vacuo to furnish the title compound as a white solid as the hydrochloride salt (160 g, quant).

$^1$H NMR (400 MHz, $D_2O$): δ ppm 3.04 (m, 2H), 3.64 (s, 3H), 3.73 (s, 3H), 4.39 (m, 1H).

Preparation 72

(3R,4S)-4-(2-Bromoacetyl)-1-(tert-butyldimethylsilyl)-3-methylazetidin-2-one (2S,3R)-1-(tert-Butyldimethylsilyl)-3-methyl-4-oxoazetidine-2-carboxylic acid (2.00 g, 8.22 mmol) was dissolved in THF (20 mL) and cooled to −25° C. Triethylamine (933 mg, 9.04 mmol) was added to the reaction mixture, followed by drop-wise addition of ethyl chloroformate (981 mg, 9.04 mmol). The reaction mixture was stirred for 30 minutes at −25° C. Freshly prepared diazomethane solution in dichloromethane (0.4 M, 41.0 mL, 16.4 mmol) was added drop-wise to the reaction mixture. The reaction was stirred 3 hours while warming to ambient temperature. The reaction mixture was filtered and the filtrate reduced to half volume in vacuo. The resulting solution was washed successively with saturated aqueous sodium bicarbonate and brine, and then dried over anhydrous magnesium sulfate and filtered. The solvent was removed in vacuo.

The residue was dissolved in acetic acid (4 mL) and 48% aqueous hydrobromic acid (665 mg, 8.22 mmol) was added drop-wise while stirring. After 30 minutes the reaction was poured over ice and the mixture was extracted two times with dichloromethane. The combined organic phase was washed with saturated aqueous sodium bicarbonate solution until fully neutralized, then dried over anhydrous magnesium sulfate, filtered and the solvent removed in vacuo. The product was purified by silica gel column chromatography eluting with 0-100% ethyl acetate in hexanes to afford the title compound (519 mg, 20%).

$^1$H NMR (400 MHz, CDCl$_3$): δ ppm 0.051 (s, 3H), 0.32 (s, 3H), 0.97 (s, 9H), 1.48 (d, 3H), 3.12 (m, 1H), 3.90 (m, 2H), 4.16 (d, 1H).

LCMS Rt=1.05 minutes MS m/z 322 [$^{79}$Br M+H]$^+$

Preparation 73

4-Fluoro-5-neopentylbenzene-1,2-diamine

A mixture of 4-bromo-5-fluorobenzene-1,2-diamine (82.1 mg, 0.400 mmol), [1,1-bis(diphenylphosphino)ferrocene]dichloropalladium(II) (20.2 mg, 0.0276 mmol), and neopentylzinc bromide in tetrahydrofuran (0.5 M, 3.0 mL, 1.5 mmol) was degassed for 5 minutes using argon. The reaction mixture was heated under microwave irradiation for 5 minutes at 140° C. The solution was concentrated in vacuo and purified by silica gel column chromatography eluting with 0-100% ethyl acetate/hexanes to afford the title compound (22 mg, 28%) as an orange oil.

LCMS Rt=0.94 minutes MS m/z 197 [M+H]$^+$

Preparation 74

4-(Adamantan-1-yl)benzene-1,2-diamine

A mixture of 4-bromobenzene-1,2-diamine (470 mg, 2.51 mmol) and [1,1-bis(diphenylphosphino)ferrocene]dichloropalladium(II) (92.2 mg, 0.126 mmol) and 0.5 M 1-adamantylzink bromide in tetrahydrofuran (15 mL, 7.54 mmol) was heated under microwave irradiation at 140° C. for 30 minutes. The reaction mixture was cooled to room temperature, diluted with dichloromethane, washed with saturated sodium bicarbonate solution. The aqueous layer was extracted with dichloromethane (2×). The combined organic phase was washed with water and brine, dried over anhydrous sodium sulfate, filtered and was concentrated. The residue was purified via silica gel column chromatography eluting with 0-10% methanol in dichloromethane to afford the title compound as a mixture of the desired product and des-bromo by-product, which was used in the next step without further purification.

LCMS Rt=0.97 minutes MS m/z 243 [M+H]$^+$

Preparation 75

4-(1,1-Dimethylpropyl)benzene-1,2-diamine

To a stirred solution of 4-(1,1-dimethylpropyl)-2-nitroaniline (Preparation 94, 11 g, 0.052 mol) in EtOH:water (240 mL:60 mL) was added iron powder (14.8 g, 0.254 mol) and calcium chloride (11.7 g, 0.105 mol). The reaction was heated to reflux for 6 hours before cooling and concentrating in vacuo. The residue was extracted with EtOAc, dried over Na$_2$SO$_4$, concentrated in vacuo and purified using silica gel column chromatography eluting with 50% EtOAc in hexane to afford the title compound (6.2 g, 65%).

$^1$H NMR (400 MHz, DMSO-d$_6$): δ ppm 0.60 (t, 3H), 1.15 (s, 6H), 1.47 (q, 2H), 4.29 (d, 4H), 6.32 (dd, 1H), 6.40 (d, 1H), 6.49 (d, 1H).

Preparation 76

4',5'-Diamino-2'-fluorobiphenyl-4-carbonitrile

To a mixture of 4'-amino-2'-fluoro-5'-nitrobiphenyl-4-carbonitrile (Preparation 90, 0.5 g, 2 mmol) and zinc dust (0.78 g, 12 mmol) in methanol (10 mL) was added ammonium chloride (0.41 g, 8 mmol) and the reaction was stirred at room temperature for 3 hours. The reaction was filtered through celite washing through with methanol (40 mL). The filtrate was concentrated to afford a solid that was purified using silica gel column chromatography eluting with EtOAc:heptanes 1:1 to afford the title compound as a brown solid (0.45 g, 99%).

$^1$H NMR (400 MHz, MeOD): δ ppm 6.52 (d, 1H), 6.82 (d, 1H), 7.62 (d, 2H), 7.68 (d, 2H).

LCMS (4.5 minute run) Rt=2.18 minutes MS m/z 228 [M+H]$^+$

Preparation 77

3',4'-Diamino-2'-fluorobiphenyl-4-carbonitrile

The title compound was prepared according to Preparation 76 using 4'-amino-2'-fluoro-5'-nitrobiphenyl-4-carbonitrile (Preparation 91). The residue was purified by silica gel column chromatography eluting with 0.5% MeOH in DCM.

$^1$H NMR (400 MHz, CDCl$_3$): δ ppm 3.42 (br s, 2H), 3.66 (br s, 2H), 6.58 (dd, 1H), 6.77 (m, 1H), 7.61 (dd, 2H), 7.67 (dd, 2H).

Preparation 78

3',4'-Diamino-2'-chlorobiphenyl-4-carbonitrile

The title compound was prepared according to Preparations 76 and 90 using 4-bromo-3-fluoro-2-nitroaniline. Taken on to the next step directly.

Preparation 79

3',4'-Diamino-2-fluorobiphenyl-4-carbonitrile

To a suspension of 4'-amino-2-fluoro-3'-nitrobiphenyl-4-carbonitrile (Preparation 92, 3 g, 11.66 mmol) in AcOH/THF (70 mL/70 mL) was added zinc dust (6.9 g, 105.6 mmol) and the reaction stirred at room temperature for 18 hours. The reaction was filtered and the filtrate concentrated in vacuo. The residue was treated with saturated aqueous NaHCO$_3$ solution (200 mL) and extracted with EtOAc (200 mL). The organic layer was collected, dried over Na$_2$SO$_4$ and concentrated in vacuo. The solid was triturated with MTBE (30 mL) and filtered to afford the title compound as a brown solid (1.5 g, 57%).

$^1$H NMR (400 MHz, MeOD): δ ppm 6.78 (d, 1H), 6.97 (m, 1H), 6.99 (d, 1H), 7.49-7.65 (m, 3H).

Preparation 80

3',4'-Diamino-2'-chloro-3-fluorobiphenyl-4-carbonitrile

To a cooled solution (0° C.) of zinc dust (9.34 g, 143 mmol) in AcOH (33 mL), THF (33 mL) and water (9.5 mL) was added 4'-amino-2'-chloro-3-fluoro-3'-nitrobiphenyl-4-carbonitrile (Preparation 93, 2.6 g, 8.93 mmol) and the reaction was allowed to warm to room temperature for 1 hour before filtering through arbocel. The filtrate was diluted with water (200 mL) and EtOAc (200 mL) and the organic layer was collected, dried over MgSO$_4$ and concentrated in vacuo to afford the title compound (2.41 g, quant).

¹H NMR (400 MHz, CDCl₃): δ ppm 3.35-4.13 (m, 4H), 6.65 (d, 1H), 6.70 (d, 1H), 7.27-7.32 (m, 2H), 7.61-7.64 (m, 1H).

Preparation 81

3',4'-Diamino-3-fluoro-[1,1'-biphenyl]-4-carbonitrile

To a warm solution of 4'-amino-3-fluoro-3'-nitro-[1,1'-biphenyl]-4-carbonitrile (Preparation 85, 0.86 g, 3.3 mmol) in ethanol (75 mL) was added saturated aqueous ammonium chloride solution (12 mL, 180 mmol) and iron (2.41 g, 43.2 mmol). The reaction solution was heated to reflux for 1 hour. The reaction mixture was allowed to cool, filtered, and the filtrate was adjusted to pH=9 with saturated aqueous sodium hydrogen carbonate solution and then the mixture was concentrated in vacuo to a residue. The residue was treated with methanol and the resulting suspension was filtered and the filtrate concentrated to dryness. The residue was purified using silica gel column chromatography eluting with 0-10% MeOH in DCM to afford the title compound (0.34 g, 45%) as a yellow solid.

¹H NMR (400 MHz, DMSO-d₆): δ ppm 4.65 (s, 2H), 5.00 (s, 2H), 6.60 (d, 1H), 6.91 (m, 1H), 6.97 (m, 1H), 7.52 (d, 1H), 7.59 (m, 1H), 7.85 (m, 1H).

LCMS Rt=0.77 minutes MS m/z 228 [M+H]⁺

Preparation 82

3',4'-Diaminobiphenyl-4-carbonitrile

To a solution of 4-amino-3-nitro-biphenyl-4-carbonitrile (Preparation 89, 1.8 g, 7.53 mmol) in EtOH/water (4:1 20 mL) were added calcium chloride (1.67 g, 15 mmol) and iron powder (2.11 g, 37.66 mmol). The reaction was heated to 100° C. for 5 hours before cooling and filtering through celite, washing through with DCM (3×30 mL). Water was added to the filtrate and the organic layer collected, dried over Na₂SO₄ and concentrated in vacuo. The residue was purified using silica gel column chromatography eluting with 2-3% MeOH in DCM to afford the title compound as a green solid (1.2 g, 76%).

¹H NMR (400 MHz, DMSO-d₆): δ ppm 4.61 (s, 2H), 4.85 (s, 2H), 6.59 (d, 1H), 6.84 (d, 1H), 6.92 (s, 1H), 7.66 (d, 2H), 7.77 (d, 2H).

LCMS Rt=2.75 minutes MS m/z 210 [M+H]⁺

Preparation 83

4-Neopentylbenzene-1,2-diamine

To a solution of 4-neopentyl-2-nitroaniline (Preparation 88, 5.23 g, 25.1 mmol) in methanol (50 mL) was added 10% palladium on carbon (800 mg, 8 mmol) and hydrogenated at 40 psi for 3.5 hours. The mixture was filtered through celite and concentrated in vacuo. The residue was purified using silica gel column chromatography eluting with a 0-10% methanol/methylene chloride gradient to provide the title compound (2.95 g, 66%) as a purple solid.

¹H NMR (400 MHz, CDCl₃): δ ppm 0.87 (s, 9H), 2.33 (s, 2H), 3.29 (br s, 2H), 3.33 (br s, 2H), 6.46 (m, 2H), 6.60 (m, 1H).

LCMS Rt=0.82 minutes MS m/z 179 [M+H]⁺

Preparation 84

4-Cyclopentylbenzene-1,2-diamine

A suspension of N-(4-cyclopentyl-2-nitrophenyl)acetamide (Preparation 86, 19.48 g, 78.46 mmol) in aqueous sodium hydroxide (6.0M, 100 mL, 600 mmol) was heated at 90° C. for 4 days. The reaction was allowed to cool and extracted with methylene chloride (3×). The organic layers were combined, dried over anhydrous magnesium sulphate, filtered, and concentrated in vacuo. The resulting residue was suspended in methanol (300 mL) and treated with palladium (2 g, 20 mmol, 10% on carbon, Degussa type). The reaction mixture was hydrogenated at 40 psi for 5 hours before filtering through celite and concentrating in vacuo. The residue was purified using silica gel column chromatography eluting with a 0-100% ethyl acetate/hexanes gradient to afford the title compound (6.85 g, 50%) as a purple solid.

¹H NMR (400 MHz, CDCl₃): δ ppm 1.51 (m, 2H), 1.61 (m, 2H), 1.75 (m, 2H), 2.01 (m, 2H), 2.82 (m, 1H), 3.33 (br s, 4H), 6.58 (m, 3H).

LCMS Rt=0.71 minutes MS m/z 177 [M+H]⁺

Preparation 85

4'-Amino-3-fluoro-3'-nitro-[1,1'-biphenyl]-4-carbonitrile

A mixture of 4-bromo-2-nitroaniline (5.02 g, 23.1 mmol), 4-cyano-3-fluorophenylboronic acid (3.62 g, 21.9 mmol), and sodium carbonate (6.1 g, 58 mmol) in water (10 mL) and tetrahydrofuran (35 mL) was sparged with nitrogen for 10 minutes. To this was added [1,1-bis(diphenylphosphino)ferrocene]dichloropalladium(II), complex with dichloromethane (1:1) (0.42 g, 0.51 mmol). The reaction mixture was heated at 65° C. for 6 hours. The mixture was allowed to cool, concentrated in vacuo, diluted with ethyl acetate, washed with saturated aqueous sodium hydrogen carbonate, water and brine. The organic layer was dried over anhydrous magnesium sulphate, filtered, and concentrated in vacuo. The residue was purified using silica gel column chromatography eluting with a 0-100% ethyl acetate/hexanes gradient to afford the title compound (3.64 g, 65%) as a yellow solid.

¹H NMR (400 MHz, CDCl₃): δ ppm 6.30 (br s, 2H), 6.95 (d, 1H), 7.43 (m, 2H), 7.68 (m, 2H), 8.42 (d, 1H).

LCMS Rt=1.17 minutes MS m/z 256 [M−H]−

Preparation 86

N-(4-Cyclopentyl-2-nitrophenyl)acetamide

To a suspension of N-(4-cyclopentylphenyl)acetamide (Preparation 97, 18.5 g, 91.0 mmol) in acetic anhydride (148 mL, 1570 mmol) cooled in an ice/brine bath was added dropwise a solution of nitric acid (5.7 mL, 140 mmol) in acetic anhydride (40 mL, 400 mmol). After stirring for 4 hours, the reaction mixture was added water and extracted with methylene chloride (3×). The organic layers were combined, dried over anhydrous magnesium sulphate, filtered, and concentrated in vacuo. This provided product (19.48 g, 86%) as a brown oil that was used without further purification.

LCMS Rt=1.29 minutes MS m/z 249 [M+H]⁺

Preparation 87

N-(4-Neopentyl-2-nitrophenyl)acetamide

To a suspension of N-(4-neopentylphenyl)acetamide (Preparation 98, 2.54 g, 12.4 mmol) in acetic anhydride (20 mL) cooled in an ice bath was added a solution of nitric acid (0.78 mL, 18 mmol) in acetic anhydride (5 mL) dropwise. The solution was allowed to warm to room temperature for 18 hours. The yellow solution was added to water and extracted with dichloromethane (3×). The organic layers were dried over anhydrous magnesium sulphate, filtered, and concentrated in vacuo. The residue was purified using silica gel column chromatography eluting with a 0-50% ethyl acetate/hexanes gradient to provide the title compound (3.0 g, 97%) as a yellow oil.
LCMS Rt=1.23 minutes MS m/z 251 [M+H]$^+$ Preparation 88

4-Neopentyl-2-nitroaniline

A suspension of N-(4-neopentyl-2-nitrophenyl)acetamide (Preparation 87, 3.0 g, 12.0 mmol) in aqueous sodium hydroxide (6.0 M, 20 mL, 120 mmol) was heated at 90° C. for 36 hours. After cooling, a small amount of water was added and the mixture extracted with dichloromethane (5×). The organic layers were combined, dried over anhydrous magnesium sulphate, filtered, and concentrated in vacuo to provide the title compound (2.15 g, 90%) as a yellow solid.
$^1$H NMR (400 MHz, CDCl$_3$): δ ppm 0.89 (s, 9H), 2.41 (s, 2H), 5.96 (br s, 2H), 6.71 (m, 1H), 7.16 (m, 1H), 7.87 (m, 1H).
LCMS Rt=1.31 minutes MS m/z 209 [M+H]$^+$ Preparation 89

4-Amino-3-nitro-biphenyl-4-carbonitrile

A solution of 4-bromo-2-nitroaniline (1.92 g, 8.85 mmol) and 4-cyanophenylboronic acid (1.3 g, 8.85 mmol) in toluene/EtOH/water (3/1/1.5, 40 mL) was degassed thoroughly before the addition of Na$_2$CO$_3$ (2.8 g, 26.55 mmol) and Pd(PPh$_3$)$_4$ (511 mg, 0.44 mmol). The reaction was heated to 100° C. for 5 hours. After cooling the reaction was filtered through celite, washing through with EtOAc (3×20 mL). The filtrate was washed with water (2×30 mL), dried over Na$_2$SO$_4$ and concentrated in vacuo. The residue was purified using silica gel column chromatography eluting with 2-3% MeOH in DCM to afford the title compound as a yellow solid (1.8 g, 85%).
$^1$H NMR (400 MHz, DMSO-d$_6$): δ ppm 7.15 (d, 1H), 7.66 (s, 2H), 7.87 (br s, 5H), 8.32 (s, 1H).

Preparation 90

4'-Amino-2'-fluoro-5'-nitrobiphenyl-4-carbonitrile

A suspension of 4-bromo-5-fluoro-2-nitroaniline (0.8 g, 3.8 mmol), 4-cyanophenylboronic acid (0.58 g, 3.87 mmol) and sodium carbonate (1 g, 9.50 mmol) in THF/water (15 mL/2 mL) was degassed with nitrogen for 10 minutes. To the suspension was added dichloro [1,1' bis(di-tert-butylphosphino)]ferrocene palladium (II) (80 mg, 0.095 mmol) and the reaction was heated to 60° C. for 18 hours. The reaction was filtered through celite and the filtrate diluted with water and EtOAc. The organic layer was collected and concentrated in vacuo to afford the title compound as a yellow solid (0.91 g, 91%).
$^1$H NMR (400 MHz, CDCl$_3$): δ ppm 6.12 (br s, 2H), 6.58 (d, 1H), 7.58 (d, 2H), 7.72 (d, 2H), 8.14 (d, 1H).

Preparation 91

4'-Amino-2'-fluoro-5'-nitrobiphenyl-4-carbonitrile

The title compound was prepared according to the method described for Preparation 90 using 4-bromo-3-fluoro-2-nitroaniline.
$^1$H NMR (400 MHz, CDCl$_3$): δ ppm 5.66 (br s, 2H), 6.70 (dd, 1H), 7.36 (dd, 1H), 7.59 (dd, 2H), 7.20 (d, 2H).

Preparation 92

4'-Amino-2-fluoro-3'-nitrobiphenyl-4-carbonitrile

The title compound was prepared according to the method described for Preparation 90 using 2-fluoro-4-cyanophenylboronic acid.
$^1$H NMR (400 MHz, CDCl$_3$): δ ppm 6.23 (br s, 2H), 6.92 (d, 1H), 7.41-7.62 (m, 4H), 8.38 (s, 1H).

Preparation 93

4'-Amino-2'-chloro-3-fluoro-3'-nitrobiphenyl-4-carbonitrile

The title compound was prepared according to Preparation 92 using 3-fluoro-4-cyanophenylboronic acid and 4-bromo-3-chloro-2-nitroaniline. The residue was purified using silica gel column chromatography eluting with 10-50% EtOAc in heptanes to afford a yellow solid (2.45 g, 52%).
$^1$H NMR (400 MHz, CDCl$_3$): δ ppm 4.81 (br s, 2H), 6.83 (d, 1H), 7.20 (d, 1H), 7.28-7.31 (m, 2H), 7.66-7.70 (m, 1H).

Preparation 94

4-(1,1-Dimethylpropyl)-2-nitroaniline

To a stirred solution of N-[4-(1,1-dimethylpropyl)-2-nitrophenyl]acetamide (Preparation 95, 15 g, 60 mmol) in MeOH:water (120 mL:80 mL) at 0° C. was added sodium hydroxide (5 g, 125.4 mmol) and the reaction stirred at room temperature for 18 hours. The reaction was concentrated in vacuo and extracted with EtOAc. The organic layer was collected, dried over Na$_2$SO$_4$ and concentrated in vacuo to afford the title compound (11 g, 88%).
$^1$H NMR (400 MHz, DMSO-d$_6$): δ ppm 0.63 (t, 3H), 1.19 (s, 6H), 1.58 (m, 2H), 6.97 (d, 1H), 7.31 (s, 2H), 7.44 (dd, 1H), 7.79 (d, 1H).

Preparation 95

N-[4-(1,1-Dimethylpropyl)-2-nitrophenyl]acetamide

To a stirred solution of N-[4-(1,1-dimethylpropyl)phenyl]acetamide (Preparation 99, 12 g, 0.058 mol) in acetic anhydride (50 mL) at −5° C. was added HNO$_3$ slowly. The reaction was maintained at 0° C. for 1 hour and then room temperature for 18 hours. The reaction was extracted with EtOAc, dried over Na$_2$SO$_4$ and concentrated in vacuo to afford the title compound (15 g, 100%).
$^1$H NMR (400 MHz, DMSO-d$_6$): δ ppm 0.63 (t, 3H), 1.25 (m, 6H), 1.62 (q, 2H), 2.04 (s, 3H), 7.53 (d, 1H), 7.66 (d, 1H), 7.76 (d, 1H), 10.18 (s, 1H).

Preparation 96

1-Cyclopentyl-4-nitrobenzene and 1-cyclopentyl-2-nitrobenzene

To a solution of cyclopentylbenzene (22.5 g, 154 mmol) in acetic anhydride (80 mL, 800 mmol) cooled in an ice water bath was added a solution of nitric acid (7.6 mL, 180 mmol) in acetic anhydride (30 mL, 300 mmol). The reaction mixture was stirred for 18 hours warming to room temperature. The next day, the reaction mixture was added to ice water and extracted with diethylether (3×). The organic layers were combined, washed with brine, dried over anhydrous magnesium sulphate, filtered, and concentrated in vacuo. This provided a mix of regioisomers (28.92 g, 98%) that was used without further purification in the next step.

Preparation 97

N-(4-Cyclopentylphenyl)acetamide

To a solution of 1-cyclopentyl-4-nitrobenzene and 1-cyclopentyl-2-nitrobenzene (Preparation 96, 28.92 g, 151.2 mmol) in methanol (300 mL) was added acetic anhydride (20.1 mL, 213 mmol) and palladium (2 g, 20 mmol) (10% on carbon, Degussa type) and the reaction mixture hydrogenated at a pressure of 40 psi for 5 hours. The mixture was filtered through celite concentrated in vacuo, and purified by silica gel column chromatography eluting with a 0-50% ethyl acetate/hexanes gradient. The isomers separated at this stage to give (16.52 g, 54%) of product as a brown solid.
$^1$H NMR (400 MHz, CDCl$_3$): δ ppm 1.55 (m, 2H), 1.65 (m, 2H), 1.79 (m, 2H), 2.04 (m, 2H), 2.12 (s, 3H), 2.93 (m, 1H), 7.14 (d, 2H), 7.39 (d, 2H), 7.82 (s, 1H).
LCMS Rt=1.29 minutes MS m/z 204 [M+H]$^+$ Preparation 98

N-(4-Neopentylphenyl)acetamide

To a solution of neopentylbenzene (9.20 g, 62 mmol) in acetic anhydride (30 mL) cooled in an ice bath was slowly added a solution of nitric acid (3.5 mL, 83 mmol) in acetic anhydride (10 mL). The reaction was allowed to warm to room temperature for 18 hours. The yellow reaction mixture was added to ice water and extracted with diethylether (3×). The organic layers were combined, washed with brine, dried over anhydrous magnesium sulphate, filtered, and concentrated in vacuo. This provided a 1:1 mixture of ortho and para nitro substituted compounds as a yellow solid. To this yellow solid dissolved in methanol (100 mL) was added acetic anhydride (8.4 mL, 89 mmol) and 10% palladium on carbon (700 mg, 7 mmol) and the reaction mixture hydrogenated at a pressure of 40 psi for 3 hours. The reaction was filtered through celite, concentrated in vacuo, and purified by silica gel column chromatography eluting with a 0-50% ethyl acetate/hexanes gradient. This provided the title compound (2.79 g, 22%) as a white solid.
$^1$H NMR (400 MHz, CDCl$_3$): δ ppm 0.90 (s, 9H), 2.15 (s, 3H), 2.44 (s, 2H), 7.07 (d, 2H), 7.38 (d, 2H), 7.61 (br s, 1H).
LCMS Rt=1.19 minutes MS m/z 205 [M+H]$^+$ Preparation 99

N-[4-(1,1-Dimethylpropyl)phenyl]acetamide

To a stirred solution of 4-(1,1-dimethylpropyl)aniline (Preparation 100, 12.5 g, 0.076 mol) in THF (100 mL) was added acetic anhydride slowly at 0° C. The reaction was stirred at room temperature for 8 hours. The reaction was extracted with EtOAc, washed with brine, dried over Na$_2$SO$_4$ and concentrated in vacuo to afford the title compound (12 g, 76%).
$^1$H NMR (400 MHz, DMSO-d$_6$): δ ppm 0.60 (t, 3H), 1.20 (s, 6H), 1.56 (q, 2H), 2.01 (s, 3H), 7.21 (d, 2H), 7.45 (d, 2H), 9.81 (s, 1H).

Preparation 100

4-(1,1-Dimethylpropyl)aniline

The title compound was prepared according to Preparation 82 for 3 hours using 1-(1,1-dimethylpropyl)-4-nitrobenzene (Preparation 101). The crude residue was used directly in the next reaction.
$^1$H NMR (400 MHz, DMSO-d$_6$): δ ppm 0.61 (t, 3H), 1.14 (s, 6H), 1.52 (m, 2H), 4.77 (s, 2H), 6.49 (d, 2H), 6.94 (d, 2H).

Preparation 101

1-(1,1-Dimethylpropyl)-4-nitrobenzene

The title compound was prepared according to Preparation 95 using (1,1-dimethylpropyl)benzene.
$^1$H NMR (400 MHz, DMSO-d$_6$): δ ppm 0.61 (m, 3H), 1.28 (m, 6H), 1.65 (q, 2H), 7.63 (d, 2H), 8.16 (d, 2H).

Preparation 102

2-[4-Cyano-2-(trifluoromethyl)phenyl]-1'-4,4,5,5-tetramethyl-1,3,2-dioxaborolane To a degassed suspension of 4-bromo-3-(trifluoromethyl)benzonitrile (0.5 g, 2 mmol), bis-pinacolatodiborane (0.559 g, 2.2 mmol) and potassium acetate (0.589 g, 6 mmol) in dioxane (9 mL) was added Pd(dppf)Cl$_2$ (0.082 g, 0.1 mmol) and the mixture heated to 100° C. for 18 hours. The reaction was cooled and concentrated to dryness, diluted with EtOAc (40 mL), washed with water (10 mL), brine (5 mL), dried over MgSO$_4$ and concentrated in vacuo. The residue was purified using silica gel column chromatography eluting with EtOAc: Heptane 1:6 to afford the title compound (252 mg, 42%).
$^1$H NMR (400 MHz, CDCl$_3$): δ ppm 1.38 (s, 12H), 7.80 (d, 1H), 7.86 (d, 1H), 7.94 (s, 1H).

Preparation 103

2,6-Difluoro-4-(4,4,5,5-tetramethyl-1,3,2-dioxaborolan-2-yl)benzonitrile

The title compound was prepared according to Preparation 102 using 4-bromo-2,6-difluorobenzonitrile. The reaction was filtered through arbocel washing through with EtOAc. The filtrate was washed with water, saturated aqueous NaHCO$_3$ solution, brine, dried over MgSO$_4$ and concentrated in vacuo. The residue was used directly in the next step.

Preparation 104

3,4-Dicyanophenylboronic acid

The title compound was prepared according to Preparation 102 using 4-iodophthalonitrile to provide a mixture of the boronic acid and boronic ester. The mixture was taken on to the next step as crude.
LCMS (2 minute run) Rt=1.71 minutes MS m/z 171 [M–H]$^-$ boronic acid Preparation 105

3,5-Difluoro-4-cyanophenylboronic acid

The title compound was prepared according to Preparation 102 using 4-bromo-2,6-difluorobenzonitrile and used crude in the next step.
LCMS Rt=2.37 minutes MS m/z 182 [M–H]–

Preparation 106

N-1-Benzyl-4-tert-butylbenzene-1,2-diamine

A 50 L autoclave was charged with methanol (37.2 L) and benzyl-(4-tert-butyl-2-nitrophenyl)lamine (Preparation 107, 6.2 kg, 21.8 mol) and the mixture stirred for ten minutes. Raney nickel (0.62 kg) was charged and the reaction maintained under hydrogen (4.0 kg) at room temperature for ten hours. After catalyst filtration and washing with methanol (1.7 L) the filtrate was concentrated under vacuum at <50° C. The residue was stirred in water (20 L) for one hour and the solids collected by filtration, washed with water (2.5 L), and dried at 45-50° C. to provide 5.1 kg of the title compound.

$^1$H NMR (400 MHz, DMSO-$d_6$): δ ppm 1.32 (s, 9H), 4.25 (d, 2H), 4.47 (s, 2H), 4.95 (m, 1H), 6.24 (d, 1H), 6.39 (d, 1H), 6.61 (s, 1H), 7.20 (m, 1H), 7.28-7.36 (m, 4H).

Preparation 107

Benzyl-(4-tert-butyl-2-nitrophenyl)amine

A reactor was charged with DMSO (6 L), followed by 4-tert-butyl-2-nitrophenylamine (Preparation 108, 3.0 kg, 15.4 mol) and potassium hydroxide (1.32 kg, 23.5 mol). The mixture was stirred at room temperature for twenty minutes. Toluene (12 L) was added and the mixture stirred for another twenty minutes. After cooling to 10° C., benzyl bromide (3.16 kg, 18.5 mol) was added slowly and the reaction mixture was stirred for 4 hours. Water (30 L) was added, the mixture stirred for 30 minutes and the layers allowed to settle. The aqueous layer was extracted with toluene (2×10 L), followed by ethyl acetate (10 L), and the combined organic extracts concentrated under vacuum at <50° C. Isopropanol (4 L) was added and the mixture cooled to −5° C. The slurry was stirred for 1 hour before collecting the solids by filtration, washing with isopropanol (2×1.5 L) and drying at 55-60° C. to provide 2.8 kg of the title compound.

$^1$H NMR (400 MHz, DMSO-$d_6$): δ ppm 1.20 (s, 9H), 4.60 (s, 2H), 6.55 (d, 1H), 7.23 (m, 1H), 7.33 (m, 4H), 7.56 (d, 1H), 7.96 (s, 1H), 8.63 (m, 1H).

Preparation 108

4-tert-Butyl-2-nitrophenylamine

A reactor was charged with methanol (13.5 L) and N-(4-tert-butyl-2-nitrophenyl) acetamide (Preparation 109, 7.0 kg, 29.6 mol). The mixture was stirred for ten minutes then a solution of 30% sodium methoxide in methanol (6.49 L, 35.5 mol) was added slowly at room temperature. The mixture was heated slowly to reflux and held at that temperature for two hours. The methanol was distilled to dryness under vacuum at 50-55° C. and the solids cooled to room temperature. The residue was stirred in water (35 L) for one hour and the solids collected by filtration, washed with water (14 L), and dried at 45-50° C. to provide 5.3 kg of the title compound.

$^1$H NMR (400 MHz, CDCl$_3$): δ ppm 1.27 (s, 9H), 5.95 (br s, 2H), 6.76 (d, 1H), 7.43 (d, 1H), 8.08 (s, 1H).

Preparation 109

N-(4-tert-Butyl-2-nitrophenyl)acetamide

A reactor was charged with acetic acid (8.7 L), followed by N-(4-tert-butylphenyl) acetamide (Preparation 110, 6.0 kg, 31.4 mol), The mixture was stirred for ten minutes, followed by the addition of acetic anhydride (6.47 kg, 63.4 mol) slowly at room temperature. The reaction was stirred for fifteen minutes. A solution of fuming nitric acid (3.56 kg, 56.5 mol) in acetic acid (2.1 L) was added slowly at 20-25° C., and stirred at that temperature for another 2 hours. The reaction mixture was added to ice water (42 L) at 10-15° C. and the mixture stirred for one hour. The resulting solids were collected by filtration, washed with water (17 L) and dried at 65-70° C. to provide 7.1 kg of the title compound.

$^1$H NMR (400 MHz, CDCl$_3$): δ ppm 1.40 (s, 9H), 2.93 (s, 3H), 7.71 (d, 1H), 8.21 (s, 1H), 8.66 (d, 1H), 10.23 (br s, 1H).

Preparation 110

N-(4-tert-Butyl phenyl)acetamide

A reactor was charged with 1,2-dichloroethane (50 L), followed by aluminum chloride (6.08 kg, 45.6 mol), The mixture was stirred for ten minutes at room temperature and then cooled to 5° C. N-phenylacetamide (5 kg, 37.0 mol) was added slowly, after which the mixture was cooled to −12° C. A solution of t-butylchloride (5.03 kg, 54.3 mol) in 1,2-dichloroethane (5 L) was added to the reaction over ten minutes and then stirred for 1 hour at that temperature. The reaction mixture was added to ice water (50 L) and concentrated hydrochloric acid (2.5 L) at 5-10° C., over one hour. The mixture was heated slowly to 40° C., held at that temperature for thirty minutes and the layers then allowed to separate. The aqueous was extracted further with dichloroethane (50 L) and the combined extracts concentrated, under vacuum, to low volume. Hexane (5 L) was added and the mixture concentrated in vacuo. The residue was slurried with hexane (25 L), cooled to 5° C. and stirred for thirty minutes. The solids were isolated by filtration and dried at room temperature to provide 6.1 kg of the title compound.

$^1$H NMR (400 MHz, CDCl$_3$): δ ppm 1.32 (s, 9H), 2.14 (s, 3H), 7.30 (d, 2H), 7.42 (d, 2H), 7.89 (brs, 1H).

Assay Method

The ability of the benzimidazole derivatives of the formula (I) to inhibit the $Na_v1.8$ channel may be measured using the assay described below.

HEK cells stably transfected with hNav1.8, purchased from Millipore (Millipore Corp., Billerica, Mass. 01821), were maintained according to manufacturer's instructions. For electrophysiological studies, cells were removed from the culture flask by brief trypsinization and re-plated at low density onto glass cover slips. Cells were typically used for electrophysiological experiments within 24 to 72 h after plating.

Electrophysiological Recording

Cover slips containing HEK cells expressing hNav1.8 were placed in a bath on the stage of an inverted microscope and perfused (approximately 1 ml/min) with extracellular solution of the following composition: 138 mM NaCl, 2 mM CaCl2, 5.4 mM KCl, 1 mM MgCl$_2$, 10 mM glucose, and 10 mM HEPES, pH 7.4, with NaOH. Pipettes were filled with an intracellular solution of the following composition: 135 mM CsF, 5 mM CsCl, 2 mM MgCl$_2$, 10 mM EGTA, 10 mM HEPES, pH 7.3 with NaOH, and had a resistance of 1 to 2 megaohms. The osmolarity of the extracellular and intracellular solutions was 300 mOsm/kg and 295 mOsm/kg, respectively. All recordings were made at room temperature (22-24° C.) using AXOPATCH 200B amplifiers and PCLAMP software (Axon Instruments, Burlingame, Calif.).

hNav1.8 currents in HEK cells were measured using the whole-cell configuration of the patch-clamp technique (Hamill et al., 1981). Uncompensated series resistance was typically 2 to 5 mega ohms and >85% series resistance compensation was routinely achieved. As a result, voltage errors were negligible and no correction was applied. Current records were acquired at 20 to 50 KHz and filtered at 5 to 10 KHz.

HEK cells stably transfected with hNav1.8 were viewed under Hoffman contrast optics and placed in front of an array of flow pipes emitting either control or compound-containing extracellular solutions. All compounds were dissolved in dimethyl sulfoxide to make 10 mM stock solutions, which were then diluted into extracellular solution to attain the final concentrations desired. The final concentration of dimethyl sulfoxide (≤0.3% dimethyl sulfoxide) was found to have no significant effect on hNav1.8 sodium currents.

The voltage-dependence of inactivation was determined by applying a series of depolarizing prepulses (8 sec long in 10 mV increments) from a negative holding potential. The voltage was then immediately stepped to 0 mV to assess the magnitude of the sodium current. Currents elicited at 0 mV were plotted as a function of prepulse potential to allow estimation of the voltage at which 50% of the channels were inactivated (midpoint of inactivation or $V_{1/2}$). Compounds were tested for their ability to inhibit hNav1.8 sodium channels by activating the channel with a 20 msec voltage step to 0 mV following an 8 second conditioning prepulse to the empirically determined $V_{1/2}$. Compound effect (% inhibition) was determined by difference in current amplitude before and after application of test compounds. For ease of comparison, "estimated $IC_{50}$" values were calculated from single point electrophysiology data by the following equation, (tested concentration, uM)×(100-% inhibition/% inhibition). Inhibition values<20% and >80% were excluded from the calculation.

In some cases electrophysiological assays were conducted with PatchXpress 7000 hardware and associated software (Molecular Devices Corp). All assay buffers and solutions were identical to those used in conventional whole-cell voltage clamp experiments described above. hNav1.8 cells were grown as above to 50%-80% confluency and harvested by trypsinization. Trypsinized cells were washed and resuspended in extracellular buffer at a concentration of $1\times10^6$ cells/ml. The onboard liquid handling facility of the PatchXpress was used for dispensing cells and application of test compounds. Determination of the voltage midpoint of inactivation was as described for conventional whole-cell recordings. Cells were then voltage-clamped to the empirically determined $V_{1/2}$ and current was activated by a 20 msec voltage step to 0 mV.

Estimated $IC_{50}$ values for the compounds of formula (I) exemplified above are as follows.

| Example No. | $Na_v1.8$ $EIC_{50}$ (nM) |
|---|---|
| 1 | 127 |
| 2 | 76 |
| 3 | 12.5 |
| 4 | 447 |
| 5 | 364 |
| 6 | 433 |
| 7 | 439 |
| 8 | 108 |
| 9 | 347 |
| 10 | 607 |
| 11 | 29.7 |
| 12 | 243 |

-continued

| Example No. | $Na_v1.8$ $EIC_{50}$ (nM) |
|---|---|
| 13 | 496 |
| 14 | 476 |
| 15 | 123 |
| 16 | 2510 |
| 17 | 468 |
| 18 | 487 |
| 19 | 176 |
| 20 | 106 |
| 21 | 32.6 |
| 22 | 108 |
| 23 | 44.6 |
| 24 | 58 |
| 25 | 74.2 |
| 26 | 31.5 |
| 27 | 153 |
| 28 | 130 |
| 29 | 390 |
| 30 | 148 |
| 31 | 125 |
| 32 | 163 |
| 33 | 266 |
| 34 | 30.6 |
| 35 | 171 |
| 36 | 227 |
| 37 | 650 |
| 38 | 41.9 |
| 39 | 54.2 |
| 40 | 77.1 |
| 41 | 648 |
| 42 | 122 |
| 43 | 842 |
| 44 | 890 |
| 45 | 203 |
| 46 | 713 |
| 47 | 781 |
| 48 | 469 |
| 49 | 1050 |
| 50 | 1840 |
| 51 | 3130 |
| 52 | 703 |
| 53 | 562 |
| 54 | 662 |
| 55 | 77.4 |
| 56 | 97.5 |
| 57 | 2530 |
| 58 | 537 |
| 59 | 105 |
| 60 | 166 |
| 61 | 698 |
| 62 | 580 |
| 63 | — |
| 64 | 1000 |
| 65 | 2710 |
| 66 | 1000 |
| 67 | — |
| 68 | 635 |
| 69 | 3900 |
| 70 | 3160 |
| 71 | 3930 |
| 72 | 2490 |
| 73 | 827 |
| 74 | 1360 |
| 75 | ND |
| 76 | ND |
| 77 | 483 |
| 78 | 59.3 |
| 79 | 168 |
| 80 | 87.6 |
| 81 | 82.8 |
| 82 | 323 |
| 83 | 872 |
| 84 | 81.9 |
| 85 | 10.5 |
| 86 | 111 |

-continued

| Example No. | Na$_v$1.8 EIC$_{50}$ (nM) |
|---|---|
| 87 | 1330 |
| 88 | 993 |
| 89 | 2390 |
| 90 | 18.7 |
| 91 | 666 |
| 92 | 17.5 |
| 93 | 746 |
| 94 | 1080 |
| 95 | 3310 |
| 96 | 188 |
| 97 | 151 |
| 98 | 1350 |
| 99 | 2490 |
| 100 | 82.5 |
| 101 | 200 |
| 102 | 71 |
| 103 | 15.4 |
| 104 | 1580 |
| 105 | 69.9 |
| 106 | 35 |
| 107 | 356 |
| 108 | 207 |
| 109 | 56.1 |
| 110 | 233 |
| 111 | 190 |
| 112 | 187 |
| 113 | 749 |
| 114 | 27.8 |
| 115 | 278 |
| 116 | 222 |
| 117 | 2490 |
| 118 | 348 |
| 119 | 671 |
| 120 | 88.5 |
| 121 | 3050 |
| 122 | 326 |
| 123 | 1080 |
| 124 | — |
| 125 | 2220 |
| 126 | 967 |
| 127 | 2770 |
| 128 | 368 |
| 129 | 510 |
| 130 | 1340 |
| 131 | 394 |
| 132 | 191 |
| 133 | 228 |
| 134 | 355 |
| 135 | 1000 |
| 136 | 508 |
| 137 | 915 |
| 138 | 486 |
| 139 | 43.5 |
| 140 | 223 |
| 141 | 797 |
| 142 | 1840 |
| 143 | 85.2 |
| 144 | 41.3 |
| 145 | 284 |
| 146 | 27.3 |
| 147 | 110 |
| 148 | 1000 |
| 149 | 303 |
| 150 | 134 |
| 151 | 45.2 |
| 152 | 101 |
| 153 | 96.3 |
| 154 | 108 |
| 155 | 208 |
| 156 | 54.6 |
| 157 | 44.5 |

Where replicate experiments were conducted resulting in multiple sets of data for a test compound, the data presented represent the average value from all replicate experiments.

The invention claimed is:

1. A compound of formula (I)

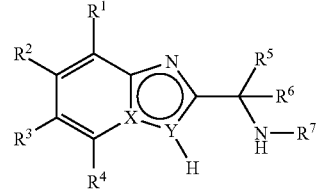

(I)

or a tautomer thereof, or a pharmaceutically acceptable salt of said compound or said tautomer, wherein:
one of X and Y is C and the other is N;
$R^1$ is selected from
    H, F, Cl and $CF_3$;
one of $R^2$ and $R^3$ is selected from
    $(C_3-C_6)$alkyl,
    $(C_3-C_6)$cycloalkyl,
    adamantyl, and
    phenyl substituted with —CN, and optionally further substituted with one or two groups independently selected from —F, —Cl, —$CF_3$ and —CN;
and the other one of $R^2$ and $R^3$ is selected from
    H and F;
$R^4$ is selected from
    H, F, Cl and $CF_3$
$R^5$ is selected from
    $(C_1-C_6)$alkyl,
    $(C_1-C_6)$alkyl substituted with a group selected from
        —CON$H_2$,
        —CONH—$(C_1-C_3)$alkyl,
        —CON$((C_1-C_3)$alkyl$)_2$ wherein the $(C_1-C_3)$alkyl groups may be the same or different,
        —OH,
        —O$(C_1-C_3)$alkyl, and
        —OCON$H_2$,
    $(C_3-C_6)$cycloalkyl, and
    phenyl,
$R^6$ is selected from
    H and $(C_1-C_3)$alkyl,
or $R^5$ and $R^6$ together with the carbon atom to which they are attached may form a 3- to 6-membered cycloalkyl moiety which may optionally be benzo-fused;
$R^7$ is H or methyl,
or, when $R^5$ and $R^6$ do not form a cycloalkyl or benzo-fused cycloalkyl moiety, $R^5$ and $R^7$ together with the carbon and nitrogen atoms to which they are attached may form 4- to 6-membered monocyclic or 6- to 8-membered bicyclic saturated nitrogen heterocycle which may optionally be substituted with 1 or 2 groups selected from —$(C_1-C_3)$alkyl, —OH, and —F.

2. The compound according to claim 1 of formula ($I^B$)

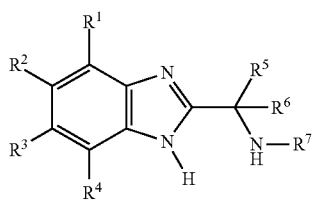

($I^B$)

or a tautomer thereof, or a pharmaceutically acceptable salt of said compound or tautomer, wherein $R^1$ is selected from H, F and Cl;
$R^2$ is selected from
  $(C_3-C_6)$alkyl,
  $(C_3-C_6)$cycloalkyl,
  adamantyl, and
  phenyl substituted with —CN, and optionally further substituted with one or two groups independently selected from —F, —Cl, —CF$_3$ and —CN; and
$R^3$ is selected from
  H and F; and
$R^4$ is selected from H and CF$_3$; and
$R^5$ is selected from
  $(C_1-C_6)$alkyl,
  $(C_1-C_6)$alkyl substituted with a group selected from
    —CONH$_2$,
    —CONH-$(C_1-C_3)$alkyl,
    —CON$((C_1-C_3)$alkyl$)_2$ wherein the $(C_1-C_3)$alkyl groups may be the same or different,
    —OH,
    —O$(C_1-C_3)$alkyl, and
    —OCONH$_2$,
  $(C_3-C_6)$cycloalkyl, and
  phenyl,
$R^6$ is selected from
  H and $(C_1-C_3)$alkyl,
or $R^5$ and $R^6$ together with the carbon atom to which they are attached may form a 3- to 6-membered cycloalkyl moiety which may optionally be benzo-fused;
$R^7$ is H or methyl,
or, when $R^5$ and $R^6$ do not form a cycloalkyl or benzo-fused cycloalkyl moiety, $R^5$ and $R^7$ together with the carbon and nitrogen atoms to which they are attached may form 4- to 6-membered monocyclic or 6- to 8-membered bicyclic saturated nitrogen heterocycle which may optionally be substituted with 1 or 2 groups selected from —$(C_1-C_3)$alkyl, —OH, and —F.

3. The compound according to claim 2 or a tautomer thereof, or a pharmaceutically acceptable salt of said compound or tautomer, wherein $R^3$ is H.

4. The compound according to claim 3 or a tautomer thereof, or a pharmaceutically acceptable salt of said compound or tautomer, wherein $R^2$ is selected from 1,1-dimethylethyl and 1,1-dimethylpropyl.

5. The compound according to claim 1 or a tautomer thereof, or a pharmaceutically acceptable salt of said compound or tautomer, wherein $R^1$ and $R^4$ are both H.

6. The compound according to claim 1 of formula ($I^E$)

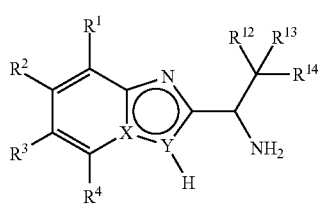

($I^E$)

or a tautomer thereof, or a pharmaceutically acceptable salt of said compound or tautomer, wherein:
  one of X and Y is C and the other is N;
  $R^1$ is selected from H, F Cl and CF$_3$;
  one of $R^2$ and $R^3$ is selected from
    $(C_3-C_6)$alkyl,
    $(C_3-C_6)$cycloalkyl,
    adamantyl, and
    phenyl substituted with —CN, and optionally further substituted with one or two groups independently selected from —F, —Cl, —CF$_3$ and —CN; and
  the other one of $R^2$ and $R^3$ is selected from
    H and F;
  $R^4$ is selected from H, F, Cl and CF3; and;
  $R^{12}$ and $R^{13}$ are each independently —H or methyl; and
  $R^{14}$ is selected from —OH, —O$(C_1-C_3)$alkyl, —OCONH$_2$ and —CONH$_2$.

7. The compound according to claim 1 selected from:
  4-{2-[(1R,2R)-1-amino-2-methoxypropyl]-1H-benzimidazol-5-yl}-2-fluorobenzonitrile,
  4-{2-[(1R,2R)-1-amino-2-methoxypropyl]-1H-benzimidazol-5-yl}benzonitrile,
  4-{2-[(1R,2R)-1-amino-2-methoxypropyl]-1H-benzimidazol-5-yl}-3-fluorobenzonitrile,
  4-{2-[(1R,2R)-1-amino-2-hydroxypropyl]-1H-benzimidazol-6-yl}-2-fluorobenzonitrile,
  4-{2-[(1R,2R)-1-amino-2-hydroxypropyl]-1H-benzimidazol-5-yl}benzonitrile,
  4-{2-[(1R,2R)-1-amino-2-methoxypropyl]-4-chloro-1H-benzimidazol-5-yl}benzonitrile,
  (2R,3S)-3-amino-3-[5-(4-cyano-3-fluorophenyl)-1H-benzimidazol-2-yl]-2-methylpropanamide,
  4-{2-[(1R,2R)-1-amino-2-methoxypropyl]-4-chloro-1H-benzimidazol-5-yl}-2-fluorobenzonitrile,
  4-{2-[(1R,2R)-1-amino-2-methoxypropyl]-1H-benzimidazol-6-yl}-3-chlorobenzonitrile,
  (1R,2R)-1-(5-tert-butyl-1H-benzimidazol-2-yl)-2-methoxypropan-1-amine,
  (2R,3S)-3-amino-3-(5-tert-butyl-1H-benzimidazol-2-yl)-2-methylpropanamide, and
  (1R,2S)-1-amino-1-(5-tert-butyl-1H-benzimidazol-2-yl)propan-2-yl carbamate;
or a pharmaceutically acceptable salt thereof.

8. A method of treating pain comprising administering a therapeutically effective amount of a compound according to claim 1, or a tautomer thereof, or a pharmaceutically acceptable salt of said compound or tautomer, to an individual in need of such treatment.

* * * * *